United States Patent
Schaus et al.

(10) Patent No.: US 11,458,132 B2
(45) Date of Patent: Oct. 4, 2022

(54) QUINOLIN-2(1H)-ONE INHIBITORS OF LATE SV40 FACTOR

(71) Applicant: TRUSTEES OF BOSTON UNIVERSITY, Boston, MA (US)

(72) Inventors: Scott Edward Schaus, Boston, MA (US); Ulla Hansen, Bedford, MA (US); Emily Ann York, Allston, MA (US); Niranjana Pokharel, Brighton, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 17/464,260

(22) Filed: Sep. 1, 2021

(65) Prior Publication Data

US 2022/0062272 A1    Mar. 3, 2022

Related U.S. Application Data

(60) Provisional application No. 63/165,278, filed on Mar. 24, 2021, provisional application No. 63/128,452, filed on Dec. 21, 2020, provisional application No. 63/073,240, filed on Sep. 1, 2020.

(51) Int. Cl.
| | |
|---|---|
| *A61K 31/4741* | (2006.01) |
| *A61P 35/00* | (2006.01) |
| *C07D 491/056* | (2006.01) |
| *C07D 215/227* | (2006.01) |

(52) U.S. Cl.
CPC ......... *A61K 31/4741* (2013.01); *A61P 35/00* (2018.01)

(58) Field of Classification Search
CPC .............................. A61K 31/4741; A61P 35/00
See application file for complete search history.

(56) References Cited

U.S. PATENT DOCUMENTS

| | | |
|---|---|---|
| 6,713,462 B2 | 3/2004 | Metcalf et al. |
| 7,081,256 B2 | 7/2006 | Kubota et al. |
| 8,440,705 B2 | 5/2013 | Lindquist et al. |
| 9,802,948 B2 | 10/2017 | Hansen et al. |
| 9,815,845 B2 | 11/2017 | Hansen et al. |
| 2003/0130505 A1 | 7/2003 | Zhi et al. |
| 2007/0287706 A1 | 12/2007 | Dickinson, Jr. et al. |
| 2009/0081183 A1 | 3/2009 | Margolis et al. |
| 2010/0004277 A1 | 1/2010 | Bulawa et al. |
| 2010/0105906 A1 | 4/2010 | Bissantz et al. |
| 2013/0158035 A1 | 6/2013 | Hansen |
| 2013/0324570 A1 | 12/2013 | Hansen et al. |
| 2015/0344491 A1 | 12/2015 | Schaus et al. |
| 2017/0044175 A1* | 2/2017 | Hansen .............. C07D 491/056 |
| 2017/0107227 A1 | 4/2017 | Hansen et al. |
| 2018/0051033 A1 | 2/2018 | Hansen et al. |
| 2019/0152949 A1 | 5/2019 | Cyr et al. |
| 2020/0039996 A1 | 2/2020 | Schaus et al. |

FOREIGN PATENT DOCUMENTS

| | | |
|---|---|---|
| CN | 101410384 A | 4/2009 |
| EP | 2433634 A2 | 3/2012 |
| WO | 1998/36641 A1 | 8/1998 |
| WO | 2003/066630 A1 | 8/2003 |
| WO | 2007/136592 A2 | 11/2007 |
| WO | 2011/123427 A2 | 10/2011 |
| WO | 2013/052465 A1 | 4/2013 |

OTHER PUBLICATIONS

Grant, Trevor J., "Antiproliferative small-molecule inhibitors of transcription factor LSF reveal oncogene addiction to LSF in hepatocellular carcinoma." Proceedings of the National Academy of Sciences 109.12 (2012): 4503-4508.*
Bortner, C. D., "A necessary role for cell shrinkage in apoptosis." Biochemical pharmacology 56.12 (1998): 1549-1559.*
Rajasekaran, D., "Small molecule inhibitors of Late SV40 Factor (LSF) abrogate hepatocellular carcinoma (HOC): Evaluation using an endogenous HOC model." Oncotarget 6.28 (2015): 26266-26277.*
Ahmed et al. "Epigenetic and genetic features of 24 colon cancer cell lines." Oncogenesis 2(9): e71 pp. 1-8 (2013).
Biagi. "Assessing the selectivity and efficacy of dihydroquinolinone inhibitors directly targeting the oncogene LSF." PhD Diss., Boston University pp. 1-159 (2017).
Broniarczyk et al. "Expression of TSG101 protein and LSF transcription factor in HPV-positive cervical cancer cells." Oncology Letters 7(5): 1409-1413 (2014).
Chang et al. "GEF-H1 couples nocodazole-induced microtubule disassembly to cell contractility via RhoA." Molecular Biology of the Cell 19(5): 2147-2153 (2008).
Chin et al. "The microtubule-associated histone methyltransferase SET8, facilitated by transcription factor LSF, methylates α-tubulin." Journal of Biological Chemistry 295(14): 4748-4759 (2020).
Chin et al. "Transcription factor LSF-DNMT1 complex dissociation by FQI1 leads to aberrant DNA methylation and gene expression." Oncotarget 7(50): 83627-83640 (2016).
Chin. "Transcription factor LSF: interactions with protein partners leading to epigenetic regulation and microtubule modifications." PhD Diss., Boston University 2017.
Chitalia et al. "Jade-1 inhibits Wnt signalling by ubiquitylating β-catenin and mediates Wnt pathway inhibition by pVHL." Nature Cell Biology 10(10): 1208-1216 (2008).
Field. "Microtubule-targeting agents are clinically successful due to both mitotic and interphase impairment of microtubule function." Bioorganic & Medicinal Chemistry 22(18): 5050-5059 (2014).

(Continued)

*Primary Examiner* — John M Mauro
(74) *Attorney, Agent, or Firm* — Nixon Peabody LLP; Ronald I. Eisenstein; Ravinderjit Braich

(57) ABSTRACT

The present invention is directed to compositions, methods and kits for treatment of cancer, e.g., hepatocellular carcinoma (HCC). In some embodiments, the present invention discloses the use of a small-molecule compounds of Formula (I) to inhibit tubulin acetylation, to inhibit cell migration, or to modulate cell compaction.

28 Claims, 67 Drawing Sheets

(56) References Cited

OTHER PUBLICATIONS

Gandalovicova at al. "Migrastatics—anti-metastatic and anti-invasion drugs: promises and challenges." Trends in Cancer 3(6): 391-406 (2017).
Ghosh et al. "The Wnt signaling pathway: a potential therapeutic target against cancer." Annals of the New York Academy of Sciences 1443(1): 54-74 (2019).
Gigant et al. "Structural basis for the regulation of tubulin by vinblastine." Nature 435(7041): 519-522 (2005).
Grant et al. "Antiproliferative small-molecule inhibitors of transcription factor LSF reveal oncogene addiction to LSF in hepatocellular carcinoma." Proceedings of the National Academy of Sciences 109(12): 4503-4508 (2012).
Hanna et al. "Signaling networks of Rho GTPases in cell motility." Cellular Signalling 25(10): 1955-1961 (2013).
Hui et al. "Dynamic microtubules regulate cellular contractility during T-cell activation." Proceedings of the National Academy of Sciences 114(21): E4175-E4183 (2017).
Janke. "The tubulin code: molecular components, readout mechanisms, and functions." Journal of Cell Biology 206(4): 461-472 (2014).
Jiang et el. "LSF expression and its prognostic implication in colorectal cancer." International Journal of Clinical and Experimental Pathology 7(9): 6024-6031 (2014).
Jung et al. "Wnt signaling in cancer: therapeutic targeting of Wnt signaling beyond β-catenin and the destruction complex." Experimental & Molecular Medicine 52(2): 183-191 (2020).
Kahn. "Can we safely target the WNT pathway?." Nature Reviews Drug Discovery 13(7): 513-532 (2014).
Kashour et al. "Late Simian virus 40 transcription factor is a target of the phosphoinositide 3-kinase/Akt pathway in anti-apoptotic Alzheimers amyloid precursor protein signalling." Biochemical Journal 370(3): 1063-1075 (2003).
Kaul. "Microtubule-targeting drugs: more than antimitotics." Journal of Natural Products 82(3): 680-685 (2019).
Kim et al. "Targeting wnt signaling for gastrointestinal cancer therapy: Present and evolving views." Cancers 12(12): 3638 pp. 1-27 (2020).
Komlodi-Pasztor et al. "Mitosis is not a key target of microtubule agents in patient tumors." Nature Reviews Clinical Oncology 8(4): 244-250 (2011).
Kotarba et al. "TFCP2/TPCP2L1/UBP1 transcription factors in cancer." Cancer Letters 420: 72-79 (2018).
Krishnamurthy at al. "Targeting the Wnt/beta-catenin pathway in cancer: Update on effectors and inhibitors." Cancer Treatment Reviews 62: 50-60 (2018).
Lawson et al. "Rho GTPase signaling complexes in cell migration and invasion." Journal of Cell Biology 217(2): 447-457 (2018).
Niethammer et al. "Stathmin-tubulin interaction gradients in motile and mitotic cells." Science 303(5685): 1862-1866 (2004).
Ogden et al. "Interphase microtubules: chief casualties in the war on cancer?." Drug Discovery Today 19(7): 824-829 (2014).
Porta-De-La-Riva et al. "LSF/TFCP2c/LBP-1c is required for Snail1-induced fibronectin gene expression." Biochemical Journal 435(3): 563-568 (2011).
Rajasekaran et al. "Small molecule inhibitors of Late SV40 Factor (LSF) abrogate hepatocellular carcinoma (HCC): Evaluation using an endogenous HCC model." Oncotarget 6(28): 26266-26277 (2015).
Santhekadur et al. "Late SV40 factor (LSF) enhances angiogenesis by transcriptionally up-regulating matrix metalloproteinase-9 (MMP-9)." Journal of Biological Chemistry 287(5): 3425-3432 (2012).
Santhekadur at al. "The transcription factor LSF: a novel oncogene for hepatocellular carcinoma." American Journal of Cancer Research 2(3): 269-285 (2012).
Shirra et al. "LSF and NTF-1 share a conserved DNA recognition motif yet require different oligomerization states to form a stable protein-DNA complex." Journal of Biological Chemistry 273(30): 19260-19268 (1998).
Steeg at al. "Metastasis: a therapeutic target for cancer." Nature Clinical Practice Oncology 5(4): 206-219 (2008).
Stoiber et al. "Expansile Nanoparticles Encapsulate Factor Quinolinone Inhibitor 1 and Accumulate in Murine Liver upon Intravenous Administration." Biomacromolecules 21(4): 1499-1506 (2020).
Takesono et al. "Microtubules regulate migratory polarity through Rho/ROCK signaling in T cells." PloS One 5(1): e8774 pp. 1-15 (2010).
Taracha et al. "Neglected functions of TFCP2/TFCP2L1/UBP1 transcription factors may offer valuable insights into their mechanisms of action." International Journal of Molecular Sciences 19(10): 2852 pp. 1-12 (2018).
Veljkovic et al. "Lineage-specific and ubiquitous biological roles of the mammalian transcription factor LSF." Gene 343(1): 23-40 (2004).
Wadsworth. "Regional regulation of microtubule dynamics in polarized, motile cells." Cell Motility and the Cytoskeleton 42(1): 48-59 (1999).
Wang et al. "Direct targeting of β-catenin in the Wnt signaling pathway: Current progress and perspectives." Medicinal Research Reviews 41(4): 2109-2129 (2021).
Willoughby et al. "Targeting the oncogene LSF with either the small molecule inhibitor FQI1 or siRNA causes mitotic delays with unaligned chromosomes, resulting In cell death or senescence." BMC Cancer 20(1): 1-15 (2020).
Xie et al. "Acetylated microtubules are required for fusion of autophagosomes with lysosomes." BMC Cell Biology 11(1): 1-12 (2010).
Xu et al. "Characterization of genome-wide TFCP2 targets in hepatocellular carcinoma: implication of targets FN1 and TJP1 in metastasis." Journal of Experimental & Clinical Cancer Research 34(1): 1-11 (2015).
Yoo et al. "Transcription factor Late SV40 Factor (LSF) functions as an oncogene in hepatocellular carcinoma." Proceedings of the National Academy of Sciences 107(18): 8357-8362 (2010).
Yuedi et al. "TFCP2 activates beta-catenin/TCF signaling in the progression of pancreatic cancer." Oncotarget 8(41): 70538 pp. 1-12 (2017).
Yunes. "The anti-cancer compound, Factor Quinolinone Inhibitor 1, inhibits stable kinetochore-microtubule attachment during mitotic progression." PhD Diss., Boston University 2020.
Zhang et al. "TFCP2 is required for YAP-dependent transcription to stimulate liver malignancy." Cell Reports 21(5); 1227-1239 (2017).
Chen et al. "Design and synthesis of 6, 7-methylenedioxy-4-substituted phenylquinolin-2 (1H)-one derivatives as novel anticancer agents that induce apoptosis with cell cycle arrest at G2/M phase." Biorganic & medicinal chemistry 21.17 (2013): 5064-5075.
Pubmed Compound Record for CID 129047524, '8-(2-Ethoxyphenyl)-2,2-difluoro-5H-[1,3]dioxolo[4,5-g]quinolin-6-one', U.S. National Library of Medicine, Aug. 4, 2017 (Aug. 4, 2017), pp. 1-8 (https://pubchem.ncbi.nlm.nih.gov/compound/129047524) p. 2.

* cited by examiner

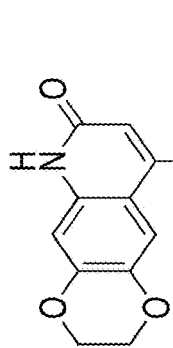
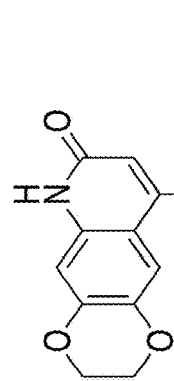
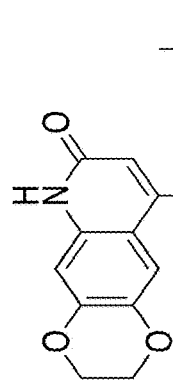
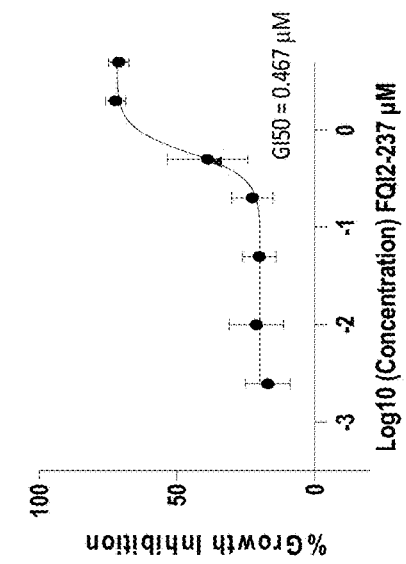
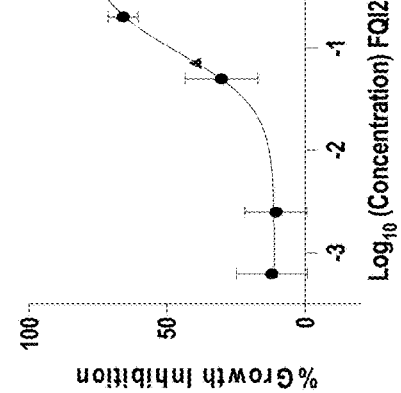
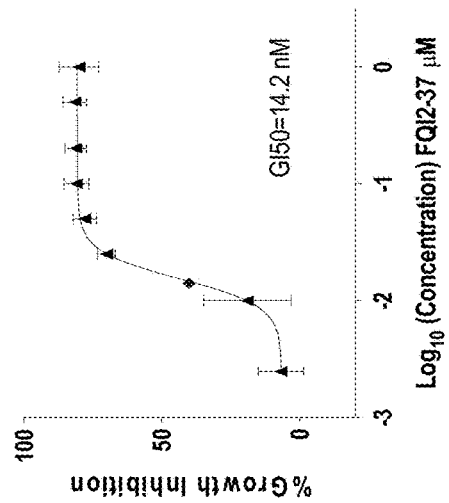
FIG. 14I
FIG. 14J
FIG. 14K

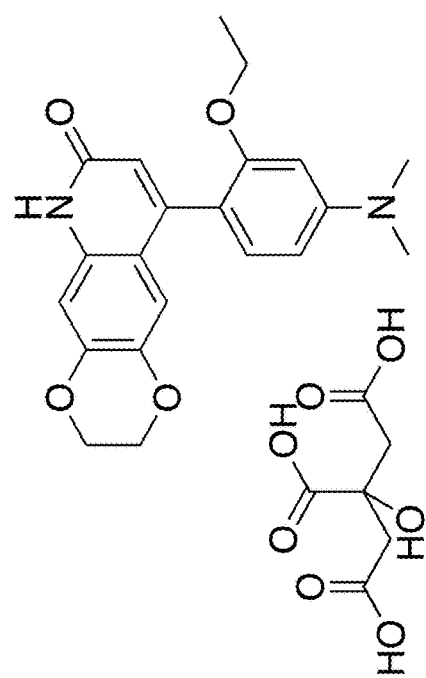
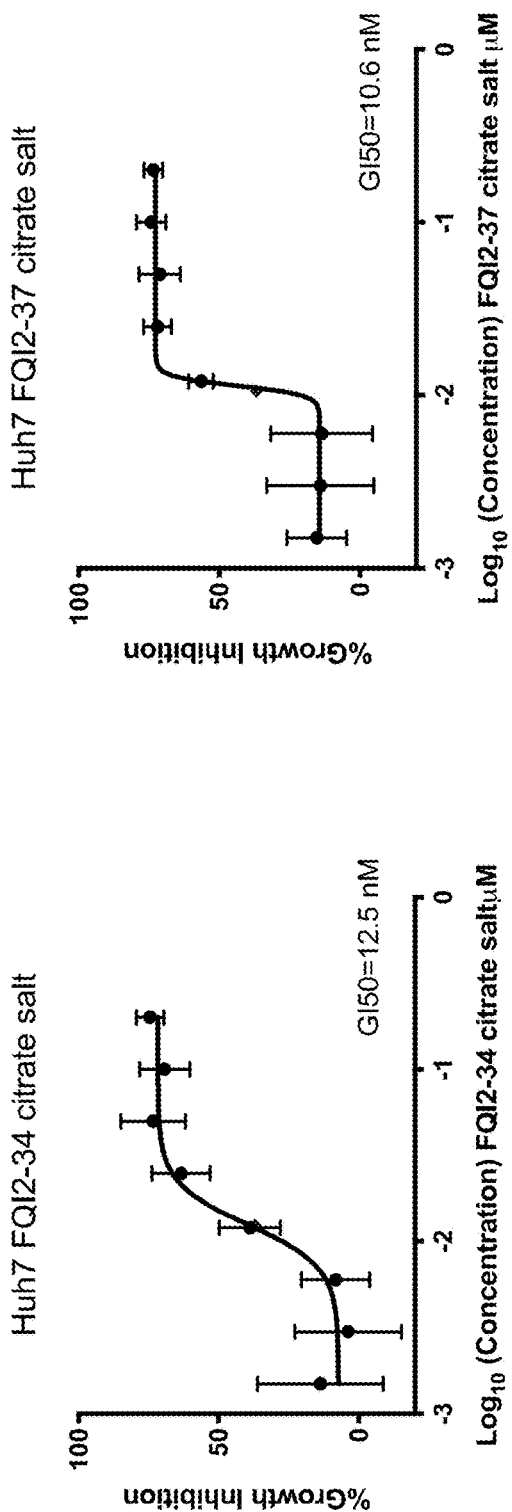
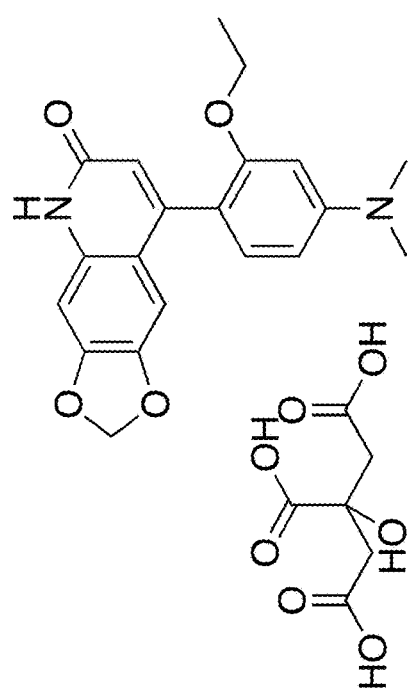
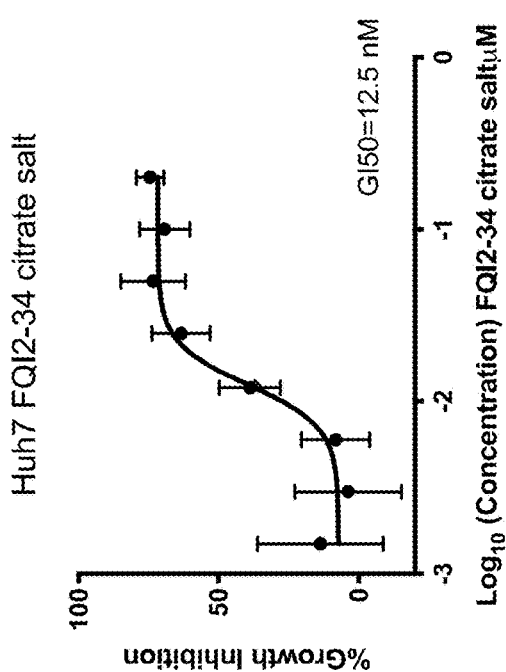
FIG. 15A
FIG. 15B

CaCo-2 Permeability pH 7.4

FQI2-34

30 x 10⁻⁶ cm/s

FQI2-37

20 x 10⁻⁶ cm/s

| Compound I.D. | Client Compound I.D. | Test Concentration | Permeability (10⁻⁶ cm/s) | | |
|---|---|---|---|---|---|
| | | | 1st | 2nd | Mean |
| A-B permeability (Caco-2, pH 7.4/7.4) | | | | | |
| 10005.4151-1 | FQI2-34 | 1.0E-05 M | 29.37 | 30.42 | 29.9 |
| 10005.4151-2 | FQI2-37 | 1.0E-05 M | 20.37 | 20.40 | 20.4 |

CaCo-2 Permeability pH 7.4

| Compound I.D. | Test Concentration | Permeability ($10^{-6}$ cm/s) | | |
|---|---|---|---|---|
| | | 1st | 2nd | Mean |
| A-B permeability (Caco-2, pH 7.4/7.4) | | | | |
| colchicine | 1.0E-05 M | 0.26 | 0.26 | 0.3 |
| labetalol | 1.0E-05 M | 20.49 | 20.04 | 20.3 |
| propranolol | 1.0E-05 M | 56.92 | 61.25 | 59.1 |
| ranitidine | 1.0E-05 M | 0.96 | 0.99 | 1.0 |

*FIG. 28*

PAMPA Assay pH 6.5

FQI2-34

$96 \times 10^{-6}$ cm / s

FQI2-37

$94 \times 10^{-6}$ cm / s

| Compound I.D. | Client Compound I.D. | Test Concentration | Permeability ($10^{-6}$ cm/s) | | |
|---|---|---|---|---|---|
| | | | 1st | 2nd | Mean |
| Parallel Artificial Membrane Permeability Assay (PAMPA, pH 6.5) | | | | | |
| 100064151-1 | FQI2-34 | 1.0E-05 M | 92.12 | 99.38 | 95.75 |
| 100064151-2 | FQI2-37 | 1.0E-05 M | 94.30 | 93.30 | 93.80 |

PAMPA Assay

Parallel Artificial Membrane Permeability Assay (PAMPA, pH 6.5)

| Compound I.D. | Test Concentration | Permeability ($10^{-6}$ cm/s) | | |
|---|---|---|---|---|
| | | 1st | 2nd | Mean |
| Furosemide | 1.0E-05 M | <1 | <1 | BLQ |
| Ketoprofen | 1.0E-05 M | 8.47 | 8.17 | 8.32 |
| Propranolol | 1.0E-05 M | 90.09 | 95.26 | 92.68 |

BLQ Compound not quantified in acceptor sample

*FIG. 30*

CYP3A4 Inhibition

FQI2-34

20% at 10 µM

FQI2-37

23% at 10 µM

| Compound I.D. | Client Compound I.D. | Test Concentration | % Inhibition of Control Values | | |
|---|---|---|---|---|---|
| | | | 1st | 2nd | Mean |
| CYP3A4 inhibition (recombinant, BFC substrate) | | | | | |
| 100054151-1 | FQI2-34 | 1.0E-05 M | 17.9 | 20.8 | 19.4 |
| 100054151-2 | FQI2-37 | 1.0E-05 M | 21.2 | 24.3 | 22.7 |

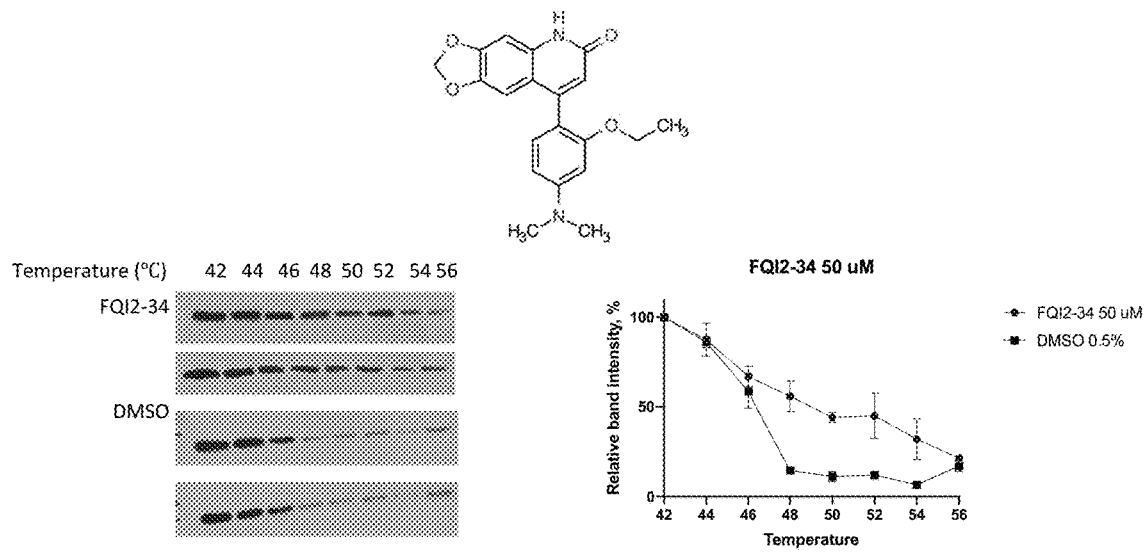
FIG. 33
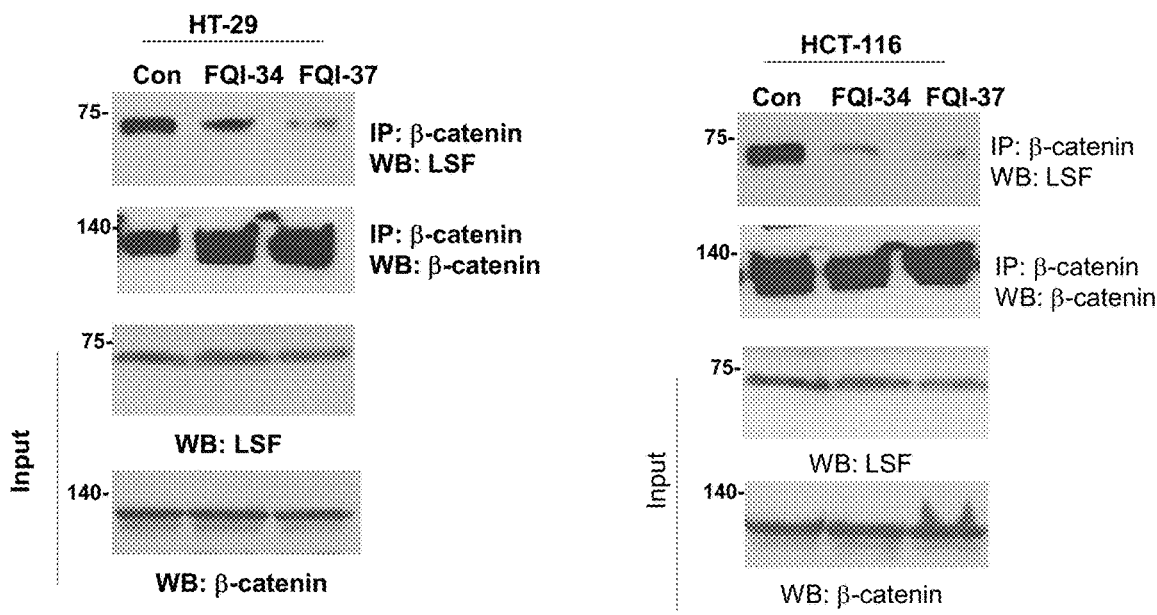
FIG. 34A
FIG. 34B

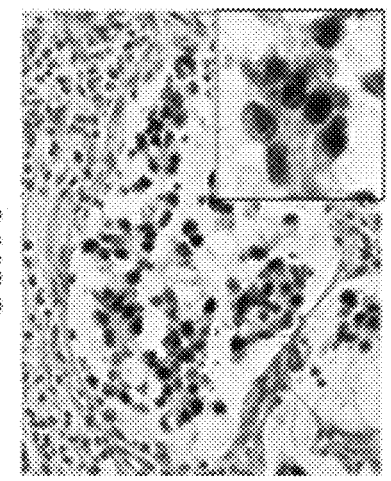 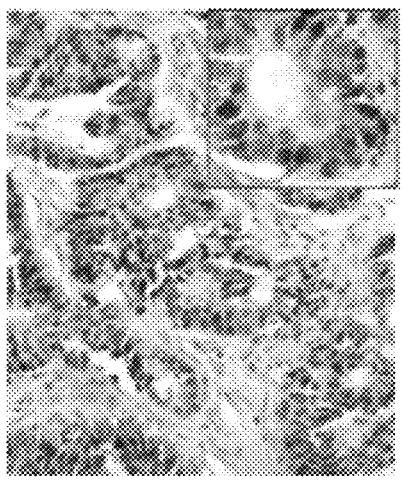
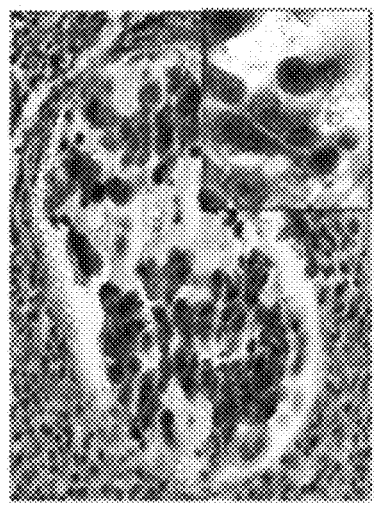 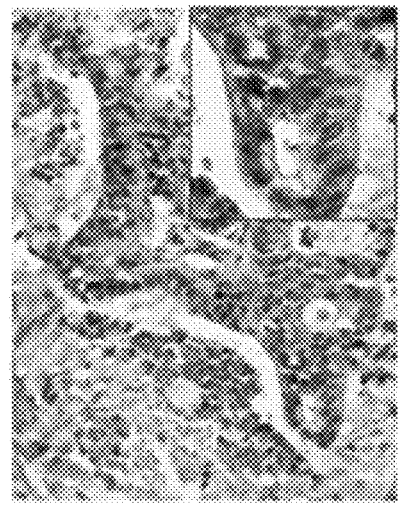
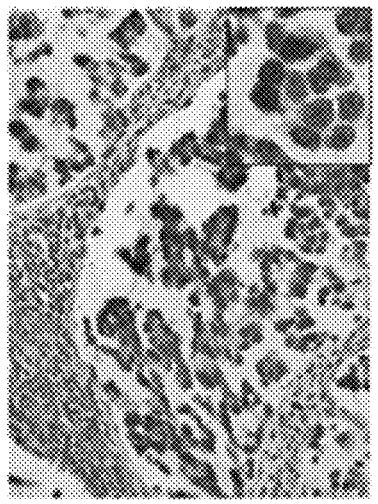 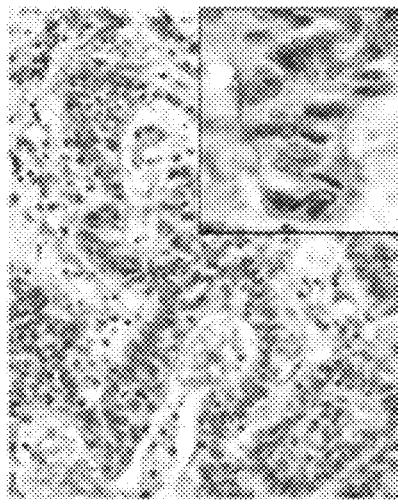
FIG. 42A  FIG. 42B

QUINOLIN-2(1H)-ONE INHIBITORS OF LATE SV40 FACTOR

RELATED APPLICATIONS

This application claims benefit under 35 U.S.C. § 119(e) of U.S. Provisional Application No. 63/073,240 filed Sep. 1, 2020, U.S. Provisional Application No. 63/128,452 filed Dec. 21, 2020, and U.S. Provisional Application No. 63/165,278 filed Mar. 24, 2021, contents of each of which are incorporated herein by reference in their entirety.

GOVERNMENT SUPPORT

This invention was made with Government support under Contract No. GM078240 awarded by the National Institutes of Health. The Government has certain rights in the invention.

TECHNICAL FIELD

The present invention generally relates to Late SV40 Factor (LSF) inhibitors and their uses, for example in a method for treating cancer, e.g., hepatocellular carcinoma (HCC) or colorectal cancer (CRC).

BACKGROUND

Microtubules are important in many cellular processes such as cell motility, protein and organelle transport, and mitosis and are a validated target for anticancer drugs. However, how tubulin is regulated or recruited for use in these cellular processes is less understood. Tubulin post-translational modifications are proposed to regulate microtubule functions and dynamics. Although many such modifications have been investigated, increasing tubulin acetylation and enzymes responsible for acetylation have only recently begun to be described. Therefore, there is need to understand the process of increasing tubulin acetylation.

Transcription factor LSF is an oncogene in Hepatocellular Carcinoma (HCC), being dramatically overexpressed in HCC cell lines and patient samples. LSF is also generally required for cell cycle progression and cell survival. Initially, LSF was described as a regulator of G1/S progression, and essential for inducing expression of the gene encoding thymidylate synthase (TYMS) in late G1. However, the inventors have discovered, inter alia, additional involvement of LSF in mitosis. Particularly, inhibiting LSF with an exemplary small molecule inhibitor of LSF abrogated the DNA-binding and corresponding transcriptional activities of LSF, as well as specific LSF-protein interactions and inhibited growth of HCC tumors in multiple mouse models. In HCC cell lines, inhibition of LSF caused cell death via mitotic defect.

Hepatocellular carcinoma is a primary malignant tumor, which develops in the liver. HCC is one of the five most common cancers and the third leading cause of cancer deaths worldwide. The incidence of HCC is increasing despite a decrease in overall incidence of all cancers. In the United States, the estimated new cases of HCC for 2008 were 21,370, of which 18,410 were expected to die. There are multiple etiologies, with subcategories displaying distinct gene expression profiles. The prognosis of HCC remains poor. The mean 5-year survival rate is less than 10%. The mortality rate of HCC parallels that of its incidence because HCC is a tumor with rapid growth and early vascular invasion that is resistant to conventional chemotherapy.

Hepatocellular carcinoma (HCC) is characterized by late stage diagnosis and a poor prognosis for treatment, usually consisting of surgical resection of the tumor and chemotherapy. Currently, the only approved systemic treatments for late stage primary malignancies are sorafenib and regorafenib. The current treatment options for HCC are not optimal, especially following metastasis. Irradiation and chemotherapies have not so far proved to be satisfactory; surgery is the most effective treatment of HCC. However, surgery is only appropriate for patients with small resectable tumors. Only two, molecularly based drugs (Sorafenib and Regorafenib), which target tyrosine kinase receptors and the MEK/ERK pathway, have generated responses in patients as a single therapy. However, increased survival times with Sorafenib are only a few months. Regorafenib, a closely related compound, has recently been approved for treatment of sorafenib-resistant patients, although again with limited survival benefit. As such, it is imperative to discover novel, effective, and targeted therapies for this highly aggressive cancer. In particular, there is a strong need in the art for improved methods for treatment of HCC with small-molecule drugs.

SUMMARY

The present invention is generally directed to methods, compositions and kits to treat cancer e.g. hepatocellular carcinoma (HCC), for example, by using inhibitors of late SV40 factor (LSF, TFCP2), tubulin acetylating compounds, cell migration inhibiting compounds, or cell compaction inducing compounds, such as a compound represented by Formula (I) as disclosed herein. In some embodiments, the LSF inhibitor, tubulin acetylating compound, cell migration inhibiting compound, or cell compaction inducing compound, e.g., a compound of Formula (I) as disclosed herein, can be used to treat other cancers, for example, cervical cancer, colon cancers, pancreatic adenocarcinoma, ductal adenocarcinoma, colorectal adenocarcinoma, rectosigmoid carcinoma, monocytic lymphoma, kidney cancer, oral squamous cell carcinoma and the like.

The compounds of Formula (I) invention differ from previously reported Quinolinone LSF inhibitors as they lack the chiral center at the 8 or 9 position phenyl group, eliminating the need for enantioselective synthesis and/or separation. The compounds exhibit high potency and selectivity, and include some of the most potent compounds to date in cancer cell antiproliferative assays. The compounds can be made by a new synthetic pathways requiring the oxidation of dihydro-quinolinone compounds using 2,3-dichloro-5,6-dicyano-1,4-benzoquinone (DDQ).

According to some embodiments, the disclosure relates to compounds of Formula (I):

FORMULA (I)

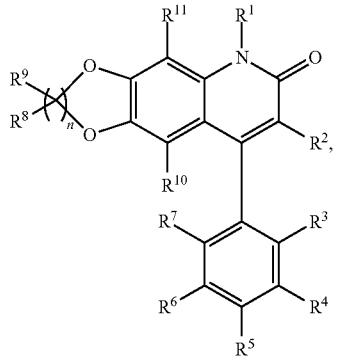

or enantiomers, prodrugs, derivatives, and pharmaceutically acceptable salts thereof.

In some compounds of Formula (I): $R^1$ is hydrogen, $C_1$-$C_6$ alkyl or $C_1$-$C_6$ haloalkyl; $R^2$, $R^4$, $R^6$, $R^7$, $R^{10}$ and $R^{11}$ are each independently selected from the group consisting of hydrogen, halogen, OH, or amino ($NH_2$); $R^3$ is $C_1$-$C_6$ alkoxy; $R^5$ is hydrogen, halogen, amino ($NH_2$), mono($C_1$-$C_6$)alkylamino, di($C_1$-$C_6$alkyl)amino, $C_1$-$C_6$ alkyl or $C_1$-$C_6$ haloalkyl; each $R^8$ and $R^9$ is selected independently from the group consisting of hydrogen and halogen; n is 1, or 2.

In some embodiments of any one of the aspects, the compound is not FQI-2 having the structure:

FQI-2

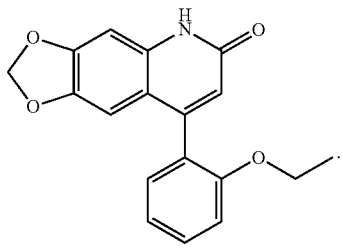

According to some embodiments, the disclosure relates to a method of increasing tubulin acetylation in a cell, the method comprising administering to the cell an effective amount of a compound of Formula (I).

According to some embodiments, the disclosure relates to a method of inducing cell compaction or inhibiting cell migration, the method comprising administering to the cell an effective amount of a compound of Formula (I).

According to some embodiments, the disclosure relates to a method for treating cancer in a subject, the method comprising administering to the cell an effective amount of a compound of Formula (I).

According to some other embodiments, the disclosure relates to a method for making the compounds of Formula (I), the method comprising treating a compound of Formula (II) with an oxidixing agent.

Formula (II)

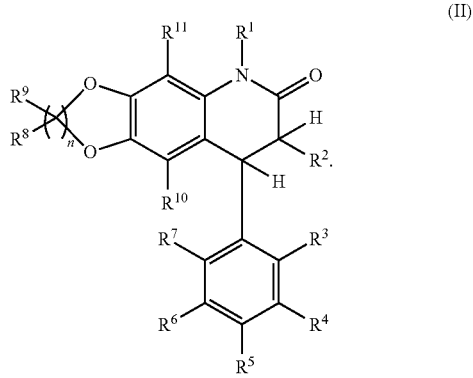

BRIEF DESCRIPTION OF THE DRAWINGS

This patent or application file contains at least one drawing executed in color. Copies of this patent or patent application publication with color drawing(s) will be provided by the Office upon request and payment of the necessary fee.

(FIG. 1A) Representative fluorescence images after staining for actin and DNA following a 30-minute treatment of FH-B cells with 4 µM FQI1, 1 µM nocodazole, or vehicle (0.01% DMSO). (FIG. 1B) The areas covered by individual cells, following 30-60 minute treatments as depicted in (a), were quantified using ImageJ and displayed as swarmplots. P-values were calculated using a paired t-test on medians of the biological replicates. The number of cells analyzed in each condition is indicated by "n" and was pooled from three independent experiments. FH-B cells treated with FQI1 for 60 minutes (replicate 3) received fresh media along with the respective treatment. (FIG. 1C) FH-B cells were stained with CellBrite™ Steady Membrane stain, treated with 4 µM FQI1 or vehicle (0.01% DMSO), and immediately imaged by time-lapse microscopy. Shown are images of representative cells taken at 2-5 minute intervals, derived from one biological replicate. Images were taken using a 20× objective. (FIG. 1D) Representative flow cytometry analysis of cellular DNA content showing cell cycle profiles of asynchronous FH-B cells treated with 4 µM FQI1 or vehicle (0.01% DMSO) for 1 hour (upper row), along with phase contrast images of cells taken prior to harvesting and fixation (lower row). Cells in this experiment received fresh media along with the respective treatment. Phase contrast images were taken using a 10× objective on an Olympus IX50 microscope. (FIG. 1E) Representative fluorescence images of RPE cells after 1-hour treatment with 4 µM FQI1, 1 µM nocodazole, or vehicle (0.01% DMSO). Cells received fresh media along with the respective treatment. (FIG. 1F) Circularity of RPE cells was quantified by processing fluorescent images of cells as in (FIG. 1E) in ImageJ. Swarmplots represent all analyzed cells from three independent experiments; p-values were calculated using an unpaired two-sample t-test. The number of cells analyzed in each condition is indicated by "n".

(FIGS. 2A and 2B) Representative immunoblots from lysates harvested at the indicated timepoints, derived from FH-B (FIG. 2A) and RPE cells (FIG. 2B) treated with 4 µM FQI1 ("F") or vehicle ("D", 0.01% DMSO) and separated into soluble and insoluble tubulin fractions using a microtubule sedimentation assay. Blots were probed for α-tubulin (upper blots), then reprobed for K40 acetyl-α-tubulin (lower blots). Microtubule-stabilizing taxol ("T", 1 µM) and microtubule-destabilizing nocodazole ("N", 1 µM) were added to the cells for 30 minutes and served as positive and negative controls, respectively. (FIGS. 2C and 2D) Quantitation of the percentage of the total α-tubulin in the insoluble fractions at the indicated time-points after addition of FQI1 or vehicle in FH-B cells (FIG. 2C) and RPE cells (FIG. 2D). Three to four independent experiments were performed for each cell line; p values were generated using an unpaired two-sample t-test. Bars and corresponding error bars represent mean±s.e.m. Numbers above brackets represent p-values. (FIGS. 2E and 2F) Quantitation of the amount of insoluble acetylated α-tubulin relative to the total insoluble α-tubulin at the indicated time-points after addition of FQI1 or vehicle in FH-B cells (FIG. 2E) and RPE cells (FIG. 2F). P-values were calculated using an unpaired two-sample t-test. Bars and error bars represent the mean±s.e.m. from 2-4 biological replicates. Numbers above brackets represent p-values.

(FIGS. 3A and 3B) After pretreatment with 1 µM taxol or vehicle (0.01% DMSO) for 30 minutes, FH-B cells were incubated in either 4 µM FQI1 or vehicle (0.02% DMSO) for another 10 minutes (replicates 4-5) or 30 minutes (replicates 1-3), before fixation, staining for actin and DNA, and analysis for cell spreading area. (FIG. 3A) Representative fluorescence images of actin- and DNA-stained FH-B cells following 30-minute treatments. (FIG. 3B) Swarmplots of cell spreading area of individual cells. Paired t-tests were performed on the medians between treatment groups from five biological replicates. (FIGS. 3C-3H) FH-B and RPE cells were pretreated with 10 µM Y-27632 for 30 minutes to maintain cell shape and then treated with either 4 µM FQI1 or vehicle (0.02% DMSO) for either 30 minutes (FH-B cells) or 10 minutes (RPE cells). After fixing, cells were immunostained for α-tubulin and γ-tubulin, followed by fluorescent Phalloidin and Hoechst 33342 staining. The Phalloidin channel (not shown) was used to measure the cell area for normalizing the number of visible ends to cell spreading area. Three independent biological replicates were performed for each cell line. Total number of cells analyzed in each condition is indicated by "n". (FIGS. 3C and 3D) Representative fluorescence images of digitally magnified FH-B (FIG. 3C) and RPE (FIG. 3D) cells are depicted. Dashed lines separating anterior and posterior portions of the cells were generated using γ-tubulin and Hoechst localization as guides. Visible microtubule ends are marked with asterisks. (FIGS. 3E and 3F) Total visible microtubule ends in FH-B (FIG. 3E) and RPE (FIG. 3F) cells were counted in both treatment groups, divided by the cell spreading area, and integrated into swarmplots. Statistical significance was determined by using an unpaired two-sample t-test on medians of the biological replicates. (FIGS. 3G and 3H) Visible microtubule ends in FH-B (FIG. 3G) and RPE (FIG. 3FH) cells were partitioned into posterior and anterior percentages, which were averaged and plotted as stacked bar charts. P-values for the posterior and anterior percentages are indicated above and below the brackets, respectively and were determined using an unpaired two-sample t-test comparing the averages for each group; numbers in stacked bar plots represent the indicated biological replicates.

(FIGS. 4A and 4B) RPE cells were grown to confluency, an X-shaped wound was drawn into the cell monolayer and the cells were monitored for 12 hours by phase contrast imaging using a 10× objective following treatment with 4 µM FQI1, 1 µM nocodazole, or vehicle (0.01% DMSO). Representative phase contrast images of a single vertex of the X-shaped wound from each treatment group over the 12-hour time-course are shown in (FIG. 4A). White lines denote the periphery of the wound. Quantitation of the averaged distances between the wound's four vertices normalized to the 0-hour distance are shown in (FIG. 4BA). Bars and error bars represent the mean±s.e.m. Three independent experiments were performed. Statistical significance was tested using an unpaired two-sample t-test. Numbers above brackets represent p-values. (FIGS. 4C and 4D) FH-B cells were synchronized by a single-thymidine block and treated with 4 µM FQI1 or vehicle (0.01% DMSO) for 1 hour. Cells were then stained with NucSpot® Live 650 dye and monitored by time-lapse fluorescence microscopy for 2 hours. The distances travelled from starting point to end point were quantified and pooled together from two separate experiments to generate swarmplots. Kymographs of representative nuclei of migrating FH-B cells from both treatment groups are shown in (FIG. 4C), while the swarmplot of distances travelled by FH-B cells is shown in (FIG. 4D). Statistical significance was tested by an unpaired two-sample t-test on the means of two biological replicates. The total number of cells analyzed in each condition is indicated by "n".

(FIG. 6A) The structure of FQI2-34. (FIG. 6A) Comparison of sensitivities of FH-B cells to FQI1 versus FQI2-34, as determined by MTS assays. Shown are curves of cell viability over the indicated concentration ranges from six technical replicates. Data indicate means±standard deviation. Calculated $GI_{50}$ values are 2.3 µM for FQI1 and 0.14 µM for FQI2-34. (FIGS. 6C and 6D) FH-B cells were treated with 200 nM FQI2-34 or vehicle (0.01% DMSO) for 30 minutes, fixed, stained with fluorescently labelled phalloidin and Hoechst 33342, and analyzed as in FIGS. 6A and 6B. Representative fluorescence images are shown in (FIG. 6C). The areas covered by individual cells in each treatment group were quantified using ImageJ and displayed as swarmplots in (FIG. 6D). P-values were calculated using an unpaired two-sample t-test on medians from two biological replicates. The number of cells analyzed in each condition is indicated by "n". (FIG. 6E) Cell extract thermal stability assays (CETSAs) were performed using Huh7 cells treated with either FQI1 or FQI2-34 as compared to treatment with vehicle alone (DMSO). Bottom panels: Representative immunoblots of soluble LSF after treatment with FQI2-34 versus DMSO (left) or FQI1 versus DMSO (right), after incubations at the indicated temperatures. Top panels: Quantitation of thermal stability of LSF after treatment of cells with each condition, as indicated. Data points are the mean±standard deviations from a total of 3 independent experiments.

(FIGS. 10A and 10B) FH-B cells were pretreated with vehicle (0.01% DMSO) or 1 µM taxol for 30 minutes, and then treated with vehicle (0.02% DMSO), 4 µM FQI1 or 1 µM nocodazole for 10 minutes. (FIG. 10A) A representative immunoblot of cell lysates probed for phospho-MLC2 (threonine 18, serine 19) and β-actin. (FIG. 10B) Quantitation of levels of phospho-MLC2 intensity relative to β-actin intensity in all treatment groups from four independent experiments. Bars and error bars represent the mean±s.e.m; circles represent individual data points. Numbers above brackets represent p-values, which were calculated using an unpaired two-sample t-test. (FIGS. 10C and 10D) FH-B cells were pretreated with either Y-27632 or vehicle (0.01% DMSO) for 30 minutes, then were incubated in either 4 µM FQI1 or vehicle (0.02% DMSO) for another 30 minutes. (FIG. 10C) Representative fluorescence images of FH-B cells from the four treatment groups, which were fixed and stained with fluorescently-labelled Phalloidin and Hoechst 33342. Images were analyzed using ImageJ. (FIG. 10D) Swarmplots depict cell spreading area of individual cells and medians from each treatment group. Paired t-tests were performed between DMSO- and FQI1-treated cells from both pretreatment groups. Data were pooled from three independent biological replicates. The total number of cells analyzed in each condition is indicated by "n". Paired p-values between the two DMSO-treated groups and the two FQI1-treated groups is 0.155 and 0.077, respectively.

(FIG. 11A) Representative histograms of DNA content are shown across all treatment groups, plus controls of an asynchronous population and a population of cells treated with a single thymidinBe block. (FIG. 11B) Quantitation of the proportion of cells in G1, S, and G2/M cell cycle phases derived from the histograms presented in (a). Bar graphs and error bars represent the mean±s.e.m. Three independent biological replicates were performed. Numbers above brackets represent p-values, which were calculated using an unpaired two-sample t-test.

FIGS. 14A-14K depict growth inhibition curves for some compounds and the structures of the compounds, according to some implementations. FIG. 14A is the plotted data for Huh7 cells with FQI2 and renders a GI50=0.141 µM. FIG. 14B is the plotted data for Huh7 cells with FQI2-34 and renders a GI50=22.2 nM. FIG. 14C is the plotted data for Huh7 cells with FQI2Br and renders a GI50=20.4 nM. FIG. 14D is the plotted data for Huh7 cells with FQI2Cl and renders a GI50=56.23 nM. FIG. 14E is the plotted data for Huh7 cells with FQI2F and renders a GI50=56.23 nM. FIG. 14F is the plotted data for Huh7 cells with FQI2-134 and renders a GI50=0.260 µM. FIG. 14G is the plotted data for Huh7 cells with FQI2-234 and renders a GI50=0.630 µM. FIG. 14H is the plotted data for Huh7 cells with FQI2F3 and renders a GI50=56.23 nM. FIG. 14I is the plotted data for Huh7 cells with FQI2-37 and renders a GI50=14.2 nM. FIG. 14J is the plotted data for Huh7 cells with FQI2-137 and renders a GI50=0.071 μM. FIG. 14K is the plotted data for Huh7 cells with FQI2-237 and renders a GI50=0.467 μM.

FIGS. 15A and 15B depict growth inhibition curves for some other compounds and the structures of the compounds, according to some implementations. FIG. 15A is the plotted data for Huh7 cells with FQI2-34 citrate salt and renders a GI50=12.5 nM. FIG. 15B is the plotted data for Huh7 cells with FQI2-37 citrate salt and renders a GI50=10.6 nM.

FIG. 16A shows immunoblots for FQI2-34 and comparative DMSO. FIG. 16B is a line plot of the CETSA data for FQI2-34 and DMSO. FIG. 16C is a plot of the FQI2-34 and DMSO data.

FIG. 17A shows immunoblots for FQI2-37 and comparative DMSO. FIG. 17B is a line plot of the CETSA data for FQI2-37 and DMSO. FIG. 17C is a plot of the FQI2-37 and DMSO data.

FIG. 18A shows immunoblots for FQI-2. FIG. 18B is a line plot of the CETSA data for FQI-2 and DMSO.

FIG. 28 depicts listed data for CaCo-2 permeability for some compounds.

FIG. 30 depicts listed data for PAMPA for some compounds.

FIG. 33 depicts the structure, CETSA immunoblots, and a line plot of the data for FQI2-34, according to some implementations.

FIGS. 34A-34D show FQI compounds reduce the interaction of LSF and β-catenin and suppress Wnt signaling in CRC cell lines. (FIG. 34A) HT-29 cells were treated with vehicle (Con), 1 μM FQI-34, or 1 μM FQI-37 for 16 hours. Top: The lysates were immunoprecipitated using β-catenin antibody and probed for LSF. The blots were stripped and reprobed for β-catenin. Bottom: 5% of the input lysates are shown as the loading controls. Representative images of three independent experiments are shown. (FIG. 34B) HT-116 cells were treated with FQIs, and processed and presented as in FIG. 34A. Representative images of three independent experiments are shown. (FIG. 34C) HT-29 cells were treated with FQI2-34 at 1 μM for 16 hours and processed and presented as above. Representative images of three independent experiments are shown. (FIG. 34D) HCT-116 cells stably expressing a β-catenin response element tethered to a firefly luciferase reporter gene were treated with vehicle, or lithium 1 mM to activate the Wnt signaling pathway. The cells were also treated with increasing concentrations of FQI2-34 overnight. Cells were lysed and luciferase activity was measured using the Promega dual luciferase assay kit. Averages of six independent readings from two independent experiments is shown. ANOVA analysis was performed. The p-value was less than 0.001. Error bars=SEM. Student's t test with Welch correction was performed. Compared to vehicle-treated control, FQI2-34 0.1 μM p=0.0051, 1.0 μM p=0.0012, 10 μM p=0.003, 20 μM p<0.0001. Compared to the lithium-treated control, FQI2-34 0.1 μM p=0.0534, 1.0 μM p=0.0043, 10 μM p=0.008, 20 μM p<0.0001.

(FIG. 35A) Approximately $1\times10^6$ HT-29 cells were injected subcutaneously in 20 female nude, athymic mice. The mice were monitored daily and the tumor volumes were calculated twice weekly. The mice were randomized into two groups with tumor volumes of 100 mm$^3$: control and FQI2-34 groups were treated as indicated and monitored for 21 days. (FIG. 35B) Images at the endpoint of one mouse from each group in FIG. 35A are shown. Individual tumors following harvest are displayed along with a scale bar. A blue asterisk marks the area of tumor ulceration in the control group. (FIG. 35C) Average tumor volumes from control group and FQI2-34 treatment group are shown. Error bars=SD. A Student's t test was performed. Compared to the controls, FQI2-34-treated mice showed significantly lower tumor volumes on day 9 (p=0.05), day 12 (p=0.05), day 17 (p=0.05), and day 21 (p=0.01).

(FIG. 36A) Paraffin embedded sections of FQI2-34-treated and control xenografts were stained for H & E. Representative images from five random images were captured at 200× magnification from each xenograft (N=10/group). Scale bars=100 μm. (FIG. 36B) Sections of xenografts from both groups were stained with β-catenin antibodies and counterstained with hematoxylin. Representative five random images captured at 200× magnification from each xenograft are shown. Black arrowheads indicate cells with nuclear β-catenin. Scale bars=100 μm. (FIG. 36C) The number of cells with nuclear β-catenin were counted by an observer blinded to the specimen. The cells positive for nuclear β-catenin from 5 randomly selected hpf from 10 different mice from each group are shown. Line corresponds to median in each group. The Student t test was performed to compare both the groups. ***p=0.0016.

(FIGS. 37A and 37C) Immunohistochemistry was performed on tumors from both the groups for AXIN-2 (FIG. 37A) and SOX-9 (FIG. 37C) and counter stained by hematoxylin. Representative images captured at 200× magnification from five random images taken per xenografts are shown. Black arrowheads indicate the nuclear Axin2 or SOX-9 in respective images. The insert shows representative xenograft cells with nucelar AXIN-2 or SOX-9. Scale bars=100 µm. (FIGS. 37B and 37D) Integrated density analysis normalized to surface area was performed using ImageJ on two to three randomly selected hpf images of each tumor. N=10 mice/group. Line corresponds to median in each group. The Student t test was performed  p=0.0025 for AXIN2 and *p=0.0009 for SOX-9). (FIG. 37E) Downregulation of Wnt target genes in FQI2-34-treated xenografts. Xenografts were harvested after three weeks and the lysates were subjected to RT-PCR performed in triplicates for AXIN2, CCND1, and SOX9. Ct values were normalized for GAPDH. Average Ct values are presented as a fold change over the control tumors (N=10/group). ANOVA was performed p<0.001. The Student t test with Welch correction was performed. All the targets were suppressed in mice treated with FQI2-34 (p=0.0001). Error bars=SEM.

(FIGS. 38A and 38C) Paraffin embedded section of xenografts from both the groups were stained for Ki-67 (FIG. 38A) and TUNEL stain (FIG. 38B) and counterstained with hematoxylin. Representatives from 2 randomly taken hpf images per xenograft (N=10 per group) are shown. Scale bars=100 µm. (FIGS. 38B and 38D) Integrated density analysis was performed and normalized to the tumor surface area on two randomly selected hpf of each xenograft using ImageJ. Line corresponds to median in each group. Student's t test was performed. *p=0.001 for Ki67 and p=0.01 for the TUNEL stain.

(FIG. 39B) Representative images of a mouse with xenograft from each group are shown. Three individual xenografts from each group following harvest are displayed along with a scale bar.

(FIG. 40A) Paraffin embedded sections of FQI2-34-treated and control xenografts were stained for H & E. Representative images from five random images were captured at 200× magnification from each xenograft (N=10/group). Scale bars=100 µm. (FIG. 40B) Sections of xenografts from both groups were stained with β-catenin antibodies and counterstained with hematoxylin. Representative two or three random images captured at 200× magnification from each xenograft are shown. A black arrowhead indicates cells with nuclear β-catenin. Scale bars=100 µm. (FIG. 40C). The number of cells with nuclear β-catenin were counted by an observer blinded to the specimen. The cells positive for nuclear β-catenin from 5 randomly selected hpf from 10 different mice from each group are shown. The Student t test was performed to compare both the groups. **p=0.0072.

(FIGS. 41A and 41C) Immunohistochemistry was performed on tumors from both the groups for AXIN-2 (A) SOX-9 (B) and counter stained by hematoxylin. Representative images captured at 200× magnification from two random images taken per xenografts are shown. Black arrowheads indicate the nuclear Axin2 or SOX-9 in respective images. The insert shows representative xenograft cells with nucelar AXIN-2 or SOX-9. Scale bars=100 µm. (FIGS. 41B and 41D) Integrated density analysis normalized to surface area was performed using ImageJ on two to three randomly selected hpf images of each tumor. N=10 mice/group. Line corresponds to median in each group. The Student t test was performed *** p=0.0003 for AXIN2 and p<0.0001 for SOX-9). (FIG. 41E) Paraffin embedded section of xenografts from both the groups were stained with Ki-67 and counterstained with hematoxylin. Representatives from 2 randomly taken hpf images per xenograft (N=10 per group) are shown. Scale bars=100 µm. (FIG. 41F) Integrated density analysis was performed and normalized to the tumor surface area on two randomly selected hpf of each xenograft using ImageJ. Line corresponds to median in each group. Student's t test was performed. *p=0.0295 for Ki-67.

FIGS. 42A-42D show relationship of expression of LSF and Wnt targets in patients with stage 4 colon cancer. (FIGS. 42A and 42B) Expression of LSF, AXIN-2 and SOX-9 in two representative stage IV CRC patients (N=19). A set of consecutive slides were stained and images were obtained at 200× magnifications. Insert shows cells stained with each marker. CRC from patient #S077 shows strong LSF expression in the nuclei, and AXIN-2 and SOX-9 expression. In contrast, patient #S1290 shows no detectable LSF expression and only few CRC cells positive for AXIN-2 and SOX-9. (FIGS. 42C and 42D) ImageJ analysis was performed on five random hpf images from each patient for normalized integrated density of LSF, AXIN-2 and SOX-9. Average of normalized integrated image density is presented for each patient. A linear correlation analysis was performed between LSF and AXIN-2 (FIG. 42C) and LSF and SOX-9 (FIG. 42D). For LSF and AXIN-2, the correlation coefficient ($R^2$)=0.42, p=0.0026. For LSF and SOX-9, the correlation coefficient ($R^2$)=0.35, p=0.0076.

DETAILED DESCRIPTION OF THE INVENTION

Figure 1A:
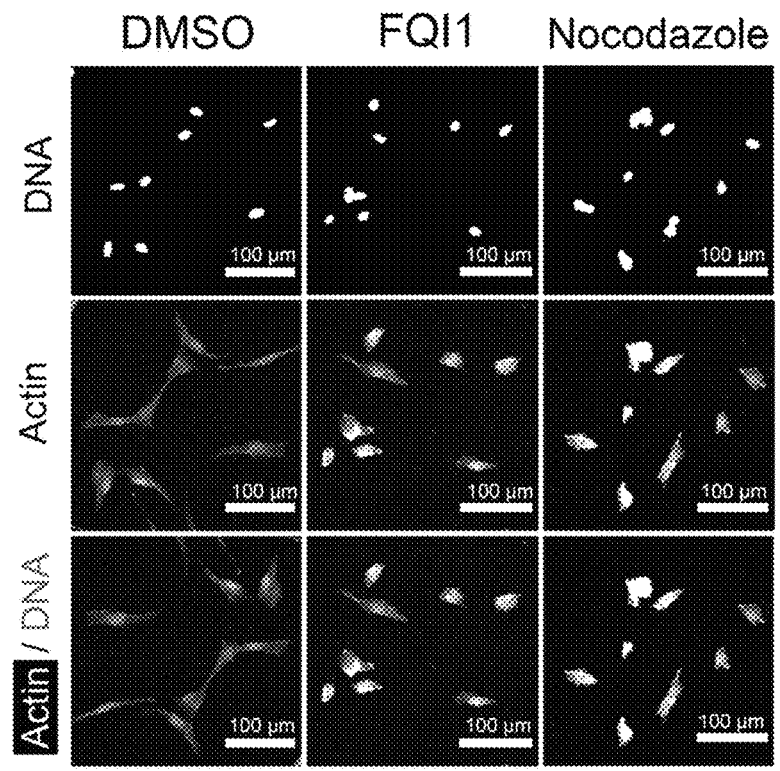
FIGS. 1A-1F show FQI1 treatment induces a rapid cell compaction in FH-B cells and increases circularity in RPE cells.

The inventors have discovered inter alia, small-molecule compounds of Formula (I). These small molecule compounds as disclosed herein can cause cell death of cancer cell lines and primary cancer cells in an in vitro assay, e.g., HCC cancer cell lines, pancreatic cancer lines, ductal cell lines, colorectal cell lines, breast cancer cell lines, colon cancer cell lines, ovarian cancer cell lines etc. Therefore, in one aspect, the disclosure provides small-molecule compounds of Formula (I). In another aspect of the present invention, the compounds disclosed herein can be used in a method for inhibiting LSF, increasing tubulin acetylation, inhibiting cell migration, inducing cell compaction and/or for treatment of cancers in subjects, e.g. HCC and other cancers.

Accordingly, in some embodiments, the disclosure relates to the disclosure relates to compounds of Formula (I):

FORMULA (I)

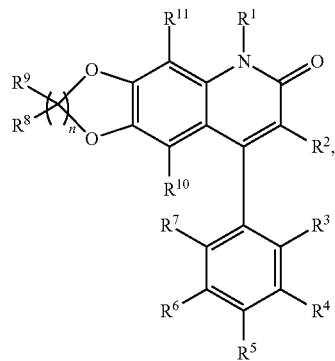

or enantiomers, prodrugs, derivatives, and pharmaceutically acceptable salts thereof.

In some compounds of Formula (I): $R^1$ is hydrogen, $C_1$-$C_6$ alkyl or $C_1$-$C_6$ haloalkyl; $R^2$, $R^4$, $R^6$, $R^7$, $R^{10}$ and $R^{11}$ are each independently selected from the group consisting of hydrogen, halogen, OH, or amino ($NH_2$); $R^3$ is $C_1$-$C_6$alkoxy; $R^5$ is hydrogen, halogen, amino ($NH_2$), mono($C_1$-$C_6$)alkylamino, di($C_1$-$C_6$alkyl)amino, $C_1$-$C_6$ alkyl or $C_1$-$C_6$ haloalkyl; each $R^8$ and $R^9$ is selected independently from the group consisting of hydrogen and halogen; n is 1, or 2; provided that the compound is not

FQI-2

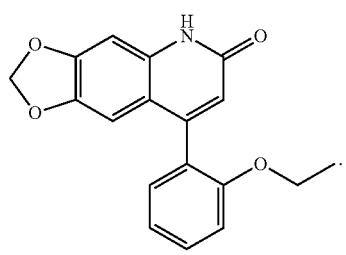

According to some embodiments of compound (I) $R^1$ is hydrogen. In some embodiments $R^2$ is hydrogen. In some embodiments $R^1$ and $R^2$ are hydrogen. In some embodiments, $R^{19}$ is hydrogen. In some embodiments $R^{11}$ is hydrogen. In some embodiments $R^{10}$ and $R^{11}$ are hydrogen. In some embodiments $R^4$ is hydrogen. In some embodiments $R^6$ is hydrogen. In some embodiments $R^7$ is hydrogen. In some embodiments, $R^4$ and $R^6$ are hydrogen, or in some other embodiments $R^4$, and $R^7$ are hydrogen, or in yet other embodiments $R^6$ and $R^7$ are hydrogen. In some embodiments $R^4$, $R^6$ and $R^7$ are hydrogen. In some embodiments, at $R^8$ is hydrogen. In some embodiments $R^9$ is hydrogen. In some embodiments, $R^8$ and $R^9$ are hydrogen.

According to some embodiments of compound (I) $R^3$ is $OCH_3$, $OCH_2CH_3$, $OCH_2CH_2CH_3$, $OCH(CH_3)_2$, $OCH_2CH_2CH_2CH_3$, $OCH_2CH(CH_3)_2$, $OCH_2CH_2CH_2CH_2CH_3$ or $OCH_2CH_2CH_2CH_2CH_2CH_3$. In some embodiments $R^3$ is $OCH_2CH_3$, $OCH_2CH_2CH_3$ or $OCH_2CH(CH_3)_2$.

In some embodiments $R^3$ is $OCH_2CH_3$. In some embodiments, $R^3$ $OCH_2CH_2CH_3$. $R^3$ is $OCH_2CH(CH_3)_2$.

In some embodiments, $R^5$ is hydrogen, halogen, amino, mono($C_1$-$C_6$)alkylamino, di($C_1$-$C_6$alkyl)amino or $C_1$-$C_6$ haloalkyl. In some embodiments, $R^5$ is hydrogen, di($C_1$-$C_6$alkyl)amino such as dimethyl amino (—$NMe_2$). In some embodiments, $R^5$ is Br, F, Cl, I, $N(CH_3)_2$, or trifluoromethane (—$CF_3$). In some embodiments, $R^5$ is H. In some embodiments, $R^5$ is F. In some embodiments, $R^5$ is Cl. In some embodiments, $R^5$ is Br. In some embodiments, $R^5$ is trifluoromethane (—$CF_3$).

According to some embodiments, n=1. In some other embodiments, n=2.

According to some embodiments, the compound of Formula (I) is selected from the group consisting of:

FQI2-34

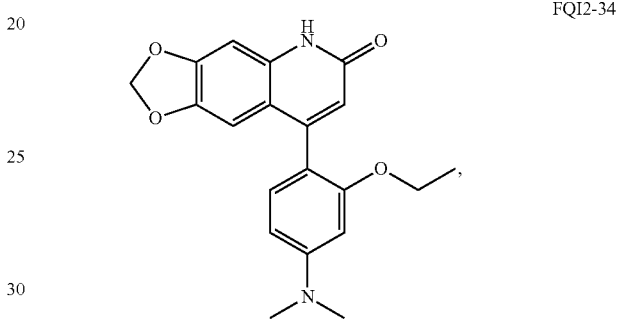

FQI2Br

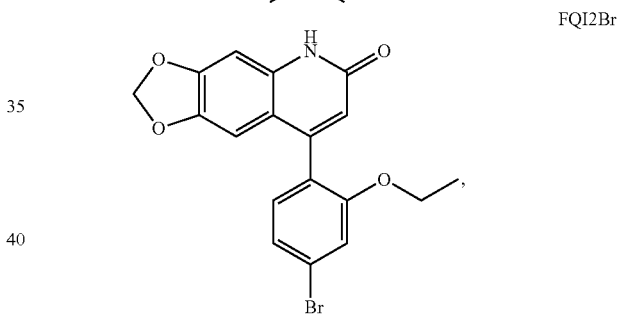

FQI2Cl

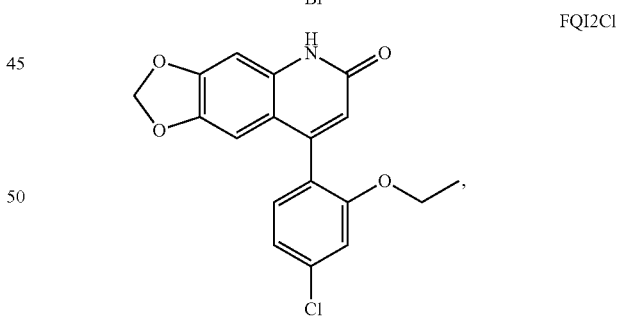

FQI2F

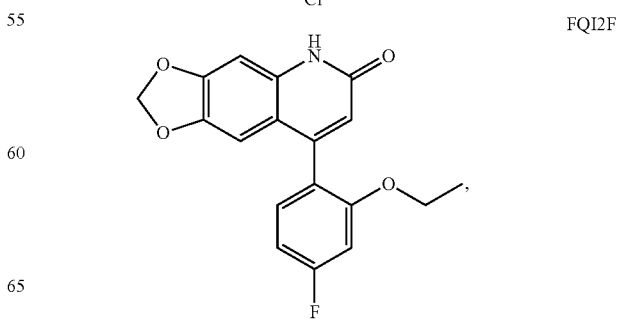

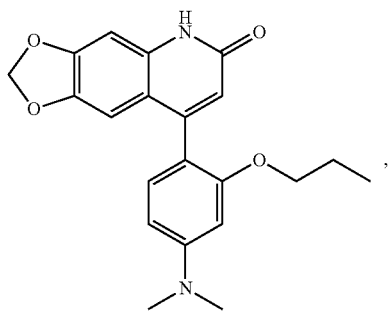
FQI2-134

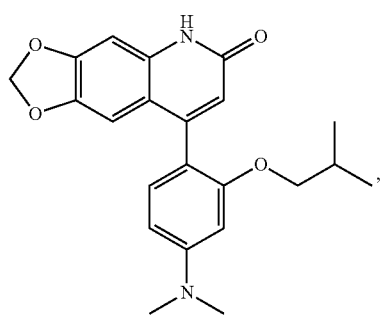
FQI2-234

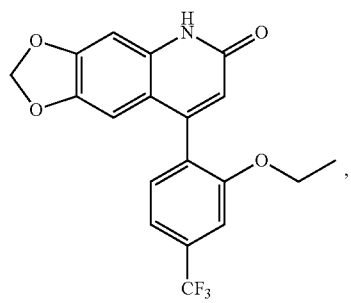
FQI2F3

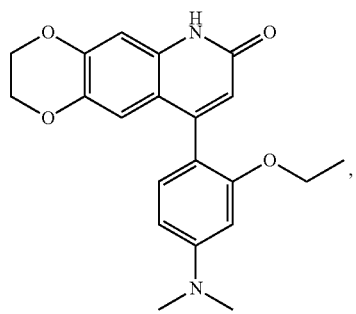
FQI2-37

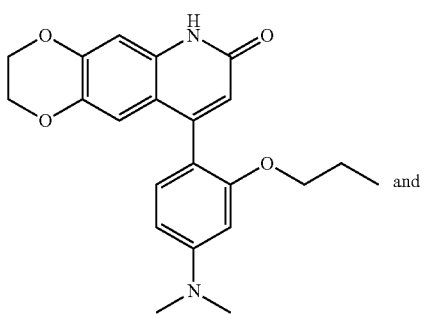
FQI2-137 and

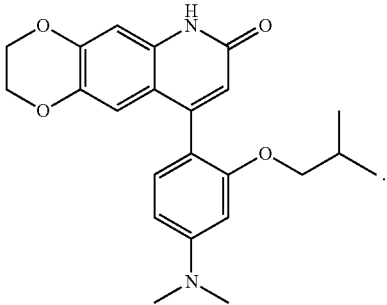
FQI2-237

In some embodiments, the compound is FQI2-34. In some other embodiments, the compound is FQI2-37.

According to some other embodiments, the disclosure relates to a method for making the compounds of Formula (I), the method comprising treating a compound of Formula (II) with an oxidizing agent. Formula (II):

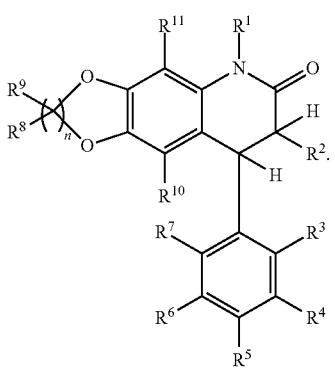

In some embodiments, the oxidizing agent is DDQ.

According to some embodiments, the disclosure relates to a method of increasing tubulin acetylation in a cell, where the method includes administering an effective amount of at least one compound having Formula (I). In some embodiments, the method comprises administering at least the compound FQI2-34 to increase tubulin acetylation in the cell. In some embodiments, the method comprises administering at least the compound FQI2-37 to increase tubulin acetylation in the cell.

According to some embodiments, the disclosure relates to a method of inducing cell compaction, the method comprising administering to the cell an effective amount of at least one compound of having Formula (I). In some embodiments, the method comprises administering at least the compound FQI2-34 to induce cell compaction. In some embodiments, the method comprises administering at least the compound FQI2-37 to induce cell compaction.

According to some embodiments, the disclosure relates to a method of inhibiting cell migration, the method comprising administering to the cell an effective amount of at least one compound of having Formula (I). In some embodiments, the method comprises administering at least the compound FQI2-34 to inhibit cell migration. In some embodiments, the method comprises administering at least the compound FQI2-37 to inhibit cell migration.

According to some embodiments, the compound (I) is an enantiomer of the compound (I), a prodrug of the compound (I), a derivative of the compound (I), or a pharmaceutically acceptable salt thereof. In some embodiments, the compound (I) is an enantiomer, a prodrug, a derivative or a pharmaceutically acceptable salt of FQI2-34, FQI2Br, FQI2Cl, FQI2F, FQI2-134, FQI2-234, FQI2-37, FQI2-137, or FQI2-237. In some embodiments, the compound (I) is an enantiomer, a prodrug, a derivative or a pharmaceutically acceptable salt of FQI2-34 or FQI2-37. In some embodiments, the compound (I) is a pharmaceutically acceptable salt of FQI2-34, FQI2Br, FQI2C, FQI2F, FQI2-134, FQI2-234, FQI2-37, FQI2-137, or FQI2-237. In some embodiments, the compound (I) is an a pharmaceutically acceptable salt of FQI2-34 or FQI2-137. In some embodiments, the salt is a citrate salt. For example, in some embodiments, the compound is the citrate salt of FQI2-34. In some embodiments, the compound is the citrate salt of FQI2-37.

In some embodiments, a compound of Formula (I) as disclosed herein can be used to treat various cancers, such as liver cancer (hepatocellular carcinoma), brain cancer, breast cancer, colon cancer, head and neck squamous cell carcinoma, lung cancer, pancreatic cancer, ductal adenocarcinoma, colorectal adenocarcinoma, rectosigmoid carcinoma, kidney cancer, monocytic lymphoma, ovarian cancer, and thyroid cancer; HIV; inflammation-related diseases such as hepatitis B virus (HBV), hepatitis C (HCV), cirrhosis and Alzheimer's disease. In some embodiments, the liver diseases can be any selected from, but not limited to, HBV, HCV, cirrhosis, hepatic adenoma, hepatic angiosarcoma and hepatic angiosarcomas; emphysema; and hereditary hemochromatosis.

In some embodiments, a compound of Formula (I) as disclosed herein can be used to treat other cancers, for example, cervical cancer, colon cancers, melanomas and the like. Other cancers which can be treated include any cancer with overexpression of LSF in the tumor, for example, but not limited to, oligodendroglioma, meningioma, GBM, breast cancer, colon cancer, Non-Hodgkin's small cell carcinoma (HNSCC), lung cancer (adrenocarcinomas), lung cancer (small cell carcinoma), pancreatic cancer, ovarian cancer, thyroid cancer and undifferentiated cancer.

In some embodiments, a compound of Formula (I) as disclosed herein can be used to treat any cancer cell type. Cancers include, but are not limited to, bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor.

In some embodiments, a compound of Formula (I) as disclosed herein is used to treat a subject with hepatocellular carcinoma (HCC).

In another implementation, a subject at high risk of developing HCC is suitable for treatment with the compositions of the invention comprising at least a LSF inhibitor, tubulin acetylating compound, cell migration inhibiting, or cell compaction inducing compound as disclosed herein.

Hepatocellular carcinoma (HCC) is one of the five most common cancers worldwide. The incidence of HCC is increasing despite a decrease in overall incidence of all cancers. In the United States, the estimated new cases of HCC for 2008 were 21,370, of which 18,410 were expected to die. The mean 5-year survival rate is less than 10%. The mortality rate of HCC parallels that of its incidence because HCC is a tumor with rapid growth and early vascular invasion that is resistant to conventional chemotherapy, and only suboptimal systemic therapy is available for the advanced disease.

To date, other than curative resection, treatments for HCC have had minimal impact on survival. Unfortunately, approximately 90% of HCC patients have unresectable HCC. Moreover, even after potentially curative hepatectomy in patients with resectable HCC, new HCC arises in the cirrhotic remnants in 70% of these patients, and frequently arises in the grafted liver following orthotopic liver transplantation. Other approaches to treating HCC, such as intralesional ethanol injection, chemoembolization, radiofrequency ablation, cryosurgery and radiation therapy have demonstrated some success in selected patient populations; however, the efficacies of these approaches have not been definitively established. Both percutaneous intralesional ethanol injection and transarterial chemoembolization have shown limited success, but not without risks of serious side effects. Radiotherapy is not usually an option because liver is very radiosensitive.

All systemic therapies for HCC to date are associated with uniformly poor outcomes, and only four chemotherapeutic agents (sorafenib, regorafenib, lenvatinib and cabozantinib), alone or in combination with other treatments, have been associated with any improvement in survival rates (Fuchs et al., 94 Cancer 3186 (2002) and Bruix et al., Lancet (2017), 389(10064), 56-66). In addition, most patients with HCC have underlying liver disease so their ability to tolerate to undergo surgery is compromised. Therefore, there is a strong need in the art to provide improved methods for treatment of HCC.

Compounds of Formula (I) unexpectedly and surprisingly show improved cell growth inhibition compared to prior art compounds. For example, the compounds described herein are better inhibitors of cell growth compared to the compounds disclosed in U.S. Pat. No. 9,597,325, 9,802,948, 9,815,845, and US Patent Application Publication US2020/0039996, the content of each of which is incorporated herein by reference in its entirety. For example, less than half the concentration of exemplary compounds of Formula (I) was as effective as the prior art compounds.

Accordingly, one aspect of the invention provides methods for therapeutic and prophylactic treatment of cancers, e.g., HCC by administering to a subject a pharmaceutical composition comprising an effective amount of a compound of Formula (I) and enantiomers, prodrugs, derivatives, and pharmaceutically acceptable salts thereof.

As described herein, compounds of Formula (I) can inhibit late SV40 factor or late Simian Virus 40 factor (LSF). LSF is also known as aliases LBP-1c (leader binding protein-1c), LBP-1d, SEF (SAA3 enhancer factor), TFCP2 (transcription factor CP2) and CP2.

LSF is a DNA-binding transcription factor that is required in multiple cell types for cell cycle progression and regulates diverse cellular and viral promoters. It binds to the alpha-globin promoter and activates transcription of the alpha-globin gene. It has been reported that LSF facilitates entry into G1/S phase of the cell cycle, promotes DNA synthesis, and functions as an antiapoptotic factor. LSF also regulates erythroid gene expression, plays a role in the transcriptional switch of globin gene promoters, and it activates many other cellular and viral gene promoters. The gene product interacts with certain inflammatory response factors, and polymorphisms of this gene can be involved in the pathogenesis of Alzheimer's disease.

A major cellular target of LSF is the thymidylate synthase (TS) gene (TYMS), which encodes the rate-limiting enzyme in the production of dTTP, required for DNA synthesis. TS has been a long-standing chemotherapeutic target for cancer treatments, and recently it was discussed that elevated levels of LSF in hepatocellular carcinoma cell lines can contribute to chemoresistance to one commonly utilized thymidylate synthetase inhibitor, 5-fluorouracil. Inhibition of LSF abrogates TS induction, induces either arrest at the G1/S transition, or in apoptosis after entry into S phase. Thus, LSF plays an important role in DNA synthesis and cell survival. In the liver, LSF is activated by inflammatory cytokines and regulates the expression of acute phase proteins.

The present invention relates in part to methods and compositions to inhibit LSF, more specifically, with small-molecule LSF inhibitors. In some embodiments, inhibitors of LSF as disclosed herein can be used to inhibit the cellular LSF activity. In some embodiments, LSF inhibitors as disclosed herein can decrease expression (level) of LSF. In some embodiments, the inhibitor of LSF is selected from the group consisting of compounds of Formula (I).

Inventors have discovered inter alia that three regulators of mitosis, SET8, LSF, and tubulin, all interact with each other both in vitro and within cells. Further, SET8 is a microtubule-associated methyltransferase that methylates lysines on α-tubulin. SET8 does not methylate LSF, but in parallel to how proteins recruit chromatin writers to target histones, LSF stimulates methylation of tubulin by SET8. LSF enhances tubulin polymerization in vitro, showing that this protein may also influence microtubule dynamics. The inventors also discovered that inhibiting LSF with an exemplary small molecule LSF abrogated LSF-tubulin interactions in cells, and disrupted mitotic spindle formation via a non-transcriptional mechanism.

Accordingly, another aspect of the present invention relates to a method of inhibiting tubulin methylation or modulating chromatin/cytoskeleton modification in a cell, the method comprising administering to the cell an effective amount of compound of Formula (I).

Inventors have also discovered inter alia that compounds of Formula (I) enhanced microtubule acetylation.

Accordingly, an aspect of the present invention relates to tubulin acetylating compound, or cell compaction inducing compounds.

It has also been shown that compounds of Formula (I), when contacted to cells, leads to cell compaction. This can be seen, for example, by a significant reduction in cell spreading in areas of compound treated cells compared to none-treated cells. Without affirming a specific mechanism, it is suggested that the cell compaction is due to microtubule destabilizing. Accordingly, another aspect of the present invention relates to a method of cell compaction, the method comprising administering to the cell an effective amount of compound of Formula (I).

Accordingly, another aspect of the present invention relates to cell compaction inducing compounds.

In yet another aspect, the disclosure relates to cell migration inhibiting compounds.

It is noted that administering the compound to the cell can be in vitro or in-vivo. Methods for administering a compound to a cell are well known and available to one of skill in the art. As used herein, administering the compound to the cell means contacting the cell with the compound so that the compound is taken up by the cell. Generally, the cell can be contacted with the compound in a cell culture e.g., in vitro or ex vivo, or the compound can be administrated to a subject, e.g., in vivo. The term "contacting" or "contact" as used herein in connection with contacting a cell includes subjecting the cells to an appropriate culture media, which comprises a compound described herein. Where the cell is in vivo, "contacting" or "contact" includes administering the compound, e.g., in a pharmaceutical composition to a subject via an appropriate administration route such that the compound contacts the cell in vivo.

For example, when the cell is in vitro, said administering to the cell can include subjecting the cell to an appropriate culture media which comprises the indicated compound. Where the cell is in vivo, said administering to the cell includes administering the compound to a subject via an appropriate administration route such that the compound is administered to the cell in vivo.

Compounds of Formula (I) can be formulated in a pharmaceutical composition described herein. Further, compounds of Formula (I) can be used in the methods, e.g., a method for increasing tubulin acetylation in a cell, a method of inhibiting cell migration, a method of inducing cell compaction, or a method for treating cancer disclosed herein.

One of the major targets of LSF is thymidylate synthase (TS) gene (TYMS), which encodes the rate-limiting enzyme in the production of dTTP, required for DNA synthesis. Additional examples of LSF-downstream genes are disclosed in Yoo et al, PNAS, 2010, 107;8357-8362, and include without limitation SPP1 (encoding osteopontin), complement factor H (CFH), TSPAN8, S100A10, CDH17, EFNB2, ZEB1, REG1A, REG3A, SAA4, TAGLN, FGFR2, EGFR, CYP2B7P1, CYP2B6, GPX2, DPYD, PKLR, LEF1, ICAM2 and IGFBP7.

In some embodiments, the genes downstream of LSF are tumor-associated genes, such as relating to invasion and metastasis, angiogenesis, epithelial-mesenchymal transition (EMT), cell growth, drug metabolism, senescence, cell adhesion, glycolysis, Wnt signaling, Hippo signaling, growth and regeneration, inflammatory response, e.g. acute phase proteins, and modulators of matrix-degrading enzymes e.g. MMP9. LSF is a transcription factor encoded by TFCP2. Thus, inhibiting LSF can disrupt or inhibit LSF binding to DNA and/or interaction of LSF with other proteins to form a complex.

Accordingly, in some embodiments, inhibition of cellular LSF activity can be determined by measuring the level of downstream genes regulated by the transcription factor LSF. The effect of LSF on expression (level) of LSF-targeted or LSF-downstream genes can be stimulatory or inhibitory. For example, one gene induced by LSF is SPP1 encoding OPN. Thus, an inhibition of biological activity of LSF results in a decrease in level of SPP1 mRNA and/or a decrease in the amount of the respective encoded protein, OPN. In another implementation, one gene inhibited by LSF is TAGLN. Thus, an inhibition of biological activity of LSF leads to an increase in level of TAGLN mRNA. In some embodiments, the cellular activity of LSF can be measured by a reduction in the level of TS.

In further embodiments, inhibition of LSF can decrease expression of LSF, for example, a reduction in protein level, and/or a decrease in gene transcript level (e.g. mRNA) of LSF.

As disclosed herein, inhibitors of LSF can decrease functional transcriptional activity or the expression of LSF (e.g., such as protein level of LSF, and/or gene transcript level of LSF), by at least about 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF. The expression of LSF can be measured by standard methods known to a skilled artisan such as western blot, ELISA, and quantitative PCR as well as the methods provided in Examples section.

In some embodiments, inhibitors of LSF as disclosed herein can inhibit or decrease cellular LSF activity by at least about 10%, relative to the activity level in the absence of inhibitors of LSF, e.g., at least about 15%, at least about 20%, at least about 30%, at least about 40%, at least about 50%, at least about 60%, at least about 70%, at least about 80%, at least about 90%, 95%, 99% or even 100%. In certain embodiments, inhibitors of LSF as disclosed herein can decrease expression of downstream genes up-regulated by LSF, e.g. SPP1 encoding OPN, by about at least 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF. In alternative embodiments, inhibitors of LSF can increase expression of downstream genes down-regulated by LSF, e.g. TAGLN, by about at least 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF.

The ability of a compound to inhibit LSF can be assessed in some instances by measuring a decrease in expression of LSF as compared to the level of LSF in the absence of inhibitors of LSF. In some embodiments, the ability of a compound to inhibit LSF can be assessed by measuring a decrease in the biological activity, e.g., transcriptional activity of LSF as compared to the level of transcriptional activity of LSF in the absence of inhibitors of LSF. The expression of LSF includes the amount of RNA transcribed from a gene, e.g. TFCP2 that encodes LSF, and/or the amount of LSF proteins that is obtained by translation of RNA transcribed from a gene, e.g. TFCP2. For example, a LSF inhibitor as disclosed herein can inhibit expression of LSF by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of a LSF inhibitor.

Additionally, ability of a compound to inhibit LSF can be also assessed by measuring a decrease in or an inhibition of biological activity of LSF as compared to a negative control, e.g. the experimental condition in the absence of LSF inhibitors. The biological activity of LSF can refer to the ability of LSF to modulate expression of LSF-targeted genes such as thymidylate synthase (TYMS) and/or LSF-downstream genes, such as secreted phosphoprotein 1 (SPP1), complement factor H (CFH) and other tumor-associated genes (see Yoo et al., PNAS, 2010, 107; 8357-8362, which is incorporated herein in its entirety by reference). Accordingly, a LSF inhibitor as disclosed herein can inhibit biological activity of LSF, such as a decrease in expression of SPP1 that encodes OPN (also known as secreted phosphoprotein 1, SPP1), by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of a LSF inhibitor. In some embodiments, ability of a compound to inhibit LSF is assessed by inhibition of LSF-induced tumorigenesis and metastasis of cancer cells, e.g. hepatocellular carcinoma cells in vitro or in an in vivo animal model as described in WO2012/050985, U.S. Pat. Nos. 9,802,948, 9,815,845 and 9,597,325, contents of all which are incorporated herein by reference in their entirety, as compared to a reference condition without treatment with such a LSF inhibitor. In such embodiments, a LSF inhibitor can decrease a tumor weight and volume by at least about 15%, at least about 20%, at least about 30%, at least about 40%, at least about 50%, at least about 60%, at least about 70%, at least about 80%, at least about 90%, 95%, 99% or even 100%, as compared to no treatment with a LSF inhibitor.

It was previously reported in Yoo et al., (PNAS, 2010; 107; 8357-8362) that the level of LSF expression is useful to identify a subject with HCC. Accordingly, a subject amenable to treatment using the methods and compositions as disclosed herein can be identified by measuring the level of LSF in a biological sample obtained from the subject and if the level of LSF in the biological sample from the subject is higher by a statistically significant amount relative to a reference level of LSF, the subject likely is at risk of having HCC, and accordingly, can be administered a composition comprising at least one small molecule inhibitor of LSF selected from any of Formula (I) as disclosed herein.

A subject is identified as suffering from HCC or having a disordered characterized by increased LSF expression, when the expression level of LSF in a biological sample obtained from the subject is higher relative to a reference level of LSF by at least about 20%, at least about 30%, at least about 40%, at least about 50%, at least about 60%, at least about 70%, at least about 80%, at least about 90%, at least about 95%, at least about 98%, about 99% or about 100%. The extent of increase in LSF expression can indicate the grades and stages of HCC (See Yoo et al., PNAS, 2010; 107; 8357-8362). Accordingly, subjects identified with HCC or having a disorder characterized by increased LSF expression can be treated with an effective dose of a pharmaceutical composition as disclosed herein comprising a LSF inhibitor selected from any of Formula (I) as disclosed herein to inhibit or delay progression of HCC.

In some embodiments, a biological sample is a tissue sample, e.g. a liver sample.

In some embodiments, the level of LSF in a biological sample is compared to a reference level, or a reference biological sample, such as a biological sample from adjacent liver tissue (not pathologically abnormal, or such as biological sample obtained from an age-matched normal control (e.g. an age-matched subject not having HCC or an age-matched normal healthy subject).

In other embodiments, in order to determine the therapeutic efficacy of the treatment (e.g. treatment of HCC), a reference level can be the level of LSF expression or the level of expression of LSF target genes measured at a previous time point from the same subject on a treatment regimen The methods of the present invention also are useful for monitoring a course of treatment being administered to a subject. The methods can be used to monitor both therapeutic treatment on symptomatic subject and prophylactic treatment on asymptomatic subject.

A treatment administered to a subject is considered to be effective if the level of expression of LSF or of LSF target genes in a biological sample obtained from the subject is decreased relative to a reference level of LSF by at least about 20%, at least about 30%, at least about 40%, at least about 50%, at least about 60%, at least about 70%, at least about 80%, at least about 90%, at least about 95%, at least about 98%, about 99% or about 100%. In such embodiments, the reference level is the measurement of LSF or of LSF target genes at a previous time point from the same subject who has been administered to the treatment regimen. Based on the outcome of treatment, the dosage and frequency of administration using the methods and compositions as disclosed herein can be adjusted accordingly by one of skill in the art.

In one implementation, the biological sample for analysis is a liver sample, wherein the sample comprises at least one cell. One can use any immunoassay to determine the level of LSF or of LSF target genes in a biological sample, such as ELISA or immunohistochemical methods of detecting LSF or LSF target genes which are commonly known in the art and are encompassed for use in the present invention.

In some embodiments, a method of determining the presence and/or level of LSF in a biological sample from a subject comprises performing a binding assay. Any reasonably specific binding partner can be used. For example, the binding partner is labeled. For example, the assay is an immunoassay, especially between LSF and an antibody that recognizes LSF, especially a labeled antibody. It can be an antibody raised against part or all of it, such as a monoclonal antibody or a polyclonal antiserum of high specificity for LSF. In some embodiments, the antibodies are specific to mammalian LSF, such as human LSF.

Thus, any anti-LSF antibody can be used in the method to determine the presence and/or level of LSF in a biological sample, which can be used to detect the increased or decreased level of LSF present in a diagnostic sample. Such antibodies can be raised by any of the methods well known in the immunodiagnostics field.

In some embodiments, an immunoassay is carried out by measuring the extent of the protein/antibody interaction of the LSF/antibody interaction. Any known method of immunoassay may be used. For example, a sandwich assay or ELISA. In this method, a first antibody to the marker protein is bound to the solid phase such as a well of a plastics microtitre plate, and incubated with the sample and with a labeled second antibody specific to the protein to be assayed. Alternatively, an antibody capture assay could be used. In some embodiments, a biological test sample is allowed to bind to a solid phase, and the anti-LSF protein antibody is then added and allowed to bind. After washing away unbound material, the amount of antibody bound to the solid phase is determined using a labeled second antibody against the first.

In some embodiments, a label is an enzyme. The substrate for the enzyme may be, for example, color-forming, fluorescent or chemiluminescent.

In some embodiments, a binding partner, e.g. an antibody or a ligand binding to LSF in the binding assay is a labeled specific binding partner, but not necessarily an antibody. The binding partner will usually be labeled itself, but alternatively it may be detected by a secondary reaction in which a signal is generated, e.g. from another labeled substance.

In some embodiments, one can use an amplified form of assay, whereby an enhanced "signal" is produced from a relatively low level of protein to be detected. One particular form of amplified immunoassay is enhanced chemiluminescent assay. Conveniently, the antibody is labeled with horseradish peroxidase, which participates in a chemiluminescent reaction with luminol, a peroxide substrate and a compound which enhances the intensity and duration of the emitted light, typically 4-iodophenol or 4-hydroxycinnamic acid.

In another implementation, an amplified immunoassay can be used which is immuno-PCR. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 23: 522-529 (1995). The signal is read out as before.

Alternatively, in some embodiments, one method to determine the level of LSF in a biological sample is to use a two dimensional gel electrophoresis to yield a stained gel and the increased or decreased level of the protein detected by an increased an increased or decreased intensity of a protein-containing spot on the stained gel, compared with a corresponding control or comparative gel.

In some embodiments, methods to determine the amount of LSF in a biological sample does not necessarily require a step of comparison of the level of LSF with a control sample (e.g. from a normal healthy subject), but it can be carried out with reference either to a control or a comparative sample. Thus, in relation to HCC, measuring the amount of LSF in a biological sample can be used to determine the stage of progression, if desired with reference to results obtained earlier from the same subject or by reference to standard values that are considered typical of the stage of the disease. In this way, the invention can be used to determine whether, for example after treatment of the subject with a LSF inhibitor, the disease has progressed or not. The result can lead to a prognosis of the outcome of the disease.

In some embodiments, one method to detect the presence and/or the level of LSF in a biological sample is to perform immunohistochemical assay on a biopsy sample, such as a liver sample. The methods for detecting the presence and/or a level of protein on a biopsy sample are well within the level of skill in the art. In alternative embodiments, the mRNA level of LSF in a biological sample is determined by quantitative PCR with primers designed according to the nucleotide sequence of LSF. The design for primers of LSF can be performed easily by one of the skill in the art.

In various embodiments, the level of LSF can be measured and used in combination with other biomarkers for HCC such as AFP to diagnose HCC in a subject. Other biomarkers for HCC include, but not limited to, those described, for example, in US 2013/0107227, content of which is incorporated herein by reference in its entirety.

All structures of Formula (I) are provided herein for illustrative purpose and disclose a particular isomer. However, one of ordinary skill in the art will recognize all possible isomers of the structures of any of Formula (I).

Therefore, other isomers such as enantiomers of any of Formula (I) are considered to fall within the scope of the invention. As used herein, the term "isomer" refers to a compound having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. The designations "R" and "S" are used to denote the absolute configuration of the molecule about its chiral center. The designations may appear as a prefix or as a suffix; they may or may not be separated from the isomer by a hyphen; they may or may not be hyphenated; and they may or may not be surrounded by parentheses. The designations "(+)" and "(−)" are employed to designate the sign of rotation of plane-polarized light by the compound, with (−) meaning that the compound is levorotatory (rotates to the left). A compound prefixed with (+) is dextrorotatory (rotates to the right). Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

In various embodiments, compounds of formula (I) include enantiomers, derivatives, prodrugs, and pharmaceutically acceptable salts thereof.

The term "derivative" as used herein refers to a chemical substance related structurally to another, i.e., an "original" substance, which can be referred to as a "parent" compound. A "derivative" can be made from the structurally-related parent compound in one or more steps. The general physical and chemical properties of a derivative are also similar to the parent compound.

In some embodiments, prodrugs of compounds selected from Formula (I) also fall within the scope of the invention. As used herein, a "prodrug" refers to a compound that can be converted via some chemical or physiological process (e.g., enzymatic processes and metabolic hydrolysis) to a compound selected from the group consisting of compounds of formula (I).

Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11,:345-365; Gaignault et al. (1996) "Designing Prodrugs and Bioprecursors I. Carrier Prodrugs," *Pract. Med. Chem.* 671-696; Asgharnej ad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Phannacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Phann. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", *Arfv. Drug Delivery Rev.* 8(1): 1-38 (1992); Fleisher et al. "Improved oral drug delivery: solubility limitations overcome by the use of prodrugs", *Arfv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.,* 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which is herein incorporated by reference in its entirety.

Compounds of Formula (I) also include pharmaceutically acceptable salts thereof. As used herein, the term "pharmaceutically-acceptable salts" refers to the conventional non-toxic salts or quaternary ammonium salts of LSF inhibitors, tubulin acetylating compound, cell migration inhibiting compound, or cell compaction inducing compound as disclosed herein, e.g., from non-toxic organic or inorganic acids. These salts can be prepared in situ in the administration vehicle or the dosage form manufacturing process, or by separately reacting a LSF inhibitor in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative pharmaceutically acceptable salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

In some embodiments, compounds of Formula (I) or a pharmaceutical composition thereof as disclosed herein can be used in conjunction with other therapeutic treatment of HCC such as hepatointralesional ethanol injection, chemoembolization, radiofrequency ablation, cryosurgery, radiation therapy, percutaneous intralesional ethanol injection, transarterial chemoembolization, and radiotherapy.

In some embodiments of the various aspects disclosed herein, the composition or method can further comprise administering an additional anti-cancer therapy to the subject. For example, administering a standard of care chemotherapeutic to the subject. Non-limiting examples of a standard of care chemotherapeutics or other anti-cancer therapy can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. Additional anti-cancer treatment can further include the use of radiation or radiation therapy. Further, the additional anti-cancer treatment can also include the use of surgical treatments.

In some embodiments of the various aspects disclosed herein, the treatment is administered to a subject currently receiving standard of care chemotherapeutics or other alternative anti-cancer treatments. Generally, cancer treatment may involve one or more of the treatment options, but not limited to surgery, radiation, chemotherapy, immunotherapy, targeted therapy and hormonal therapy. The single agent therapy or current combination therapies for the treatment of cancer cause side effects such as nausea, rashes, swelling, flu-like symptoms, fatigue, digestive tract problems, allergic reactions and immunosuppression. In some embodiments, the invention described herein provides a more effective treatment of cancer by administering one or more compounds represented by Formula (I) in combination with other cancer treatments. In some embodiments, the combination therapy induces additive or synergistic therapeutic effect. In some embodiments, the method described herein can reduce or prevent one or more adverse effects or toxicities associated with the administration of a chemotherapeutic agent or radiation therapy. In some embodiments, the method described herein can increase the anti-tumor activity of a chemotherapeutic agent or radiation therapy or increase the selective cytotoxicity of a chemotherapeutic agent.

The phrase "combination therapy" as described herein means administration of one or more compounds represented by Formula (I) and a therapeutic agent as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period. The time period may be in minutes, hours, days or weeks depending upon the combination selected.

Combination therapy includes administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be done, for example, by administering to the subject a single pill having a fixed ratio of each therapeutic agent or in multiple, single pills for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered may or may not be important.

Combination therapy also can mean the administration of one or more compounds represented by Formula (I) in further combination with other compounds and non-drug therapies, such as, but not limited to, surgery or radiation treatment. Where the combination therapy further comprises radiation treatment, the radiation treatment may be conducted at any suitable time so long as a beneficial effect from the co-action of the combination of the therapeutic agents and radiation treatment is achieved.

In some embodiments, compounds represented by Formula (I) as disclosed herein or a pharmaceutical composition thereof can be used to treat HCC subjects who are not responsive to any prior treatment of HCC, or show little/no improvement from any prior treatment of HCC, e.g. continued progression or worsening of HCC. In such embodiments, the HCC subjects can be treated again with the previous therapeutic method in combination with an inhibitor of LSF. In alternative embodiments, they can be administered with a LSF inhibitor or a pharmaceutical composition thereof alone, or concurrently with alternative therapeutic methods.

It has been previously reported that LSF is a downstream gene of astrocyte elevated gene-1 (AEG-1), which is overexpressed in >90% of human HCC patients and induces chemoresistance of HCC to a chemotherapeutic agent, such as 5-fluorouracil (5-FU). Accordingly, in some embodiments, an inhibitor of LSF described herein can be administered prior to, or concurrently with at least one chemotherapeutic agent such as 5-FU. Other exemplary chemotherapeutic agents include Doxorubicin, 5-FU, Paclitaxel, Irinotecan, Patupilone, Everolimus, multikinase inhibitors (Sorafenib and Sunitinib), and EGFR inhibitors (Cetuximab, Erlotinib, Gefitinib, Brivanib, Lapatinib). In one implementation, a LSF inhibitor or a pharmaceutical composition thereof as disclosed herein can be combined with Sorafenib for treatment of HCC.

As a prophylactic measure against HCC recurrence or metastasis, compounds represented by Formula (I) as disclosed herein or a pharmaceutical composition thereof can be administered after surgery or after aforementioned treatments for HCC where solid tumors have been removed or eliminated. In some embodiments, subjects with resectable HCC can be treated with any of compounds represented by Formula (I) or a pharmaceutical composition thereof after hepatectomy or liver transplantation to prevent the recurrence of HCC.

Most cases of HCC are developed from either chronic infection with hepatitis B or hepatitis C virus (HBV or HCV, respectively), or hepatic cirrhosis due to alcoholism. Chronic hepatitis can progress into cirrhosis (a noncancerous liver disease associated with fibrosis and abnormal nodules), which increases the risk of developing HCC. Subjects with chronic hepatitis and/or cirrhosis, therefore form a high risk population. Accordingly, in some embodiments, any of compounds represented by Formula (I) can be used in conjunction with other therapeutic treatment for liver diseases such as infection with HBV, HCV or cirrhosis, as a preventive measure against the onset of HCC.

In some embodiments, any of compounds of Formula (I) as disclosed herein can be administered to a subject with a high risk of developing hepatocellular carcinoma. For example, subjects amenable to treatment by methods and compositions as disclosed herein, e.g. using an inhibitor of LSF, are subjects having a risk factor for HCC. Examples of risk factors for HCC include, but not limited to, HBV, HCV, chronic alcohol consumption, exposure to aflatoxin B1 in food (which is a liver carcinogenic chemical produced by a mold called *Aspergillus flavus* after exposure of food to a hot and humid environment), hepatic adenoma resulted from the use of female hormones (estrogens) and protein-building (anabolic) steroids, exposure to thorotrast (a previously used contrast agent for imaging, which caused a cancer of the blood vessels in the liver called hepatic angiosarcoma), hepatic angiosarcomas (resulted from a prolonged exposure to vinyl chloride, a compound used in the plastics industry), hereditary hemochromatosis (a disorder that causes the body to accumulate excessive amounts of iron), emphysema and cirrhosis (resulted from alpha 1 anti-trypsin deficiency) and hereditary tyrosinemia. In some embodiments, a LSF inhibitor can be used alone or combined with other therapeutic treatment of the aforementioned diseases or disorders. In further embodiments, subjects who have been previously subjected to high risk of developing HCC can be continually treated with an inhibitor of LSF or a pharmaceutical composition thereof, even after they have discontinued treatment of liver diseases such as HBV, HCV or cirrhosis.

Other indications that can be contemplated for the use of LSF inhibitors of the invention as disclosed herein include diseases or disorders, in which expression and/or biological activity of LSF is up-regulated, e.g. by inflammatory cytokines, or in which it is desirable to decrease or inhibit LSF. Non-limiting examples of such diseases or disorders include HIV and inflammation-associated diseases including Alzheimer's disease.

It has been previously reported that LSF activates cell survival-regulating pathways, such as MEK/ERK and NF-κB pathways, and is up-regulated in various cancers (see Yoo et al., PNAS, 2010, 107; 8357-8362 and Kotarba et al., Cancer Lett. (2018), 28 (420), 72-79). Accordingly, in some embodiments, a LSF inhibitor disclosed herein can be used alone or in combination with chemotherapeutic agents for treatment of other various cancers such as brain cancer, breast cancer, colon cancer, cervical cancer, head and neck squamous cell carcinoma, lung cancer, pancreatic cancer, ovarian cancer, and thyroid cancer. Exemplary chemotherapeutic agents include Doxorubicin, 5-FU, Paclitaxel, Irinotecan, Patupilone, Everolimus, multikinase inhibitors (Sorafenib and Sunitinib), and EGFR inhibitors (Cetuximab, Erlotinib, Gefitinib, Brivanib, Lapatinib). In some embodiments, diseases or disorders associated with LSF-induced MEK/ERK activation can be contemplated for treatment with a LSF inhibitor as disclosed herein alone or in combination with inhibitors of MEK/ERK pathway such as PD98059 and U0126.

In some embodiments, a subject amenable or suitable for treatment with a composition comprising any of compounds of Formula (I) as disclosed herein can be selected based on an increased level of LSF expression in a biological sample, or tumor or cancer sample as compared to a control reference LSF expression level, e.g., in a normal non-cancerous sample. In some embodiments, a subject is at risk of having a cancer if the level of LSF expression in the biological sample from the subject is above a pre-determined reference LSF expression threshold level. In some embodiments, the reference LSF expression threshold level is based on the level of LSF expression in a non-cancer cell or non-tumor tissue, or a control cell line, or cells from a normal tissue sample, where the tissue sample is from adjacent, non-pathological tissue of the subject, or a biological tissue sample from a tissue matched, and species matched and age matched biological sample. In some embodiments, the reference level is based on a reference sample is from a non-cancer matched tissue sample.

In some embodiments, the level of LSF expression is measured in a biological sample comprising a tumor sample. In some embodiments, a biological sample obtained from the subject comprises cancer cells, and can be a biological sample which is serum plasma, blood or tissue sample. In some embodiments, a biological sample is selected from the group consisting of; a tissue sample; a tumor sample; a tumor cell; a biopsy sample; ex vivo cultivated sample; ex vivo cultivated tumor sample; surgically dissected tissue sample, blood sample, plasma sample, cancer sample, lymph fluid sample or primary ascite sample. In alternative embodiments, the biological sample includes, for example blood, plasma, serum, urine, spinal fluid, plural fluid, nipple aspirates, lymph fluid, external secretions of the skin, respiratory, internal and genitoururinary tracts, bile, tears, sweat, saliva, organs, milk cells and primary ascite cells, biopsy tissue sample, a cancer biopsy tissue sample, an in vitro or ex vivo cultivated biopsy tissue sample.

Screening for HCC: In some embodiments, a subject amenable to treatment according to the methods as disclosed herein is screened for HCC. A convention biomarker for HCC is alpha-fetoproteins (AFP). Yang et al., 123 J. Cancer Res Clin Oncol. 357 (1997). Individuals with elevated serum levels of AFP can be an indication of hepatocellular carcinoma. Other biomarkers for HCC include, but not limited to, the ones disclosed in the U.S. Patent Application Nos.: US2009/0317844, US2010/0015605, US 2010/0120631, and International Patent Application Nos.: WO 2010/048304, WO 2005/0233392, and WO2008/056854, which are incorporated herein in their entirety by reference. One of the skill in the art can easily perform the measurement of mRNA or protein level of these biomarkers in a biological sample e.g. blood from a subject such as human, using the standard methods in the art. In some embodiments, a subject identified with HCC is administered a LSF inhibitor according to the methods as disclosed herein.

As disclosed herein, a subject with HCC can also be selected by detecting a high level of LSF expression in a biological sample such as a liver sample from the subject as compared to a reference level. In one implementation, the reference level is the level of LSF in a normal healthy subject.

In addition, a biopsy can be used to diagnose HCC. (Walter et al., 24 Curr Opin Gastroenterol. 312 (2008)). Other diagnostic methods for HCC known to one of the skill in the art include imaging methods such as ultrasound, computed tomography (CT) scan and MRI (Scholmerich et al., 52 Gut. 1224 (2004)). In various embodiments, a pharmaceutical composition comprising compounds of Formula (I) as disclosed herein can be administered to a subject diagnosed with HCC or HCC susceptibility.

In some embodiments, a subject undergoing treatment of HCC, e.g. chemotherapy, can be treated alone or in combination with the methods and compositions of the invention as disclosed herein. For example, the inventors have previously reported in collaboration with other scientists that inhibition of LSF can increase sensitivity of HCC cells to chemotherapeutic agents, such as, but not limited to 5-fluorouracil (5-FU) (see Yoo et al., PNAS, 2010; 107; 8357-8362). Accordingly, in some embodiments, subjects with no response to current HCC therapeutic treatment, e.g. HCC subjects who have shown chemoresistance to chemotherapeutic agents such as 5-FU, can be administered with a LSF small molecule inhibitor as disclosed herein using the methods and compositions of the invention, prior to or concurrently with chemotherapy.

Detection of hepatocellular carcinoma can be difficult as most of the patients who develop this tumor have no symptoms other than those inflicted with their longstanding liver disease. The onset of abdominal pain, weight loss, early satiety, jaundice and a palpable mass in the upper abdomen usually indicate an advanced cancer. Accordingly, in some embodiments, subjects at high risk for HCC can be administered an inhibitor of LSF as disclosed herein in the methods and compositions for prevention of the development of HCC (e.g. prophylactic treatment). For example, subjects highly susceptible to HCC are subjects with HBV, HCV, chronic alcohol consumption, an exposure to aflatoxin B1 in food (which is a liver carcinogenic chemical produced by a mold called *Aspergillus flavus* after food has been stored in a hot and humid environment), hepatic adenoma resulted from the use of female hormones (estrogens) and protein-building (anabolic) steroids, an exposure to thorotrast (a previously used contrast agent for imaging, which caused a cancer of the blood vessels in the liver called hepatic angiosarcoma), hepatic angiosarcomas (resulted from a prolonged exposure to vinyl chloride, a compound used in the plastics industry), hereditary hemochromatosis (a disorder that causes the body to accumulate excessive amounts of iron), emphysema and cirrhosis (resulted from alpha 1 anti-trypsin deficiency) and hereditary tyrosinemia.

In additional embodiments, for prophylactic treatment (e.g. to prevent reoccurence of HCC), subjects who was diagnosed with HCC before and HCC is in remission can be selected for treatment with a LSF inhibitor as disclosed herein using the methods and compositions of the invention. For example, subjects who had their HCC tumor removed by hepatectomy and/or liver transplantation, or who had their HCC tumor reduced or stabilized by other therapeutic methods are amenable to administration of a LSF inhibitor or a pharmaceutical composition thereof as disclosed herein.

In yet other embodiments, subjects amenable to therapeutic treatment with methods and compositions of the invention, e.g. using a LSF inhibitor as disclosed herein, include subjects in need of inhibition of LSF. For example, it has been reported that HIV patients, or individuals in need for a decrease in inflammatory response or immune function can be treated by inhibiting LSF (Bovolenta et al, 163 J. Immuno. 6892, (1999), U.S. Patent Application No.: US2009/0081183 and International Application No.: WO1998/36641, which are incorporated herein in their entirety by reference). Accordingly, a LSF inhibitor of the invention as disclosed herein can be administered alone, or concurrently with other LSF inhibitors such as IL2, or peptides, antibodies or antisense RNA against LSF, to subjects in which inhibition of LSF is desirable, such as HIV.

In still another implementation, a subject who has other cancers such as breast cancer but has an up-regulated expression of LSF as compared to a reference level can be selected for therapeutic treatment with methods and compositions of the invention using a LSF inhibitor as disclosed herein. In some embodiments, a reference level is the expression of LSF in a normal healthy subject. In other embodiments, a reference level is the expression of LSF in the same subject measured at the previous time point of the treatment regime. Other cancer indications that can be used for the purposes of the invention include brain cancer, colon cancer, head and neck squamous cell carcinoma, lung cancer, pancreatic cancer, cervical cancer, ovarian cancer, and thyroid cancer.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Amount of compounds of Formula (I) in the pharmaceutical composition can be based on weight, moles, or volume. In some embodiments, the pharmaceutical composition comprises at least 0.0001% of compounds of Formula (I). In some embodiments, the pharmaceutical composition comprises at least 0.1% of compounds of Formula (I). In some embodiments, the pharmaceutical composition comprises at least 0.5% of compounds of Formula (I). In some embodiments, the pharmaceutical composition comprises at least 1% of compounds of Formula (I). In some embodiments, the pharmaceutical composition comprises at least 2% of compounds of Formula (I). In some embodiments, the pharmaceutical composition comprises at least 3% of compounds of Formula (I). In some embodiments, the pharmaceutical composition comprises at least 4% of compounds of Formula (I). In some embodiments, the pharmaceutical composition comprises at least 5% of compounds of Formula (I). In some embodiments, the pharmaceutical composition comprises at least 10% of compounds of Formula (I). In some embodiments, the pharmaceutical composition comprises 0.01%-99% of the compounds of Formula (I). In some embodiments, the pharmaceutical composition comprises 0.05%-90% of the compounds of Formula (I). In some embodiments, the pharmaceutical composition comprises 0.1%-85% of the compounds of Formula (I). In some embodiments, the pharmaceutical composition comprises 0.5%-80% of the compounds of Formula (I). In some embodiments, the pharmaceutical composition comprises 1%-75% of the compounds of Formula (I). In some embodiments, the pharmaceutical composition comprises 2%-70% of the compounds of Formula (I). In some embodiments, the pharmaceutical composition comprises 3%-65% of the compounds of Formula (I). In some embodiments, the pharmaceutical composition comprises 4%-60% of the compounds of Formula (I). In some embodiments, the pharmaceutical composition comprises 5%-50% of the compounds of Formula (I).

It will also be appreciated that certain of the compounds of Formula (I) can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compounds of Formula (I) which upon administration to a patient in need is capable of providing, directly or indirectly, a compound as otherwise described herein, or a metabolite or residue thereof.

As described above, the pharmaceutical compositions of the present invention optionally comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, antioxidants, solid binders, lubricants, and the like, as suited to the particular dosage form desired.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) C2-C12 alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Useful pharmaceutical carriers for the preparation of the compositions hereof, can be solids, liquids or gases. Suitable pharmaceutical carriers and their formulation are described in Remington's Pharmaceutical Sciences by E. W. Martin. Such compositions will, in any event, contain an effective amount of the compounds of Formula (I) together with a suitable carrier so as to prepare the proper dosage form for proper administration to the recipient.

Liquid dosage forms for oral administration include, but are not limited to, pharmaceutically acceptable emulsions, microemulsions, solutions, suspensions, syrups and elixirs. In addition to the compounds of Formula (I), the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the compounds of Formula (I) are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcelhdose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monosteamte, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polethylene glycols, and the like.

The compounds of Formula (I) can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the compounds of Formula (I) can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for parenteral administration conveniently include sterile aqueous preparations of the agents that are preferably isotonic with the blood of the recipient. Suitable excipient solutions include phosphate buffered saline, saline, water, lactated Ringer's or dextrose (5% in water). Such formulations can be conveniently prepared by admixing the agent with water to produce a solution or suspension, which is filled into a sterile container and sealed against bacterial contamination. Preferably, sterile materials are used under aseptic manufacturing conditions to avoid the need for terminal sterilization. Such formulations can optionally contain one or more additional ingredients, which can include preservatives such as methyl hydroxybenzoate, chlorocresol, metacresol, phenol and benzalkonium chloride. Such materials are of special value when the formulations are presented in multidose containers.

Buffers can also be included to provide a suitable pH value for the formulation. Suitable buffer materials include sodium phosphate and acetate. Sodium chloride or glycerin can be used to render a formulation isotonic with the blood.

If desired, a formulation can be filled into containers under an inert atmosphere such as nitrogen and can be conveniently presented in unit dose or multi-dose form, for example, in a sealed ampoule.

Those skilled in the art will be aware that the amounts of the various components of the compositions of the invention to be administered in accordance with the method of the invention to a subject will depend upon those factors noted above.

Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable media prior to use.

In order to prolong the effect of a drug, it is often desirable to slow the absorption of the drug from subcutaneous or intramuscular injection. This can be accomplished by the use of a liquid suspension or crystalline or amorphous material with poor water solubility. The rate of absorption of the drug then depends upon its rate of dissolution that, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are in some embodiments suppositories which can be prepared by mixing the compounds of Formula (I) with suitable non-irritating excipients or carriers such as cocoa butter, polyethylene glycol, or a suppository wax which are solid at ambient temperature but liquid at body temperature and therefore melt in the rectum or vaginal cavity and release the active compound.

A typical suppository formulation includes the compound or a pharmaceutically acceptable salt thereof which is active when administered in this way, with a binding and/or lubricating agent, for example, polymeric glycols, gelatins, cocoa-butter, or other low melting vegetable waxes or fats. Typical transdermal formulations include a conventional aqueous or nonaqueous vehicle, for example, a cream, ointment, lotion, or paste or are in the form of a medicated plastic, patch or membrane.

Typical compositions for inhalation are in the form of a solution, suspension, or emulsion that can be administered in the form of an aerosol using a conventional propellant such as dichlorodifluoromethane or trichlorofluoromethane.

Another aspect of the present invention relates to pharmaceutical compositions for treatment of diseases or disorders where it is therapeutically beneficial to inhibit LSF, increasing tubulin acetylation, inhibiting cell migration, or inducing cell compaction, e.g for treatment of hepatocellular carcinoma. In some embodiments, a pharmaceutical composition of the invention comprises a therapeutically effective amount of at least one LSF inhibitor selected from any of the compounds represented by Formula (I) disclosed herein. In one implementation, a LSF inhibitor is a compound of Formula (I). In some embodiments, a LSF inhibitor is a compound selected from the group consisting of compounds of Formula (I). In some embodiments, a LSF inhibitor is the compound FQI2-34 or FQI2-37. In some embodiments, a LSF inhibitor is FQI2-34, FQI2Br, FQI2Cl, FQI2F, FQI2-134, FQI2-234, FQI2-37, FQI2-137, or FQI2-237. In various embodiments, a LSF inhibitor is an enantiomer, a prodrug, a derivative, or a pharmaceutically acceptable salt of a compound of any of formula (I)

As LSF inhibitor, tubulin acetylating compound, cell migration inhibiting compound, or cell compaction inducing compound as disclosed herein selected from any of Formula (I) can be used in an amount of about 0.001 to 10 mg/kg of body weight or about 0.005 to 8 mg/kg of body weight or about 0.01 to 6 mg/kg of body weight or about 0.1 to 0.2 mg/kg of body weight or about 1 to 2 mg/kg of body weight. In some embodiments, an inhibitor of LSF can be used in an amount of about 0.1 to 1000 mg/kg of body weight or about 1 to 100 mg/kg of body weight or about 10 to 50 µg/kg of body weight. In some embodiments, a LSF inhibitor as disclosed herein selected from any of Formula (I) can be used at a concentration of about 0.001 mg/ml or 0.1 mg/ml or a higher concentration of 0.1 mg/ml. In some embodiments, a pharmaceutical composition comprises at least one LSF inhibitor at a concentration of about 0.01 µM to 300 µM, or about 0.1 µM to 150 µM, or about 1 µM to 50 µM, or about 1 µM to 25 µM. The dosage may vary within this range depending upon the dosage form employed and the route of administration utilized. In some embodiments, a pharmaceutical composition does not comprise inhibitors described in U.S. application Ser. No. 15/713,956, U.S. Pat. Nos. 9,802,948, 9,815,845, 9,597,325 and WO 2012/050985 which are incorporated herein in their entirety by reference.

Depending on routes of administration, one of skill in the art can determine and adjust an effective dosage of a LSF inhibitor, tubulin acetylating compound, cell migration inhibiting compound, or cell compaction inducing compound disclosed herein to a subject such as a human subject accordingly, by determining pharmacokinetics and bioavailability of a LSF inhibitor, tubulin acetylating compound, cell migration inhibiting compound, or cell compaction inducing compound and analyzing dose-response relationship specific to an LSF inhibitor, tubulin acetylating compound, cell migration inhibiting compound, or cell compaction inducing compound in animal models such as a mouse.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices, are preferred.

The data obtained from the cell culture assays and animal studies can be used in formulating a range of dosage for use in humans. The therapeutically effective dose can be determined by one of ordinary skill in the art, e.g. using cell culture assays. An effective dose of a LSF inhibitor, tubulin acetylating compound, cell migration inhibiting compound, or cell compaction inducing compound can be determined in an animal model by measuring the tumor weight and tumor volume over the course of treatment with a LSF inhibitor, tubulin acetylating compound, cell migration inhibiting compound, or cell compaction inducing compound as compared to no treatment. In some embodiments, a dosage comprising a LSF inhibitor, tubulin acetylating compound, cell migration inhibiting compound, or cell compaction inducing compound is considered to be effective if the dosage inhibits or decreases the growth of tumor weight and/or tumor volume by at least about 15%, at least about 20%, at least about 30%, at least about 40%, at least about 50%, at least about 60%, at least about 70%, at least about 80%, at least about 90%, 95%, 99% or even 100%, as compared to a control (e.g. in the absence of a LSF inhibitor, tubulin acetylating compound, cell migration inhibiting compound, or cell compaction inducing compound). In some embodiments, a therapeutically effective amount of a LSF inhibitor, tubulin acetylating compound, cell migration inhibiting compound, or cell compaction inducing compound administered to a subject is dependent upon factors known to a person of ordinary skill, including bioactivity and bioavailability of a LSF inhibitor, tubulin acetylating compound, cell migration inhibiting compound, or cell compaction inducing compound (e.g. half-life and stability of a LSF inhibitor, tubulin acetylating compound, cell migration inhibiting compound, or cell compaction inducing compound in the body), chemical properties of a LSF inhibitor, tubulin acetylating compound, cell migration inhibiting compound, or cell compaction inducing compound (e.g molecular weight, hydrophobicity and solubility); route and frequency of administration, time of administration (e.g. before or after a meal), and the like. Further, it will be understood that the specific dose of the pharmaceutical composition comprising a LSF inhibitor, tubulin acetylating compound, cell migration inhibiting compound, or cell compaction inducing compound as disclosed herein to provide the therapeutic or prophylactic benefits can depend on a variety of factors including physical condition of the subject (e.g. age, gender, weight), medical history of the subject (e.g. medications being taken, other diseases or disorders) and clinical condition of the subject (e.g. health condition, stage of the disease). The precise dose of a pharmaceutical composition comprising a LSF inhibitor, tubulin acetylating compound, cell migration inhibiting compound, or cell compaction inducing compound can be determined by methods known to a skilled artisan such as pharmacologists and physicians.

According to the invention, a LSF inhibitor, tubulin acetylating compound, cell migration inhibiting compound, or cell compaction inducing compound as disclosed herein selected from Formula (I) can be administered prophylactically or therapeutically to a subject prior to, simultaneously or sequentially with other therapeutic regimens or agents (e.g. multiple drug regimens), in a therapeutically effective amount. In some embodiments, a LSF inhibitor, tubulin acetylating compound, cell migration inhibiting compound, or cell compaction inducing compound administered concurrently with other therapeutic agents can be administered in the same or different compositions.

In some embodiments, a pharmaceutical composition comprising at least one LSF inhibitor, tubulin acetylating compound, cell migration inhibiting compound, or cell compaction inducing compound further comprises a second therapeutic agent. In one implementation, the second therapeutic agent is a chemotherapeutic agent such as Sorafenib or 5-FU. In some embodiments, the second therapeutic agent is a second LSF inhibitor, tubulin acetylating compound, cell migration inhibiting compound, or cell compaction inducing compound, e.g. a compound selected from any of formula (I). In some embodiments, a second LSF inhibitor is an enantiomer of a first LSF inhibitor as disclosed herein. In other embodiments, the second therapeutic agent is a therapeutic for liver diseases such as HBV, HCV and cirrhosis.

In prophylactic applications, pharmaceutical compositions (or medicaments) comprising a LSF inhibitor, tubulin acetylating compound, cell migration inhibiting compound, or cell compaction inducing compound can be administered to a subject susceptible to, or otherwise at risk of, a disease or disorder mediated by elevated levels of LSF in an amount sufficient to eliminate or reduce the risk or delay the onset of the disease. In one implementation, the disease or disorder to be prevented is hepatocellular carcinoma (HCC). As most HCCs are generated from the background of hepatitis B virus (HBV) or hepatitis C virus (HCV), a subject with HBV or HCV can be subjected to an effective amount or dose of a pharmaceutical composition comprising a LSF inhibitor, tubulin acetylating compound, cell migration inhibiting compound, or cell compaction inducing compound described herein. In one implementation, a pharmaceutical composition of the invention disclosed herein comprises a compound of Formula (I), or enantiomers, prodrugs, derivatives or pharmaceutically acceptable salts thereof. In some embodiments, an effective amount or dose of a pharmaceutical composition comprising a LSF inhibitor, tubulin acetylating compound, cell migration inhibiting compound, or cell compaction inducing compound disclosed herein can be administered to a subject at high risk of HCC. In additional embodiments, a pharmaceutical composition further comprises a second therapeutic agent, e.g. therapeutics to treat high-risk factors such as liver diseases (e.g HBV). Representative high-risk factors of HCC include hepatic cirrhosis, chronic alcohol consumption, (prolonged) exposure to liver carcinogenic chemicals such as aflatoxin B1 in food, thorotrast in diagnostic contrast agent and vinyl chloride, hepatic adenoma, hepatic angiosarcoma, hepatic angiosarcomas, hereditary hemochromatosis, emphysema and cirrhosis resulted from alpha 1 anti-trypsin deficiency, and hereditary tyrosinemia. In various embodiments, individuals that have discontinued treatment for high-risk factors of HCC can still be subjected to a pharmaceutical composition comprising an effective dose of compound selected from any of Formula (I) as disclosed herein for prevention of development of HCC. For such embodiments, an effective dose of a LSF inhibitor can be higher or lower than the previous dosage.

In therapeutic applications, according to the invention provided herein, when an effective amount or effective dose of a pharmaceutical composition comprising a LSF inhibitor, tubulin acetylating compound, cell migration inhibiting compound, or cell compaction inducing compound selected from any of Formula (I) of the present invention is administered to the subject with cancer, e.g. hepatocellular carcinoma, progression of cancer, e.g. HCC, can be delayed or inhibited. In some embodiments, administration of an effective amount or effective dose of a pharmaceutical composition comprising a LSF inhibitor, tubulin acetylating compound, cell migration inhibiting compound, or cell compaction inducing compound selected from any of Formula (I) to a subject with hepatocellular carcinoma can inhibit or delay progression of HCC. In further embodiments, treating subjects with an effective dose of a pharmaceutical composition comprising a LSF inhibitor, tubulin acetylating compound, cell migration inhibiting compound, or cell compaction inducing compound can prevent or delay metastasis of HCC in the subject. In some embodiments, a LSF inhibitor, tubulin acetylating compound, cell migration inhibiting compound, or cell compaction inducing compound used for therapeutic treatment of various diseases, e.g. HCC, using the methods and compositions disclosed herein is the compound FQI2-34 or FQI2-37. In some embodiments, a LSF inhibitor used for therapeutic treatment of various diseases, e.g. HCC, using the methods and compositions disclosed herein is the compound FQI2-34, FQI2Br, FQI2Cl, FQI2F, FQI2-134, FQI2-234, FQI2-37, FQI2-137, or FQI2-237 or enantiomers, prodrugs, derivatives or pharmaceutically acceptable salts thereof.

In therapeutic applications, a relatively high dosage in relatively short intervals is sometimes required until progression of the disease is reduced or terminated, or until the subject shows partial or complete amelioration of symptoms of disease. Thereafter, the subject can be administered a prophylactic regime. For example, subjects with HCC can be treated with a LSF inhibitor, tubulin acetylating compound, cell migration inhibiting compound, or cell compaction inducing compound as disclosed herein at an effective dose in a therapeutic regimen accordingly to prevent or delay the progression of HCC or metastasis. In other embodiments, a LSF inhibitor, tubulin acetylating compound, cell migration inhibiting compound, or cell compaction inducing compound can be administered using the methods and compositions as disclosed herein to chemotherapy subjects in order to increase sensitivity to chemotherapy. In some embodiments, an inhibitor of LSF, tubulin acetylating compound, cell migration inhibiting compound, or cell compaction inducing compound as disclosed herein can be administered to subjects prior to, concurrently with, or sequentially to treatment with chemotherapeutic drugs, e.g. Sorafenib. In further embodiments, HCC subjects selected for other therapeutic procedures or surgeries, such as hepatectomy, intralesional ethanol injection, or chemoembolization, can be subjected to a treatment with a LSF inhibitor, tubulin acetylating compound, cell migration inhibiting compound, or cell compaction inducing compound as disclosed herein. For example, a pharmaceutical composition of the invention can be administered prior to, during or after therapeutic procedures. Route of administration can vary with therapeutic procedures or surgeries and can be determined by a skilled artisan. In yet another implementation, compositions and methods of the invention can be used as an adjuvant therapy.

In some embodiments, the subject is a human, and in alternative embodiments the subject is a non-human mammal. Treatment dosages need to be titrated to optimize safety and efficacy. The amount of a LSF inhibitor, tubulin acetylating compound, cell migration inhibiting compound, or cell compaction inducing compound depends on the stage of the disease, e.g. HCC as well as whether a second therapeutic agent is also administered. The second therapeutic agent can be an agent to treat a different disease or disorder. In some embodiments, the second therapeutic agent can be a chemotherapeutic agent such as Doxorubicin, 5-FU, Paclitaxel, Irinotecan, Patupilone, Everolimus, multikinase inhibitors (Sorafenib and Sunitinib), and EGFR inhibitors (Cetuximab, Erlotinib, Gefitinib, Brivanib, Lapatinib). In alternative embodiments, the second therapeutic agent can be a second LSF inhibitor, tubulin acetylating compound, cell migration inhibiting compound, or cell compaction inducing compound. In some embodiments, a second LSF inhibitor, tubulin acetylating compound, cell migration inhibiting compound, or cell compaction inducing compound can be selected from the group consisting of compounds of Formula (I), and enantiomers, prodrugs and pharmaceutically acceptable salts thereof. In one implementation, a second LSF inhibitor, tubulin acetylating compound, cell migration inhibiting compound, or cell compaction inducing compound can be an enantiomer of a first LSF inhibitor, tubulin acetylating compound, cell migration inhibiting compound, or cell compaction inducing compound. In further embodiments, a second therapeutic agent is another therapeutics to target another disease, or another disorder, or a different symptom. In combination with other therapeutics, the dosage of a LSF inhibitor, tubulin acetylating compound, cell migration inhibiting compound, or cell compaction inducing compound can be reduced, compared to the standard dosage of a LSF inhibitor, tubulin acetylating compound, cell migration inhibiting compound, or cell compaction inducing compound when administered alone.

In some embodiments, the frequency of administration can vary significantly from once a day, once every other day, once every 3 days, once weekly, once monthly to once a year, depending on the disease of cancer (e.g., stage of cancer) such as HCC stage, and/or mode of administration.

Generally, effective dosages and dosing schedules can be adjusted based on, for example, the outcome of the treatment such as whether the progression rate of HCC is slower or terminated, or whether at least one of the symptoms associated with HCC is reduced. In accordance with the teachings provided herein, the effectiveness of the treatment can be monitored by obtaining a biological sample from a subject, e.g. a blood serum sample, and determining the level of biomarkers for HCC, such as AFP in the serum sample, using methods well known in the art and the diagnostic methods. The efficacy of the treatment can also be monitored by imaging modalities such as CT scan, MRI, ultrasound, and the like that are known to a skilled artisan.

In some embodiments, the daily dose administered to a subject in a form of a bolus composition comprising a LSF inhibitor, tubulin acetylating compound, cell migration inhibiting compound, or cell compaction inducing compound can be given in a single dose, in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease. It is also within the skill of the art to start doses at levels lower than required to achieve the desired therapeutic effect and to gradually increase the dosage until the desired effect is achieved.

In various embodiments, an LSF inhibitor, tubulin acetylating compound, cell migration inhibiting compound, or cell compaction inducing compound selected from any of Formula (I) can be a pro-drug, where it is activated by a second agent. Accordingly, in such embodiments, administration of such the second agent which activates the pro-drug into its active form can be administered the same time, concurrent with, or prior to, or after the administration of the pharmaceutical composition comprising an LSF, tubulin acetylating compound, cell migration inhibiting compound, or cell compaction inducing compound inhibitor as disclosed herein.

In some embodiments, an LSF inhibitor, tubulin acetylating compound, cell migration inhibiting compound, or cell compaction inducing compound selected from any of Formula (I) as disclosed herein is often administered as pharmaceutical compositions comprising an active therapeutic agent, i.e. a LSF inhibitor, tubulin acetylating compound, cell migration inhibiting compound, or cell compaction inducing compound and a variety of other pharmaceutically acceptable components. See Remington's Pharmaceutical Science (15th ed., Mack Publishing Company, Easton, Pa., 1980). The formulation of the compositions depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, non-therapeutic, non-immunogenic stabilizers and the like. However, some reagents suitable for administration to animals may not necessarily be used in compositions for human use.

Exemplary embodiments of the various aspects descried herein can be described with the following numbered embodiments:

Embodiment 1: A compound of Formula (I),

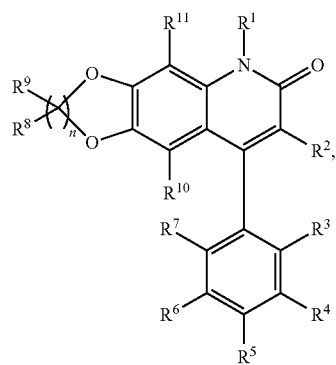

(I)

or enantiomers, prodrugs, derivatives, and pharmaceutically acceptable salts thereof; wherein: $R^1$ is hydrogen, $C_1$-$C_6$ alkyl or $C_1$-$C_6$ haloalkyl; $R^2$, $R^4$, $R^6$, $R^7$, $R^{10}$ and $R^{11}$ are each independently selected from the group consisting of hydrogen, halogen, OH, or amino ($NH_2$); $R^3$ is $C_1$-$C_6$ alkoxy; $R^5$ is hydrogen, halogen, amino ($NH_2$), mono($C_1$-$C_6$)alkylamino, di($C_1$-$C_6$alkyl)amino, $C_1$-$C_6$ alkyl or $C_1$-$C_6$ haloalkyl; each $R^8$ and $R^9$ is selected independently from the group consisting of hydrogen and halogen; and n is 1, or 2, and, optionally provided that the compound is not

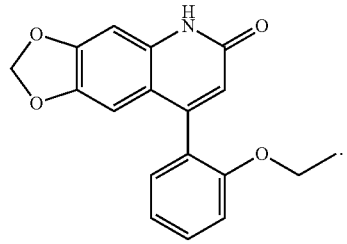

FQI-2

Embodiment 2: The compound according to Embodiment 1, wherein $R^1$ and $R^2$ are hydrogen.

Embodiment 3: The compound according to Embodiment 1 or 2, wherein $R^{10}$ and $R^{11}$ are hydrogen.

Embodiment 4: The compound according to any one of Embodiments 1 to 4, wherein $R^4$, $R^6$ and $R^7$ are hydrogen.

Embodiment 5: The compound according to any one of Embodiments 1 to 4, wherein $R^3$ is $OCH_3$, $OCH_2CH_3$, $OCH_2CH_2CH_3$, $OCH(CH_3)_2$, $OCH_2CH_2CH_2CH_3$, $OCH_2CH(CH_3)_2$, $OCH_2CH_2CH_2CH_2CH_3$ or $OCH_2CH_2CH_2CH_2CH_2CH_3$.

Embodiment 6: The compound according to any one of Embodiments 1 to 5, wherein $R^3$ is $OCH_2CH_3$, $OCH_2CH_2CH_3$ or $OCH_2CH(CH_3)_2$.

Embodiment 7: The compound according to any one of Embodiments 1 to 6, wherein $R^5$ is hydrogen, halogen, amino, mono($C_1$-$C_6$)alkylamino, di($C_1$-$C_6$alkyl)amino or $C_1$-$C_6$ haloalkyl.

Embodiment 8: The compound according to any one of Embodiments 1 to 7, wherein $R^5$ is H, Br, F, Cl, I, $N(CH_3)_2$, or trifluoromethane ($-CF_3$).

Embodiment 9: The compound according to any one of Embodiments 1 to 8, wherein $R^5$ is $N(CH_3)_2$.

Embodiment 10: The compound according to any one of Embodiments 1 to 9, wherein $R^5$ is trifluoromethane ($-CF_3$)

Embodiment 11: The compound according to any one of Embodiments 1 to 10, wherein $R^8$ and $R^9$ are hydrogen.

Embodiment 12: The compound according to any one of Embodiments 1 to 11, wherein n is 1.

Embodiment 13: The compound according to any one of Embodiments 1 to 12, wherein n is 2.

Embodiment 14: The compound according to Embodiment 1, wherein the compound is selected from the group consisting of:

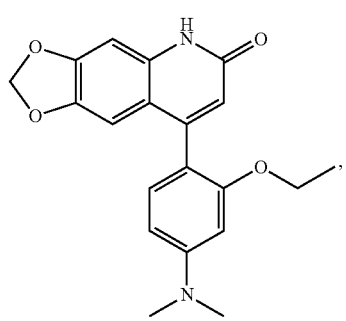

FQI2-34

FQI2Br
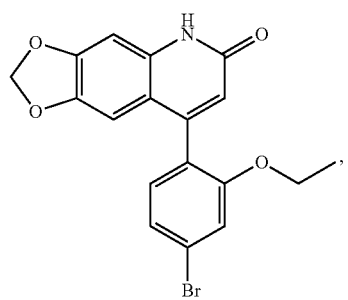
FQI2Cl
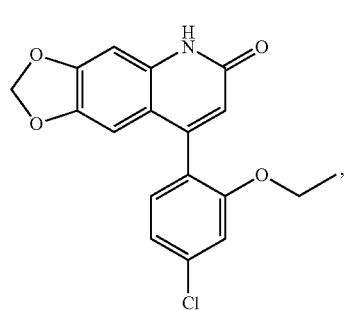
FQI2F
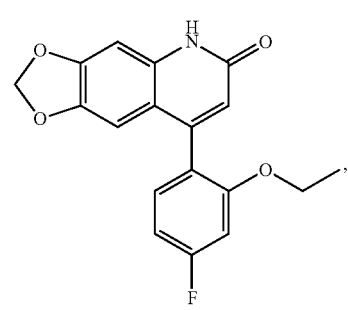
FQI2-134
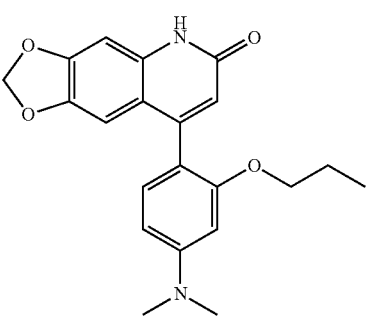
FQI2-234
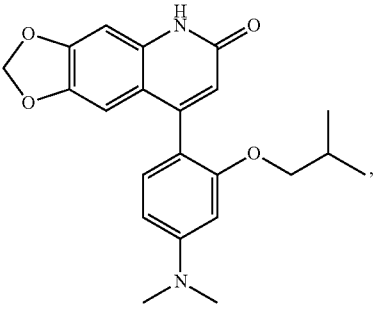
FQI2F3
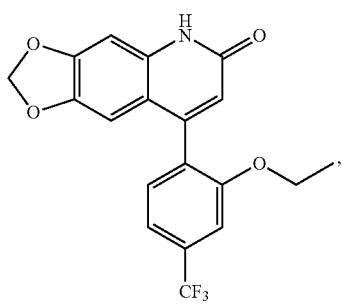
FQI2-37
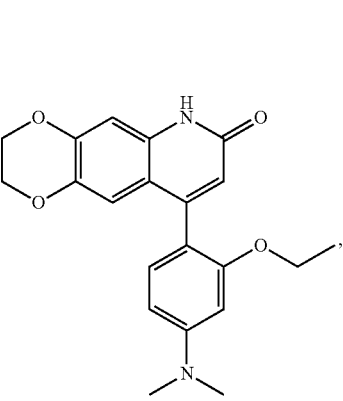
FQI2-137
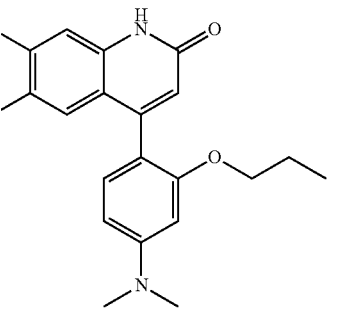
and
FQI2-237
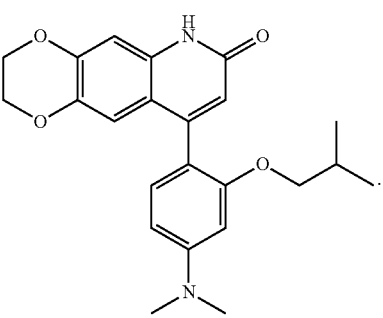
Embodiment 15: The compound according to Embodiment 14, wherein the compound is selected from the group consisting of:

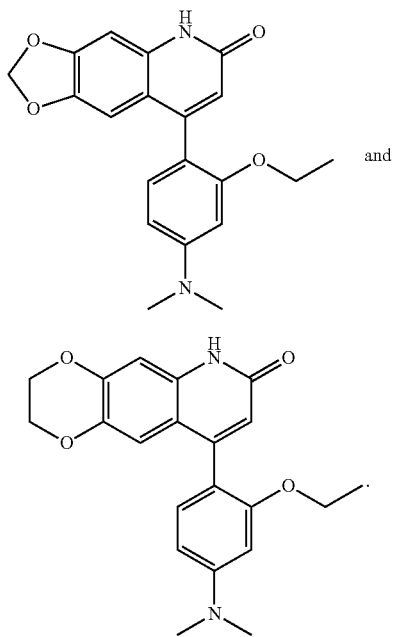

FQI2-34 and

FQI2-37

Embodiment 16: A method of increasing tubulin acetylation in a cell, the method comprising administering to the cell an effective amount of a compound of any one of Embodiments 1 to 15.

Embodiment 17: A method of inducing cell compaction, the method comprising administering to the cell an effective amount of a compound of any one of Embodiments 1 to 15.

Embodiment 18: A method of inhibiting cell migration, the method comprising administering to the cell an effective amount of a compound of any one of Embodiments 1 to 15.

Embodiment 19: A method for treating cancer in a subject, the method comprising administering an effective amount of a compound of any one of Embodiments 1 to 15.

Embodiment 20: A method for making the compounds according to any one of Embodiments 1 to 15, wherein the method comprising treating a compound of Formula (II),

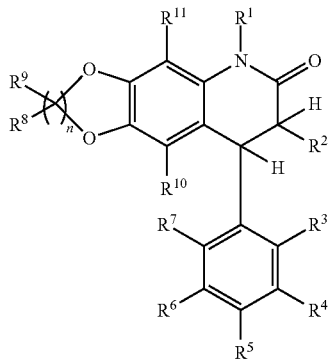

with an oxidixing agent.

Embodiment 21: The method according to Embodiment 20, wherein the oxidizing agent is 2,3-dichloro-5,6-dicyano-1,4-benzoquinone (DDQ).

Definitions

The structure definitions such as "alkyl" are provided below for nomenclature purposes. They do not exclude the meaning as those acquired in the art to which this invention pertains. The term "alkyl" as used herein refers to a linear, branched, or cyclic saturated hydrocarbon group typically although not necessarily containing 1 to about 24 carbon atoms, 1 to about 12 carbon atoms, 1 to about 6 carbon atoms or a lower alkyl, such as methyl, ethyl, n-propyl, isopropyl, n-butyl, isobutyl, sec-butyl, tert-butyl, pentyl, hexyl, and the like, as well as cycloalkyl groups such as cyclopropyl, cyclobutryl, cyclopentyl, cyclohexyl, cycloheptyl, cyclooctyl and the like. The term "cycloalkyl" intends a cyclic alkyl group, typically having 3 to 10, or 3 to 8, carbon atoms. The term "substituted alkyl" refers to alkyl substituted with one or more substituent groups, and the terms "heteroalkyl" and "heteroatom-containing alkyl" refer to alkyl in which at least one carbon atom is replaced with a heteroatom. The term "haloalkyl" as used herein refers to an alkyl structure with at least one substituent of fluorine, chorine, bromine or iodine, or with combinations thereof. If not otherwise indicated, the term "alkyl" includes linear, branched, cyclic, unsubstituted, substituted, and/or heteroatom-containing alkyl, respectively.

The term "alkenyl" as used herein refers to a linear, branched, or cyclic hydrocarbon group of 2 to about 16 carbon atoms containing at least one double bond, such as ethenyl, n-propenyl, isopropenyl, n-butenyl, isobutenyl, n-pentenyl, iso-pentenyl, hexenyl, heptenyl, octenyl, decenyl, tetradecenyl, hexadecenyl, eicosenyl, tetracosenyl, and the like. In some embodiments, alkenyl groups herein contain 2 to about 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the term "alkenyl" includes linear, branched, cyclic, unsubstituted, substituted, and/or heteroatom-containing alkenyl, respectively.

The term "alkynyl" as used herein refers to a linear or branched-chain hydrocarbon group having one or more carbon-carbon triple-bonds and having from 2 to about 8 carbon atoms. Examples of alkynyl groups include ethynyl, propynyl, butynyl, pentynyl and the like.

The term "alkoxy" as used herein intends an alkyl group bound through a single, terminal ether linkage; that is, an "alkoxy" group may be represented as —O-alkyl where alkyl is as defined herein. Exemplary alkoxy groups include, but are not limited to O-methyl, O-ethyl, O-n-propyl, O-iso-propyl, O-n-butyl, O-isobutyl, O-sec-butyl, O-tert-butyl, O-pentyl, O-hexyl, O-cyclopropyl, O-cyclobutyl, O-cyclopentyl, O-cyclohexyl and the like.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). In some embodiments, aryl groups contain 5 to 24 carbon atoms, or 5 to 14 carbon atoms. Exemplary aryl groups contain one aromatic ring or two fused or linked aromatic rings, e.g., phenyl, 1-naphthyl, 2-naphthyl, biphenyl, pyridine, quinoline, furan, thiophene, pyrrole, imidazole, pyrazole, diphenylether, diphenylamine, benzophenone, and the like. "Substituted aryl" refers to an aryl moiety substituted with one or more, (e.g., one, two, three, four or more) substituent groups, and the terms "heteroatom-containing aryl" and "heteroaryl" refer to aryl substituents in which at least one carbon atom is replaced with a heteroatom such as oxygen, nitrogen and sulfur. The term "heteroaryl" includes ring systems such as pyridine, quinoline, furan, thiophene, pyrrole, imidazole and pyrazole and the like.

The term "heterocycyl" as used herein refers to a single ring or multiple rings that are fused together, directly linked, or indirectly inked (such that the different rings are bound to a common group such as a methylene or ethylene moiety), in which at least one carbon atom is replaced with a heteroatom such as oxygen, nitrogen and sulfur. In some embodiments, heterocycyl groups contain 3 to 24 carbon atoms, or 3 to 14 carbon atoms. For example, a heterocycyl group can be a five-membered ring with at least one carbon replaced by oxygen or nitrogen.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic. In one implementation, the bicyclic or polycyclic ring may be fused ring. The fusion of the ring may be across a bond between two atoms, i.e. two cyclic rings share one bond or two atoms, for example, a decalin; the fusion of the ring may be across a sequence of atoms, i.e. two cyclic rings share three or more atoms, for example a norbornane.

By "substituted" as in "substituted alkyl," "substituted aryl," and the like, as alluded to in some of the definitions as described herein, is meant that in the alkyl, aryl, or other moiety, at least one hydrogen atom bound to a carbon (or other) atom is replaced with one or more non-hydrogen substituents. Examples of such substituents include, without limitation: halogen, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aryl alkoxy, $C_6$-$C_{24}$ alkyl aryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$), phospho (—PO$_2$), phosphino (—PH$_2$); and the hydrocarbyl moieties $C_1$-$C_{24}$ alkyl (e.g., $C_1$-$C_{12}$ alkyl, or $C_1$-$C_6$ alkyl), $C_2$-$C_{24}$ alkenyl (e.g., $C_2$-$C_{12}$ alkenyl, or $C_2$-$C_6$ alkenyl), $C_2$-$C_{24}$ alkynyl (e.g., $C_2$-$C_{12}$ alkynyl, or $C_2$-$C_6$ alkynyl), and $C_5$-$C_{24}$ aryl (e.g., $C_5$-$C_{14}$ aryl). In some embodiments, the substituents as used herein are halogen, $C_1$-$C_4$ alkyl, $C_1$-$C_4$ haloalkyl, $C_1$-$C_4$ heteroalkyl, $C_1$-$C_6$ alkoxy, mono($C_1$-$C_6$alkyl)amino or di($C_1$-$C_6$alkyl)amino.

In addition, the functional groups as described herein may, if a particular group permits, be further substituted with one or more additional functional groups or with one or more hydrocarbyl moieties such as those specifically enumerated herein. Analogously, the hydrocarbyl moieties described herein may be further substituted with one or more functional groups or additional hydrocarbyl moieties such as those specifically enumerated.

The term 'disorder' or 'disease' used interchangeably herein, refers to any alteration in the state of the body or of some of its organs, interrupting or disturbing the performance of the functions and/or causing symptoms such as discomfort, dysfunction, distress, or even death to the person afflicted or those in contact with the person. A disease or disorder can also relate to distemper, ailing, ailment, malady, disorder, sickness, illness, complaint, indisposition, affection. In one implementation, the disorder or disease is cancer. In one implementation, the disease or disorder is liver cancer, e.g., hepatocellular carcinoma. In one implementation, the disease or disorder is a cancer selected from the group selected from: colon cancer, breast cancer, ovarian cancer, melanomia, endometrium cancer, pancreatic cancer, prostate cancer, bone cancer, kidney cancer, leukemia, large intestine cancer, lung cancer, small cell lung carcinoma (SSLC), stomach cancer and other cancers.

The term 'cancer' and 'malignancy' are used interchangeably herein, and refer to a disease that is characterized by uncontrolled, abnormal growth of cells. Cancer cells can spread locally or through the bloodstream and lymphatic system to other parts of the body. The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer. The term cancer also includes metastases which are cancer cells (e.g. a primary tumor, or a metastasis tumor) which has migrated to other locations in the subject and to establish new tumors at such locations. A small molecule LSF inhibitor as disclosed herein which "inhibits" cancer metastasis may result in the delayed appearance of secondary tumors, slowed development of primary or secondary tumors, decreased occurrence of secondary tumors, slowed or decreased severity of secondary effects of disease, arrested tumor growth and regression of tumors, among others. In the extreme, complete inhibition is referred to herein as prevention (e.g., virtually complete inhibition, no metastasis if it had not occurred, no further metastasis if there had already been metastasis of a cancer, or virtually complete inhibition of the growth of a primary tumor caused by re-seeding of the tumor by a metastasized cell).

A "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage dependence, proliferation, malignancy, lack of contact inhibition and density limitation of growth, lack of growth factor or serum dependence, tumor specific markers levels, invasiveness, tumor growth in suitable animal hosts such as nude mice, and the like, in vitro, in vivo, and ex vivo (see also Freshney, Culture of Animal Cells: A Manual of Basic Technique (3rd ed. 1994)).

A "tumorigenic cell," as used herein, is a cell that, when introduced into a suitable site in a subject, can form a tumor. The cell may be non-metastatic or metastatic. A variety of types of tumorigenic and/or metastatic cells can be used in a method of the invention, including cells from metastatic epithelial cancers, carcinomas, melanoma, leukemia, etc. The tumor cells may be, e.g., from cancers of breast, lung, colon, bladder, prostate, liver, gastrointestinal tract, endometrium, tracheal-bronchial tract, pancreas, uterus, ovary, nasopharynges, prostate, bone or bone marrow, brain, skin or other suitable tissues or organs. In some embodiments, the cancer cells are of human origin.

The term "tumor" or "tumor cell" are used interchangeably herein, refers to the tissue mass or tissue type of cell that is undergoing abnormal proliferation.

A "metastatic" cell, as used herein, refers to a cell that has a potential for metastasis and, when used in a method of the invention, is able to seed a tumor or a cell colony of interest. A "highly metastatic" cell, as used herein, refers to a cell that has a high potential for metastasis; e.g., cells from a cell line such as, but not limited to LM2, MDA-MB-231, PC-3, DU-145, Lewis Lung carcinoma, can be considered to be highly metastatic cells. Metastatic cells can be generated in a variety of ways, which are discussed further below.

A "sarcoma" refers to a type of cancer cell that is derived from connective tissue, e.g., bone (osteosarcoma) cartilage (chondrosarcoma), muscle (rhabdomyosarcoma or rhabdosarcoma), fat cells (liposarcoma), lymphoid tissue (lymphosarcoma), collagen-producing fibroblasts (fibrosarcoma). Sarcomas may be induced by infection with certain viruses, e.g., Kaposi's sarcoma, Rous sarcoma virus, etc.

The term "tissue" is intended to include intact cells, blood, blood preparations such as plasma and serum, bones, joints, muscles, smooth muscles, and organs.

The term "subject" includes human and other mammalian subjects that receive either prophylactic or therapeutic treatment. Accordingly, the term "subject" refers to any living organism which can be administered compound and/or pharmaceutical compositions of the present invention. The term includes, but is not limited to, humans, non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult and newborn subjects, whether male or female, are intended to be covered. The term "subject" is also intended to include living organisms susceptible to conditions or disease states as generally disclosed, but not limited to, throughout this specification. Examples of subjects include humans, dogs, cats, cows, goats, and mice. The term subject is further intended to include transgenic species. The term "subject" and "individual" are used interchangeably herein, and refer to an animal, for example a human or non-human mammals/animals, to whom treatment, including prophylactic treatment, with the compounds and compositions according to the present invention, is provided. The term "non-human animals" and "non-human mammals" are used interchangeably herein and include all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one implementation, the subject is human. In another implementation, the subject is an experimental animal or animal substitute as a disease model.

The terms "a reference sample" or "a reference level" as used interchangeably herein refer to a negative control of the condition. For example, in the context of treatment, a reference level is the level if a subject is not treated. In some embodiments, a reference level in the context of diagnosis is the level present in a normal healthy subject. The term "normal healthy subject" refers to a subject who has no symptoms of any diseases or disorders, or who is not identified with any diseases or disorders, or who is not on any medication treatment, or a subject who is identified as healthy by physicians based on medical examinations. In some embodiments, a reference level or sample used herein refers to the level measured at a previous time point from a subject being treated.

The term "tissue" is intended to include intact cells, blood, blood preparations such as plasma and serum, bones, joints, muscles, smooth muscles, and organs. In one implementation, the tissue is liver tissue.

The terms "treat", "treatment" and "treating" used interchangeably, with respect to treatment of a disease or disorder, mean preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis in a subject who is at risk of the disease, as well as slowing or reducing progression of existing disease. The term treating encompasses reducing or alleviating at least one adverse effect or symptom of a condition, disease or disorder associated with inappropriate proliferation, for example cancer. As used herein with respect to cancer, the term treating is used to refer to the reduction of a symptom and/or a biochemical marker of inappropriate proliferation, for example a reduction in at least one biochemical marker of cancer by at least 10%. For example, but are not limited to, a reduction in a biochemical marker of cancer, for example a reduction in, as an illustrative example only, at least one of the following biomarkers; CD44, telomerase, TGF-α, TGF-β, erbB-2, erbB-3, MUC1, MUC2, CK20, PSA, CA125, FOBT, osteopontin (OPN), alpha-fetoprotein (AFP) by 10%, or a reduction in the rate of proliferation of the cancer cells by 10%, would be considered effective treatments by the methods as disclosed herein. As alternative examples, a reduction in a symptom of cancer, for example, a slowing of the rate of growth of the cancer by 10% or a cessation of the increase in tumor size, or a reduction in the size of a tumor by 10% or a reduction in the tumor spread (i.e. tumor metastasis) by 10% would also be considered as effective treatments by the methods as disclosed herein. In other embodiments, treatment can be therapeutic in terms of eliminating or reducing at least one symptom of the condition or disease. For example, in the case of HCC, therapeutic treatment refers to inhibiting or delaying the progression of HCC in a subject that is already inflicted with HCC. Measurable lessening includes any statistically significant decline in a measurable marker or symptom, such as measuring a tumor size or level of a biomarker.

As used herein, the term "treating" includes preventing the progression and/or reducing or reversing at least one adverse effect or symptom of a condition, disease or disorder associated with inappropriate proliferation, for example cancer. Accordingly, in some embodiments, treatment can be prophylactic in terms of completely or partially preventing a disease or sign or symptom of cancer. For example, subjects at high risk of cancer, e.g., HCC, such as HBV or HCV, can be subjected to prophylactic treatment to prevent the onset of HCC. In some embodiments, prophylactic treatment can be administered to subjects who had prior treatment of a disease and the disease is in remission. For example, for subjects who have their HCC tumors removed or stabilized by previous therapeutic methods can be prophylactically treated (e.g. with a LSF inhibitor as disclosed herein) to prevent the recurrence and metastasis of HCC.

As used herein, the terms "prevent," "preventing" and "prevention" refer to the avoidance or delay in manifestation of one or more symptoms or measurable markers of a disease or disorder. A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the complete avoidance or prevention of symptoms or markers, but also a reduced severity or degree of any one of those symptoms or markers, relative to those symptoms or markers arising in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

In some embodiments, treatment is therapeutic and does not include prophylactic treatment.

The terms "up-regulate", "increase" or "activate" are all used herein to generally mean an increase by a statically significant amount; for the avoidance of any doubt, the terms "up-regulate", "increase" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or a 100% increase or more, or any increase between 10-100% as compared to a reference level, or an increase greater than 100%, for example, an increase at least about a 2-fold, or at least about a 3-fold, or at least about a 4-fold, or at least about a 5-fold or at least about a 10-fold increase, or any increase between 2-fold and 10-fold or greater as compared to a reference level. When "increase" is used in the context of the expression or activity of a gene or protein, it refers to a positive change in protein or nucleic acid level or activity in a cell, a cell extract, or a cell supernatant. For example, such an increase may be due to increased RNA stability, transcription, or translation, or decreased protein degradation. In some embodiments, this increase is at least 5%, at least about 10%, at least about 25%, at least about 50%, at least about 75%, at least about 80%, at least about 100%, at least about 200%, or even about 500% or more over the level of expression or activity under control conditions.

The terms "lower", "reduced", "reduction" or "decrease", "down-regulate" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level. When "decrease" or "inhibition" is used in the context of the level of expression or activity of a gene or a protein, e.g. LSF or LSF target genes, it refers to a reduction in protein or nucleic acid level or activity in a cell, a cell extract, or a cell supernatant. For example, such a decrease may be due to reduced RNA stability, transcription, or translation, increased protein degradation, or RNA interference. In some embodiments, the small-molecule LSF inhibitors as disclosed herein decrease the activity or expression of LSF. In some embodiments, this decrease is at least about 5%, at least about 10%, at least about 25%, at least about 50%, at least about 75%, at least about 80%, or even at least about 90% of the level of expression or activity under control conditions. The term "level" as used herein in reference to LSF refers to expression or activity of LSF.

The terms "significantly different than,", "statistically significant," and similar phrases refer to comparisons between data or other measurements, wherein the differences between two compared individuals or groups are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

A "pharmaceutical composition" refers to a chemical or biological composition suitable for administration to a mammalian subject. Such compositions may be specifically formulated for administration via one or more of a number of routes, including but not limited to, oral, parenteral, intravenous, intraarterial, subcutaneous, intranasal, sublingual, intraspinal, intracerebroventricular, and the like.

The phrase "effective amount" as used herein means that amount of a compound, material, or composition comprising a compound described herein which is effective for producing some desired therapeutic effect in at least a sub-population of cells at a reasonable benefit/risk ratio applicable to any medical treatment. Thus, "effective amount" means that amount which, when administered to a subject for treating a disease, is sufficient to affect such treatment for the disease, for example, to the amount of a compound of Formula (I) to reduce or stop at least one symptom of the abnormal proliferation, for example a symptom of a cancer or malignancy. In one non-limiting example, an effective amount using the methods as disclosed herein would be considered as the amount sufficient to reduce a symptom of the abnormal proliferation, for example at least one symptom of a cancer or malignancy by at least 10%. An effective amount as used herein would also include an amount sufficient to prevent or delay the development of a symptom of the disease, alter the course of a symptom disease (for example but not limited to, slow the progression of a symptom of the disease), or reverse a symptom of the disease. Accordingly, the term "effective amount" or "therapeutically effective amount" as used herein refers to the amount of therapeutic agent (e.g. at least one small molecule inhibitor of LSF, tubulin acetylation, cell migration inhibiting compound, or inducing cell compaction of Formula (I) as disclosed herein) of pharmaceutical composition to alleviate at least some of the symptoms of cancer e.g. HCC. In some embodiments, small molecule inhibitors of Formula (I) can be used. Stated another way, "therapeutically effective amount" of a small molecule LSF inhibitor, increasing tubulin acetylation, cell migration inhibiting compound, or inducing cell compaction, as disclosed herein is the amount of a LSF inhibitor, increasing tubulin acetylation, cell migration inhibiting compound, or inducing cell compaction which exerts a beneficial effect on, for example, cancer, e.g., HCC. Beneficial effects include inhibition or delay of cancer, e.g., HCC progression. The dosage administered, as single or multiple doses, to an individual will vary depending upon a variety of factors, including pharmacokinetic properties of a LSF inhibitor, the route of administration, conditions and characteristics (sex, age, body weight, health, size) of subjects, extent of symptoms, concurrent treatments, frequency of treatment and the effect desired.

Depending on the route of administration, effective doses can be calculated according to the body weight, body surface area, or organ size of the subject to be treated. Optimization of the appropriate dosages can readily be made by one skilled in the art in light of pharmacokinetic data observed in human clinical trials. Alternatively, or additionally, the dosage to be administered can be determined from studies using animal models for the particular type of condition to be treated, and/or from animal or human data obtained from agents which are known to exhibit similar pharmacological activities. The final dosage regimen will be determined by the attending surgeon or physician, considering various factors which modify the action of active agent, e.g., the agent's specific activity, the agent's specific half-life in vivo, the severity of the condition and the responsiveness of the patient, the age, condition, body weight, sex and diet of the patient, the severity of any present infection, time of administration, the use (or not) of other concomitant therapies, and other clinical factors.

Determination of an effective amount is well within the capability of those skilled in the art. Generally, the actual effective amount can vary with the specific compound, the use or application technique, the desired effect, the duration of the effect and side effects, the subject's history, age, condition, sex, as well as the severity and type of the medical condition in the subject, and administration of other pharmaceutically active agents. Accordingly, an effective dose of compound described herein is an amount sufficient to produce at least some desired therapeutic effect in a subject.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of use or administration utilized.

The effective dose can be estimated initially from cell culture assays. A dose can be formulated in animal models to achieve a circulating plasma concentration range that includes the $IC_{50}$ (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay. The effective plasma concentration for a compound as disclosed herein can be about 0.01 µM to about 10 µM, about 0.2 µM to about 5 µM, or about 0.8 to about 3 µM in a subject, such as a rat, dog, or human.

Generally, the compositions are administered so that a compound of the disclosure herein is used or given at a dose from 1 µg/kg to 1000 mg/kg; 1 µg/kg to 500 mg/kg; 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 µg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this disclosure, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

The compounds described herein can be administered at once, or can be divided into a number of smaller doses to be administered at intervals of time. It is understood that the precise dosage and duration of treatment will be a function of the location of where the composition is parenterally administered, the carrier and other variables that can be determined empirically using known testing protocols or by extrapolation from in vivo or in vitro test data. It is to be noted that concentrations and dosage values can also vary with the age of the individual treated. It is to be further understood that for any particular subject, specific dosage regimens can need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The compound can be administered as a single bolus or multiple boluses, as a continuous infusion, or a combination thereof. For example, the compound can be administered as a single bolus initially, and then administered as a continuous infusion following the bolus. The rate of the infusion can be any rate sufficient to maintain effective concentration, for example, to maintain effective plasma concentration. Some contemplated infusion rates include from 1 mg/kg/min to 100 mg/kg/min, or from 1 µg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to maintain effective plasma concentration and the rate of elimination of the compound, such that the compound is administered via infusion at a rate sufficient to safely maintain a sufficient effective plasma concentration of compound in the bloodstream.

An "agent" is a chemical molecule of synthetic or biological origin. In the context of the present invention, an agent is generally a molecule that can be used in a pharmaceutical composition. In some embodiments, the agent is chemotherapeutic agents. In some embodiments, the agent is small-molecule LSF inhibitors as disclosed herein. In some embodiments, the agent can provide a therapeutic value. In some embodiments, the small molecule LSF inhibitors as disclosed herein can be used as a preventative or prophylactic treatment for prevention of cancer, e.g., where a subject is at risk or is likely to develop cancer. In other embodiments, the agent is used solely to implement the invention, e.g. pharmaceutically acceptable carriers as disclosed herein.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably.

The terms "administered" and "subjected" are used interchangeably in the context of treatment of a disease or disorder. Both terms refer to a subject being treated with an effective dose of pharmaceutical composition comprising a LSF inhibitor of the invention by methods of administration such as parenteral or systemic administration.

In jurisdictions that forbid the patenting of methods that are practiced on the human body, the meaning of "administering" of a composition to a human subject shall be restricted to prescribing a controlled substance that a human subject will be administer to the subject by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, administration will generally be local rather than systemic The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of a pharmaceutical composition comprising at least an inhibitor of LSF as disclosed herein such that it enters the animal's system and, thus, is subject to metabolism and other like processes, for example, subcutaneous administration. In some embodiments, the administration is oral administration. Without limitations, oral administration can be in the form of solutions, suspensions, tablets, pills, capsules, sustained-release formulations, oral rinses, powders and the like.

The term "consisting of" refers to compositions, methods, and respective components thereof as described herein, which are exclusive of any element not recited in that description of the implementation.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following, including the Examples, but the scope of the invention should not be limited thereto.

The term "inhibit LSF" as used herein refers to inhibiting expression (level) of LSF and/or biological activity of LSF. In some embodiments, the term "inhibit LSF" refers to a decrease in the protein level of LSF and/or gene transcript level of LSF. For example, inhibition of LSF can result in a reduction in the gene expression of TFCP2 encoding LSF.

The term "inhibit LSF" also refers to a down-regulation or an inhibition of biological activity of LSF, e.g. the function of LSF to modulate expression of LSF-regulated downstream genes such as; thymidylate synthetase (TYMS), secreted phosphoprotein 1 (SPP1), complement factor H (CFH) and fibronectin 1 (FN1) (see Porta-de-la-Riva M, et al (2011) J. Biochem. 435:563-8, which is incorporated herein in its entirety by reference).

The terms "cellular LSF activity" and "biological activity of LSF" are used herein interchangeably. Both terms refer to the ability of LSF to regulate cellular processes downstream of LSF, for example, to modulate the expression of genes that are downstream of LSF. In some embodiments, the biological activity of LSF can elicit a stimulatory effect on expression of LSF-downstream genes. In other embodiments, the biological activity of LSF can induce an inhibitory effect on expression of LSF-downstream genes. In yet other embodiments, the biological activity of LSF may be due to interactions with other cellular proteins.

The phrase "level of LSF" as used herein encompasses the expression and/or biological activity of LSF. As described herein, the term "expression" refers to the amount of the protein obtained by translation of RNA transcribed from a gene, and/or the amount of RNA transcribed from a gene.

The term "regulate" used herein in reference to expression of a gene, refers to producing an effect on, for example, gene expression. In some embodiments, the effect can be stimulatory, such as increasing expression of a gene. In some embodiments, the effect can be inhibitory, such as decreasing expression of a gene. The terms "regulate" and "modulate" are interchangeably used herein.

The terms "inhibitors of LSF" and "LSF inhibitors" used interchangeably herein, generally refers to agents that inhibit LSF. They can be of synthetic or biological origins. They can be organic, or inorganic molecules, or peptides, antibodies or antisense RNA that inhibit LSF. Inhibitors of LSF of the invention are chemical entities or molecules that can inhibit expression of LSF and/or biological activity of LSF, as disclosed herein, for example, compounds of any of Formula (I), and enantiomers, prodrugs, derivatives and pharmaceutically acceptable salts thereof. In some embodiments, LSF inhibitors also increase tubulin acetylation, inhibit cell migration, or induce cell compaction.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

Example 1: Synthesis and Characterization of Exemplary Compounds $^1$H NMR spectra were obtained at 400 MHz and referenced to the CHCl$_3$ singlet at 7.26 ppm, or the DMSO singlet at 2.50 ppm. $^{13}$C NMR spectra were obtained at 100 MHz, and referenced to the center peak of the CDCl$_3$ triplet at 77.16 ppm, or the center of the DMSO-d$_6$ septet at 39.51 ppm. Chemical shifts are reported in parts per million as follows: chemical shift, multiplicity (s=singlet, d=doublet, t=triplet, q=quartet, m=multiplet), coupling constant, and integration. High resolution mass spectrometry data were obtained on a Waters Qtof (hybrid quadrupolar/time-of-flight) API US system by electrospray (ESI) in the positive mode. Mass correction was done by an external reference using a Waters Lockspray accessory. Mobile phases were water and acetonitrile with 0.1% formic acid. The MS settings were: capillary voltage=3 kV, cone voltage=35, source temperature=120° C. and dissolvation temperature=350° C. Flash column chromatography was performed on Sorbent Technologies 60 Å silica gel.

FQI1 was synthesized as previously described (Grant et al., *Proc. Natl. Acad. Sci. USA*. 109, 4503-4508 (2012)). FQI1 was prepared in anhydrous dimethyl sulfoxide (DMSO) (Sigma Aldrich, D2650) to a final concentration of 40 mM. For experiments assessing cell spreading area, pelleted microtubule levels, microtubule depletion by microscopy, wound healing assay and cell motility, FQI1 and DMSO, along with nocodazole, taxol (Sigma Aldrich, T7402), and Y-27632 (Med Chem Express, 129830-38-2), were added directly into the cell culture dish from the stock solutions (final DMSO concentration 0.01%-0.02%), unless noted otherwise.

FQI-34 and FQI2-34 were generally prepared according to the method described in U.S. Pat. No. 9,815,845 to Hansen et al. and U.S. Provisional Application No. 63/073, 240), with a few modifications. The preparation of FQI1 and FQI2 compounds is detailed in the following as detailed in the following step-by-step protocol.

N-(benzo[d][1,3]dioxol-5-yl)-2-bromoacetamide

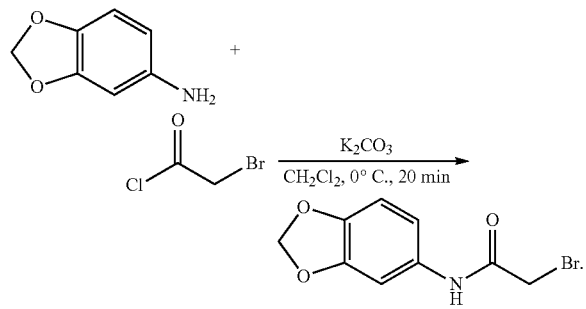

A flame-dried 500-mL round bottomed flask equipped with a Teflon-coated magnetic stirbar under an argon atmosphere was charged with 3,4-(methylenedioxy)aniline (5.88 g, 42.9 mmol) and dry dichloromethane (100 mL, 0.43 M). (Note: 3,4-(methylenedioxy)aniline was recrystallized from hexanes prior to use). Vacuum oven-dried potassium carbonate (8.30 g, 60 mmol, 1.40 equiv) was added, and the reaction was cooled to 0° C. Bromoacetyl chloride (4.64 mL, 55.7 mmol, 1.30 equiv) was added via syringe and the reaction was stirred at 0° C. for 20 min and then allowed to warm to room temperature. Saturated aqueous sodium bicarbonate was added (100 mL) and the mixture was extracted with dichloromethane (3×150 mL). The combined organic layers were washed with saturated aqueous sodium chloride (100 mL), and dried over anhydrous sodium sulfate ($Na_2SO_4$). The filtrate was concentrated via rotary evaporation to afford N-(benzo[d][1,3]dioxol-5-yl)-2-bromoacetamide as a tan solid (9.73 g, 37.7 mmol, 88% yield, >97% purity), that was used without purification. $^1$H NMR (DMSO-$d_6$, 400 MHz) δ 10.30 (s, 1H), 7.27 (d, J=2.0 Hz, 1H), 6.96 (dd, J=8.4, 2.0 Hz, 1H), 6.87 (d, J=8.4 Hz, 1H), 5.98 (s, 2H), 4.00 (s, 2H). $^{13}$C NMR (DMSO-$d_6$, 100 MHz) δ 164.4, 147.1, 142.9, 133.0, 112.2, 108.1, 101.3, 101.1, 30.4. HRMS m/z 257.9771 [(M+H$^+$) calcd for $C_9H_9BrNO_3^+$: 257.9766].

N-(2,3-dihydrobenzo[b][1,4]dioxin-6-yl)-2-bromo-acetamide

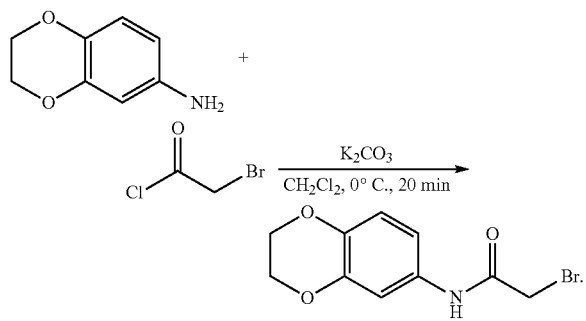

A flame-dried 100-mL round bottomed flask equipped with a stirbar under an argon atmosphere was charged with freshly purified 3,4-(ethylenedioxy)aniline (3.02 g, 20 mmol) and dry dichloromethane (45 mL, 0.43 M). Vacuum oven-dried potassium carbonate (3.87 g, 28 mmol, 1.40 equiv) was then added, and the reaction was cooled to 0° C. Then, bromoacetyl chloride (2.17 mL, 26 mmol, 1.30 equiv) was added via syringe and the reaction was stirred at 0° C. for 20 min and then allowed to warm to room temperature. Saturated aqueous sodium bicarbonate was added (50 mL) and the mixture was extracted with dichloromethane (3×75 mL). The combined organic layers were washed with brine (150 mL), and dried over anhydrous sodium sulfate. The solution was concentrated via rotary evaporation to afford N-(2,3-dihydrobenzo[b][1,4]dioxin-6-yl)-2-bromoacetamide as a purple-gray solid (3.88 g, 14.2 mmol, 71% yield). $^1$H NMR (CDCl3, 400 MHz) δ 8.00 (s, 1H), 7.15 (d, J=2.5 Hz, 1H), 6.90 (dd, J=8.7, 2.5 Hz, 1H), 6.83 (d, J=8.7, 1H), 4.25 (s, 4H), 4.02 (s, 2H).

Dimethyl (2-(benzo[d][1,3]dioxol-5-ylamino)-2-oxoethyl)phosphonate

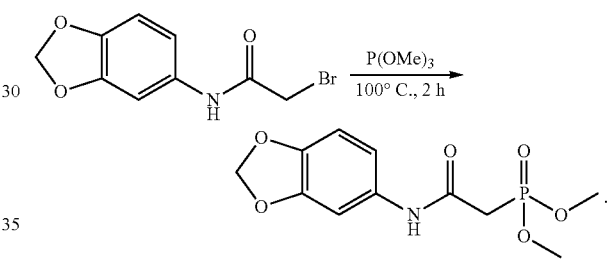

A flame dried 50-mL round-bottomed flask equipped with a Teflon-coated magnetic stirbar under an argon atmosphere was charged with N-(benzo[d][1,3]dioxol-5-yl)-2-bromoacetamide (4.00 g, 15.5 mmol) and trimethyl phosphite (9.62 g, 9.16 mL, 77.5 mmol). The flask was fitted with a reflux condenser, rubber septum, and argon balloon. The reaction was heated to 100° C. for 2 hours, at which time the reaction was poured into a 500-mL separatory funnel, diluted with dichloromethane (250 mL), and washed with water (3×200 mL). The organic layer was rinsed with saturated aqueous sodium chloride (50 mL), and dried over anhydrous sodium sulfate ($Na_2SO_4$). The filtrate was concentrated in vacuo to afford a viscous oil that was left under high vacuum (0.4 mmHg) overnight. Then, the product was dissolved in dry toluene (50 mL) and concentrated via rotary evaporation to azeotrope any remaining trimethyl phosphite. The product was further dried under high vacuum (0.4 mmHg) to afford dimethyl (2-(benzo[d][1,3]dioxol-5-ylamino)-2-oxoethyl) phosphonate as a pale pink/purple solid (3.43 g, 77% yield, >98% purity) that was used without further purification. $^1$H NMR (CDCl$_3$, 400 MHz) δ 8.89 (s, 1H), 7.18 (d, J=2.1 Hz, 1H), 6.79 (dd, J=8.4, 2.1 Hz, 1H), 6.65 (d, J=8.4 Hz, 1H), 5.91 (s, 2H), 3.82 (d=11.2 Hz, 6H), 3.01 (d, J=21.0 Hz, 2H). $^{13}$C NMR (CDCl$_3$, 100 MHz) δ 161.7, 147.5, 144.0, 132.3, 112.8, 107.8, 102.4, 53.4, 35.9, 34.6. HRMS m/z 288.0630 [(M+H$^+$) calcd for $C_{11}H_{15}BrNO_6P^+$: 288.0637].

Dimethyl (2-((2,3-dihydrobenzo[b][1,4]dioxin-6-yl)amino)-2-oxoethyl) phosphonate

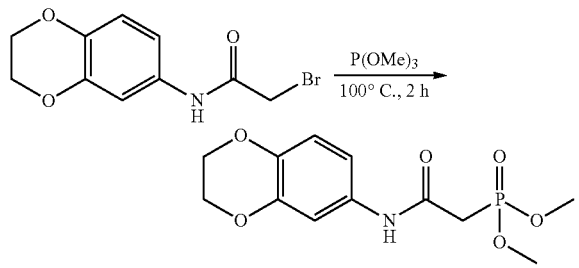

A flame dried 25-mL round-bottomed flask equipped with a stirbar under an argon atmosphere was charged with N-(2,3-dihydrobenzo[b][1,4]dioxin-6-yl)-2-bromoacetamide (2.03 g, 7.46 mmol) and trimethyl phosphite (4.63 g, 4.41 mL, 37.3 mmol). The flask was fitted with a reflux condenser, rubber septum, and argon balloon. The reaction was then heated to 100° C. for 2 hours, at which time the reaction was poured into a 500-mL separatory funnel, diluted with 150 mL dichloromethane, and washed 3×100 mL water. The organic layer was rinsed with 50 mL brine, dried over anhydrous sodium sulfate, and concentrated in vacuo to afford a viscous oil that was left under high vacuum overnight (0.4 mmHg). Then, the product was dissolved in dry toluene and concentrated via rotary evaporation to afford dimethyl (2-02,3-dihydrobenzo[b][1,4]dioxin-6-yl)amino)-2-oxoethyl)phosphonate as a pale-purple solid (3.43 g, 77% yield). $^1$H NMR (CDCl3, 400 MHz) δ 8.69 (s, 1H), 7.15 (d, J=2.5 Hz, 1H), 6.88 (dd, J=8.7, 2.5 Hz, 1H), 6.75 (d, J=8.7 Hz, 1H), 4.22 (s, 4H), 3.82 (d, J=11.2 Hz, 6H), 3.00 (d, J=20.8 Hz, 2H).

4-(dimethylamino)-2-ethoxybenzaldehyde

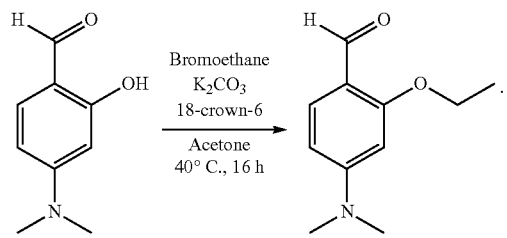

A flame-dried 250-mL round-bottomed flask equipped with a Teflon-coated magnetic stirbar under an argon atmosphere was charged with 4-(dimethylamino)-2-hydroxybenzaldehyde (4.13 g, 25 mmol) in acetone (83 mL, 0.30 M). Anhydrous potassium carbonate (5.18 g, 37.5 mmol), 18-crown-6 (330 mg, 1.25 mmol) and bromoethane (13.6 g, 125 mmol, 9.27 mL) were added to the reaction. The reaction mixture was fitted with a reflux glycol condenser and heated at 40° C. for 16 hours, then cooled to room temperature. The reaction was filtered and the filtered solid was washed with acetone. The filtrate was evaporated via rotary evaporation to yield 4-(dimethylamino)-2-ethoxybenzaldehyde as a brown solid (3.87 g, >99% yield, 90% pure) that was used without further purification. $^1$H NMR (CDCl$_3$, 400 MHz) δ 10.20 (s, 1H), 7.72 (d, J=8.8 Hz, 1H), 6.29 (dd, J=8.8, 2.3 Hz, 1H), 6.02 (d, J=2.3 Hz, 1H), 4.11 (q, J=7.0 Hz, 2H), 3.06 (s, 6H), 1.46 (t, J=7.0 Hz, 3H). $^{13}$C NMR (CDCl$_3$, 100 MHz) 187.6, 163.4, 155.9, 129.8, 114.6, 104.50, 93.7, 70.0, 63.7, 40.2, 14.7. HRMS m/z 194.1176 [(M+H$^+$) calcd for C$_{11}$H$_{16}$NO$_2$$^+$: 194.1181].

4-chloro-2-ethoxybenzaldehyde

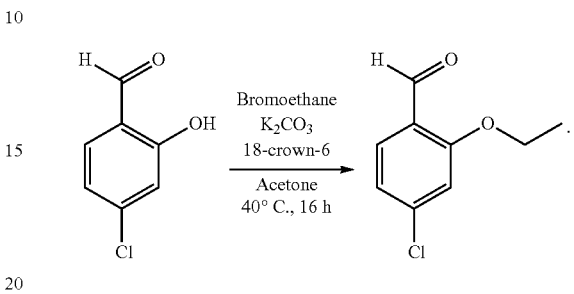

A flame-dried 25-mL round-bottomed flask equipped with a stirbar under an argon atmosphere was charged with 4-chloro-2-hydroxy-benzaldehye (0.783 g, 5 mmol) in acetone (17 mL, 0.30 M), followed by the addition of anhydrous potassium carbonate (1.04 g, 7.50 mmol), 18-crown-6 (66 mg, 0.25 mmol) and bromoethane (2.72 g, 25 mmol, 1.85 mL). The reaction mixture was fitted with a reflux glycol condenser and heated at 40° C. for 16 hours, and then cooled to room temperature. The reaction was filtered and the filtered solid was washed with acetone. The filtrate was evaporated via rotary evaporation to yield 4-chloro-2-ethoxybenzaldehyde as a yellow solid in quantitative yield that was used without further purification. $^1$H NMR (CDCl3, 400 MHz) δ 10.41 (s, 1H), 7.76 (d, J=8.2 Hz, 1H), 6.98 (overlap, 2H), 4.14 (q, J=7.0 Hz, 2H), 1.49 (t, J=7.0 Hz, 3H).

4-bromo-2-ethoxybenzaldehyde

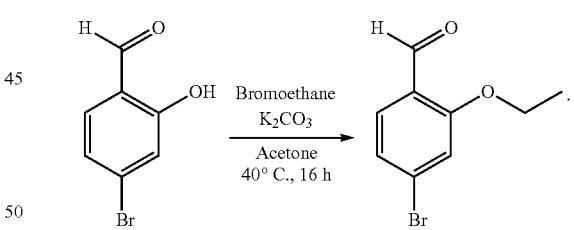

A flame-dried 100-mL round-bottomed flask equipped with a stirbar under an argon atmosphere was charged with 4-bromo-2-hydroxy-benzaldehyde (1.14 g, 8.14 mmol) in acetone (38 mL), followed by the addition of anhydrous potassium carbonate (1.69 g, 12.20 mmol), and bromoethane (4.43 g, 40.7 mmol, 3.04 mL). The reaction mixture was fitted with a reflux glycol condenser and heated at 40° C. for 16 hours, and then cooled to room temperature. The reaction was filtered and the filtered solid was washed with acetone. The filtrate was evaporated via rotary evaporation to yield 4-bromo-2-ethoxybenzaldehyde as a yellow-orange solid (1.37 g, 75% yield) that was used without further purification. $^1$H NMR (CDCl3, 400 MHz) δ 10.43 (s, 1H), 7.68 (d, J=8.0 Hz, 1H), 7.17-7.14 (overlap, 2H), 4.15 (q, J=8.0 Hz, 2H), 1.49 (t, J=8.0 Hz, 3H).

4-fluoro-2-ethoxybenzaldehyde

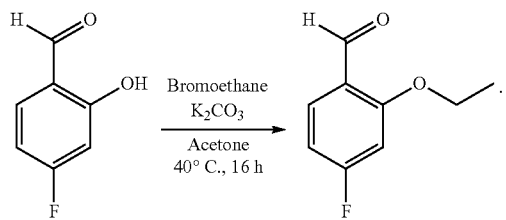

A flame-dried 100-mL round-bottomed flask equipped with a stirbar under an argon atmosphere was charged with 4-fluoro-2-hydroxy-benzaldehye (1.20 g, 5.97 mmol) in acetone (27 mL), followed by the addition of anhydrous potassium carbonate (1.24 g, 8.95 mmol), and bromoethane (3.25 g, 29.85 mmol, 2.23 mL). The reaction mixture was fitted with a reflux glycol condenser and heated at 40° C. for 16 hours, and then cooled to room temperature. The reaction was filtered and the filtered solid was washed with acetone. The filtrate was evaporated via rotary evaporation to yield 4-fluoro-2-ethoxybenzaldehyde as a yellow-orange solid (1.37 g, 93% yield) that was used without further purification. $^1$H NMR (CDCl3, 400 MHz) δ 10.41 (s, 1H), 7.85 (m, 1H), 6.73-6.62 (overlap, 2H), 4.13 (q, J=8.0 Hz, 2H), 1.49 (t, J=8.0 Hz, 3H).

4-(dimethylamino)-2-propoxybenzaldehyde

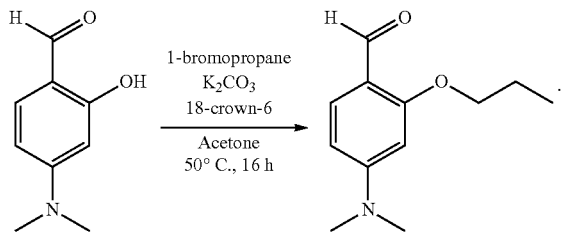

A flame-dried 25-mL round-bottomed flask equipped with a stirbar under an argon atmosphere was charged with 4-(dimethylamino)-2-hydroxybenzaldehyde (0.826 g, 5 mmol) in acetone (17 mL, 0.30 M), followed by the addition of anhydrous potassium carbonate (1.04 g, 7.50 mmol), 18-crown-6 (66 mg, 0.25 mmol) and 1-bromopropane (3.07 g, 25 mmol, 2.28 mL). The reaction mixture was fitted with a reflux glycol condenser and heated at 50° C. for 16 hours, and then cooled to room temperature. The reaction was filtered and the filtered solid was washed with acetone. The filtrate was evaporated via rotary evaporation to yield 4-(dimethylamino)-2-propoxybenzaldehyde as a yellow solid in quantitative yield that was used without further purification. $^1$H NMR (CDCl3, 400 MHz) δ 10.24 (s, 1H), 7.73 (d, J=8.8 Hz, 1H), 6.30 (dd, J=8.8, 2.3 Hz, 1H), 6.03 (d, J=2.3 Hz, 1H), 4.01 (t, J=6.4 Hz, 2H), 3.10 (s, 6H), 1.87 (qt, J=7.5, 6.4 Hz, 2H), 1.07 (t, J=7.5 Hz, 3H).

4-(dimethylamino)-2-isobutoxybenzaldehyde

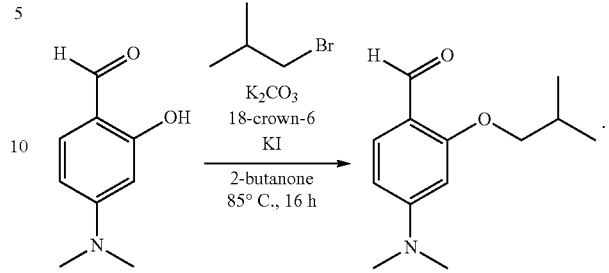

A flame-dried 25-mL round-bottomed flask equipped with a stirbar under an argon atmosphere was charged with 4-(dimethylamino)-2-hydroxybenzaldehyde (0.826 g, 5 mmol) in 2-butanone (17 mL, 0.30 M), followed by the addition of anhydrous potassium carbonate (1.04 g, 7.50 mmol), 18-crown-6 (132 mg, 0.50 mmol), potassium iodide (83 mg, 0.50 mmol), and 1-bromo-2-methylpropane (1.37 g, 10 mmol, 1.09 mL). The reaction mixture was fitted with a reflux glycol condenser and heated at 85° C. for 16 hours, and then cooled to room temperature. The reaction was filtered and the filtered solid was washed with acetone. The filtrate was evaporated via rotary evaporation to afford 4-(dimethylamino)-2-isobutoxybenzaldehyde as a yellow solid in quantitative yield that was used without further purification. $^1$H NMR (CDCl3, 400 MHz) δ 10.23 (s, 1H), 7.72 (d, J=8.8 Hz, 1H), 6.28 (dd, J=8.8, 2.4 Hz, 1H), 6.00 (d, J=2.4 Hz, 1H), 3.79 (d, J=6.4 Hz, 2H), 3.06 (s, 6H), 2.14 (m, 1H), 1.05 (d, J=6.8 Hz, 6H).

2-ethoxy-4-(trifluoromethyl)benzaldehyde

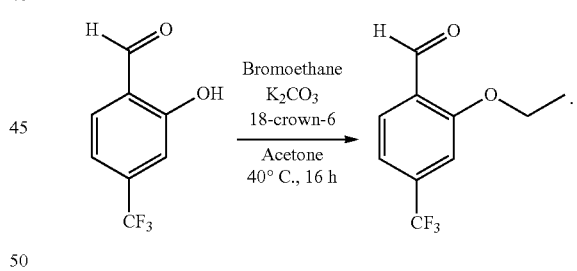

A flame-dried 25-mL round-bottomed flask equipped with a stirbar under an argon atmosphere was charged with 2-hydroxy-4-(trifluoromethyl)benzaldehyde (1.00 g, 5.26 mmol) in acetone (18 mL, 0.30 M), followed by the addition of anhydrous potassium carbonate (1.09 g, 7.89 mmol), 18-crown-6 (70 mg, 0.26 mmol) and bromoethane (2.87 g, 26.3 mmol, 1.95 mL). The reaction mixture was fitted with a reflux glycol condenser and heated at 40° C. for 16 hours, and then cooled to room temperature. The reaction was filtered and the filtered solid was washed with acetone. The filtrate was evaporated via rotary evaporation to afford 2-ethoxy-4-(trifluoromethyl)benzaldehyde as a yellow solid in quantitative yield that was used without further purification. $^1$H NMR (CDCl3, 400 MHz) δ 10.53 (s, 1H), 7.21 (s, 1H), 7.92 (d, J=8.0 Hz, 1H), 7.27 (d, J=8.0 Hz, 1H), 4.21 (q, J=7.0 Hz, 2H), 1.52 (t, J=7.0 Hz, 3H).

General Procedure a for the Synthesis of Acrylamides (Horner-Wadsworth-Emmons Reactions)

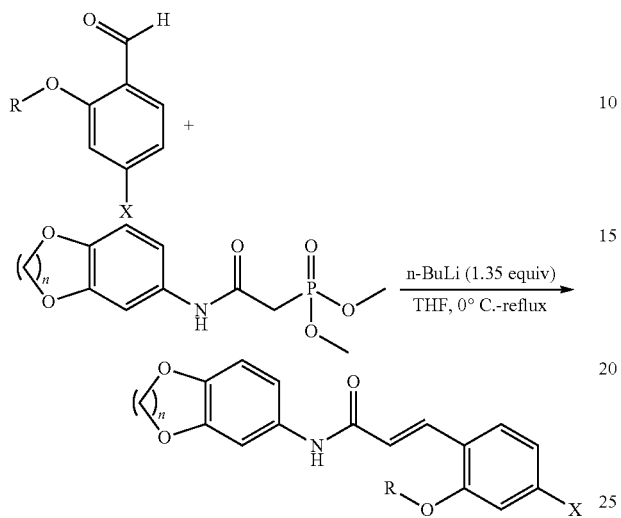

where for example n=1 or 2; X=H, —NH$_2$, halide; —CF$_3$. R=H, alkyl.

A flame dried 25-mL round-bottomed flask equipped with a stirbar was charged with either dimethyl (2-(benzo[d][1,3]dioxol-5-ylamino)-2-oxoethyl)phosphonate (n=1) or dimethyl (2-((2,3-dihydrobenzo[b][1,4]dioxin-6-yl)amino)-2-oxoethyl)phosphonate and THF (0.30 M) (n=2). The flask was flushed with argon and fitted with a rubber septum and argon balloon, then cooled to 0° C. in an ice-water bath. n-Butyllithium (1.6 M in hexanes, 1.35 equiv) was added dropwise, and the mixture was allowed to warm to RT and stir for 30 min, at which time the corresponding aldehyde (1.50 mmol) was added as a single portion. The flask was fitted with a reflux condenser and argon balloon, and the mixture was heated to reflux for 22 h. The mixture was cooled to RT and quenched with saturated ammonium chloride (5 mL). The mixture was transferred to a 500 mL separatory funnel, and diluted with 150 mL dichloromethane and 50 mL water. The dichloromethane layer was removed and washed with an additional 3×50 mL water, then dried over anhydrous sodium sulfate, filtered, and concentrated by rotary evaporation. The crude product was used without further purification unless otherwise indicated.

(E)-N-(benzo[d][1,3]dioxol-5-yl)-3-(4-(dimethyl-amino)-2-ethoxyphenyl)acrylamide

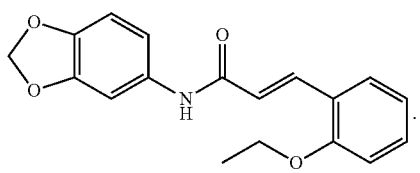 [SMILES: CCOc1ccccc1/C=C/C(=O)Nc1ccc2c(c1)OCO2]

The reaction was setup according to general procedure A using dimethyl (2-(benzo[d][1,3]dioxol-5-ylamino)-2-oxoethyl)phosphonate (539 mg, 1.88 mmol) in THF (5 mL), n-butyl lithium (1.27 mL, 2.03 mmol), and 2-ethoxybenzaldehyde (225 mg, 1.50 mmol, 0.2 mL). The product was isolated as a yellow brown solid (450 mg, 87% yield). $^1$H NMR (CDCl3, 400 MHz) □ 8.01 (d, 15.6 Hz, 1H), 7.50 (d, J=7.8 Hz, 1H), 7.39 (s, 1H), 7.31 (dd, J=7.8, 7.8 Hz, 1H), 7.17 (s, 1H), 6.98-6.85 (overlap, 3H), 6.67 (d, J=8.2 Hz, 1H), 6.63 (d, J=15.6 Hz, 1H), 5.96 (s, 2H), 4.17 (q, J=7.1 Hz, 2H), 1.49 (t, J=7.1 Hz, 3H).

(E)-N-(benzo[d][1,3]dioxol-5-yl)-3-(4-(dimethyl-amino)-2-ethoxyphenyl) acrylamide

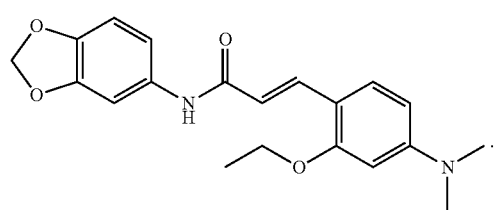 [SMILES: CCOc1cc(N(C)C)ccc1/C=C/C(=O)Nc1ccc2c(c1)OCO2]

The reaction was setup according to general procedure A using dimethyl (2-(benzo[d][1,3]dioxol-5-ylamino)-2-oxoethyl)phosphonate (718 mg, 2.50 mmol) in THF (8.3 mL), n-butyl lithium (1.69 mL, 2.70 mmol), and 4-(dimethylamino)-2-ethoxybenzaldehyde (387 mg, 2.0 mmol). The product was isolated as a yellow brown solid (671 mg, 95% yield, 3:1 E:Z). $^1$H NMR (CDCl3, 400 MHz) δ 7.90 (d, J=15.3 Hz, 1H), 7.07 (s, 1H), 7.35 (d, J=8.2 Hz, 1H), 6.84 (d, J=8.2 Hz, 1H), 6.73 (d, J=8.5 Hz, 1H), 6.44 (d, J=15.3 Hz, 1H), 6.27 (dd, J=8.5, 2.4 Hz, 1H), 6.14 (d, J=2.4 Hz, 1H), 5.93 (s, 2H), 4.09 (q, J=6.9 Hz, 2H), 3.00 (s, 6H), 1.47 (t, J=6.9 Hz, 3H).

(E)-N-(2,3-dihydrobenzo[b][1,4]dioxin-6-yl)-3-(4-(dimethylamino)-2-ethoxyphenyl)acrylamide

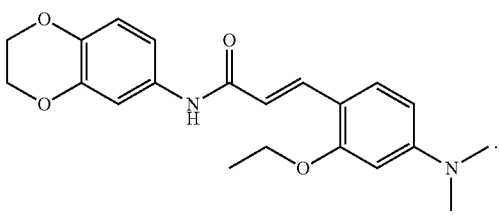 [SMILES: CCOc1cc(N(C)C)ccc1/C=C/C(=O)Nc1ccc2c(c1)OCCO2]

The reaction was setup according to general procedure A using dimethyl (2-((2,3-dihydrobenzo[b][1,4]dioxin-6-yl)amino)-2-oxoethyl)phosphonate (1.39 g, 4.61 mmol) in THF (10 mL), n-butyl lithium (3.12 mL, 5.0 mmol), and 4-(dimethylamino)-2-ethoxybenzaldehyde (715 mg, 3.70 mmol). The product was isolated as a yellow brown solid (1.24 g, 90% yield, 6:1 E:Z). $^1$H NMR (CDCl3, 400 MHz) □ 7.91 (d, J=15.2 Hz, 1H), 7.37 (d, J=8.8 Hz, 1H), 7.05-6.94 (overlap, 2H), 6.81 (d, J=8.8 Hz, 1H), 6.45 (d, J=15.2 Hz, 1H), 6.29 (dd, J=8.8, 2.3 Hz, 1H), 6.15 (d, J=2.3 Hz, 1H), 4.25 (m, 4H), 4.10 (q, J=6.7 Hz, 2H), 3.32 (s, 1H), 3.01 (s, 6H), 1.48 (t, J=6.7 Hz, 3H).

(E)-N-(benzo[d][1,3]dioxol-5-yl)-3-(4-bromo-2-ethoxyphenyl)acrylamide

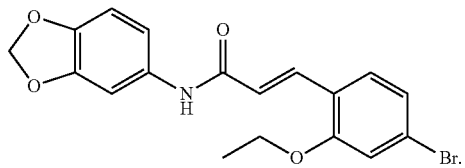 [SMILES: CCOc1cc(Br)ccc1/C=C/C(=O)Nc1ccc2c(c1)OCO2]

The reaction was setup according to general procedure A using dimethyl (2-(benzo[d][1,3]dioxol-5-ylamino)-2-oxoethyl)phosphonate (539 mg, 1.88 mmol) in THF (5 mL), n-butyl lithium (1.27 mL, 2.03 mmol), and 2-ethoxy-4-bromobenzaldehyde (344 mg, 1.50 mmol). The product was isolated as a yellow brown solid (500 mg, 85% yield, 6:1 E:Z). $^1$H NMR (CDCl3, 400 MHz) □ 7.92 (d, J=15.7 Hz, 1H), 7.44-7.26 (overlap, 3H), 7.07 (d, J=9.1 Hz, 1H), 7.04 (s, 1H), 6.88 (d, J=8.1 Hz, 1H), 6.76 (d, J=8.1 Hz, 1H), 6.60 (d, J=15.7 Hz, 1H), 4.09 (q, J=7.1 Hz, 2H), 1.48 (t, J=7.1 Hz, 3H).

(E)-N-(benzo[d][1,3]dioxol-5-yl)-3-(2-ethoxy-4-fluorophenyl)acrylamide

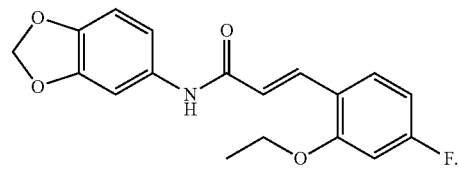 [SMILES: CCOc1cc(F)ccc1/C=C/C(=O)Nc1ccc2c(c1)OCO2]

The reaction was setup according to general procedure A using dimethyl (2-(benzo[d][1,3]dioxol-5-ylamino)-2-oxoethyl)phosphonate (539 mg, 1.88 mmol) in THF (5 mL), n-butyl lithium (1.27 mL, 2.03 mmol), and 2-ethoxy-4-fluorobenzaldehyde (252 mg, 1.50 mmol). The product was isolated as a yellow brown solid (428 mg, 87% yield, 3:1 E:Z). $^1$H NMR (CDCl3, 400 MHz) □ 7.94 (d, J=15.6 Hz, 1H), 7.45 (dd, J=6.9, 6.9 Hz, 1H), 7.39 (s, 1H), 6.87 (d, J=8.2 Hz, 1H), 6.76 (d, J=8.2 Hz, 1H), 6.68-6.50 (overlap, 4H), 5.96 (s, 2H), 4.09 (q, J=7.1 Hz, 2H), 1.50 (t, J=7.1 Hz, 3H).

(E)-N-(benzo[d][1,3]dioxol-5-yl)-3-(2-ethoxy-4-chlorophenyl)acrylamide

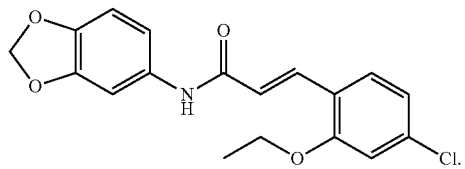 [SMILES: CCOc1cc(Cl)ccc1/C=C/C(=O)Nc1ccc2c(c1)OCO2]

The reaction was setup according to general procedure A using dimethyl (2-(benzo[d][1,3]dioxol-5-ylamino)-2-oxoethyl)phosphonate (539 mg, 1.88 mmol) in THF (5 mL), n-butyl lithium (1.27 mL, 2.03 mmol), and 2-ethoxy-4-chlorobenzaldehyde (277 mg, 1.50 mmol). The product was isolated as a yellow brown solid (484 mg, 93% yield, 3:1 E:Z).

(E)-N-(benzo[d][1,3]dioxol-5-yl)-3-(4-(dimethylamino)-2-propoxyphenyl) acrylamide

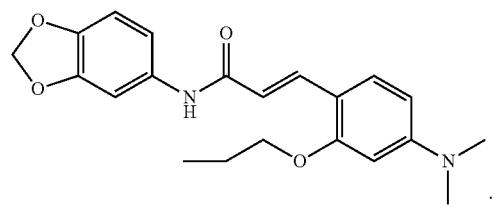

The reaction was setup according to general procedure A using dimethyl (2-(benzo[d][1,3]dioxol-5-ylamino)-2-oxoethyl)phosphonate (539 mg, 1.88 mmol) in THF (5 mL), n-butyl lithium (1.27 mL, 2.03 mmol), and 4-(dimethylamino)-2-propoxybenzaldehyde (311 mg, 1.50 mmol). The product was isolated as a yellow brown solid (508 mg, 92% yield, 5:1 E:Z). $^1$H NMR (CDCl3, 400 MHz) □ 7.92 (d, J=15.3 Hz, 1H), 7.37 (d, J=8.6 Hz, 1H), 7.09 (s, 1H), 6.85 (d, J=8.0 Hz, 1H), 6.75 (d, J=8.0 Hz, 1H), 6.45 (d, J=15.3 Hz, 1H), 6.28 (d, J=8.6 Hz, 1H), 6.15 (s, 1H), 5.95 (s, 2H), 3.99 (q, J=6.4 Hz, 2H), 1.87 (m, 2H), 1.08 (t, J=7.5 Hz, 3H).

(E)-N-(2,3-dihydrobenzo[d][1,4]dioxin-6-yl)-3-(4-(dimethylamino)-2-propoxyphenyl) acrylamide

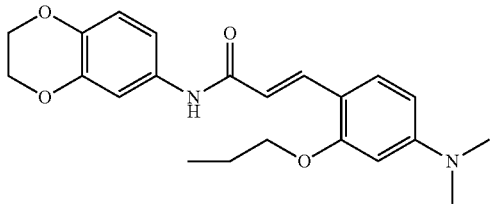

The reaction was setup according to general procedure A using dimethyl (2-((2,3-dihydrobenzo[b][1,4]dioxin-6-yl)amino)-2-oxoethyl)phosphonate (565 mg, 1.88 mmol) in THF (5 mL), n-butyl lithium (1.27 mL, 2.03 mmol), and 4-(dimethylamino)-2-propoxybenzaldehyde (311 mg, 1.50 mmol). The product was isolated as a yellow brown solid (508 mg, 92% yield, >20:1 E:Z). $^1$H NMR (CDCl3, 400 MHz) □ 7.92 (d, J=15.4 Hz, 1H), 7.36 (d, J=8.7 Hz, 1H), 7.02 (s, 1H), 6.81 (d, J=8.7 Hz), 6.45 (d, J=15.4 Hz, 1H), 6.29 (d, J=8.7 Hz, 1H), 6.15 (s, 1H), 4.25 (s, 4H), 3.99 (q, J=6.3 Hz, 2H), 1.87 (m, 2H), 1.08 (t, 7.5 Hz, 3H).

(E)-N-(benzo[d][1,3]dioxol-5-yl)-3-(4-(dimethylamino)-2-isobutoxyphenyl) acrylamide

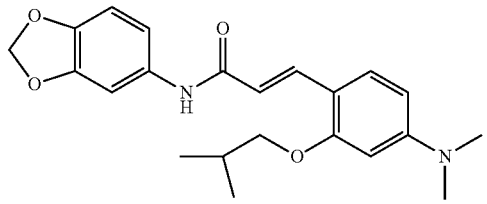

The reaction was setup according to general procedure A using dimethyl (2-(benzo[d][1,3]dioxol-5-ylamino)-2-oxoethyl)phosphonate (539 mg, 1.88 mmol) in THF (5 mL), n-butyl lithium (1.27 mL, 2.03 mmol), and 4-(dimethylamino)-2-isobutoxybenzaldehyde (332 mg, 1.50 mmol). The product was isolated as a yellow brown solid (574 mg, >99% yield, 5:1 E:Z). $^1$H NMR (CDCl3, 400 MHz) □ 7.95 (d, J=15.4 Hz, 1H), 7.37 (d, J=8.5 Hz, 1H), 6.87 (d, J=8.0 Hz, 1H), 6.74 (d, J=8.0 Hz, 1H), 6.46 (d, J=15.4 Hz, 1H), 6.26 (dd, J=8.5, 2.3 Hz, 1H), 6.13 (d, J=2.3 Hz, 1H), 5.94 (s, 2H), 3.77 (d, J=6.4 Hz, 2H), 1.85 (m, 1H), 1.07 (d, J=6.4 Hz, 6H).

(E)-N-(2,3-dihydrobenzo[b][1,4]dioxin-6-yl)-3-(4-(dimethylamino)-2-isobutoxyphenyl) acrylamide

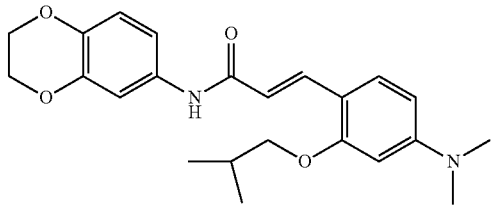 [SMILES: CC(C)COc1cc(N(C)C)ccc1/C=C/C(=O)Nc1ccc2c(c1)OCCO2]

The reaction was setup according to general procedure A using dimethyl (2-((2,3-dihydrobenzo[b][1,4]dioxin-6-yl)amino)-2-oxoethyl)phosphonate (565 mg, 1.88 mmol) in THF (5 mL), n-butyl lithium (1.27 mL, 2.03 mmol), and 4-(dimethylamino)-2-isobutoxybenzaldehyde (332 mg, 1.50 mmol). The product was isolated as a yellow brown solid (536 mg, 90% yield, >20:1 E:Z). $^1$H NMR (CDCl3, 400 MHz) □ 7.94 (d, J=15.5 Hz, 1H), 7.38 (d, J=8.7 Hz, 1H), 7.04-6.96 (overlap, 2H), 6.80 (d, J=8.7 Hz, 1H), 6.45 (d, J=15.5 Hz, 1H), 6.28 (dd, J=8.7, 2.4 Hz, 1H), 6.13 (d, J=2.4 Hz, 1H), 4.25 (s, 4H), 3.79 (d, J=6.4 Hz, 2H), 2.19 (m, 2H), 1.07 (d, J=6.7 Hz, 6H).

(E)-N-(benzo[d][1,3]dioxol-5-yl)-3-(2-ethoxy-4-(trifluoromethyl)phenyl) acrylamide

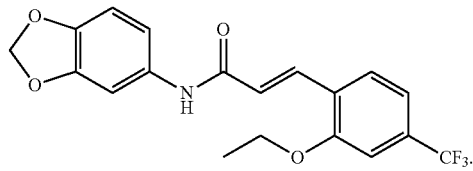 [SMILES: CCOc1cc(C(F)(F)F)ccc1/C=C/C(=O)Nc1ccc2c(c1)OCO2]

The reaction was setup according to general procedure A using dimethyl (2-(benzo[d][1,3]dioxol-5-ylamino)-2-oxoethyl)phosphonate (539 mg, 1.88 mmol) in THF (5 mL), n-butyl lithium (1.27 mL, 2.03 mmol), and 2-ethoxy-4-(trifluoromethyl)benzaldehyde (332 mg, 1.50 mmol). The product was isolated as a yellow brown solid (519 mg, >91% yield, 3:1 E:Z). 1H NMR (CDCl3, 400 MHz) δ 8.00 (d, J=15.6 Hz, 1H), 7.58 (d, J=8.0 Hz, 1H), 7.38 (s, 1H), 7.20 (d, J=8.1 Hz, 1H), 7.11 (s, 1H), 6.90 (d, J=8.1 Hz, 1H), 6.77 (d, J=8.0 Hz, 1H), 6.73-6.64 (overlap, 2H), 5.97 (s, 2H), 4.16 (q, J=7.5 Hz, 2H), 1.51 (t, J=7.5 Hz, 3H).

General Procedure B for the Synthesis of Saturated FQI Compounds (Intramolecular Friedel-Crafts Cyclization)

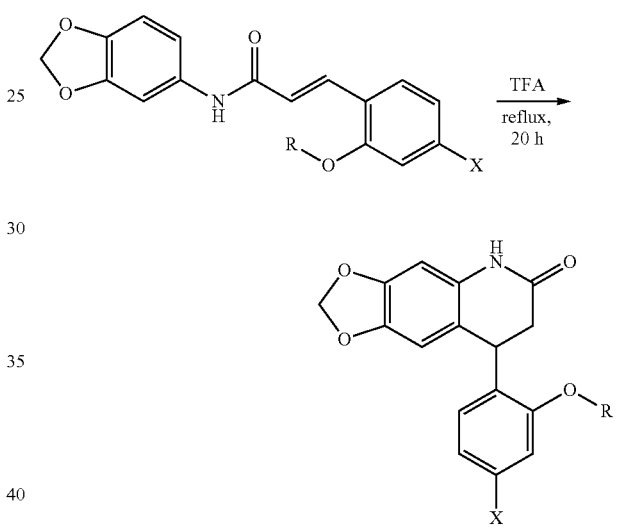

where for example n=1 or 2; X=H, —NH$_2$, halide; —CF$_3$. R=H, alkyl.

A flame-dried 25-mL round-bottomed flask equipped with a stirbar was charged with the acrylamide and trifluoroacetic acid (0.15 M). The flask was flushed with argon, and fitted with a reflux condenser, a rubber septum, and an argon balloon and refluxed for 20 h. The resulting mixture was cooled to room temperature, and transferred to a 500-mL Erlenmeyer flask. The mixture was diluted with dichloromethane (150 mL) and cooled to 0° C. in an ice bath. The reaction mixture was quenched with saturated aqueous sodium bicarbonate (~100 mL) and then transferred to a 500-mL separatory funnel. The organic layer was removed, and the aqueous layer was extracted with dichloromethane (2×50 mL). The combined organic layers were washed with brine (50 mL), dried over anhydrous sodium sulfate, filtered, and concentrated via rotary evaporation. The crude product was purified via column chromatography (gradient from hexanes to 1:1 hexanes: ethyl acetate to afford the desired quinolinones.

FQI-1 8-(2-ethoxyphenyl)-7,8-dihydro-[1,3]dioxolo[4,5-g]quinolin-6(5H)-one

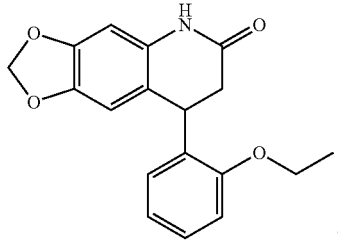

The reaction was setup according to general procedure B using (E)-N-(benzo[d][1,3]dioxol-5-yl)-3-(2-ethoxyphenyl)acrylamide (449 mg, 1.44 mmol) in TFA (9.6 mL). The product was isolated as an orange-yellow solid (237 mg, 53% yield). $^1$H NMR (CDCl3, 400 MHz) ☐ 8.03 (s, 1H), 7.20 (m, 1H), 6.90-6.80 (overlap, 2H), 6.45 (s, 1H), 6.39 (s, 1H), 5.90 (s, 2H), 4.60 (dd, J=6.7, 6.7 Hz, 1H), 4.07 (q, J=6.8 Hz, 2H), 2.94 (dd, J=16.3, 6.7 Hz), 2.83 (dd, J=16.3, 6.7 Hz, 1H), 1.41 (t, J=6.8 Hz, 3H).

FQI-34 (8-(4-(dimethylamino)-2-ethoxyphenyl)-7,8-dihydro-[1,3]dioxolo[4,5-g]quinolin-6(5H)-one)

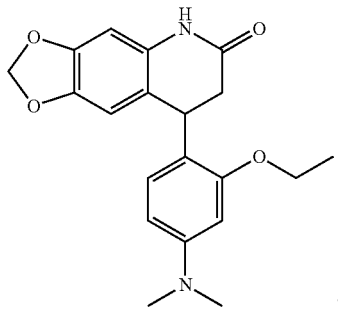

The reaction was setup according to general procedure B using (E)-N-(benzo[d][1,3]dioxol-5-yl)-3-(4-(dimethylamino)-2-ethoxyphenyl)acrylamide (580 mg, 1.64 mmol) in TFA (11 mL). The product was isolated as an orange-yellow solid (400 mg, 69% yield). $^1$H NMR (CDCl3, 400 MHz) ☐ 7.79 (s, 1H), 6.73 (d, J=8.4 Hz, 1H), 6.47 (s, 1H), 6.35 (s, 1H), 6.27 (d, J=2.4 Hz, 1H), 6.22 (J=8.4, 2.4 Hz, 1H), 5.88 (s, 2H), 4.49 (dd, J=7.0, 7.0 Hz, 1H), 4.05 (m, 2H), 2.94-2.87 (overlap, 7H), 2.76 (dd, J=16.2, 6.4 Hz, 1H), 1.38 (t, 6.9 Hz, 3H).

FQIBr (8-(4-bromo-2-ethoxyphenyl)-7,8-dihydro-[1,3]dioxolo[4,5-g]quinolin-6(5H)-one)

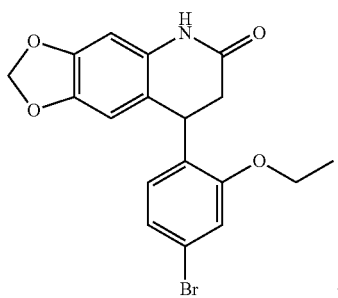

The reaction was setup according to general procedure B using (E)-N-(benzo[d][1,3]dioxol-5-yl)-3-(4-bromo-2-ethoxyphenyl)acrylamide (478 mg, 1.23 mmol) in TFA (8.2 mL) The product was isolated as a tan solid (333 mg, 70% yield). $^1$H NMR (CDCl3, 400 MHz) δ 7.83 (s, 1H), 7.00 (s, 1H), 6.96 (s, J=8.2 Hz, 1H), 6.66 (d, J=8.2 Hz, 1H), 6.45 (s, 1H), 6.38 (s, 1H), 5.93 (s, 1H), 4.51 (dd, J=6.1, 6.1 Hz, 1H), 4.05 (q, J=7.6 Hz, 2H), 2.88 (dd, J=15.9, 6.4 Hz, 1H), 2.81 (d, J=15.9, 6.4 Hz, 1H), 1.43 (t, J=7.6 Hz, 2H).

FQIF (8-(2-ethoxy-4-fluorophenyl)-7,8-dihydro-[1,3]dioxolo[4,5-g]quinolin-6(5H)-one)

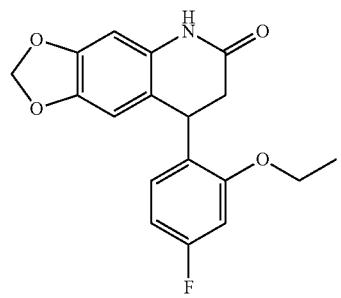

The reaction was setup according to general procedure B using (E)-N-(benzo[d][1,3]dioxol-5-yl)-3-(4-fluoro-2-ethoxyphenyl)acrylamide (428 mg, 1.30 mmol) in TFA (8.7 mL) The product was isolated as a tan solid (272 mg, 64% yield). $^1$H NMR (CDCl3, 400 MHz) δ 7.80 (s, 1H), 6.73 (m, 1H), 6.60 (m, 1H), 6.52 (m, 1H), 6.46 (s, 1H), 6.38 (s, 1H), 5.93 (s, 2H), 4.52 (dd, J=6.4, 6.4 Hz 1H), 4.04 (m. 2H), 2.89 (dd, J=16.3, 6.2 Hz, 1H), 2.81 (dd, J=16.3, 6.2 Hz, 1H), 1.43 (t, J=7.0 Hz, 3H).

FQICI (8-(2-ethoxy-4-chlorophenyl)-7,8-dihydro-[1,3]dioxolo[4,5-g]quinolin-6(5H)-one)

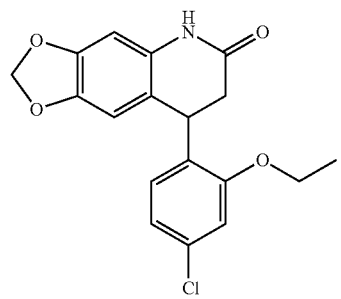

The reaction was setup according to general procedure B using (E)-N-(benzo[d][1,3]dioxol-5-yl)-3-(4-cloro-2-ethoxyphenyl)acrylamide (483 mg, 1.40 mmol) in TFA (9.3 mL) The product was isolated as a tan solid (246 mg, 51% yield). $^1$H NMR (CDCl3, 400 MHz) ☐ 7.99 (s, 1H), 6.85 (d, J=2.0 Hz, 1H), 6.80 (dd, J=8.2, 2.0 Hz, 1H), 6.72 (d=8.2 Hz, 1H), 6.44 (s, 1H), 6.38 (s, 1H), 4.52 (dd, J=6.4, 6.4 Hz), 4.06 (m, 2H), 2.88 (dd, J=16.3, 6.2 Hz, 1H), 2.82, (dd, J=16.3, 6.2 Hz, 1H), 1.42 (t, J=7.0 Hz, 3H FQI-I34 (8-(4-(dimethylamino)-2-propoxyphenyl)-7,8-dihydro-[1,3]dioxolo[4,5-g]quinolin-6(5H)-one):

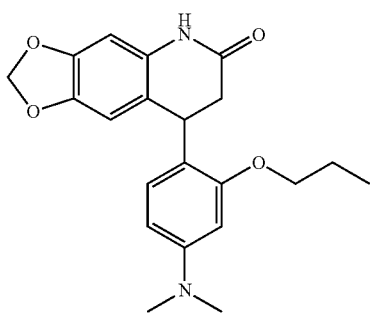

The reaction was setup according to general procedure B using (E)-N-(benzo[d][1,3]dioxol-5-yl)-3-(4-(dimethylamino)-2-propoxyphenyl)acrylamide (453 mg, 1.23 mmol) in TFA (8.2 mL). The product was isolated as a tan solid (246 mg, 51% yield). $^1$H NMR (CDCl3, 400 MHz) δ 7.75 (s, 1H), 6.73 (d, J=8.5 Hz, 1H), 6.46 (s, 1H), 6.34 (s, 1H), 6.27 (s, 1H), 6.22 (d, J=8.5 Hz, 1H), 5.88 (s, 2H), 4.48 (dd, J=7.2, 7.2 Hz, 1H), 3.94 (m, 2H), 2.96-2.89 (overlap, 7H), 2.76 (dd, J=16.1, 6.4 Hz, 1H), 1.78 (qt, J=7.4, 6.8 Hz, 2H), 0.99 (t, J=7.4 HzD FQI-234 (8-(4-(dimethylamino)-2-isobutoxyphenyl)-7,8-dihydro-[1,3]dioxolo[4,5-g]quinolin-6(5H)-one

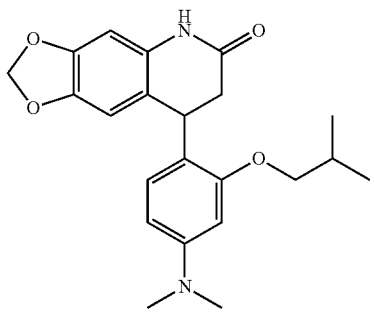

The reaction was setup according to general procedure B using (E)-N-(benzo[d][1,3]dioxol-5-yl)-3-(4-(dimethylamino)-2-isobutoxyphenyl)acrylamide (574 mg, 1.50 mmol) in TFA (10 mL). The product was isolated as a tan solid (383 mg, 67% yield). 1H NMR (CDCl3, 400 MHz) δ 8.66 (s, 1H), 6.89 (d, J=2.2 Hz, 1H), 6.81 (d, J=8.3 Hz), 6.67 (dd, J=8.3, 2.2 Hz, 1H), 6.45-6.41 (overlap, 2H), 5.93-5.89 (overlap, 2H), 4.52 (dd, J=6.5, 6.5 Hz, 1H), 3.79 (m, 2H), 3.07 (s, 6H), 2.91 (dd, J=16.3, 6.0 Hz, 1H), 2.84 (dd, J=16.3, 6.0 Hz, 1H), 2.10 (m, 1H), 1.01 (d, J=6.8 Hz, 6H).

FQI-34F3 (8-(2-ethoxy-4-(trifluoromethyl)phenyl)-7,8-dihydro-[1,3]dioxolo[4,5-g]quinolin-6(5H)-one)

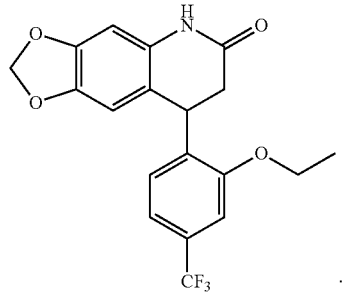 [SMILES: CCOc1cc(C(F)(F)F)ccc1C1CC(=O)Nc2cc3c(cc21)OCO3]

The reaction was setup according to general procedure B using (E)-N-(benzo[d][1,3]dioxol-5-yl)-3-(2-ethoxy-4-(trifluoromethyl)phenyl)acrylamide (500 mg, 1.32 mmol) in TFA (9 mL). The product was isolated as a yellow-orange solid (126 mg, 25% yield) that was used without further purification. 1H NMR (CDCl3, 400 MHz) δ 8.05 (s, 1H), 7.12-7.04 (overlap, 2H), 6.91 (d, J=7.8 Hz, 1H), 6.45 (s, 1H), 6.42 (s, 1H), 5.92 (s, 2H), 4.61 (dd, J=6.2, 6.2 Hz, 1H), 4.12 (m, 2H), 2.88 (m, 2H), 1.46 (t, J=7.0 Hz, 3H).

General Procedure C for the Synthesis of Saturated FQI Compounds (Intramolecular Friedel-Crafts Cyclization)

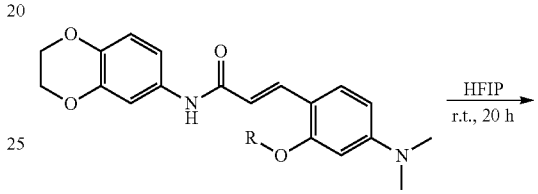

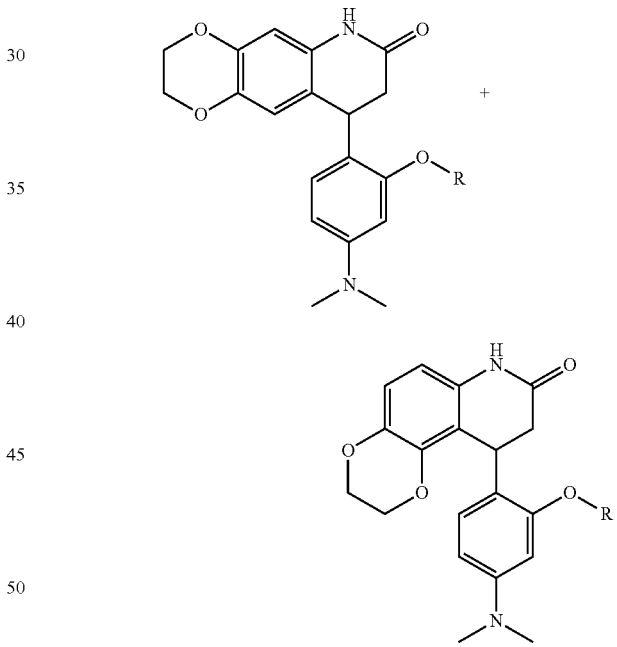

for example where R is H, alkyl.

A flame-dried 250-mL round-bottomed flask equipped with a stirbar was charged with (E)-N-(2,3-dihydrobenzo[b][1,4]dioxin-6-yl)-3-(4-(dimethylamino)-2-ethoxyphenyl)acrylami de and 1,1,1,3,3,3-hexafluoropropan-2-ol (0.025 M). The reaction was stirred at RT for 20 h and then concentrated via rotary evaporation. The crude product was purified via column chromatography (20% ethyl acetate in hexanes to 70% ethyl acetate in hexanes. The product and purified via recrystallization with dichloromethane/hexanes to afford the desired products.

FQI-37 (9-(4-(dimethylamino)-2-ethoxyphenyl)-2,3,8,9-tetrahydro-[1,4]dioxino[2,3-g]quinolin-7(6H)-one)

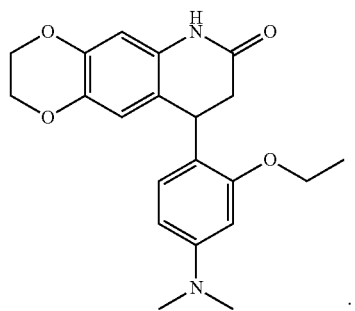 [SMILES: CCOc1cc(N(C)C)ccc1C1CC(=O)Nc2cc3c(cc21)OCCO3]

The reaction was setup according to general procedure C using (E)-N-(2,3-dihydrobenzo[b][1,4]dioxin-6-yl)-3-(4-(dimethylamino)-2-ethoxyphenyl)acrylamide (720 mg, 1.95 mmol) and 1,1,1,3,3,3-hexafluoropropan-2-ol (78 mL). After column, the product (361 mg, 50% yield) contained 3% of the undesired FQI-38 isomer (10-(4-(dimethylamino)-2-ethoxyphenyl)-2,3,9,10-tetrahydro-[1,4]dioxino[2,3-f]quinolin-8(7H)-one) which was separated in the recrystallization. The final product was isolated as a white solid. $^1$H NMR (CDCl3, 400 MHz) □ 7.42 (s, 1H), 6.75 (d, J=8.4 Hz, 1H), 6.50 (s, 1H), 6.30 (s, 1H), 6.26 (d, J=2.4 Hz, 1H), 6.23 (dd, J=8.4, 2.4 Hz, 1H), 4.50 (dd, J=7.2, 7.2 Hz, 1H), 4.21 (m, 2H), 4.17 (m, 2H), 4.04 (m, 2H), 2.92 (s, 6H), 2.90 (dd, J=16.1, 6.4 Hz, 1H), 2.75 (dd, J=16.1, 6.4 Hz, 1H), 1.38 (t, J=7.0 Hz, 3H).

FQI-137 (9-(4-(dimethylamino)-2-propoxyphenyl)-2,3,8,9-tetrahydro-[1,4]dioxino[2,3-g]qinolin-7(6H)-one)

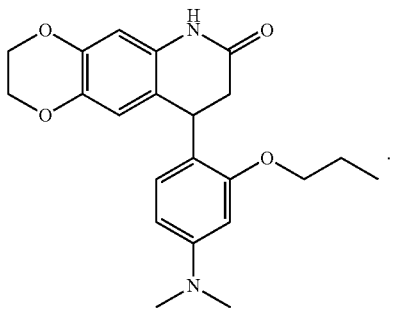 [SMILES: CCCOc1cc(N(C)C)ccc1C1CC(=O)Nc2cc3c(cc21)OCCO3]

The reaction was setup according to general procedure C using (E)-N-(2,3-dihydrobenzo[b][1,4]dioxin-6-yl)-3-(4-(dimethylamino)-2-propoxyphenyl)acrylamide (482 mg, 1.26 mmol) and 1,1,1,3,3,3-hexafluoropropan-2-ol (50 mL). After column, the product (361 mg, 42% yield) contained ~10% of the undesired FQI-138 isomer (10-(4-(dimethylamino)-2-propoxyphenyl)-2,3,9,10-tetrahydro[1,4]dioxino[2,3-f]quinolin-8(7H)-one) which was separated in the recrystallization. The final product was isolated as a white solid. $^1$H NMR (CDCl3, 400 MHz) □7.52 (s, 1H), 6.75 (d, J=8.4 Hz), 6.48 (s, 1H), 6.31 (s, 1H), 6.27 (s, 1H), 6.22 (d, J=8.4 Hz, 1H), 4.48 (dd, J=6.5, 6.5 Hz, 1H), 4.21 (m, 2H), 4.17 (m, 2H), 3.93 (m, 2H), 2.96-2.87 (overlap, 7H), 2.74 (dd, J=16.2, 6.3 Hz, 1H), 1.78 (qt, J=7.4, 7.1 Hz, 2H), 0.98 (t, J=7.4 Hz, 3H).

FQI-237 9-(4-(dimethylamino)-2-isobutoxyphenyl)-2,3,8,9-tetrahydro-[1,4]dioxino[2,3-g]quinolin-7(6H)-one

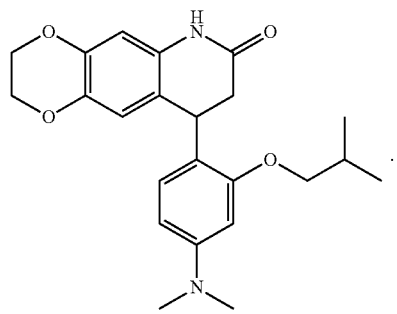 [SMILES: CC(C)COc1cc(N(C)C)ccc1C1CC(=O)Nc2cc3c(cc21)OCCO3]

The reaction was setup according to general procedure C using (E)-N-(2,3-dihydrobenzo[b][1,4]dioxin-6-yl)-3-(4-(dimethylamino)-2-isobutoxyphenyl)acrylamide (520 mg, 1.31 mmol) and 1,1,1,3,3,3-hexafluoropropan-2-ol (52 mL). After column, the product (198 mg, 38% yield) contained >1% of the undesired FQI-238 isomer and the tan solid was used without further purification. $^1$H NMR (CDCl3, 400 MHz) □ 7.75 (s, 1H), 6.75 (d, J=8.2 Hz, 1H), 6.47 (s, 1H), 6.33 (s, 1H), 6.25 (s, 1H), 6.22 (d, J=8.2 Hz, 1H), 4.47 (dd, J=7.5, 7.5 Hz, 1H), 4.20 (m, 2H), 4.16 (m, 2H), 3.73 (m, 2H), 2.99-2.87 (overlap, 7H), 2.75 (dd, J=16.1, 6.4 Hz, 1H), 2.04 (m, 1H), 0.96 (m, 6H)

General Procedure D for the Synthesis of Unsaturated FQI Compounds (DDQ Oxidation)

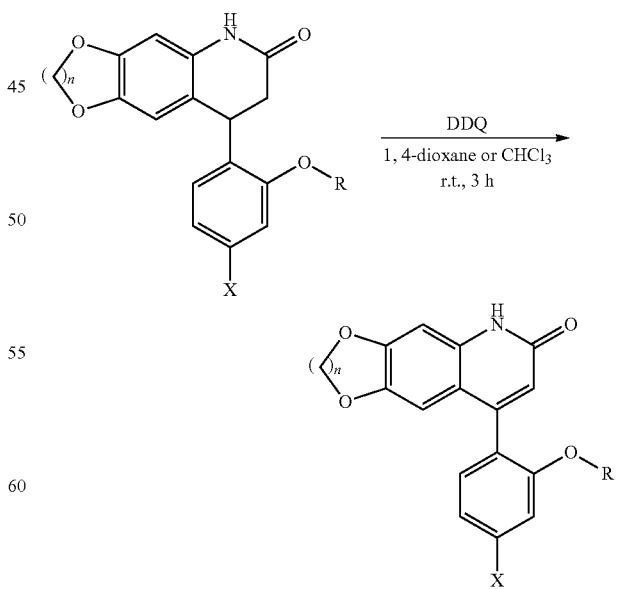

where for example n=1 or 2; X=H, —NH$_2$, halide; —CF$_3$. R=H, alkyl.

An oven-dried 25-mL round bottomed flask under argon was charged with the quinolinone and chloroform (0.02 M) unless otherwise noted. Then, DDQ (1.0 equiv) was added and the reaction was stirred at room temperature and stirred for 3 hours and then concentrated via rotary evaporation. The resulting residue was dissolved in 2.5% aqueous potassium carbonate solution (30 mL) and extracted with dichloromethane (3×50 mL). The combined organic layers were washed with brine, (50 mL) then dried over anhydrous sodium sulfate. The solid crude product was purified via column chromatography (gradient from 80% ethyl acetate in hexanes to 100% ethyl acetate to afford the desired unsaturated quinolinones quinolinones.

FQI-2

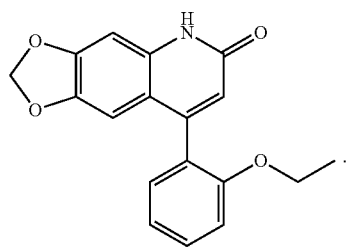 [SMILES: CCOc1ccccc1-c1cc(=O)[nH]c2cc3c(cc12)OCO3]

The reaction was setup according to general procedure D using 8-(2-ethoxyphenyl)-7,8-dihydro-[1,3]dioxolo[4,5-g]quinolin-6(5H)-one (156 mg, 0.50 mmol), chloroform (25 mL, 0.02 M), and DDQ (114 mg, 0.50 mmol). The product was isolated as a tan solid (107 mg, 69% yield). $^{1H}$ NMR (CDCl3, 400 MHz) δ 12.39 (s, 1H), 7.42 (ddd, J=7.9, 7.9, 1.7 Hz, 1H), 7.22 (dd, J=7.3, 1.7 Hz, 1H), 7.09-6.99 (overlap, 2H), 6.95 (s, 1H), 4.03 (m, 2H), 1.19 (t, J=7.0, 3H).

FQI2-34 (8-(4-(dimethylamino)-2-ethoxyphenyl)-[1,3]dioxolo[4,5-g]quinolin-6(5H)-one)

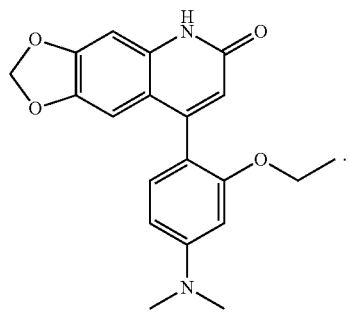 [SMILES: CCOc1cc(N(C)C)ccc1-c1cc(=O)[nH]c2cc3c(cc12)OCO3]

The reaction was setup according to general procedure D using 8-(4-(dimethylamino)-2-ethoxyphenyl)-[1,3]dioxolo[4,5-g]quinolin-6(5H)-one (280 mg, 0.79 mmol), 1,4-dioxane (13 mL, 0.06 M), and DDQ (179 mg, 0.79 mmol). The product was isolated as an off-white solid (203 mg, 73% yield). 1H NMR (CDCl3, 400 MHz) δ 12.14 (s, 1H), 7.10 (J=8.4 Hz, 1H), 6.92 (s, 1H), 6.76 (s, 1H), 6.53 (s, 1H), 6.41 (dd, J=8.4, 2.2 Hz, 1H), 6.33 (d, J=2.2 Hz, 1H), 5.99 (m, 1H), 5.96 (m, 1H), 4.00 (q, J=7.1 Hz, 2H), 3.04 (s, 6H), 1.19 (t, J=7.1 Hz, 3H).

FQI2-37 (9-(4-(dimethylamino)-2-ethoxyphenyl)-2,3-dihydro-[1,4]dioxino[2,3-g]quinolin-7(6H)-one)

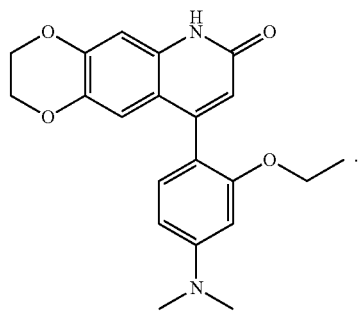 [SMILES: CCOc1cc(N(C)C)ccc1-c1cc(=O)[nH]c2cc3c(cc12)OCCO3]

The reaction was setup according to general procedure D using 9-(4-(dimethylamino)-2-ethoxyphenyl)-2,3,8,9-tetrahydro-[1,4]dioxino[2,3-g]quinolin-7(6H)-one (184 mg, 0.50 mmol), 1,4-dioxane (8.33 mL, 0.06 M), and DDQ (114 mg, 0.50 mmol). The product was isolated as an off-white solid (133 mg, 72% yield). 1H NMR (CDCl3, 400 MHz) δ 11.08 (s, 1H), 7.07 (d, J=8.4 Hz, 1H), 6.86 (s, 1H), 6.83 (s, 1H), 6.48 (s, 1H), 6.38 (dd, J=8.4, 2.2 Hz, 1H), 6.32 (d, J=2.4 Hz, 1H), 4.28 (m, 2H), 4.20 (m, 2H), 4.00 (q, J=6.9 Hz, 2H), 3.01 (s, 6H), 1.17 (t, J=6.9 Hz, 3H).

FQI2Br (8-(4-bromo-2-ethoxyphenyl)-[1,3]dioxolo[4,5-g]quinolin-6(5H)-one)

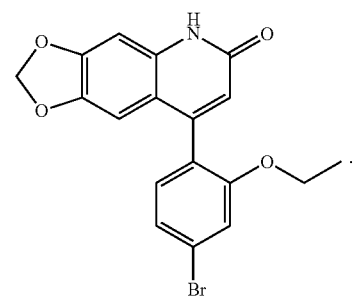 [SMILES: CCOc1cc(Br)ccc1-c1cc(=O)[nH]c2cc3c(cc12)OCO3]

The reaction was setup according to general procedure D using 8-(4-bromo-2-ethoxyphenyl)-7,8-dihydro-[1,3]dioxolo[4,5-g]quinolin-6(5H)-one (195 mg, 0.50 mmol), chloroform (25 mL, 0.02 M), and DDQ (114 mg, 0.50 mmol). The product was isolated as a tan solid (137 mg, 71% yield). $^1$H NMR (CDCl3, 400 MHz) δ 12.45 (s, 1H), 7.21 (dd, J=7.9, 1.8 Hz, 1H), 7.15 (d, J=1.8 Hz, 1H), 7.09 (d, J=7.9 Hz, 1H), 6.95 (s, 1H), 6.56 (s, 1H), 6.50 (s, 1H), 6.01 (m, 1H), 5.98 (m, 1H), 4.02 (q, J=7.0 Hz, 2H), 1.20 (t, J=7.0 Hz, 3H).

FQI2F (8-(2-ethoxy-4-fluorophenyl)-[1,3]dioxolo[4,5-g]quinolin-6(5H)-one)

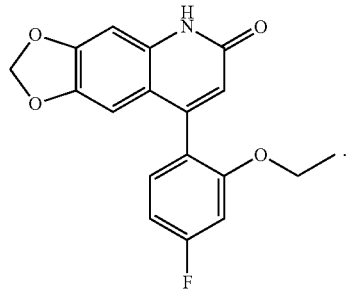 [SMILES: CCOc1cc(F)ccc1-c1cc(=O)[nH]c2cc3c(cc12)OCO3]

The reaction was setup according to general procedure D using 8-(4-fluoro-2-ethoxyphenyl)-7,8-dihydro-[1,3]dioxolo[4,5-g]quinolin-6(5H)-one (114 mg, 0.35 mmol), dichloromethane (6 mL, 0.06M), and DDQ (114 mg, 0.50 mmol). The product was isolated as a tan solid (66 mg, 58% yield). $^{1H}$ NMR (CDCl3, 400 MHz) δ 12.18 (s, 1H), 7.17 (dd, J=7.5, 7.5 Hz, 1H), 6.93 (s, 1H), 6.80-6.70 (overlap, 2H), 6.59 (s, 1H), 6.50 (s, 1H), 6.01 (m, 1H), 5.99 (m, 1H), 4.00 (m, 2H), 1.21 (t, J=7.0 Hz, 3H).

FQI2Cl (8-(2-ethoxy-4-chlorophenyl)-[1,3]dioxolo[4,5-g]quinolin-6(5H)-one)

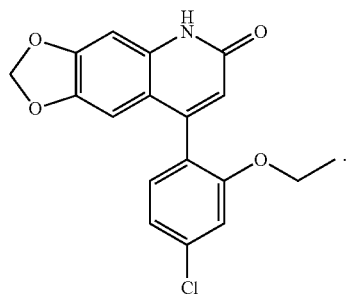 [SMILES: CCOc1cc(Cl)ccc1-c1cc(=O)[nH]c2cc3c(cc12)OCO3]

The reaction was setup according to general procedure D using 8-(4-chloro-2-ethoxyphenyl)-7,8-dihydro-[1,3]dioxolo[4,5-g]quinolin-6(5H)-one (173 mg, 0.50 mmol), chloroform (25 mL, 0.02 M), and DDQ (114 mg, 0.50 mmol). The product was isolated as a tan solid (132 mg, 77% yield). $^1$H NMR (CDCl3, 400 MHz) δ 11.82 (s, 1H), 7.15 (d, J=8.0 Hz, 1H), 7.05 (d, J=8.0 Hz, 1H), 7.00 (s, 1H), 6.89 (s, 1H), 6.57 (s, 1H), 6.49 (s, 1H), 6.01 (m, 1H), 5.98 (m, 1H), 4.01 (q, J=7.0 Hz, 2H), 1.21 (t, J=7.0 Hz, 3H)

FQI2-134 8-(4-(dimethylamino)-2-propoxyphenyl)-[1,3]dioxolo[4,5-g]quinolin-6(5H)-one

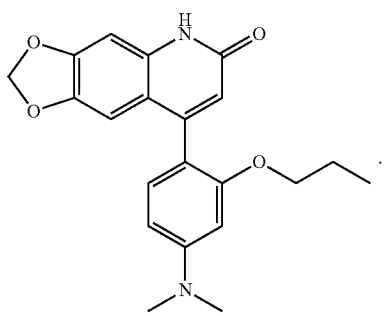 [SMILES: CCCOc1cc(N(C)C)ccc1-c1cc(=O)[nH]c2cc3c(cc12)OCO3]

The reaction was setup according to general procedure D using 8-(4-(dimethylamino)-2-propoxyphenyl)-7,8-dihydro-[1,3]dioxolo[4,5-g]quinolin-6(5H)-one (173 mg, 0.50 mmol), chloroform (25 mL, 0.02 M), and DDQ (114 mg, 0.50 mmol). The product was isolated as a tan solid (86 mg, 47% yield). 11.71 (s, 1H), 7.09 (d, J=8.4 Hz, 1H), 6.87 (s, 1H), 6.76 (s, 1H), 6.52 (s, 1H), 6.41 (d, J=8.4 Hz, 1H), 6.34 (s, 1H), 5.97 (m, 1H), 5.96 (m, 1H), 3.89 (m, 2H), 3.04 (s, 6H), 1.58 (m, 2H), 0.76 (t, J=7.4 Hz, 3H).

FQI2-137 (9-(4-(dimethylamino)-2-propoxyphenyl)-2,3-dihydro-[1,4]dioxino[2,3-g]quinolin-7(6H)-one)

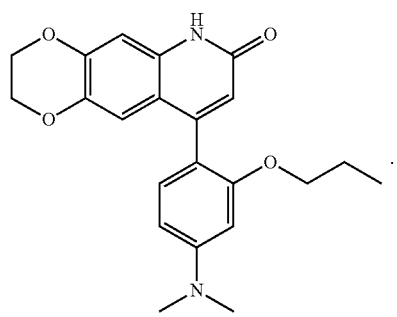 [SMILES: CCCOc1cc(N(C)C)ccc1-c1cc(=O)[nH]c2cc3c(cc12)OCCO3]

The reaction was setup according to general procedure D using 9-(4-(dimethylamino)-2-propoxyphenyl)-2,3,8,9-tetrahydro-[1,4]dioxino[2,3-g]quinolin-7(6H)-one (84 mg, 0.22 mmol), chloroform (11 mL, 0.02 M), and DDQ (50 mg, 0.22 mmol). The product was isolated as a tan solid (45 mg, 53% yield). 10.57 (s, 1H), 7.08 (d, J=8.4 Hz, 1H), 6.88 (s, 1H), 6.79 (s, 1H), 6.48 (s, 1H), 6.39 (d, J=8.4 Hz, 1H), 6.32 (s, 1H), 4.29 (m, 1H), 4.21 (m, 1H), 3.88 (m, 2H), 3.02 (s, 6H), 1.57 (m, 2H), 0.76 (t, J=7.5 Hz, 3H).

FQI2-234 (8-(4-(dimethylamino)-2-isobutoxyphenyl)-[1,3]dioxolo[4,5-g]quinolin-6(5H)-one)

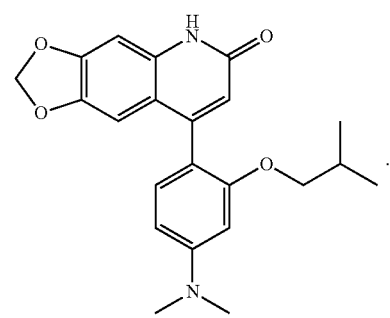 [SMILES: CC(C)COc1cc(N(C)C)ccc1-c1cc(=O)[nH]c2cc3c(cc12)OCO3]

The reaction was setup according to general procedure D using 8-(4-(dimethylamino)-2-isobutoxyphenyl)-7,8-dihydro-[1,3]dioxolo[4,5-g]quinolin-6(5H)-one (48 mg, 0.13 mmol), chloroform (6.3 mL, 0.02 M), and DDQ (28 mg, 0.13 mmol). The product was isolated as a tan solid (19 mg, 40% yield). 1H NMR (CDCl3, 400 MHz) δ 11.14 (s, 1H), 7.09 (d, J=8.4 Hz, 1H), 6.81 (s, 1H), 6.76 (s, 1H), 6.51 (s, 1H), 6.41 (d, J=8.4 Hz, 1H), 6.33 (s, 1H), 5.97 (m, 1H), 5.96 (m, 1H), 3.68 (m, 2H), 3.04 (s, 6H), 1.82 (m, 1H), 0.77 (m, 3H), 0.72 (m, 3H).

FQI2-237 (9-(4-(dimethylamino)-2-isobutoxyphenyl)-2,3-dihydro-[1,4]dioxino[2,3-g]quinolin-7(6H)-one)

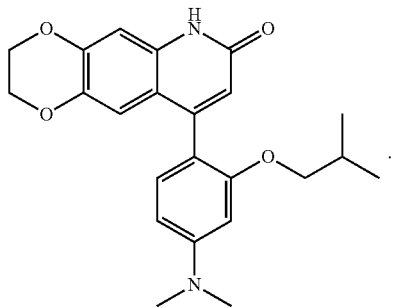 [SMILES: CC(C)COc1cc(N(C)C)ccc1-c1cc(=O)[nH]c2cc3c(cc12)OCCO3]

The reaction was setup according to general procedure D using 9-(4-(dimethylamino)-2-isobutoxyphenyl)-2,3,8,9-tetrahydro-[1,4]dioxino[2,3-g]quinolin-7(6H)-one (189 mg, 0.48 mmol), chloroform (24 mL, 0.02 M), and DDQ (108 mg, 0.48 mmol). The product was isolated as a tan solid (71 mg, 38% yield). $^1$H NMR (CDCl3, 400 MHz) □ 9.99 (s, 1H), 7.09 (d, J=8.4 Hz, 1H), 6.87 (s, 1H), 6.73 (s, 1H), 6.47 (s, 1H), 8.39 (d, J=8.4 Hz, 1H), 6.31 (s, 1H), 4.29 (m, 2H), 4.20 (m, 2H), 3.67 (t, J=6.5 Hz, 2H), 3.02 (s, 6H), 1.83 (m, 1H), 0.77 (m, 3H), 0.72 (m, 3H).

FQI2F3 (8-(2-ethoxy-4-(trifluoromethyl)phenyl)-[1,3]dioxolo[4,5-g]quinolin-6(5H)-one)

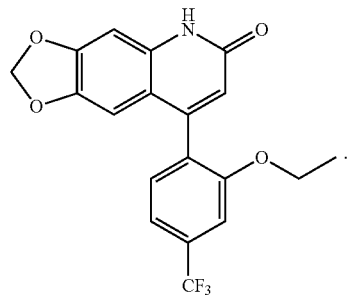 [SMILES: CCOc1cc(C(F)(F)F)ccc1-c1cc(=O)[nH]c2cc3c(cc12)OCO3]

The reaction was setup according to general procedure D using 8-(2-ethoxy-4-(trifluoromethyl)phenyl)-7,8-dihydro-[1,3]dioxolo[4,5-g]quinolin-6(5H)-one (93 mg, 0.25 mmol), chloroform (12 mL, 0.02 M), and DDQ (56 mg, 0.25 mmol). The product was isolated as a tan solid (32 mg, 35% yield). $^1$H NMR (CDCl3, 400 MHz) δ 11.71 (s, 1H), 7.34 (s, 1H), 7.22 (s, 1H), 6.90 (s, 1H), 6.52 (s, 1H), 6.50 (s, 1H), 6.02 (m, 1H), 5.99 (m, 1H), 4.08 (q, J=7.0 Hz, 2H), 1.23 (t, J=7.0 Hz, 3H).

Example 2: Factor Quinolinone Inhibitors Alter Cell Morphology and Motility by Destabilizing Interphase Microtubules Factor Quinolinone Inhibitors are promising anti-cancer compounds, initially characterized as specific inhibitors of the oncogenic transcription factor LSF (TFCP2). These compounds exert anti-proliferative activity at least in part by disrupting mitotic spindles. Herein, we report additional interphase consequences of the initial lead compound, FQI1, in telomerase immortalized cell lines. FQI1 rapidly reduces cell spreading and increases circularity in interphase fetal hepatocyte and retinal pigment epithelial cells, respectively. A sudden breakdown and depolarization of the microtubule network precedes and gives rise to these FQI1-induced morphological changes. Surprisingly, this microtubule breakdown is accompanied by an increase in tubulin acetylation, indicating the mechanism of microtubule destabilization by FQI1 to involve increasing access to the microtubule lumen. FQI1 decreases the rate and range of locomotion of interphase cells, supporting an impact of FQI1-induced microtubule breakdown on cell motility. Taken together, our results show that FQI1 interferes with microtubule-associated functions in interphase, specifically cell morphology, polarity, and motility. Because these processes are fundamental to cell migration, an integral part of cancer malignancy, our findings support FQI1 as anti-migration agent and expand the potential of FQIs, including more potent compounds in this class, as effective and clinically successful anti-cancer compounds.

Cell migration is a fundamental biological process at the heart of orchestrating the organization and rearrangement of cells and tissues into complex multi-cellular structures. During development, collective cell movement is required for tissue morphogenesis and gastrulation, while individual cell migration is observed during primordial germ cell movement[1,2]. In adult organisms, cell migration is needed for wound healing, movement of immune and platelet cells[3,4], and neuronal migration[5,6]. Understanding the underlying mechanisms of cell migration is also crucial in elucidating how certain disease states operate, such as metastatic cancer and autoimmune diseases[6,7].

Although actin arrays are regarded as the main cytoskeletal regulator of cell migration due to the propelling and contracting forces they exert, microtubules are becoming increasingly more recognized as important players in many aspects of cell migration including cell polarity, lamellipodia formation, focal adhesion turnover, and trailing-edge contractility[8-10]. The multifunctionality of microtubules in regulating cell migration is attributed to their ability to undergo dynamic instability at their plus ends and to organize differing rates of dynamic instability asymmetrically across the migrating cell: microtubules near the leading edge display relatively frequent bouts of growth, while microtubules towards the trailing-edge show much higher rate of instability and shrinkage[8,11]. Because of the importance of cell migration in exacerbating cancer severity via metastasis, there is growing interest in developing therapeutics targeting cell locomotion[12,13]. Although proteins linked to actin polymerization and organization are considered potential targets given their central position in cell migration, microtubule-targeting agents have also been acknowledged as promising anti-migration therapeutics due to their advantage of potentially targeting both cell migration in interphase and cell proliferation via mitotic microtubules[14].

Here we report that Factor Quinolinone Inhibitor 1 (FQI1), the initial lead of a first-in-class set of novel anti-cancer agents, destabilizes the microtubule network in interphase cells and impairs cell movement. FQI1 has previously been identified as a potent and specific inhibitor of the transcription factor LSF[15] (TFCP2) and has demonstrated promising efficacy against hepatocellular carcinoma in mouse tumor models[16]. Exploring the mechanism behind FQI1's anti-proliferative activity revealed that FQI1 causes mitotic arrest with disrupted spindles and condensed, but unaligned chromosomes in vivo, as does siRNA specifically targeting LSF[17,18]. Notably, LSF also specifically interacts with α-tubulin[19]. Because FQI1 treatment disrupts mitotic microtubules, we hypothesized that FQI1 would impact microtubule-associated processes beyond mitosis. Herein we describe the effects of FQI1 on microtubule dynamics and cell movement in interphase cells: i) FQI1 triggers rapid cell compaction in telomerase-immortalized human fetal hepatocytes (FH-B cells) and renders telomerase-immortalized retinal pigment epithelial (RPE) cells more circular in shape; ii) microtubules are rapidly destabilized in FH-B cells and RPE cells upon FQI1 addition with microtubule disruption occurring in both the anterior and posterior portions of polarized cells; and iii) FH-B and RPE cells exhibit defective cell motility in the presence of FQI1.

Results

Figure 1B:
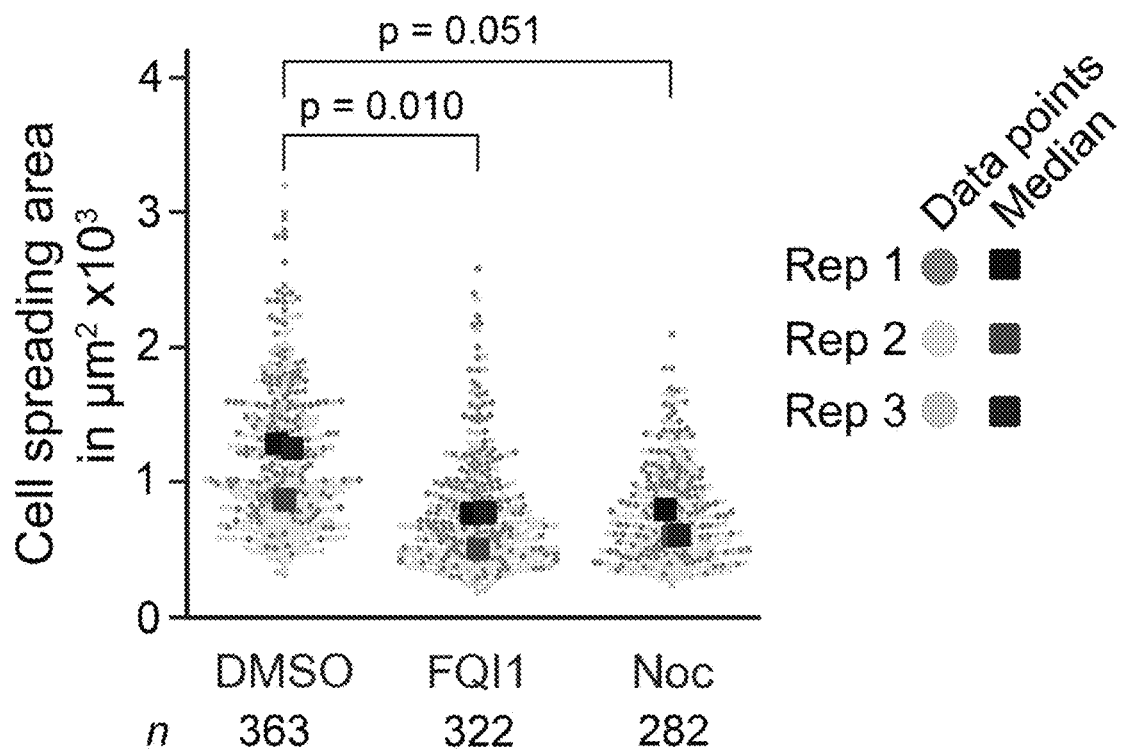
Figure 1C:
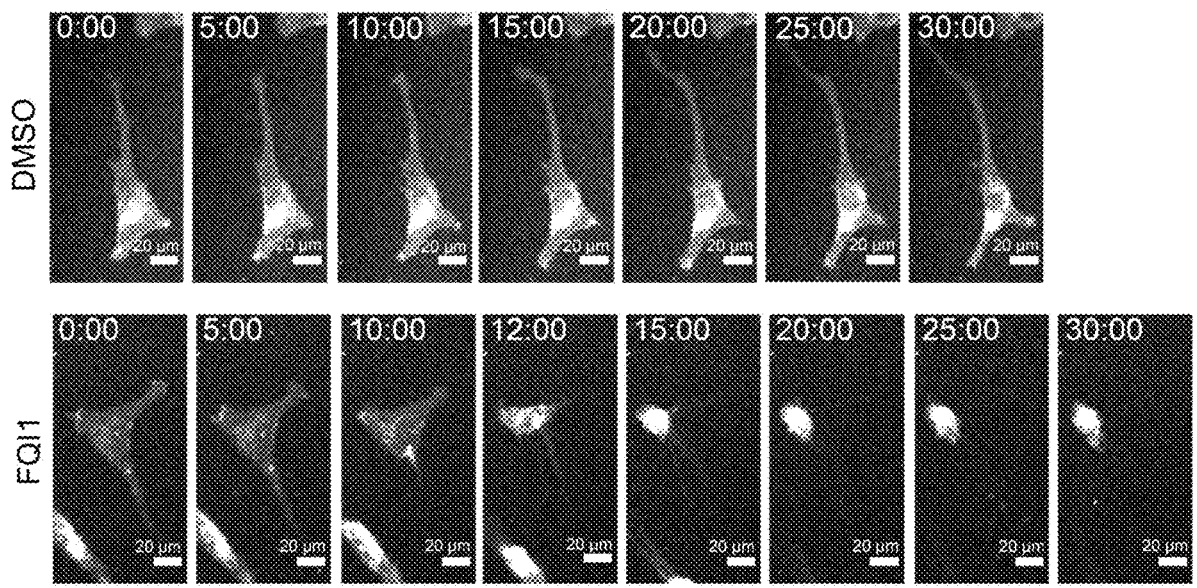
Figure 1D:
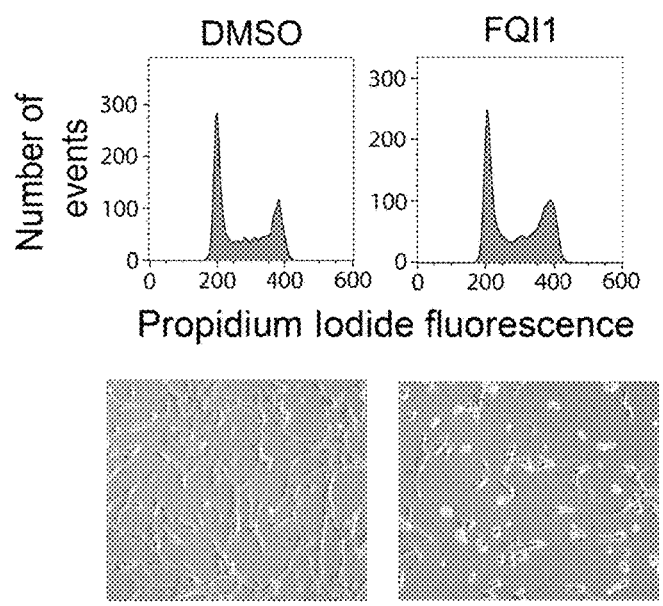
Figure 5:
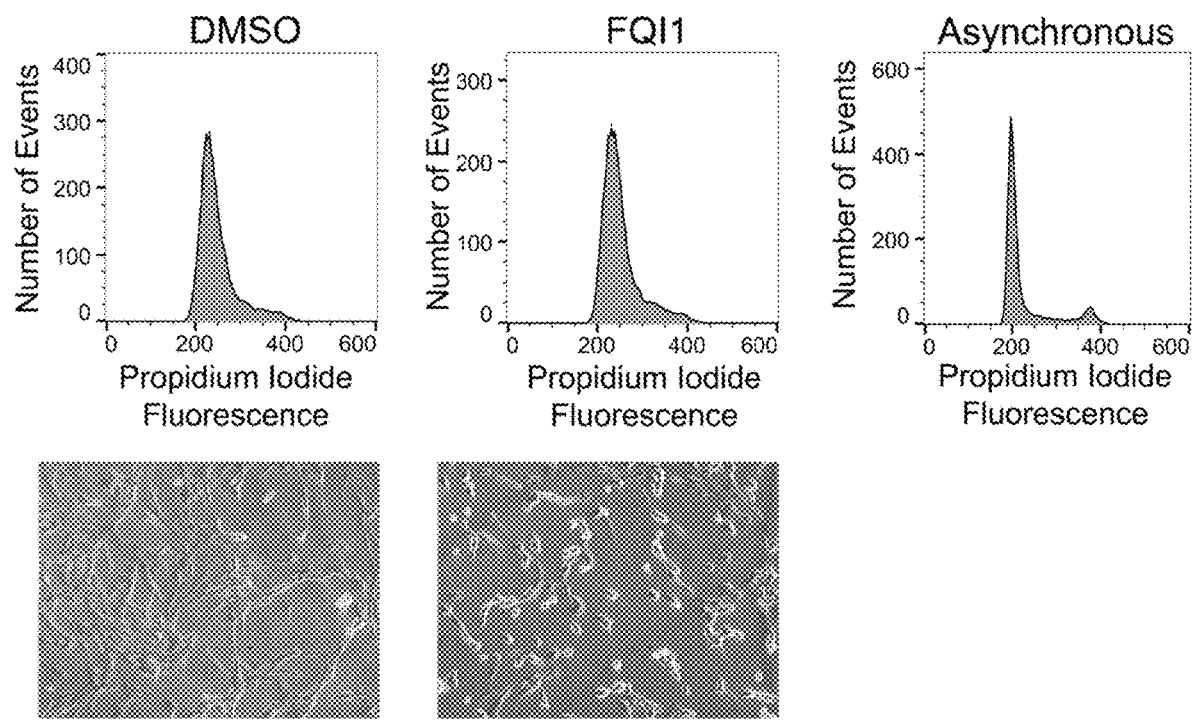
FIG. 5 shows FQI1-induced cell compaction in FH-B cells is not due to mitotic arrest. Representative flow cytometry analysis of cellular DNA content showing cell cycle profiles of thymidine-blocked FH-B cells treated with 4 µM FQI1 or vehicle (0.01% DMSO) for 1 hour (upper row), along with phase contrast images of cells taken prior to harvesting and fixation (lower row). FH-B cells in this experiment received fresh media along with the respective treatments. Phase contrast images were taken using a 10× objective on an Olympus IX50 microscope. Two biological replicates exhibited identical findings.

FQI1 treatment induces rapid compaction in immortalized human fetal hepatocytes: In order to study the interphase effects of FQI1, we first investigated FH-B cells, because our previous study indicated that FQI1 exerted a cytostatic, rather than a cytotoxic effect on these cells[20]. This allowed addition of FQI1 to FH-B cells at effective concentrations without inducing cell death. Upon treatment of asynchronous FH-B cells for a short time (30 minutes) with FQI1, the cells underwent a notable compaction, as visualized by staining for actin (FIG. 1A). Quantification revealed statistically significant, 1.7-fold reduction in cell spreading area in FQI1-treated cells compared to vehicle-treated cells (FIG. 1B). This decrease in cell spreading area was phenocopied by treatment with nocodazole, a microtubule-destabilizing compound (FIGS. 1A and 1B). As monitored by time-lapse microscopy, the overall spreading of FH-B cells was substantially reduced within 10 minutes after addition of FQI1, accompanied by a retreat of cellular protrusions between 10-15 minutes (FIG. 1C). Since FQI1 can cause cells to undergo mitotic arrest[17,18], which also results in cells "rounding-up", although not as quickly, the cell cycle stage of cells exhibiting this compact phenotype was examined by cellular DNA profiling. By this analysis, there was no apparent shift in cell cycle phases upon such a short incubation with FQI1 (FIG. 1D). Furthermore, when FH-B cells were synchronized by a single thymidine block, the cells arrested around the $G_1$/S transition and into early S-phase displayed the same change in morphology as did asynchronous FH-B cells after 1 hour of treatment with FQI1 (FIG. 5), confirming that this FQI1-induced phenotype is the consequence of a novel, non-mitotic action.

Figure 6A:
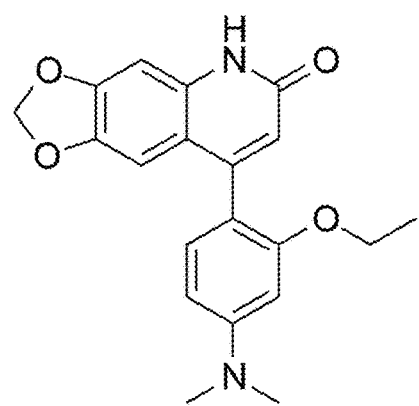
FIGS. 6A-6E show FH-B cells undergo compaction upon FQI2-34 treatment at a 20-fold lower concentration relative to that of FQI1.
Figure 6B:
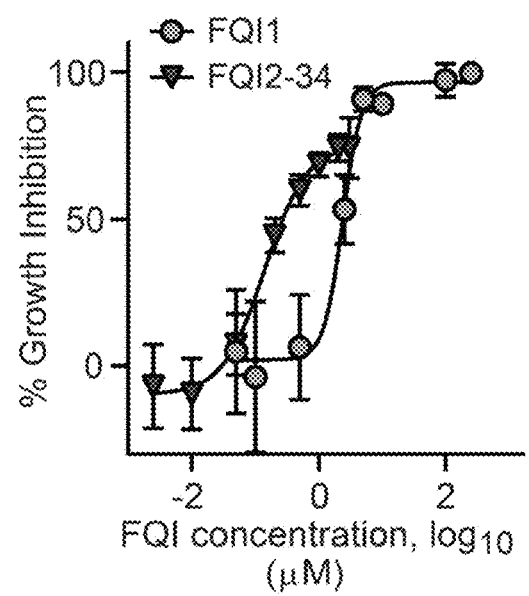
Figure 6C:
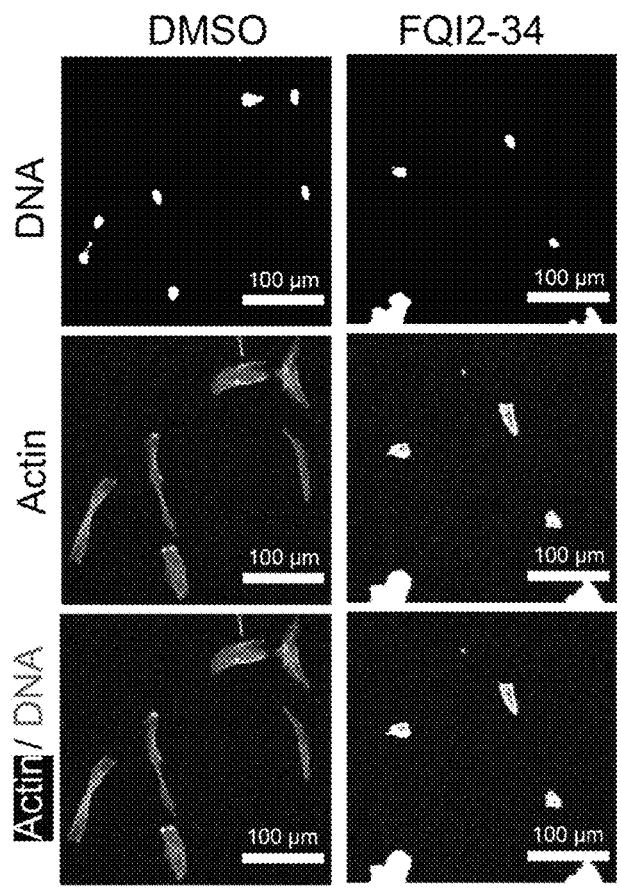
Figure 6D:
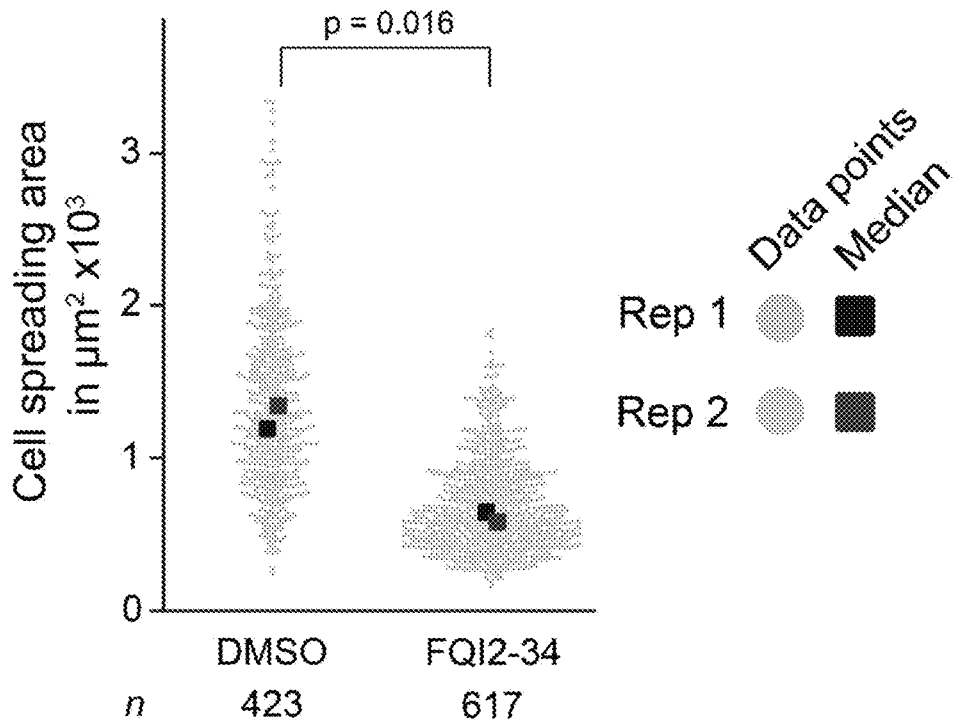
Figure 6E:
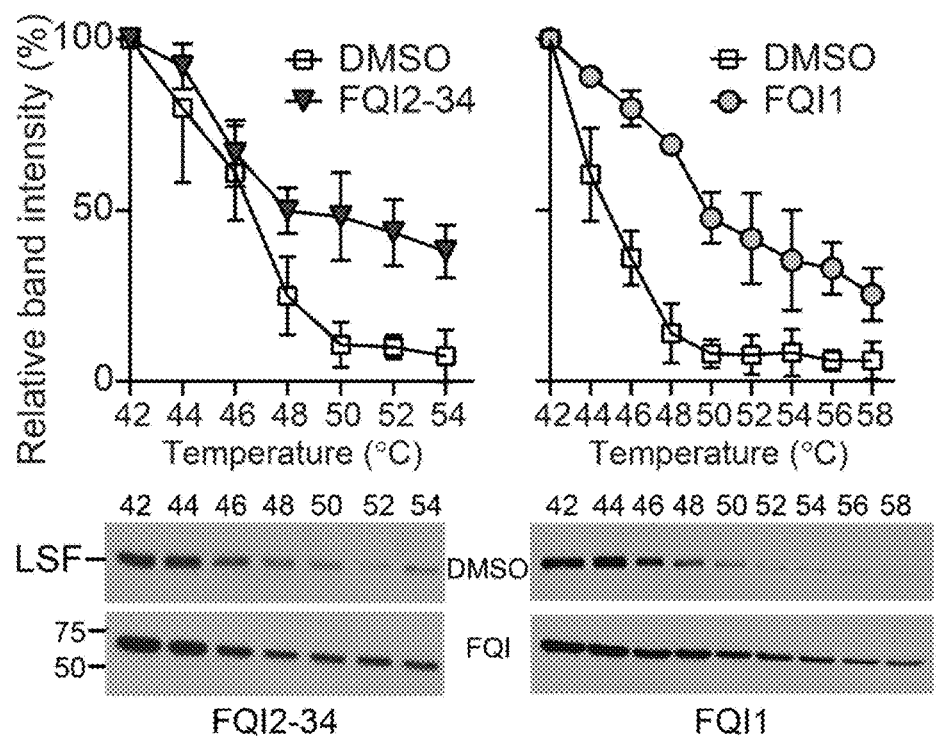

To test whether the sudden cell compaction is related to the previously described activities of FQI1[15,17] we tested whether the phenotype was replicated using a recently developed FQI family member, FQI2-34 (FIG. 6A). FQI2-34 is more potent than FQI1, exhibiting 17-fold higher efficacy than FQI1 in inhibiting proliferation of FH-B cells (FIG. 6B). Cell spreading of FH-B cells was decreased 2.1-fold by FQI2-34 at a 20-fold lower concentration than the effective concentrations for FQI1 (FIGS. 6C and -6D). Therefore, this novel and rapid morphological change in interphase FH-B cells is likely due to disruption of similar cellular target(s) specific to FQI1 that lead to mitotic defects in other cell types, such as cancer cells. In cell extract thermal shift assays (CETSA)[21,22], FQI2-34, like FQI1, enhanced the stability of LSF to thermal denaturation, indicating that both compounds directly bind LSF (FIG. 6E). These data are consistent with the involvement of LSF as the target of FQIs resulting in the changes in cell shape, although other mechanisms remain possible.

Figure 1E:
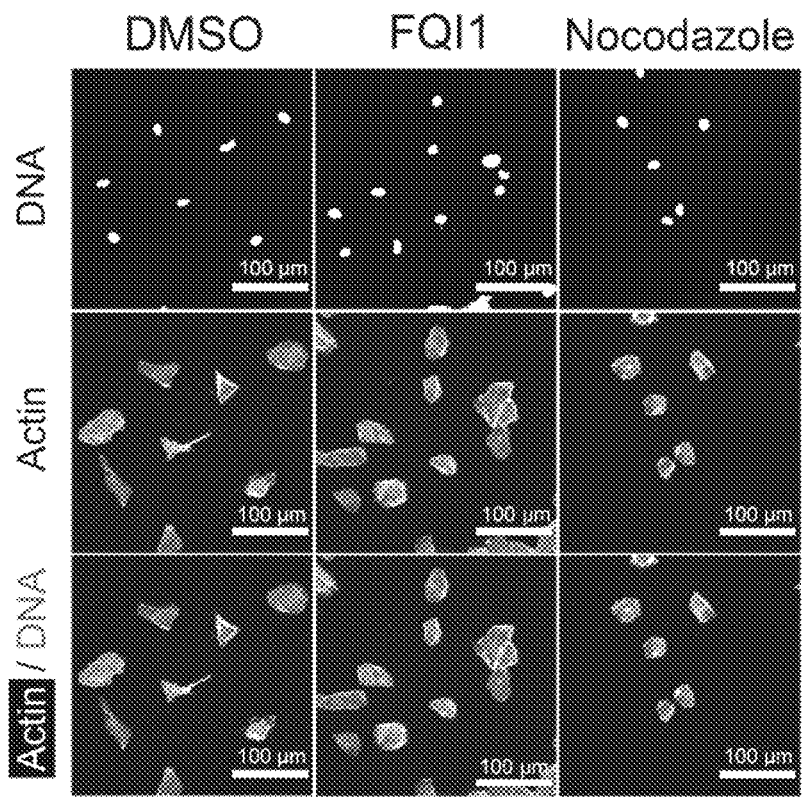
Figure 1F:
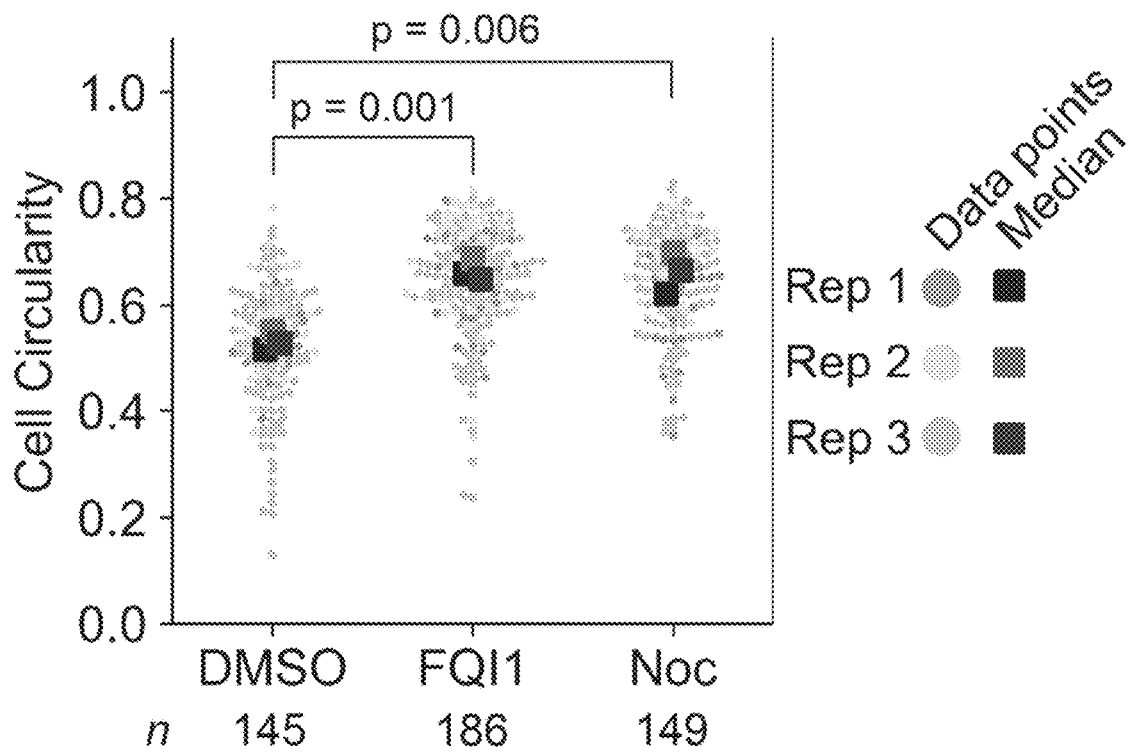
Figure 7:
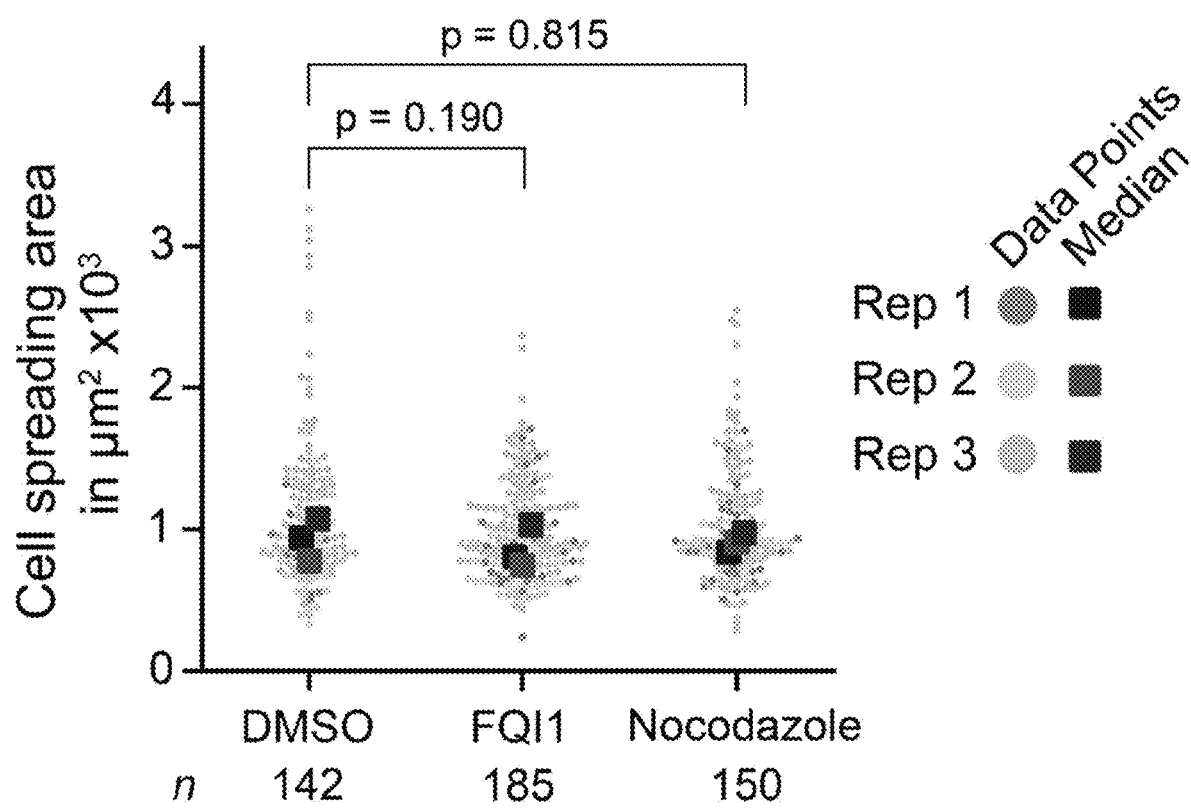
FIG. 7 shows RPE cells do not undergo significant compaction in the presence of FQI1. Quantitation of cell surface area covered by RPE cells upon treatment with 4 µM FQI1 or 1 µM nocodazole for 1 hour. Fluorescent images of actin staining in RPE cells as shown in FIG. 1E were processed using ImageJ to measure cell spreading area. The cells received fresh media along with the respective treatment. P-values were calculated using a paired two-sample t-test on medians from each biological replicate. Swarmplots include all analyzed cells from three independent experiments. The number of cells analyzed in each condition is indicated by "n".

Immortalized retinal pigmented epithelial cells become more circular with FQI1 treatment: In order to determine whether the FQI1-induced cell shape change in interphase occurs across multiple cell types, we tested whether the phenotype could be replicated in a different cell line. RPE cells are frequently used as a model cell line for investigating cell morphology and cell migration. In contrast to FH-B cells, RPE cells did not respond to FQI1 with significant change in cell spreading area (FIG. 7). However, the RPE cells became significantly more circular in shape (FIGS. 1E and 1F) in the presence of either FQI1 or nocodazole as compared to control cells. This increase in circularity indicates that RPE cells are losing their front-rear polarization[23] and thus could implicate processes governing cell polarity in the FQI1-induced phenotype.

Figure 8A:
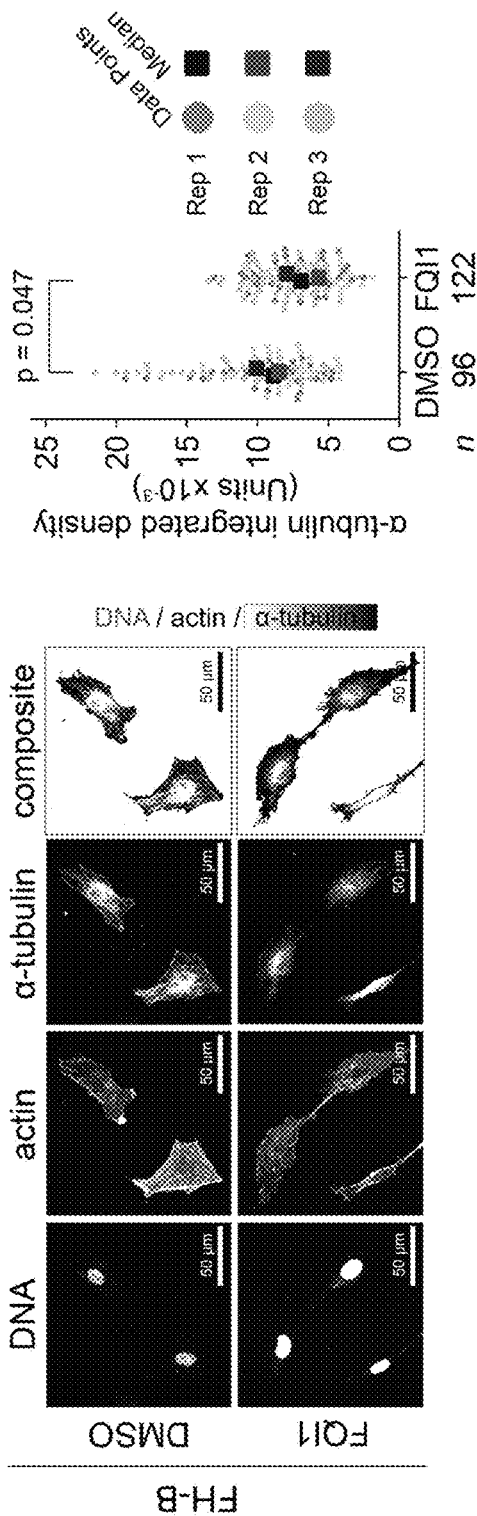
FIGS. 8A and 8B show FQI1 decreases the total density of microtubules detected in fixed FH-B and RPE cells. FH-B (FIG. 8A) and RPE (FIG. 8B) cells were pretreated with 10 µM Y-27632 for 30 minutes in order to maintain cell shape and then treated for 30 minutes (FH-B cells) or 10 minutes (RPE cells) with either 4 µM FQI1 or vehicle (0.01% DMSO). After fixing, cells were immunostained for α-tubulin, followed by fluorescently labelled Phalloidin and Hoechst 33342 staining. The actin staining was used to determine the cellular space as a region of interest for the measurement of α-tubulin intensity. To generate the composite images, the actin channel was thresholded, inverted and combined with the other channels using ImageJ. To better visualize the α-tubulin staining, the "Red Hot" lookup table was applied to the α-tubulin channel; the white-yellow and red-black colors represent the high and low intensities of the α-tubulin channel, respectively. Purple color represents the overlap of the blue and red colors. P-values were calculated using an unpaired two-sample t-test and the integrated density values of all cells from 3-4 independent experiments were incorporated into swarmplots. The total number of cells analyzed in each condition from all independent experiments is indicated by "n".
Figure 8B:
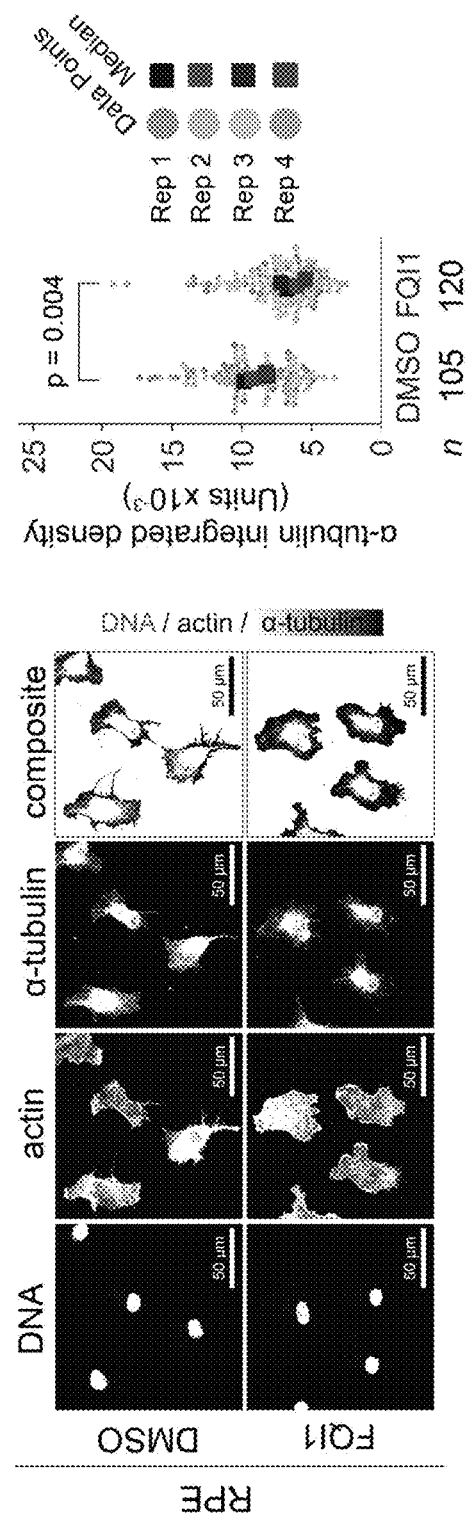

Interphase microtubules are rapidly depleted in the presence of FQI1: The swift FQI1-mediated reduction in cell spreading in FH-B cells and the more rounded morphology in RPE cells are similar to morphological changes caused by nocodazole in both cell types (FIGS. 1A, 1B, 1E and 1F). This indicates that FQI1 directly or indirectly destabilizes microtubules. Consistent with this, FQI1 treatment results in mitotic arrest in multiple cell types, at least in part by disruption of spindle microtubules[18]. To directly address whether microtubule destabilization occurs in interphase after addition of FQI1, we performed microtubule sedimentation assays, which separate the cellular tubulin pool into soluble and pellet fractions representing free tubulin and microtubule-associated tubulin, respectively. Performing a time-course following addition of FQI1 demonstrated that not only is FQI1 effective at reducing stable microtubule levels in both FH-B and RPE cells, but also that this decrease in microtubules occurs extremely quickly, as a drop in pelleted tubulin is observed only 1 minute after FQI1 addition (FIGS. 2A-2D). Upon monitoring the effect of FQI1 on the microtubule network by immunofluorescence, results were consistent with the microtubule sedimentation assay. A significant decrease in overall α-tubulin intensity was observed after fixation of both FQI1-treated FH-B and RPE cells, compared to their respective cells treated with vehicle (FIGS. 8A and 8B).

Figure 2A:
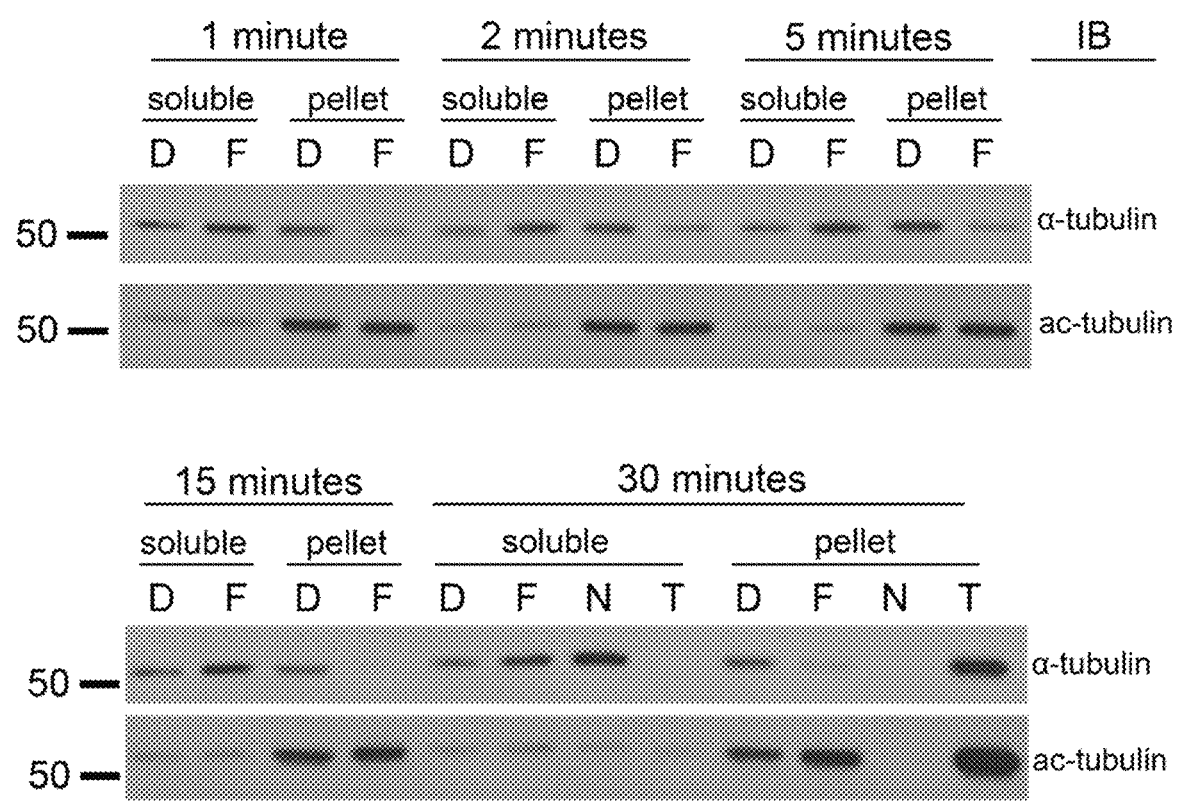
FIGS. 2A-2F show stable microtubule levels are rapidly diminished upon FQI1 treatment.
Figure 2B:
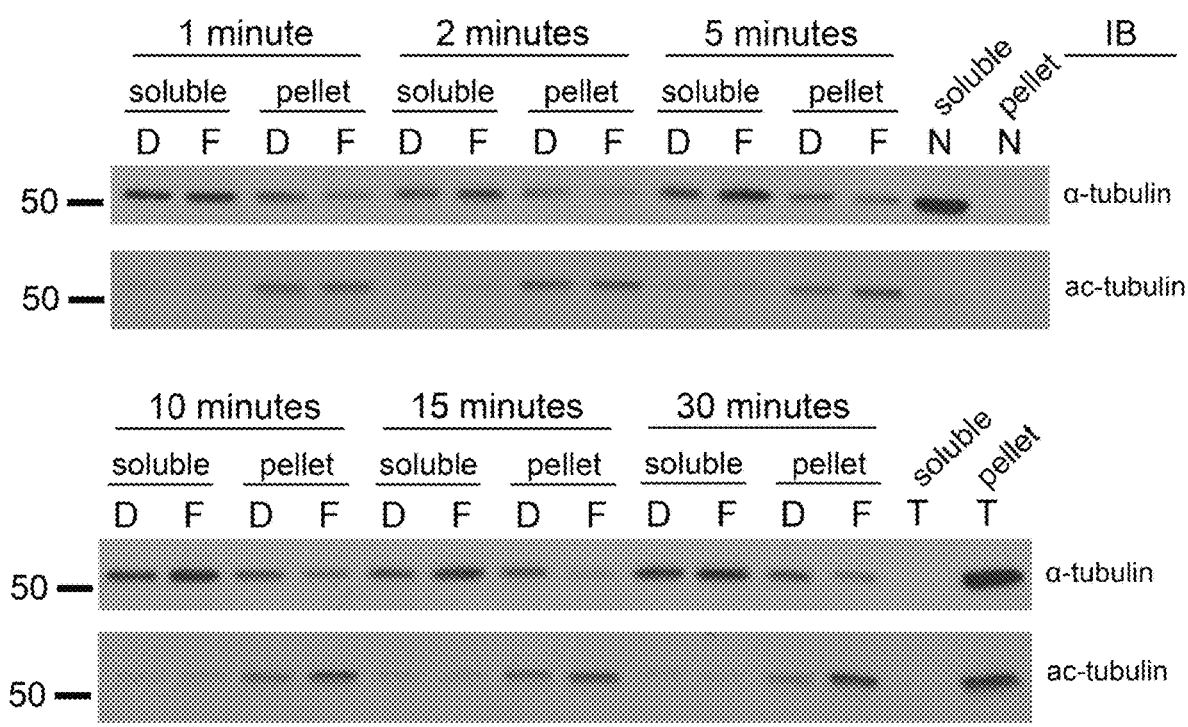
Figure 2C:
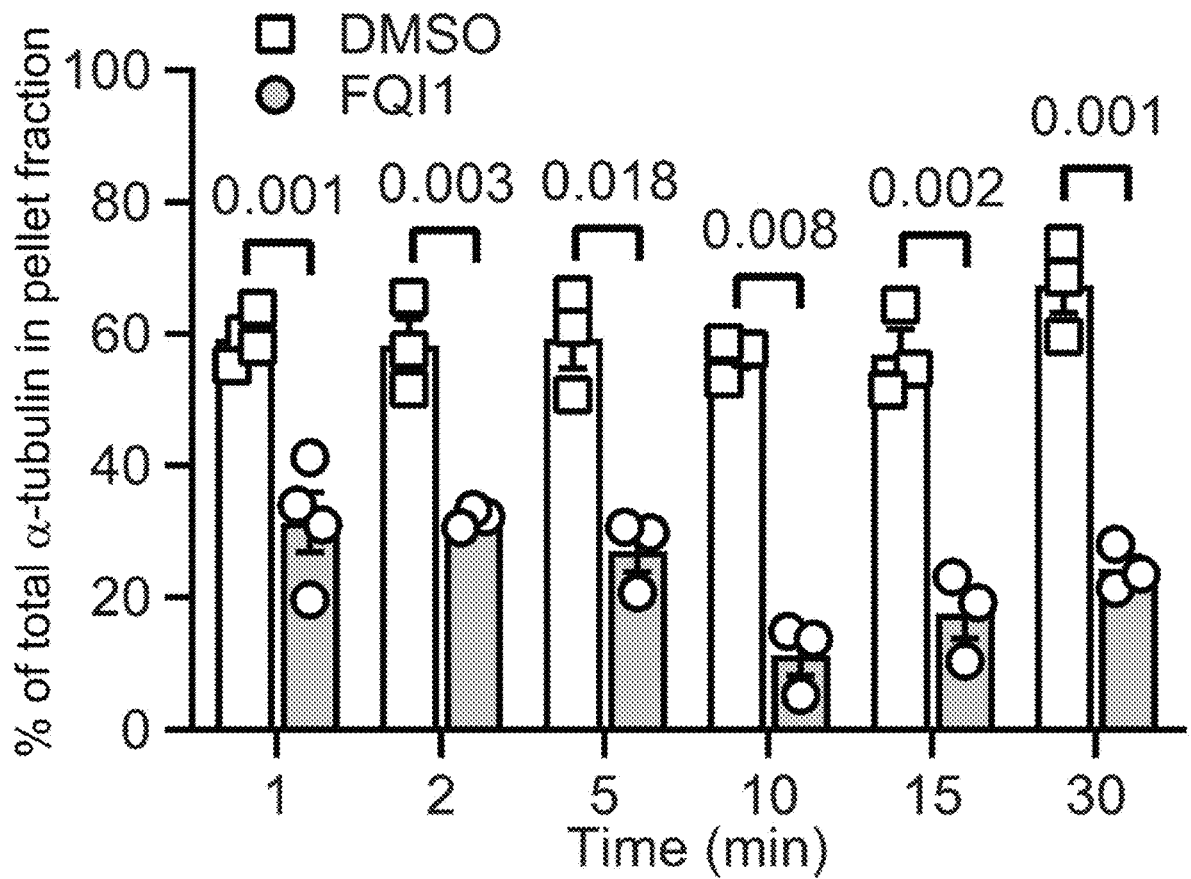
Figure 2D:
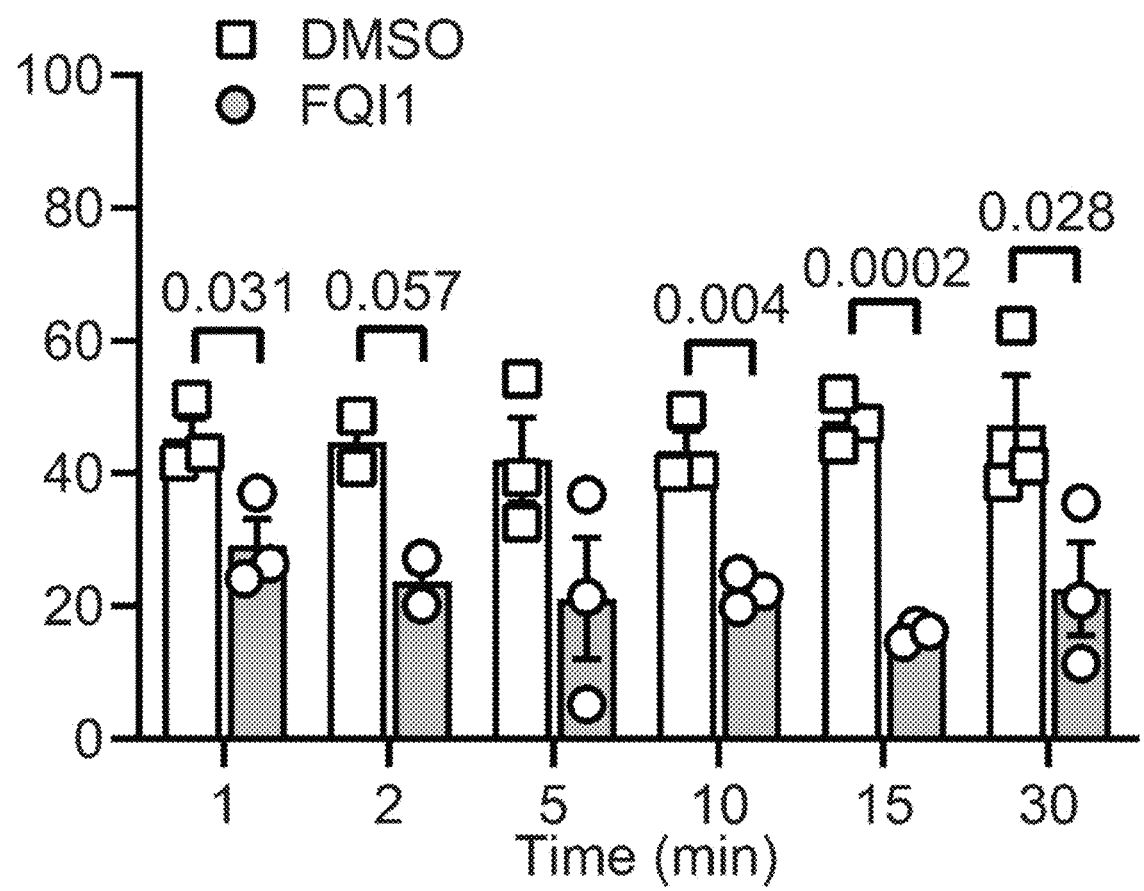
Figure 2E:
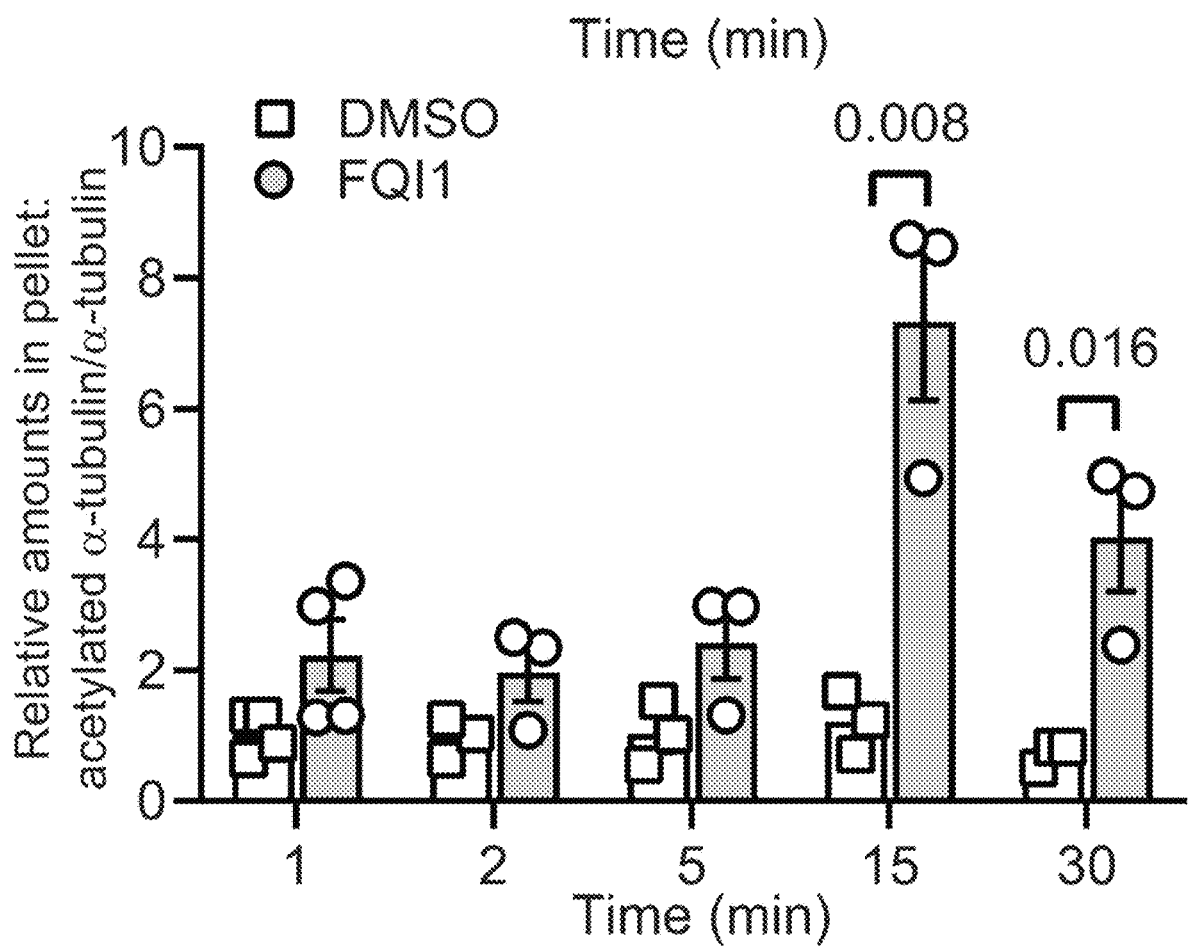
Figure 2F:
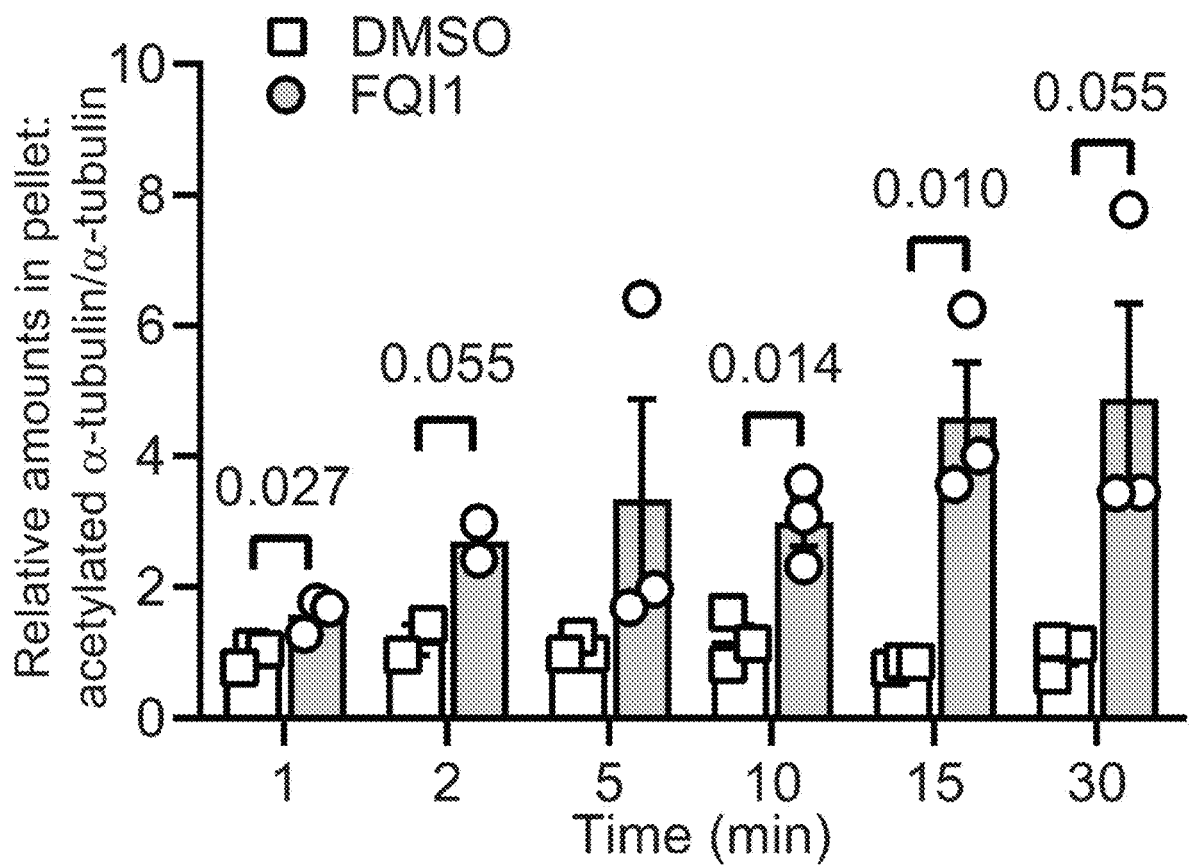

Unexpectedly, FQI1-induced microtubule destabilization was accompanied by an increase in the amount of acetylated α-tubulin in the microtubule fraction, despite the significant depletion of microtubules (FIGS. 2E and 2F, 15- and 30-minute pellets). This combination of microtubule acetylation and destabilization is distinct from the effects observed by nocodazole, which destabilizes and deacetylates microtubules, and taxol, which stabilizes and hyperacetylates microtubules (FIGS. 2A and 2B, "N" and "T" lanes). Because α-tubulin acetylation occurs inside the microtubule lumen, microtubule hyperacetylation by FQI1 treatment could provide a clue into the structural impact of FQI1 on the microtubule lattice. Recent reports have demonstrated that tubulin acetylation occurs either at the polymer ends[24,25] or on curved regions, which feature openings between the protofilaments allowing access for the tubulin acetyltransferase αTAT1[26-28].

Figure 9A:
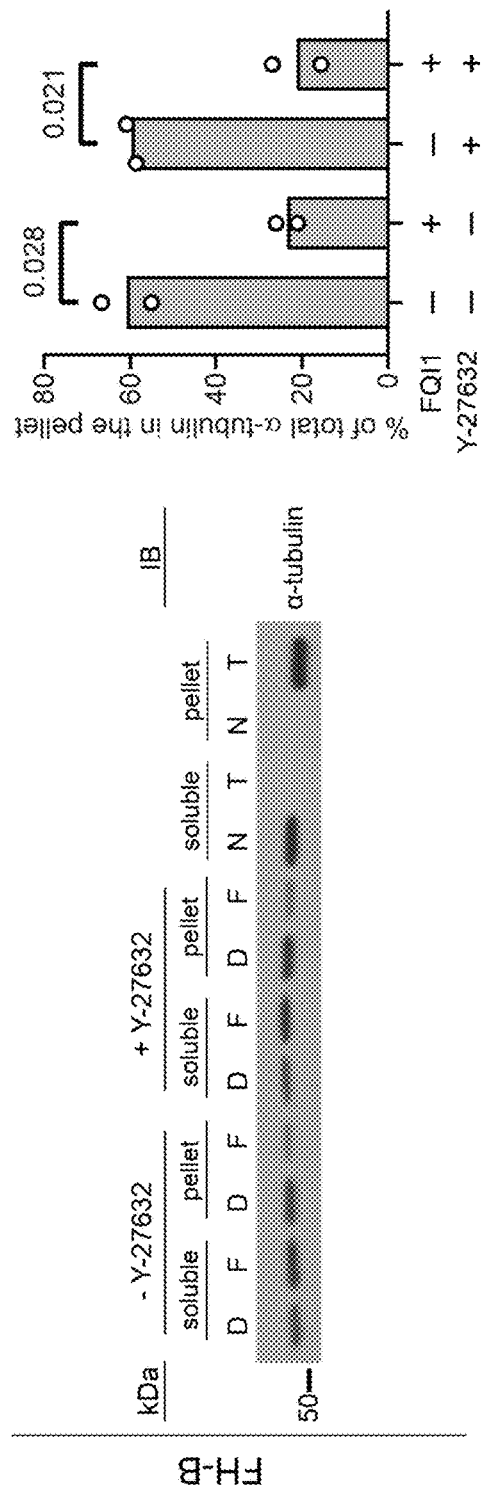
FIGS. 9A and 9B show ROCK inhibitor does not prevent FQI1-induced decrease in stable microtubule levels. FH-B and RPE cells were pretreated with 10 µM Y-27632 or vehicle (0.01% DMSO) for 30 minutes, followed by treatment with either 4 µM FQI1 or vehicle (0.02% DMSO) for another 30 minutes. As positive and negative controls, taxol ("T", 1 µM) and nocodazole ("N", 1 µM), respectively, were also added after the pretreatment. Cells were then fractionated using the microtubule sedimentation assay, followed by an analysis of soluble and insoluble α-tubulin. Two independent biological replicates were performed for each cell line. Left panels: Representative α-tubulin immunoblots of FH-B (FIG. 9A) and RPE (FIG. 9B) lysate fractions from the DMSO- and FQI1-treated cells. Right panels: quantitation of immunoblots. Numbers above brackets represent p-values, which were calculated using an unpaired two-sample t-test. Bars represent means and circles represent individual data points.
Figure 9B:
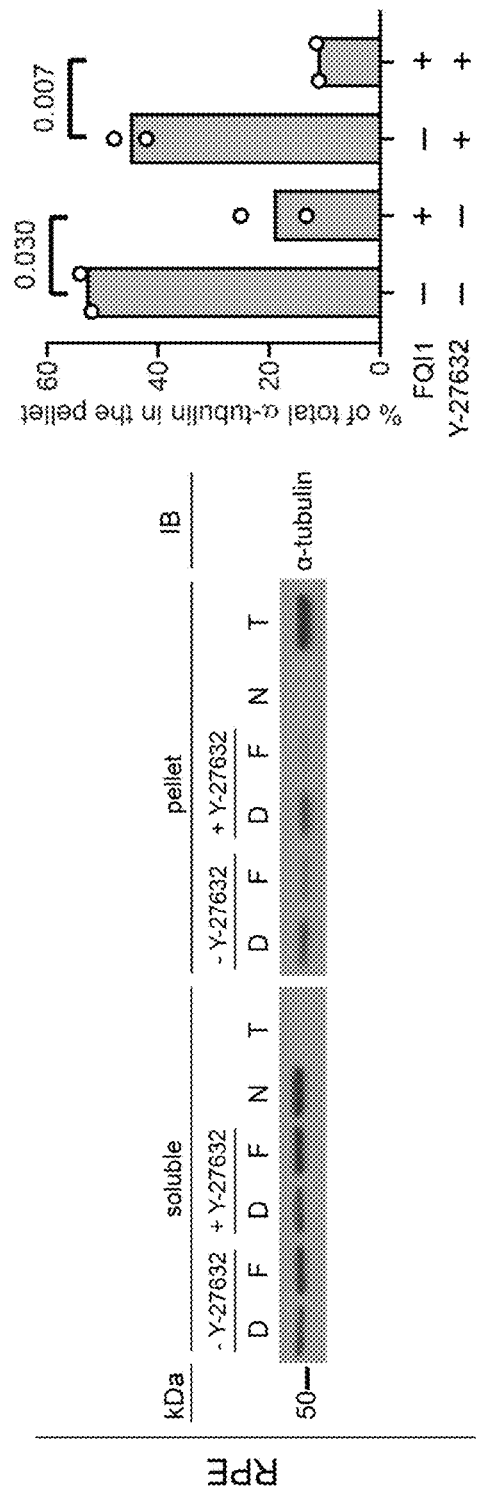

It has been reported that the complete collapse of microtubules by nocodazole can involve, in part, a mechanical compression of nocodazole-resistant microtubules by myosin-mediated contraction resulting from RhoA activation[27]. Thus, we tested whether inactivating the RhoA/ROCK pathway with Y-27632 could rescue FQI1-mediated microtubule depletion. However, FH—B and RPE cells pre-exposed to Y-27632 experienced quantitatively the same decline in stable microtubules as seen in control cells (FIGS. 9A and 9B). This indicates that FQI1-activated microtubule disruption is not a downstream consequence of the RhoA/ROCK signaling pathway. Overall, these data demonstrate that FQI1 significantly and rapidly decreases the pool of stable microtubules in interphase in these two cell types.

Figure 3A:
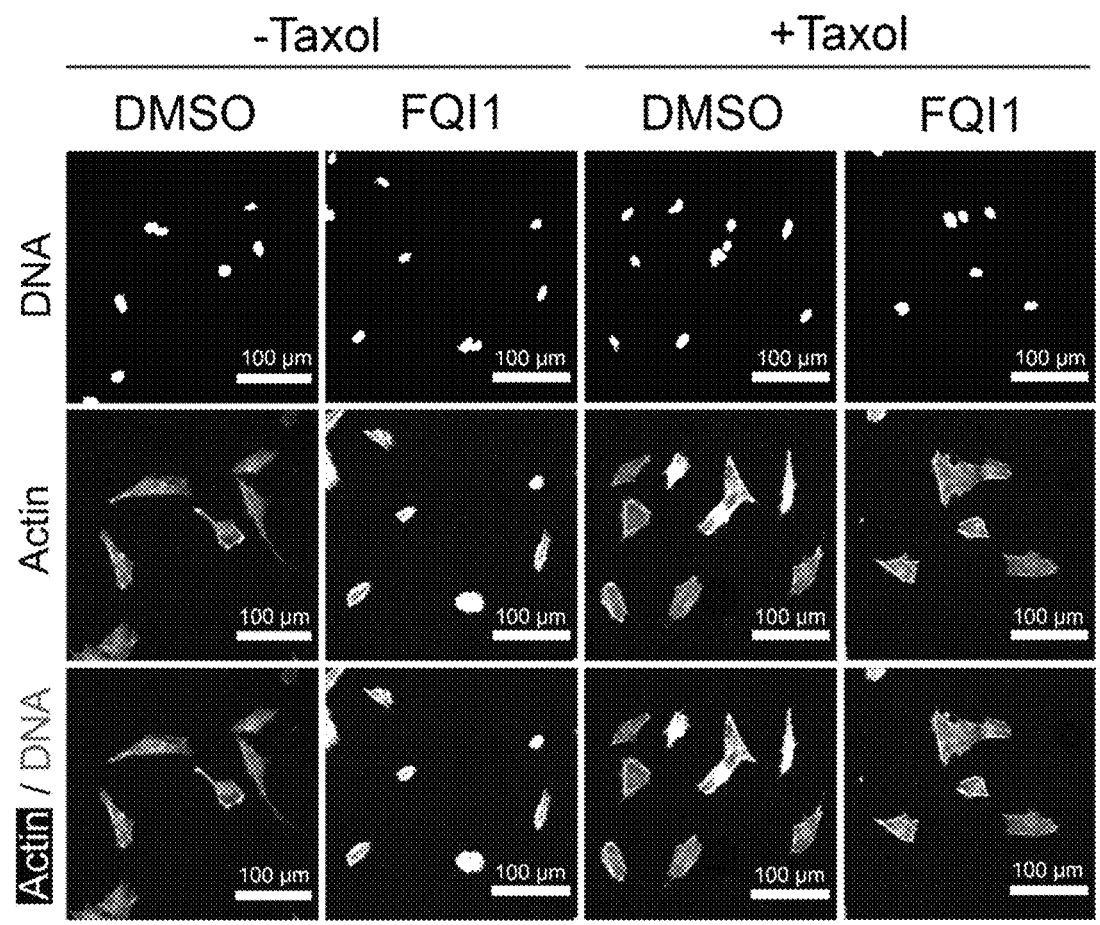
FIGS. 3A-3H show FQI1-induced morphology changes are based on disruption of the microtubule network.
Figure 3B:
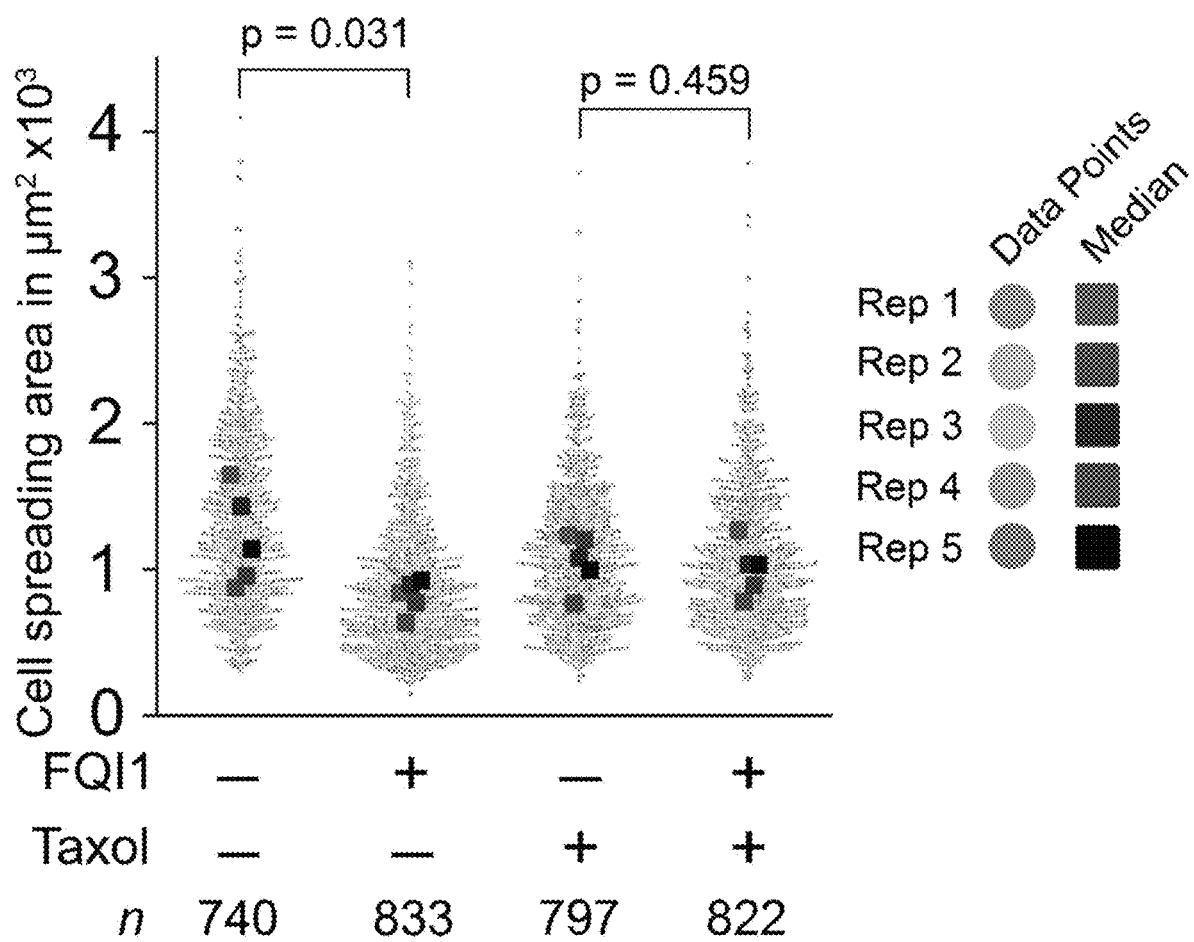

Microtubule depletion is the basis for FQI1-induced morphological phenotypes: Because the decline in stable microtubules temporally precedes the FQI1-induced reduction in cell spreading in FH-B cells, this indicates a microtubule-based mechanism for the phenotypes. In order to test the connection between the morphological changes and the prior depletion of microtubules, we investigated whether taxol, a microtubule-stabilizing agent, would rescue the cell compaction of FH-B cells resulting from exposure to FQI1 (FIGS. 3A and 3B). Indeed, when FH-B cells were incubated first with taxol, subsequent FQI1 treatment did not visibly lead to the compressed phenotype (FIG. 3A). Upon quantitation, the median cell spreading area upon incubation with FQI1 was decreased 1.5-fold on average, which was statistically significant (FIG. 3B), whereas there was no detectable effect of FQI1 on cell spreading area when cells were pretreated with taxol. This supports the interpretation that FQI1-induced reduction in cell spreading is mediated through destabilization of microtubules.

In RPE cells, the proposed connection between cell shape alterations and microtubule depolymerization was tested by examining changes in the microtubule network upon FQI1 addition. Cell polarity is closely linked to polarized patterning of microtubule dynamics across the anterior-posterior axis of a migrating cell. Therefore, we hypothesized that a disruption of microtubule polarization would accompany the increase in cell circularity upon FQI1 treatment. A closer look at the microtubule network in FQI1-versus vehicle-treated cells revealed a striking 2.7- to 2.5-fold increase in the number of exposed and individually discernible microtubule ends in the presence of FQI1 in FH-B and RPE cells, respectively (FIGS. 3C-3F). We interpreted these individually discernible microtubule ends as indicators that the microtubule network was undergoing depolymerization to such an extent that individual microtubule ends were becoming more visible, rather than being embedded in a dense meshwork. This observation is also consistent with the decrease in total tubulin density (FIGS. 8A and 8B) and the decrease in stable microtubules (FIGS. 2A-2D). We hypothesize that these unembedded microtubule ends may provide access for αTAT1 to the lumen of the microtubules, resulting in the enhanced tubulin acetylation that is observed (FIGS. 2A, 2B, 2E and 2F).

Figure 3C:
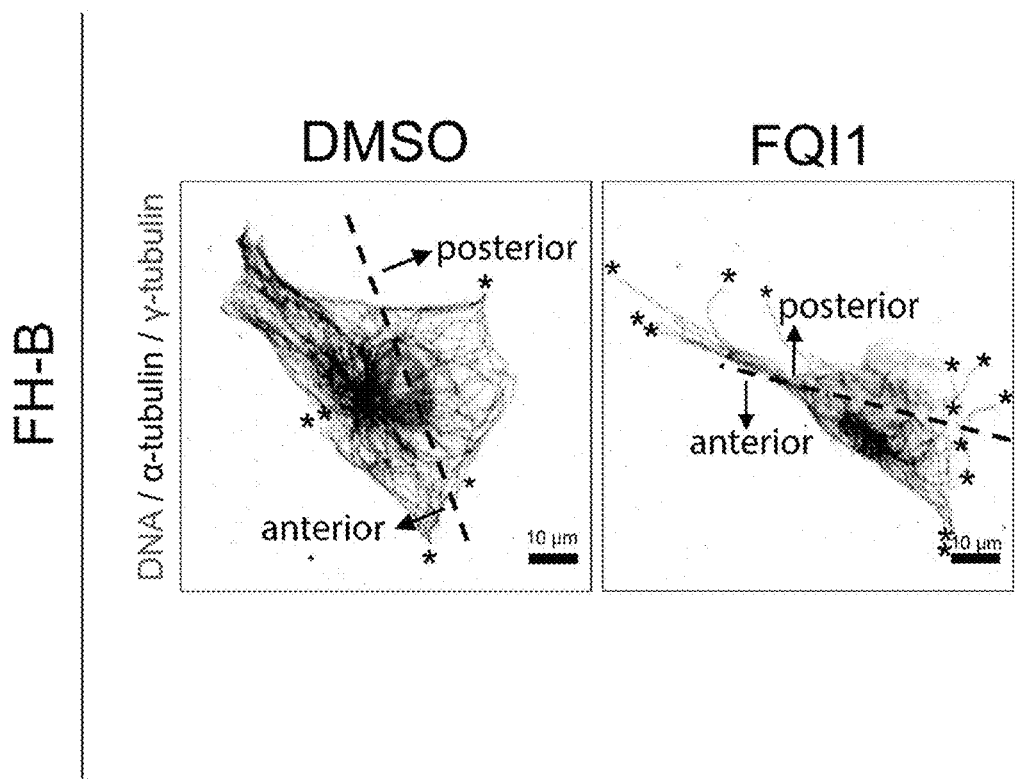
Figure 3D:
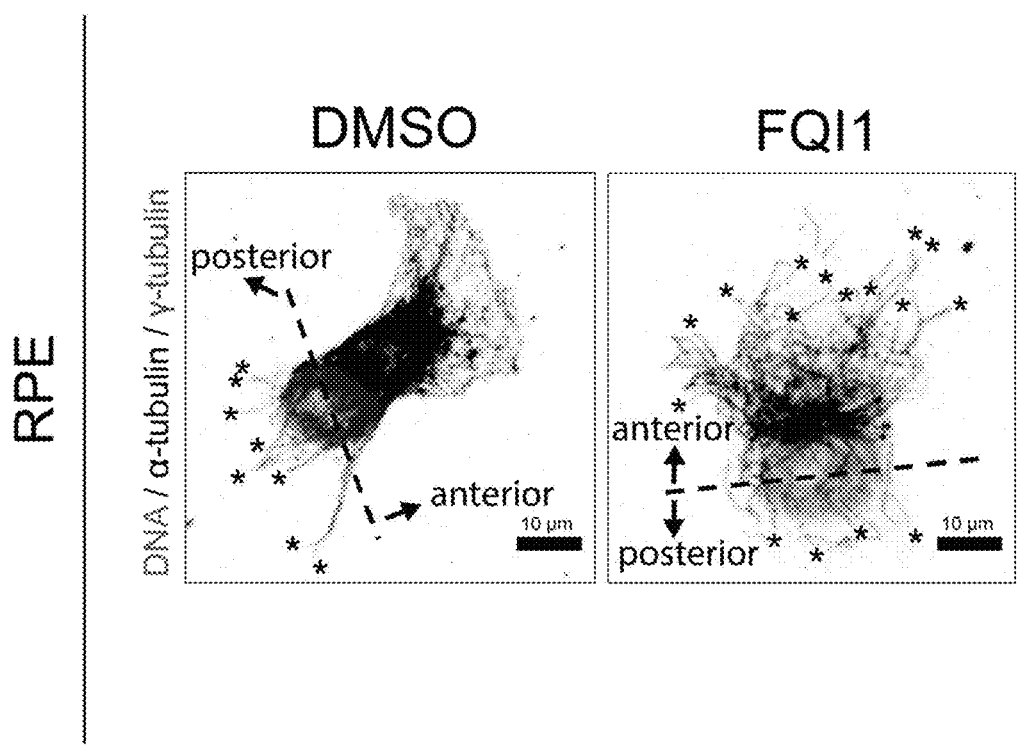
Figure 3E:
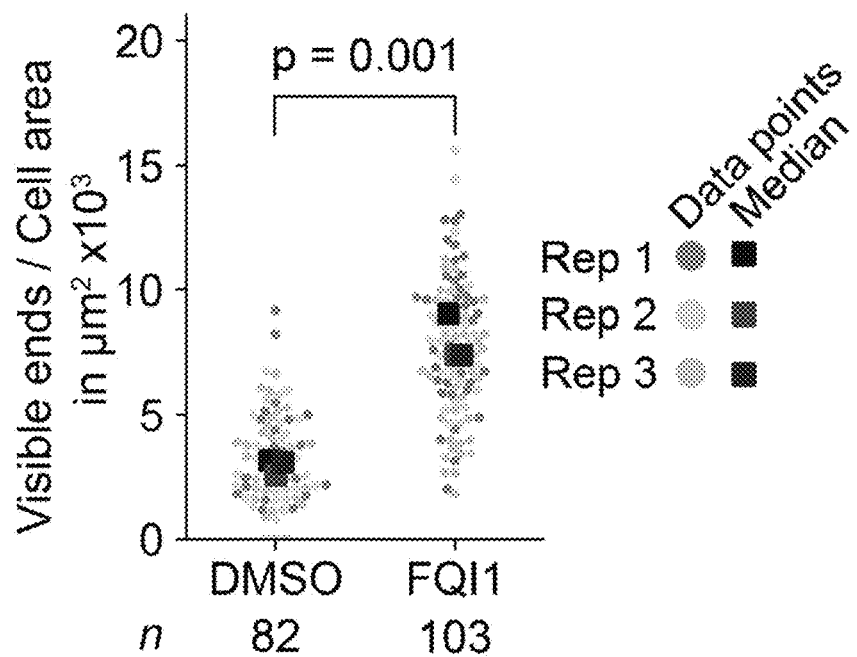
Figure 3F:
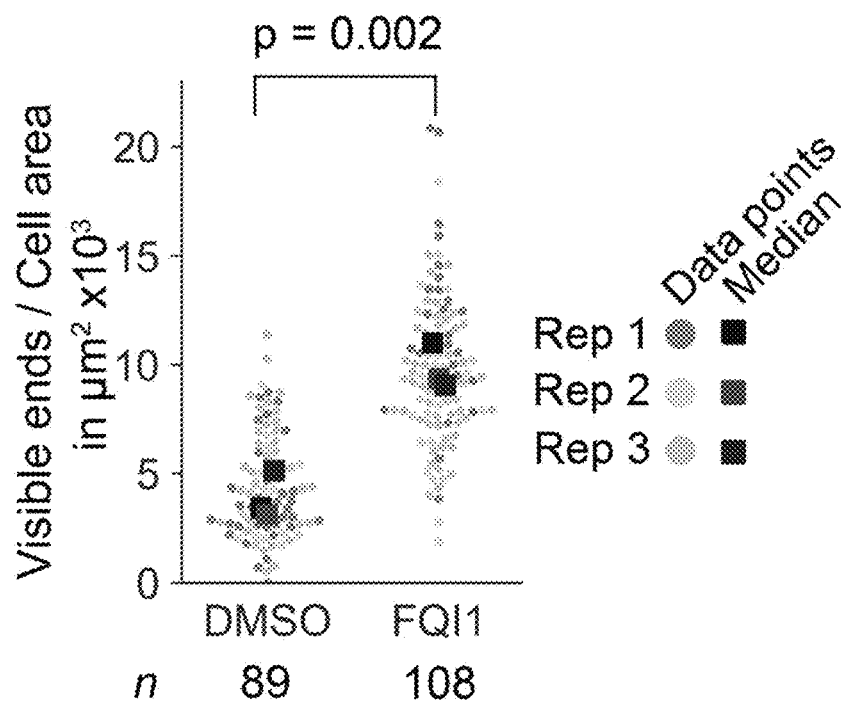
Figure 3G:
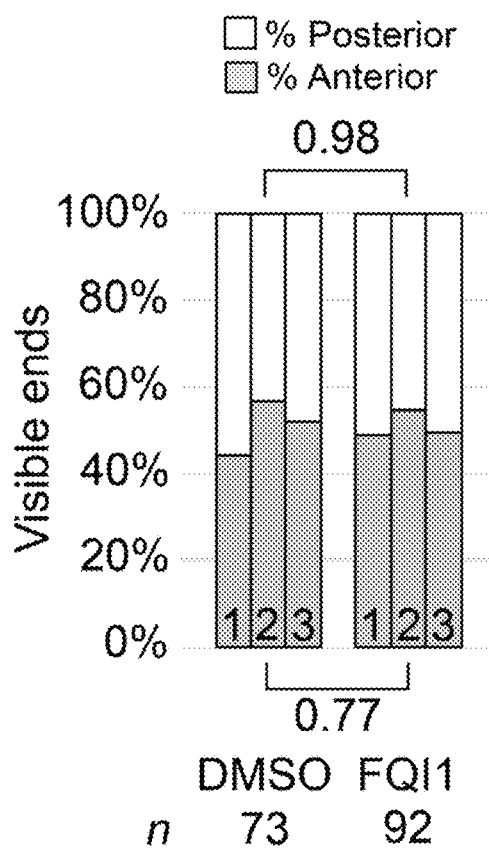
Figure 3H:
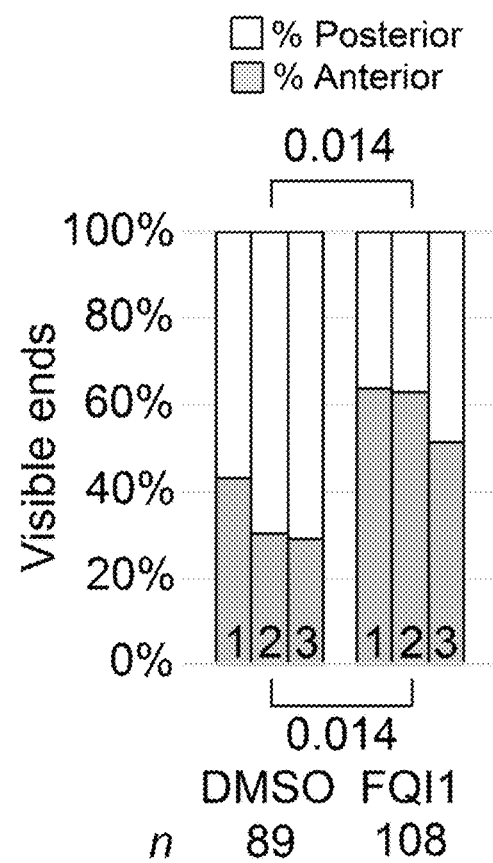

Using these visible microtubule ends as markers for microtubule depletion, we analyzed whether the ends were distributed differentially along the anterior-posterior orientation of the cell in FQI1-versus control-treated cells. In order to identify the front-rear axis, the nucleus and γ-tubulin were stained to establish the polarity of the cell so that the visible microtubule ends could be sorted into anterior and posterior fractions (FIGS. 3C and 3D). The position of the centrosome, the main microtubule organizing center of the cell, relative to the nucleus is historically regarded as a strong indicator for the anterior leading edge of a migrating cell, thereby rendering the opposite side the posterior of the cell[29]. Although the anterior positioning can vary with cell type and substrate, in RPE cells the centrosome is predominantly anterior, independent of the migratory mode[30]. Regions containing visible microtubule ends in control migrating RPE cells occurred largely at the posterior edge, while microtubules at the anterior edge formed a meshwork in which individual microtubule ends were much less discernible (FIGS. 3D and 3H). This validates use of the centrosome position to assign anterior segments, as microtubules undergoing higher rates of catastrophes at the trailing edge, in which the local microtubule network is depleted[31,32], should render individual microtubules more visible. In contrast, the front-rear pattern of visible microtubule ends in FQI1-treated RPE cells shifted to a more anterior distribution (FIGS. 3D and 3H). This indicates that the microtubule instability normally restricted to the trailing edge becomes more prevalent throughout the cell periphery in the presence of FQI1. This is consistent with the increase in circularity observed in FQI1-treated RPE cells, because a more circular shape could indicate a loss in cell polarization, which a depletion of microtubules towards the anterior portion of the cells would reflect. In the case of FH-B cells, the anterior-posterior patterning of visible microtubule ends was largely unaffected by FQI1 (FIGS. 3C and 3G). As the morphological response to FQI1 of FH-B cells is much more substantial than that of RPE cells, an unchanged distribution of front-rear microtubule depletion indicates that the cell compaction is caused by an even depletion of microtubules throughout the cell with no preference for anterior or posterior edges. Overall, we demonstrated that the FQI1-mediated decrease in microtubule levels is necessary for the reduction in cell spreading in FH-B cells, that the FQI1-mediated decrease in microtubule levels in RPE cells is accompanied by a reduction in microtubule polarization. Without wishing to be bound by a theory, this underlies the increase in cell circularity in these cells.

Figure 10A:
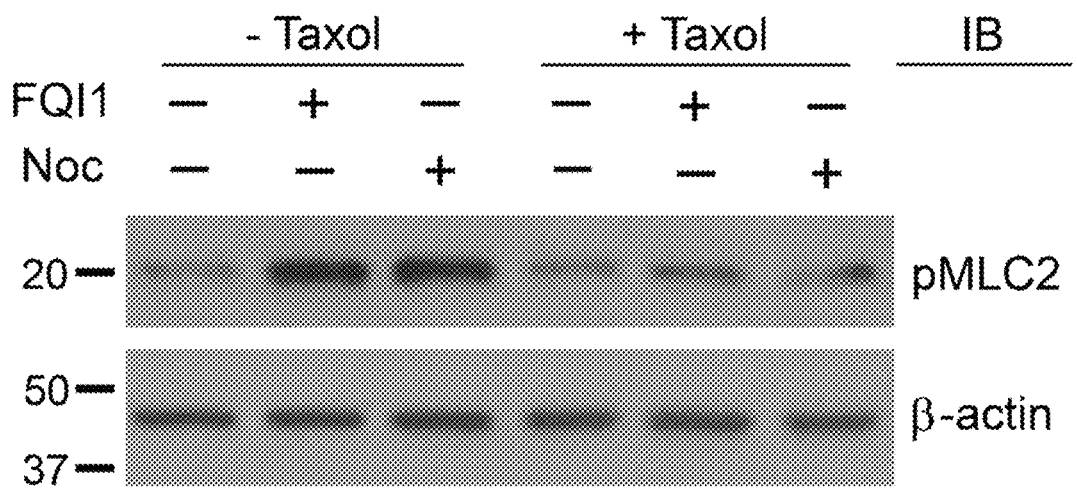
FIGS. 10A-10D show activation of the RhoA/ROCK pathway may be only partially responsible for FQI1-induced cell compaction.
Figure 10B:
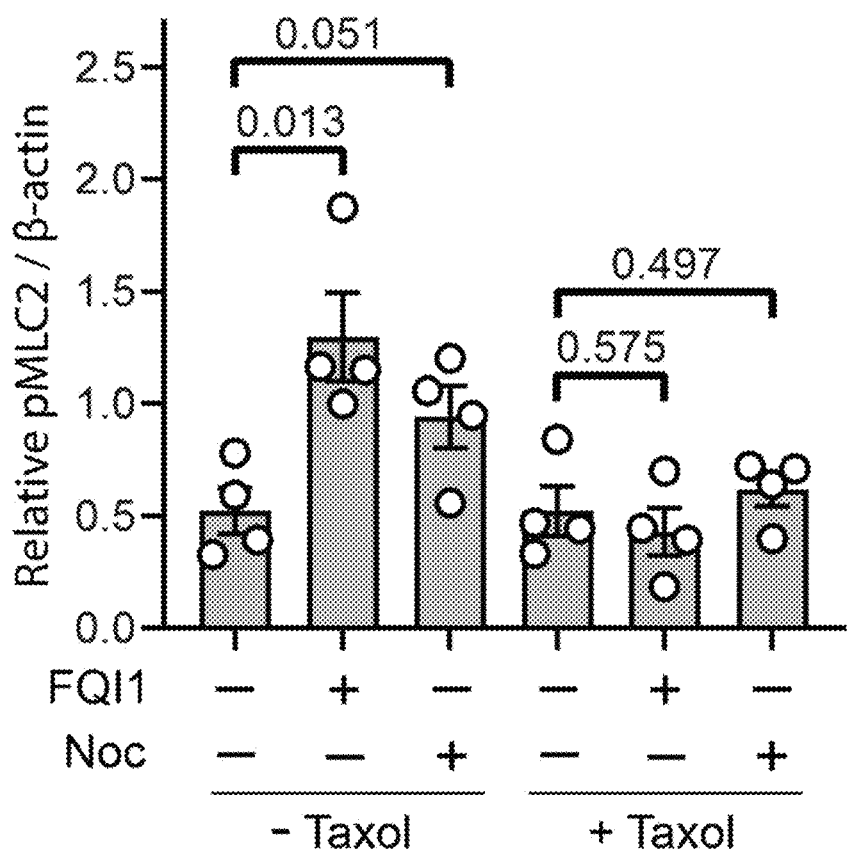
Figure 10C:
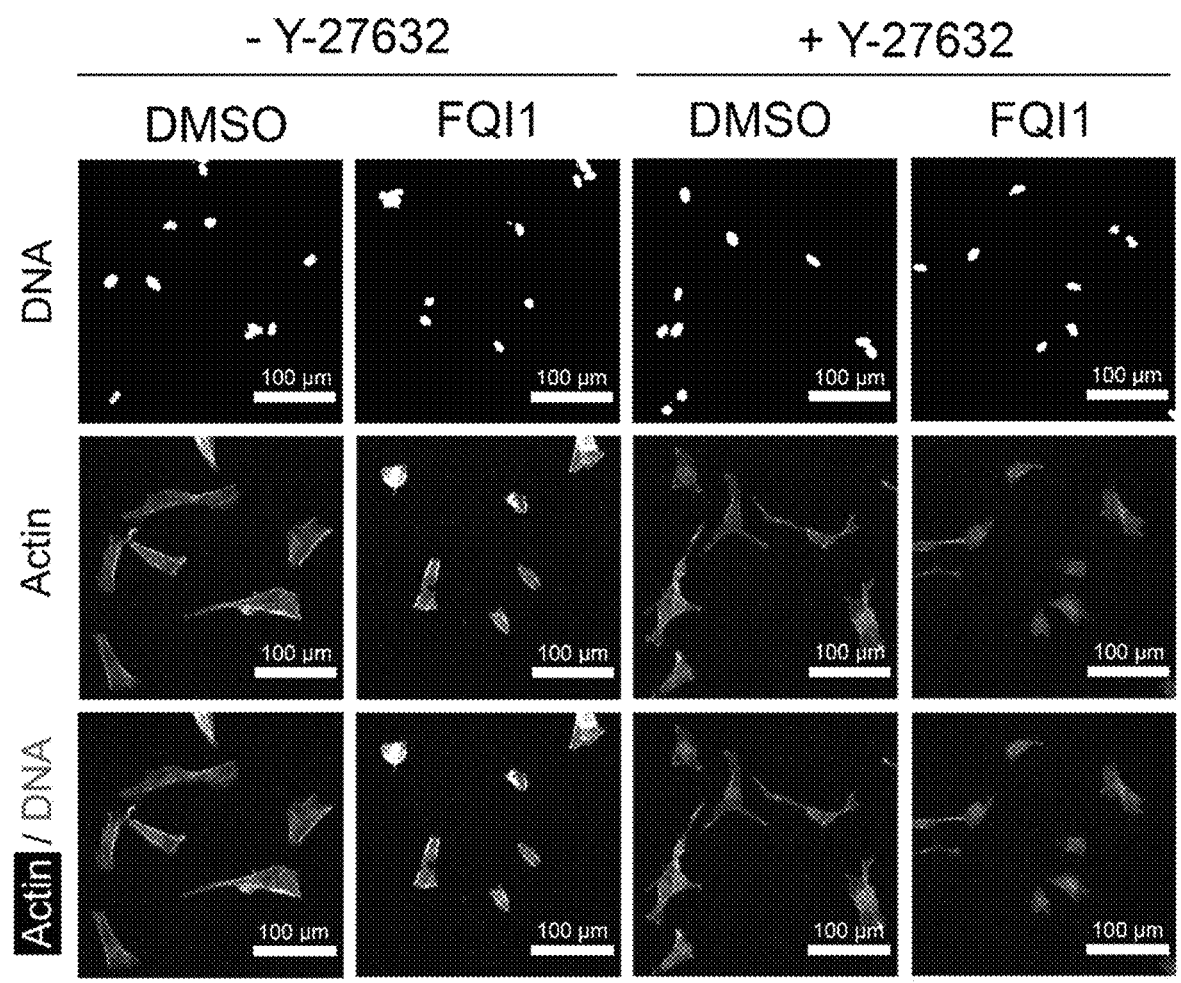
Figure 10D:
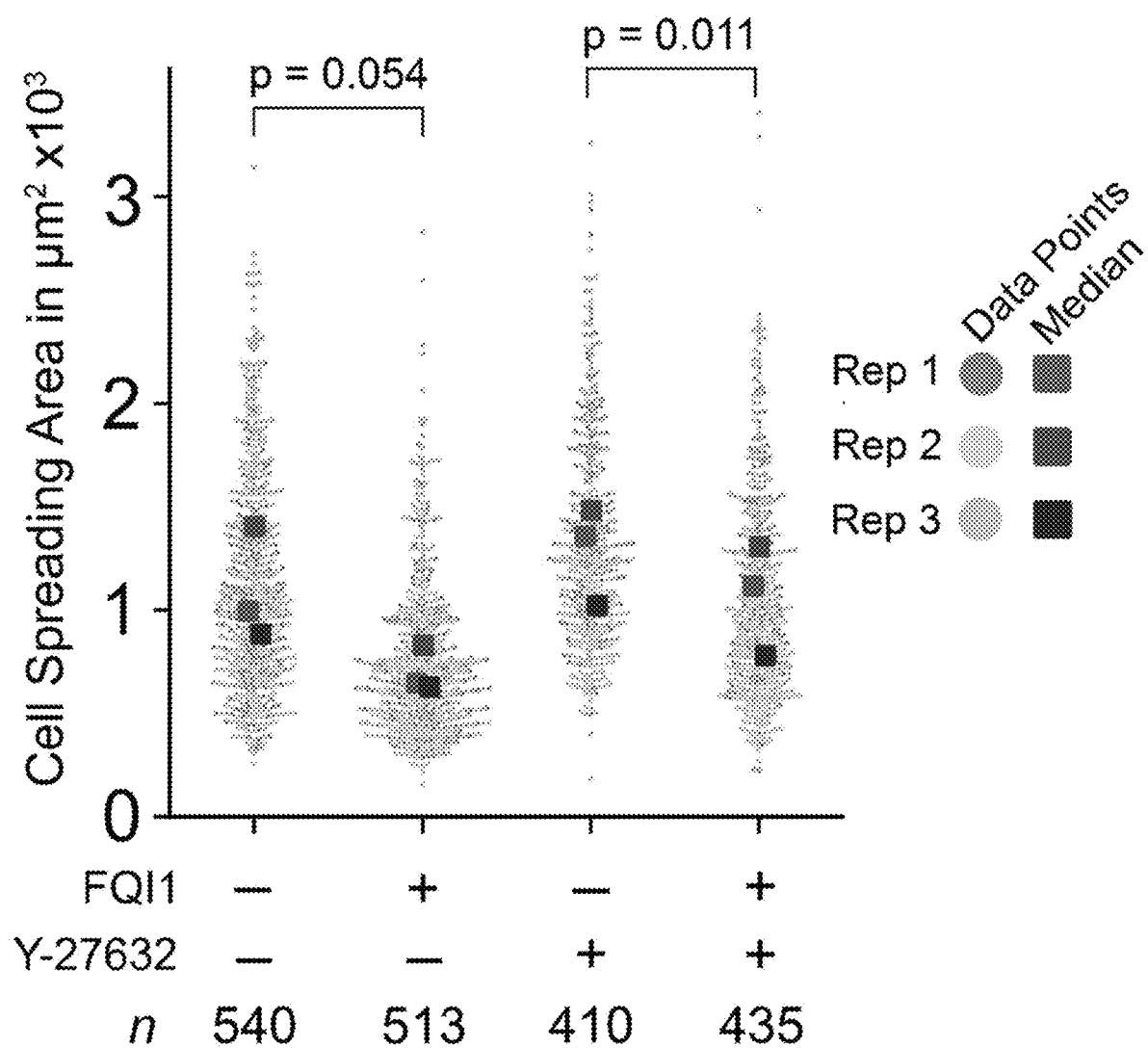

Activation of the RhoA/ROCK pathway is not required for FQI1-induced cell compaction: In considering how the rapid microtubule disruption resulting from FQI1 treatment could trigger cell compaction and disruption of cell motility, we examined whether it was similar to the pathway downstream of nocodazole. Depolymerization of microtubules by nocodazole results in dissociation of GEF-H1 from microtubules, which then activates the small GTPase RhoA[8,33-35]. One of the most crucial effector proteins of RhoA is ROCK, which targets several downstream proteins for phosphorylation in order to execute the contractile response[36,37]. To test whether FQI1 also activates the RhoA/ROCK pathway, phosphorylation levels of myosin regulatory light chain 2 (MLC2), a well-known ROCK substrate, were measured in the presence and absence of FQI1. Indeed, phosphorylation of MLC2 was elevated 10-minutes after FQI1 addition (FIGS. 10A and 10B). Furthermore, the increase in MLC2 phosphorylation was abrogated when FH-B cells were pre-incubated with taxol, strongly indicating that FQI1-mediated microtubule depletion is needed in order to activate the RhoA/ROCK pathway. To explore whether FQI1-mediated compaction of FH-B cells is dependent on the RhoA/ROCK pathway, we tested whether inhibiting ROCK would counteract the ability of FQI1 to reduce the cell spreading area. Cells were pretreated with either ROCK2 inhibitor Y-27632 or vehicle, followed by addition of FQI1 or vehicle for an additional 30-minutes (FIGS. 10C and 10D). FQI1 still caused a statistically significant decrease in cell spreading area in the presence of Y-27632, although the reduction in cell spreading area when cells were pretreated with Y-27632 was slightly diminished (1.2-fold) compared to the control group (1.6-fold). This indicates that the RhoA/ROCK pathway, although activated by FQI1 in a microtubule-dependent manner, is only a partial, but not the sole mediator of FQI1-induced cell compaction, and that factors other than the ROCK pathway can enable FQI1's control over cell shape. Overall, these data show that FQI1 activates the RhoA/ROCK pathway by directly or indirectly depolymerizing microtubules in FH-B cells, but that the RhoA/ROCK pathway is not required for the FQI1-induced cell compaction.

Figure 11A:
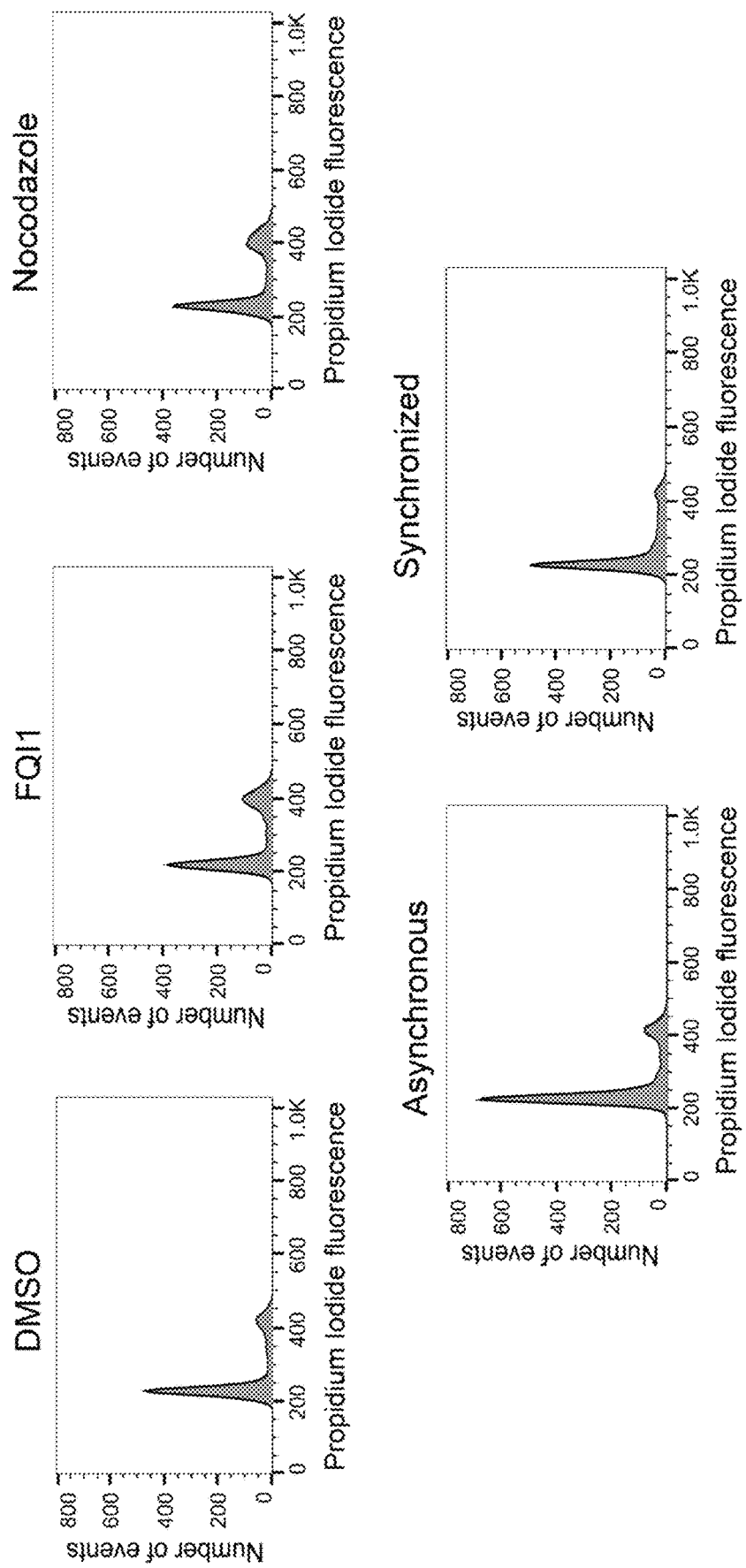
FIGS. 11A and 11B show cell cycle alterations do not account for reduced wound-closing ability in FQI1-treated RPE cells. At the end of the wound healing experiment (FIGS. 11A and 11B), RPE cells were harvested for flow cytometry analysis of cellular DNA content to assess the proportion of cells with a 4n DNA content in FQI1-treated cells compared to vehicle-treated cells.
Figure 11B:
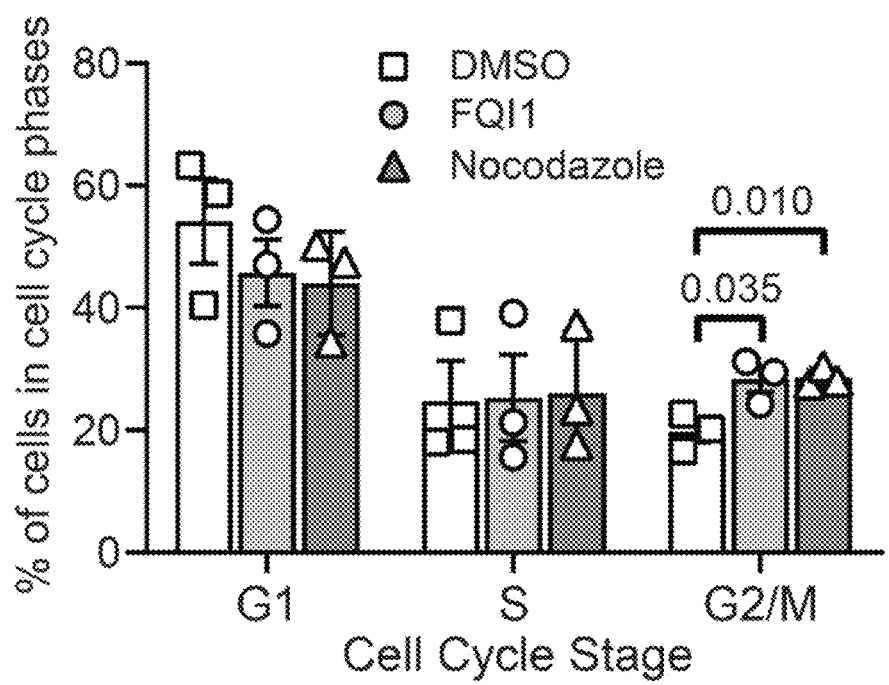

FQI1 impairs cell motility: Concentrations of nocodazole that fully depolymerize the microtubule network also suppress directional cell migration, by forcing a random, directionless, and blebbing-based migratory behavior[11,34]. Because nocodazole abrogates persistent cell migration and also mimics the morphological phenotypes of FQI1-treated FH-B and RPE cells, we hypothesized that FQI1 would likewise impede cell migration. This was investigated using a wound-healing assay in RPE cells, which, in contrast to the fibroblast-like FH-B cells, are able to form stable monolayer sheets. An X-shaped scratch was drawn on confluent monolayers of cells and the rate of wound-closure under different treatment conditions was monitored for 12 hours. Similarly to nocodazole, FQI1 hindered RPE cells from migrating into the wound (FIGS. 4A and 4B), which was detectable even by 4 hours. To rule out the possibility that the slow migration was due to FQI1-mediated mitotic arrest, we also analyzed the cell cycle profiles of the treatment groups at the end of the experiment. Although the FQI1 group contained ~30% cells with a 4n DNA content compared to ~20% in the control group (FIGS. 11A and 11B), only a fraction of cells at the wound edge displayed a mitotic "rounded-up" phenotype (FIG. 4A) and FQI1 inhibited migration by 4 hours, well before the 12-hour time-point at which the cell cycle profiling was performed. Therefore, the increase in the percentage of presumptive mitotic cells is unlikely to account for the reduction in cell migration by FQI1. Instead, the reduction in wound healing rate is likely due to a FQI1-mediated effect on cell migration.

Figure 12A:
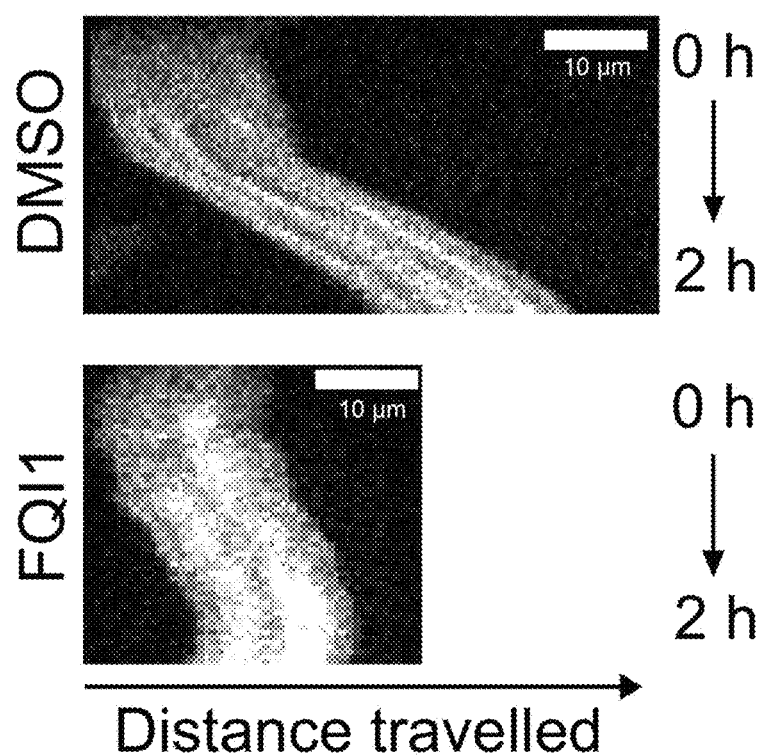
FIGS. 12A and 12B show RPE cell motility is not statistically significantly reduced during 2 hours of FQI1 treatment. RPE cells were synchronized, treated, and imaged the same way as FH-B cells in FIGS. 4C and D. Representative kymographs of RPE nuclei are shown in (FIG. 12A) and the swarmplot of distances travelled by migrating RPE cells is shown in (FIG. 12B). The p-value was calculated using an unpaired two-sample t-test. The total number of cells analyzed in each condition is indicated by "n".
Figure 12B:
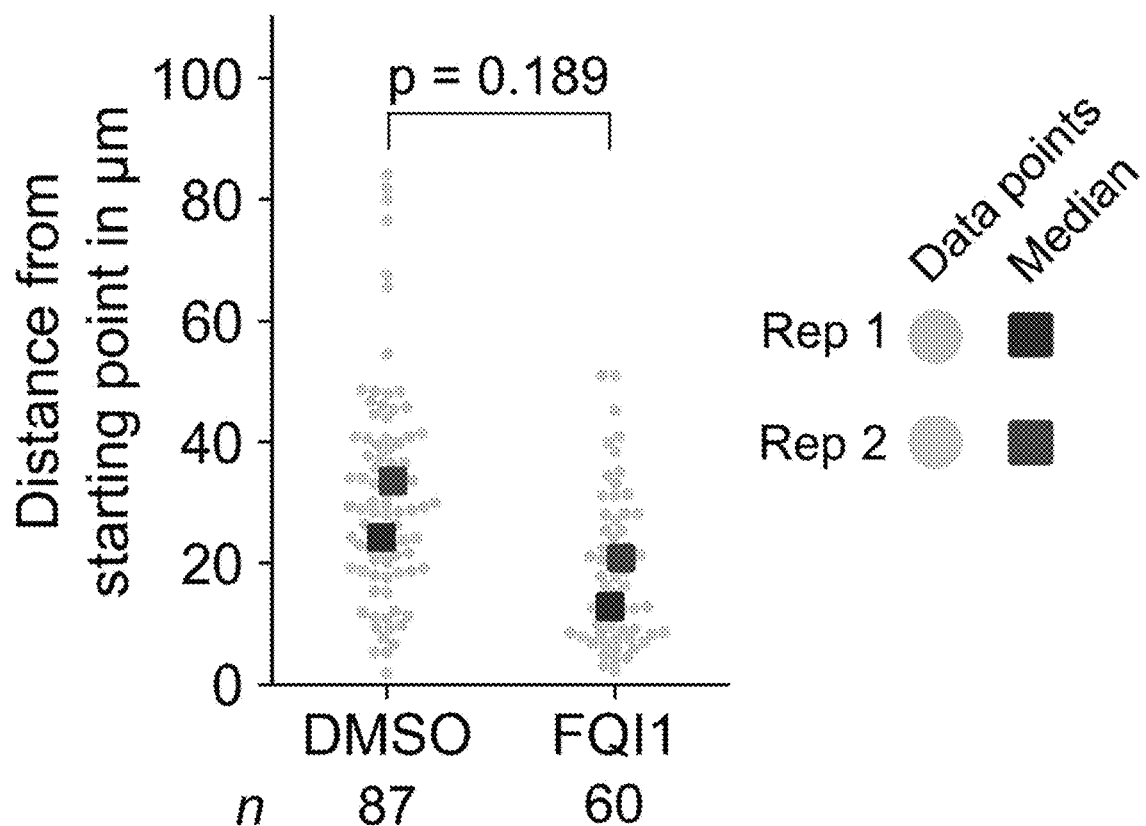

The migratory behaviors of both FH-B and RPE cells in the presence or absence of FQI1 were directly analyzed by tracking the paths of individual cells using time-lapse microscopy. This experiment was performed in cells arrested in the cell cycle by a thymidine block, to avoid any possible concerns regarding cell cycle effects of FQI1. Cells were treated with FQI1 or vehicle for 1 hour and then stained with a live-cell nuclear dye for cell tracking, while maintaining cells in either FQI1 or vehicle treatment. Measuring the cell displacement over a 2-hour period from starting point to end point demonstrated that FQI1-treated FH-B cells display a significantly smaller range of motion than do control cells (FIGS. 4C and 4D). In RPE cells, there was also a clear trend towards motility being reduced in the presence of FQI1, although it did not reach the level of statistical significance (FIGS. 12A and 12B). This is consistent with the results from the wound healing assay performed with RPE cells, in which the difference in cell movement between FQI1- and control-treated cells was not statistically significant after 2 hours. The extent of FQI1-mediated changes to cell locomotion also appear to be cell type dependent, as the movement of FH-B cells was more oscillatory and stochastic in the presence of FQI1 (FIG. 4C), while the majority of RPE cells were simply decelerated by FQI1 (FIGS. 12A and 12B). Overall, the data indicate that FQI1 treatment diminishes directional cell motility.

Discussion

FQI1 is an anti-proliferative compound, which has demonstrated promise in curbing cancer cell growth in vitro and in vivo[15,16] Recent investigations showed that FQI1 causes mitotic arrest with condensed, but unaligned chromosomes by disrupting microtubule spindles[17,18] Interphase microtubules are also important in regulating cancer-promoting processes, such as cell migration[14]. Here, we present the significant cytoskeletal and morphological impact of FQI1 also on interphase cells, due to disruption of microtubules and microtubule-associated processes. Specifically, we demonstrate first that treatment with FQI1 initiates a rapid, microtubule-dependent compaction in immortalized human fetal hepatocytes (FH-B cells). Compaction occurred around 10-15 minutes after addition of FQI1. Microtubule depolymerization preceded this phenotype, with biochemical fractionation demonstrating a widespread reduction in the stable microtubule pool by 1 minute after FQI1 addition. The microtubule stabilizer taxol prevented FQI1-mediated cell compaction, signifying that microtubule depolymerization drives this cellular compression. The immediate perturbation of microtubules by FQI1 appears to be a general response, as it also occurs in immortalized retinal pigment epithelium (RPE) cells. Increases in cellular circularity and in visible microtubule ends at the cell anterior in FQI1-treated RPE cells also implicates FQI1 in perturbing cell polarization. FQI1-induced disruption of the microtubule network and of cell polarization led to the hypothesis that FQI1 would impede cell movement. Indeed, FQI1 treatment diminishes the ability of RPE cells to close a wound gap and overall reduces the rate and directionality of FH-B and RPE cells' movement. Taken together, our findings support a role for FQI1 in disrupting interphase microtubules, which reduces cell spreading and polarity, and overall impedes cell motility.

Our findings that FQI1 inhibits cell movement also argue for FQI1 being a so-called "migrastatic" compound[13] in parallel with being an anti-proliferative agent[15-17]. Due to the central role that cell migration plays in metastasis, FQI1's ability to impair cell motility could expand the repertoire of anti-cancer activities of the FQI family of compounds by dampening the metastatic potential. There is increasing acknowledgment that agents that disrupt microtubules have clinical success as chemotherapeutics due to their ability to dysregulate both mitotic and interphase microtubules[38-40]. The historical misconception that a higher mitotic index sets cancer cells apart from healthy cells, while in reality less than 10% of tumor cells are in mitosis[41-43], has been blamed for the clinical failure of anti-cancer agents targeting mitosis-specific targets, such as the cyclin-dependent, Aurora, and Polo-like kinases. What differentiates agents disrupting microtubules from these mitosis-specific agents is the ability to also inhibit interphase microtubules[14,40]. Beyond roles in mitosis, microtubules contribute to cancer survival and proliferation in numerous ways[44-46,] notably through metastasis' and neoangiogenesis by migrating endothelial cells[48]. Given the importance of non-mitotic microtubules in promoting tumor survival and growth, the demonstration that exposure to FQI1 causes disruption of interphase microtubules and impairment of cell motility further supports candidacy of FQIs as promising chemotherapeutics.

How microtubules are mechanistically destabilized upon exposure of cells to FQI1 is not yet defined. An insight is provided by the enhanced microtubule acetylation, a post-translational modification of α-tubulin located inside the microtubule lumen, which is generally associated with long-lived and stable microtubules[49]. The combination of depolymerization and hyperacetylation sets FQI1 apart from the tested microtubule targeting agents: nocodazole depolymerized and deacetylated microtubules, while taxol stabilized and hyperacetylated microtubules. However, vinblastine can both disrupt microtubules and enhance acetylation of the remaining microtubules, likely due its idiosyncratic conformational restructuring of protofilaments to generate spiral aggregates[50,51]. Similarly, the distinct impact of FQI1 exposure on microtubules could indicate a unique type of FQI1-induced microtubule injury. Multiple mechanisms have been proposed for the tubulin acetyltransferase, αTAT1, to access the microtubule lumen to acetylate α-tubulin. Either open microtubule ends or gaps in the polymer lattice due to mechanical damage or bending can provide entry points for αTAT1[25-28]. Initially, a patch of acetylated α-tubulin is generated at the site of entry, followed by slower extension of the acetylated region down the lumen. In the case of FQI1, the increase in visible microtubule ends at the cellular periphery indicates that αTAT1 could enter the microtubule lumen mainly through these open polymer ends. On the other hand, given the significant increase in microtubule acetylation of the remaining microtubule structures, FQI1 treatment might either directly or indirectly also mechanically injure the microtubule lattice, by means of polymer bending or breaking, or alter the conformation of adjacent protofilaments thereby allowing additional access of αTAT1 to the microtubule lumen. Whether tubulin acetylation is enhanced by microtubule lumen accessibility solely through open ends or in combination with lattice breaks or conformational effects remains to be explored.

A crucial aspect of the mechanism behind FQI1's impact on microtubules is whether or not it involves FQI1's intended target protein, the transcription factor LSF (TFCP2). FQI1 was originally identified as a lead compound capable of inhibiting LSF's ability to transactivate target genes. Given that elevated LSF expression can promote oncogenesis, such as in hepatocellular carcinoma[15,52], these small molecule LSF inhibitors were viewed as having potential for development of cancer chemotherapeutics. An increasing number of cancer types are being identified in which LSF is overexpressed and contributes to tumorigenic phenotypes[53-55]. The mechanism of action through which FQI1 inhibits proliferation of cancer cells in culture has uncovered disruption of mitotic microtubules and induction of a mitotic arrest[16-18]. Although the possibility that FQI1 exerts antimitotic activity through off-target effects has not been ruled out, several lines of evidence point towards LSF being the specific target of FQI1. Notably, knocking down LSF via siRNA generated a similar mitotic arrest to that of FQI1[17]. Furthermore, the $IC_{50}$ of FQI1-mediated inhibition of LSF linearly correlates with the $GI_{50}$ of FQI1-induced cell growth inhibition[56]. Finally, LSF directly binds α-tubulin[19] and can enhance tubulin polymerization in vitro[57], indicating that LSF was a microtubule-associated protein. In support of this notion, mass spectrometry analysis of LSF interacting proteins in mitotic cell lysates showed association between LSF and a number of microtubule-associated proteins that are involved in spindle assembly and dynamics[18]. In interphase, although LSF is predominantly localized in the nucleus, as consistent with its role as a transcription factor, LSF is also localized in the cytoplasm, with levels varying in a cell-type and condition-dependent manner[58-60]. With regards specifically to the effects of FQIs on interphase microtubules, we demonstrate here that the more efficacious FQI2-34, which also binds LSF, induces cell compaction in FH-B cells at concentrations 20-fold lower than the effective FQI1 concentrations (FIGS. 6C and 6D). Because the concentration of FQI2-34 that alters interphase cell shape is comparable to the concentration needed to inhibit cell growth, this is consistent with LSF being the mediator of the effects of the compound on interphase microtubules.

LSF has been shown to regulate cell migration, invasion, and metastasis, although these functions were reported to result from transcriptional regulation of genes important for these processes[52,59,61,62]. In addition to FQI1 inhibiting the DNA-binding activity of LSF[15], which requires oligomerization of the LSF stable dimers to homo-tetramers, FQI1 also inhibit the interaction of LSF with other specific protein partners, including several microtubule-associated proteins[18,63]. Given the speed with which microtubules and cell shapes respond to FQI1 treatment in the FH-B and RPE cells, we therefore hypothesize that, if FQI1 effects are a faithful readout of LSF functionality, LSF is regulating these processes through dynamic protein-protein interactions. In particular, LSF may interact in interphase in a FQI1-sensitive manner with microtubule-associated proteins that stabilize the plus ends of microtubules at the cell periphery, or interfere with functions of microtubule-destabilizing proteins on the microtubules. Such dynamic LSF-protein interactions that directly and rapidly alter microtubule stability could function alongside slower LSF-mediated transcriptional outputs that could more permanently alter the cellular state.

Methods

Cell culture: FH-B cells were obtained from Sanjeev Gupta, Albert Einstein College of Medicine[64] and were cultured in DMEM with 10% FBS at 37° C. in 5% $CO_2$. FH-B cells were verified by assessing ALB and CYP2B expression, and confirming lack of FOXA2 expression. The RPE-hTERT Flp-In™ cell line[65] from Patrick Meraldi, Université de Genève), called RPE cells here, was cultured in HyClone DMEM with 10% FBS at 37° C. in 5% $CO_2$ and had been cultured periodically in 400 μg/mL zeocin to ensure maintenance.

Inhibitor treatments: FQI1 was synthesized as previously described[15] and dissolved in anhydrous DMSO. FQI1 and DMSO, along with nocodazole, taxol (Sigma Aldrich, T7402), and Y-27632 (Med Chem Express, 129830-38-2), were added directly into the cell culture dish from the stock solutions (final DMSO concentration 0.01%-0.02%), unless noted otherwise.

Microscopy for cell shape analysis: After seeding overnight in 35 mm, high μ-dishes (ibidi USA Inc., 81156), cells were treated as indicated in figure legends, washed twice in PBS and incubated in fixation buffer (3.7% formaldehyde in 100 mM PIPES at pH 6.8, 10 mM EGTA, 1 mM magnesium chloride, and 0.2% Triton X-100) for 10 minutes at room temperature. Cells were washed as before, treated with Phalloidin-iFluor 488 Reagent (abcam, ab176753) for 1 hour in 1-5% BSA in PBS, followed by Hoechst 33342 (Thermo Fisher Scientific, H3570) for 5 minutes. Mounting medium (Fisher Scientific, P10144) and cover slips were applied onto dried cells. Individually discernible cells were imaged on an Olympus Fluoview 10i. Using ImageJ, the phalloidin channel was thresholded and area and circularity values were measured and integrated into swarmplots using Python's seaborn library.

For time lapse microscopy, FH-B cells in high μ-dishes were incubated with CellBrite™ Steady Membrane stain (Biotium, 30108-T) for 30-40 minutes in the environmental chamber of a Nikon $C_2$ Si microscope at 37° C. and 5% $CO_2$. Treatments were added to the cells through a syringe to reach final concentrations of 4 μM FQI1 or 0.01% DMSO. Immediately thereafter, a time-lapse series was acquired by imaging every 30 seconds for 30 minutes at 20× magnification.

Cell cycle analysis by flow cytometry: After trypsinization, subsequent steps prior to staining were performed at 4° C. Cells in PBS were transferred dropwise into ethanol (final concentration of 70%) for overnight incubation. Fixed cells were washed with PBS and then incubated in 50 μg/ml propidium iodide and 10 µg/ml RNase A in PBS for 45 minutes at room temperature. After passage through a cell strainer, cell fluorescence was measured using a Becton Dickinson FACSCalibur. Ten thousand events were counted per sample. Histogram plots were generated using FlowJo.

Wound healing analysis: Confluent RPE cells were synchronized by incubating with 2 mM thymidine for 18-20 hours. Two intersecting lines were drawn into the confluent cells using a pipette tip. A phase-contrast image was acquired of the intersection point ("0 h" time-point) on an Olympus IX50 inverted microscope, immediately followed by treatment with the respective inhibitor and 2 mM thymidine. Phase-contrast images of the intersection point were acquired every 2 hours for 12 hours, continuing incubation at 37° C. in 5% $CO_2$ in-between time points. Using ImageJ, the distances between each pair of neighboring vertices of the intersection point at each time-point were measured and normalized to the "0 h" sample.

All the samples, including a "0 hour" synchronized and an asynchronous sample, were harvested and prepared for flow cytometry, as described above. The proportion of cells in their respective cell cycle phases was determined by applying the Dean-Jett-Fox model in the FlowJo Cell Cycle analysis tool.

Cell motility tracking: After overnight seeding in high µ-dishes, cells were synchronized by incubating in 2 mM thymidine for 18-20 hours. Thereafter, cells were treated with 4 µM FQI1 or vehicle (0.01% DMSO) for 1 hour, followed by a 10-min incubation in NucSpot® Live 650 dye (Biotium, 40082) following the manufacturer's instructions. Subsequently, cells were imaged every 2 minutes for 2 hours in an environmental chamber of a Nikon $C_2$ Si microscope at 37° C. and 5% $CO_2$ at 20× magnification. Cells that underwent mitosis during the 2-hour period were excluded from the analysis. Using ImageJ, individual nuclei were monitored using the Manual Tracking tool and the distances between starting and end points were integrated into swarmplots using Python's seaborn library.

Cell lysate preparation: For microtubule sedimentation assays, cells were treated as indicated in the figure legends, washed with PBS and incubated in 250 µl of microtubule sedimentation assay lysis buffer (100 mM PIPES pH 6.8, 2 M glycerol, 2 mM EGTA, 5 mM $MgCl_2$, 0.1% Triton X-100) supplemented with 1 µM taxol, protease inhibitor cocktail (1:200, Abcam, ab201111) and phosphatase inhibitor cocktail (1:100, Abcam, ab201115) for 20 minutes at 37° C. Two hundred µl of scraped lysate was centrifuged at 21,000×g for 10 minutes at room temperature. Supernatants were saved as soluble fractions. Pellets were resuspended in 200 µl RIPA buffer (50 mM Tris HCl pH 8.0, 150 mM NaCl, 1% IGEPAL CA630, 0.05% deoxycholic acid) supplemented with 1.05% SDS, protease inhibitor cocktail (1:200) and phosphatase inhibitor cocktail (1:100) and incubated at 100° C. for 15 minutes. Pellet suspensions were centrifuged as before and supernatants were saved as pellet fractions.

For analysis of phosphorylated MLC2, FH-B cells were treated as indicated in the figure legend, washed with PBS and incubated for 5 minutes in lysis buffer (50 mM Tris-HCl pH 8.0, 50 mM NaF, 5 mM $MgCl_2$, 150 mM NaCl, 1% Triton X-100) supplemented with Tricine Sample Buffer (Bio-rad, 1610739), protease inhibitor cocktail (1:200), phosphatase inhibitor cocktail (1:100), and 1% (3-mercaptomethanol. Lysates were incubated at 100° C. for 15 minutes and centrifuged at 21,000×g for 10 minutes prior to SDS-PAGE.

Gel electrophoresis and immunoblotting: Microtubule sedimentation fractions and MLC2 analysis samples were separated by electrophoresis through tris-glycine and tricine polyacrylamide gels, respectively, which were transferred to PVDF membranes. Membranes with microtubule sedimentation fractions and MLC2 analysis samples were blocked in 5% milk in TBST and in 5% BSA in TBST, respectively. After overnight incubation with primary antibody at 4° C., the membranes were washed and incubated with secondary antibody for 1 hour at room temperature. Primary antibodies included anti-α-tubulin (1:2,000, Thermo Fisher Scientific, PA529444), anti-acetylated tubulin (1:1,000, Sigma-Aldrich, T7451), anti-phospho MYL9 (1:200, Thermo Fisher Scientific, PA517727), and anti-β-actin (1:5,000, Sigma-Aldrich, A1978). Secondary antibodies included Goat anti-Rabbit HRP (Thermo Fisher Scientific, 31460; 1:10,000 for anti-α-tubulin; 1:5,000 for anti-phospho MYL9), and Goat anti-Mouse HRP (Thermo Fisher Scientific, 62-6520; 1:5,000 for anti-acetylated tubulin; 1:10,000-1:20,000 for anti-β-actin). Membranes were placed into Pierce™ ECL Western Blotting Substrate (Thermo Fisher Scientific, 32106). Autoradiography film was exposed to each membrane for various times to ensure acquisition of non-saturated exposures. Band intensities were quantified from scanned films by densitometry using ImageJ.

For reblotting, membranes were incubated in stripping buffer (200 mM glycine, 0.1% SDS, 1% Tween-20, pH 2.2) twice for 10 minutes, followed by two 10-minute washes in PBS and two 5-minute washes in TBST.

Analysis of microtubule features by immunofluorescence: Because Y-27632 diminishes FQI1-induced cell compaction (FIGS. 10C and 10D) without affecting microtubule levels (FIGS. 9A and 9B), cells were pretreated with Y-27632 in order to maintain overall cellular shape, facilitating capture of structural or positional impact of FQI1 on microtubules. In addition, only cells with cell spreading areas larger than 1000 µm$^2$ were considered. Cells were seeded overnight in high n-dishes, treated as indicated in the figure legends, fixed with formaldehyde as described above, blocked in 5% BSA in PBS and stained overnight at 4° C. with anti-γ-tubulin (1:500, Abcam, ab11316) and anti-α-tubulin (1:500, Fisher Scientific, 62204). Samples were then incubated in goat anti-rabbit Cy5 (1:1000, Invitrogen, A10523), goat anti-mouse Alexa Fluor 546 (1:1000, Thermo Fisher Scientific, A11003), and Phalloidin-iFluor 488 Reagent. Hoechst 33342 and mounting medium were applied, before acquiring Z stack images at 60× magnification on an Olympus Fluoview 10i microscope.

Using ImageJ, binary Z projections of Phalloidin and Hoechst channel stacks were merged with Z projections with average intensity of the α-tubulin channels. The Phalloidin channel was used as the region of interest for measurement of "integrated density" of the total α-tubulin intensity, which was plotted into swarmplots.

To assess distribution of visible microtubule ends, the Hoechst, γ-tubulin, and α-tubulin stacks were converted into Z projections with maximum intensity. The Hoechst and γ-tubulin Z projections were thresholded and all channels were merged. A line was generated between the γ-tubulin signal and the center of the nucleus to identify the axis of cell movement; a line perpendicular to the first line and running through the center point of the nucleus divided the cell into posterior and anterior portions. Visible microtubule ends were counted using the Cell Counter plugin, excluding unattached microtubule fragments.

Statistical analysis: In experiments involving large numbers of n, data points of each biological replicate were plotted with the respective median in swarmplots. Medians were chosen due to the non-normal distributions of these datasets. Due to batch effects, paired two-sample t-tests were used to assess statistical significance in cell spreading area experiments. Otherwise, unpaired two-sample t-tests were used. Outliers were excluded using Grubb's test ($\alpha=0.05$). P-values less than 0.05 were regarded as statistically significant.

References

1. Kunwar, P. S., Siekhaus, D. E. & Lehmann, R. In vivo migration: a germ cell perspective. *Annu. Rev. Cell Dev. Biol.* 22, 237-265 (2006).
2. Aman, A. & Piotrowski, T. Cell migration during morphogenesis. *Dev. Biol.* 341, 20-33 (2010).
3. Gaertner, F. et al. Migrating platelets are mechano-scavengers that collect and bundle bacteria. *Cell* 171, 1368-1382 (2017).
4. Hampton, H. R. & Chtanova, T. Lymphatic migration of immune cells. *Front. Immunol.* 10, 1168 (2019).
5. Kaneko, N., Sawada, M. & Sawamoto, K. Mechanisms of neuronal migration in the adult brain. *J. Neurochem.* 141, 835-847 (2017).
6. Luster, A. D., Alon, R. & von Andrian, U. H. Immune cell migration in inflammation: present and future therapeutic targets. *Nat. Immunol.* 6, 1182-1190 (2005).
7. Lambert, A. W., Pattabiraman, D. R. & Weinberg, R. A. Emerging biological principles of metastasis. *Cell* 168, 670-691 (2017).
8. Etienne-Manneville, S. Microtubules in cell migration. *Annu. Rev. Cell Dev. Biol.* 29, 471-499 (2013).
9. Garcin, C. & Straube, A. Microtubules in cell migration. *Essays Biochem.* 63, 509-520 (2019).
10. Seetharaman, S. & Etienne-Manneville, S. Microtubules at focal adhesions—a double-edged sword. *J. Cell Sci.* 132, jcs232843 (2019).
11. Ganguly, A., Yang, H., Sharma, R., Patel, K. D. & Cabral, F. The role of microtubules and their dynamics in cell migration. *J. Biol. Chem.* 287, 43359-43369 (2012).
12. Steeg, P. S. & Theodorescu, D. Metastasis: a therapeutic target for cancer. *Nat. Clin. Pract. Oncol.* 5, 206-219 (2008).
13. Gandalovičová, A. et al. Migrastatics-anti-metastatic and anti-invasion drugs: promises and challenges. *Trends in Cancer* 3, 391-406 (2017).
14. Ogden, A., Rida, P. C. G., Reid, M. D. & Aneja, R. Interphase microtubules: chief casualties in the war on cancer? *Drug Discov. Today* 19, 824-829 (2014).
15. Grant, T. J. et al. Antiproliferative small-molecule inhibitors of transcription factor LSF reveal oncogene addiction to LSF in hepatocellular carcinoma. *Proc. Natl. Acad. Sci. U.S.A.* 109, 4503-4508 (2012).
16. Rajasekaran, D. et al. Small molecule inhibitors of Late SV40 Factor (LSF) abrogate hepatocellular carcinoma (HCC): evaluation using an endogenous HCC model. *Oncotarget* 6, 26266-26277 (2015).
17. Willoughby, J. L. S. et at Targeting the oncogene LSF with either the small molecule inhibitor FQI1 or siRNA causes mitotic delays with unaligned chromosomes, resulting in cell death or senescence. *BMC Cancer* 20, 552 (2020).
18. Yunes, S. A. The anti-cancer compound, Factor Quinolinone Inhibitor 1, inhibits stable kinetochore-microtubule attachment during mitotic progression. *PhD Thesis, Boston University* (2020).
19. Chin, H. G. et al. The microtubule-associated histone methyltransferase SET8, facilitated by transcription factor LSF, methylates α-tubulin. *J. Biol. Chem.* 295, 4748-4759 (2020).
20. Stoiber, P. et al. Expansile nanoparticles encapsulate Factor Quinolinone Inhibitor 1 and accumulate in murine liver upon intravenous administration. *Biomacromolecules* 21, 1499-1506 (2020).
21. Molina, D. M. et al. Monitoring drug target engagement in cells and tissues using the cellular thermal shift assay. *Science* 341, 84-87 (2013).
22. Jafari, R. et al. The cellular thermal shift assay for evaluating drug target interactions in cells. *Nat. Protoc.* 9, 2100-2122 (2014).
23. Rappel, W.-J. & Edelstein-Keshet, L. Mechanisms of cell polarization. *Curr. Opin. Syst. Biol.* 3, 43-53 (2017).
24. Ly, N. et al. αTAT1 controls longitudinal spreading of acetylation marks from open microtubules extremities. *Sci. Rep.* 6, 35624 (2016).
25. Coombes, C. et at Mechanism of microtubule lumen entry for the α-tubulin acetyltransferase enzyme αTAT1. *Proc. Natl. Acad. Sci. U.S.A.* 113, E7176-E7184 (2016).
26. Portran, D., Schaedel, L., Xu, Z., Théry, M. & Nachury, M. V. Tubulin acetylation protects long-lived microtubules against mechanical ageing. *Nat. Cell Biol.* 19, 391-398 (2017).
27. Xu, Z. et at Microtubules acquire resistance from mechanical breakage through intralumenal acetylation. *Science* 356, 328-332 (2017).
28. Eshun-Wilson, L. et at Effects of α-tubulin acetylation on microtubule structure and stability. *Proc. Natl. Acad. Sci. U.S.A.* 116, 10366-10371 (2019).
29. Luxton, G. W. G. & Gundersen, G. G. Orientation and function of the nuclear-centrosomal axis during cell migration. *Curr. Opin. Cell Biol.* 23, 579-588 (2011).
30. Zhang, J. & Wang, Y.-L. Centrosome defines the rear of cells during mesenchymal migration. *Mol. Biol. Cell* 28, 3240-3251 (2017).
31. Wadsworth, P. Regional regulation of microtubule dynamics in polarized, motile cells. *Cell Motil. Cytoskeleton* 42, 48-59 (1999).
32. Niethammer, P., Bastiaens, P. & Karsenti, E. Stathmin-tubulin interaction gradients in motile and mitotic cells. *Science* 303, 1862-1866 (2004).
33. Chang, Y.-C., Nalbant, P., Birkenfeld, J., Chang, Z.-F. & Bokoch, G. M. GEF-H1 couples nocodazole-induced microtubule disassembly to cell contractility via RhoA. *Mol. Biol. Cell* 19, 2147-2153 (2008).
34. Takesono, A., Heasman, S. J., Wojciak-Stothard, B., Garg, R. & Ridley, A. J. Microtubules regulate migratory polarity through Rho/ROCK signaling in T cells. *PLoS One* 5, e8774 (2010).
35. Hui, K. L. & Upadhyaya, A. Dynamic microtubules regulate cellular contractility during T-cell activation. *Proc. Natl. Acad. Sci. U.S.A.* 114, E4175-E4183 (2017).
36. Hanna, S. & El-Sibai, M. Signaling networks of Rho GTPases in cell motility. *Cell. Signal.* 25, 1955-1961 (2013).
37. Lawson, C. D. & Ridley, A. J. Rho GTPase signaling complexes in cell migration and invasion. *J. Cell Biol.* 217, 447-457 (2018).
38. Komlodi-Pasztor, E., Sackett, D., Wilkerson, J. & Fojo, T. Mitosis is not a key target of microtubule agents in patient tumors. *Nat. Rev. Clin. Oncol* 8, 244-250 (2011).
39. Field, J. J., Kanakkanthara, A. & Miller, J. H. Microtubule-targeting agents are clinically successful due to both mitotic and interphase impairment of microtubule function. *Bioorg. Med. Chem.* 22, 5050-5059 (2014).
40. Kaul, R., Risinger, A. L. & Mooberry, S. L. Microtubule-targeting drugs: more than antimitotics. *J. Nat. Prod.* 82, 680-685 (2019).

41. Mitchison, T. J. The proliferation rate paradox in antimitotic chemotherapy. *Mol. Biol. Cell* 23, 1-6 (2012).
42. Yan, V. C. et al. Why great mitotic inhibitors make poor cancer drugs. *Trends in Cancer* 6, 924-941 (2020).
43. Dominguez-Brauer, C. et al. Targeting mitosis in cancer: emerging strategies. *Mol. Cell* 60, 524-536 (2015).
44. Schnaeker, E.-M. et al. Microtubule-dependent matrix metalloproteinase-2/matrix metalloproteinase-9 exocytosis: prerequisite in human melanoma cell invasion. *Cancer Res.* 64, 8924-8931 (2004).
45. Sevko, A. et al. Antitumor effect of paclitaxel is mediated by inhibition of myeloid-derived suppressor cells and chronic inflammation in the spontaneous melanoma model. *J. Immunol.* 190, 2464-2671 (2013).
46. Poruchynsky, M. S. et al. Microtubule-targeting agents augment the toxicity of DNA-damaging agents by disrupting intracellular trafficking of DNA repair proteins. *Proc. Natl. Acad. Sci. U.S.A.* 112, 1571-1576 (2015).
47. Fife, C. M., McCarroll, J. A. & Kavallaris, M. Movers and shakers: cell cytoskeleton in cancer metastasis. *Br. J. Pharmacol.* 171, 5507-5523 (2014).
48. Pasquier, E., Honoré, S. & Braguer, D. Microtubule-targeting agents in angiogenesis: where do we stand? *Drug Resist. Updat.* 9, 74-86 (2006).
49. Janke, C. The tubulin code: molecular components, readout mechanisms, and functions. *J. Cell Biol.* 206, 461-472 (2014).
50. Gigant, B. et al. Structural basis for the regulation of tubulin by vinblastine. *Nature* 435, 519-522 (2005).
51. Xie, R., Nguyen, S., McKeehan, W. L. & Liu, L. Acetylated microtubules are required for fusion of autophagosomes with lysosomes. *BMC Cell Biol.* 11, 89 (2010).
52. Yoo, B. K. et al. Transcription factor Late SV40 Factor (LSF) functions as an oncogene in hepatocellular carcinoma. *Proc. Natl. Acad. Sci. U.S.A.* 107, 8357-8362 (2010).
53. Jiang, H. et al. LSF expression and its prognostic implication in colorectal cancer. *Int. J. Clin. Exp. Pathol* 7, 6024-6031 (2014).
54. Yuedi, D. et al. TFCP2 activates beta-catenin/TCF signaling in the progression of pancreatic cancer. *Oncotarget* 8, 70538-70549 (2017).
55. Kotarba, G., Krzywinska, E., Grabowska, A. I., Taracha, A. & Wilanowski, T. TFCP2/TFCP2L1/UBP1 transcription factors in cancer. *Cancer Lett.* 420, 72-79 (2018).
56. Biagi, J. M. Assessing the selectivity and efficacy of dihydroquinolinone inhibitors directly targeting the oncogene LSF. *PhD Thesis, Boston University* (2017).
57. Chin, H. G. Transcription factor LSF: interactions with protein partners leading to epigenetic regulation and microtubule modifications. *PhD Thesis, Boston University* (2017).
58. Kashour, T., Burton, T., Dibrov, A. & Amara, F. M. Late Simian virus 40 transcription factor is a target of the phosphoinositide 3-kinase/Akt pathway in anti-apoptotic Alzheimer's amyloid precursor protein signalling. *Biochem. J.* 370, 1063-1075 (2003).
59. Porta-de-la-Riva, M. et al. TFCP2c/LSF/LBP-1c is required for Snail1-induced fibronectin gene expression. *Biochem. J.* 435, 563-568 (2011).
60. https://www.proteinatlas.org/ENSG00000135457-TFCP2/cell
61. Santhekadur, P. K. et al. Late SV40 factor (LSF) enhances angiogenesis by transcriptionally up-regulating matrix metalloproteinase-9 (MMP-9). *J. Biol. Chem.* 287, 3425-3432 (2012).
62. Xu, X. et al. Characterization of genome-wide TFCP2 targets in hepatocellular carcinoma: implication of targets FN1 and TJP1 in metastasis. *J. Exp. Clin. Cancer Res.* 34, 6 (2015).
63. Chin, H. G. et al. Transcription factor LSF-DNMT1 complex dissociation by FQI1 leads to aberrant DNA methylation and gene expression. *Oncotarget* 7, 83627-83640 (2016).
64. Wege, H. et al. Telomerase reconstitution immortalizes human fetal hepatocytes without disrupting their differentiation potential. *Gastroenterology* 124, 432-444 (2003).
65. Klebig, C., Korinth, D. & Meraldi, P. Bub1 regulates chromosome segregation in a kinetochore-independent manner. *J. Cell Biol.* 185, 841-858 (2009).

Supplementary Information

Synthesis of FQI2-34: Scheme 1 is a summary of the series of steps for synthesizing the final product, FQI2-34. Details are included in the Materials and Methods. The yields for each step are indicated underneath each arrow.

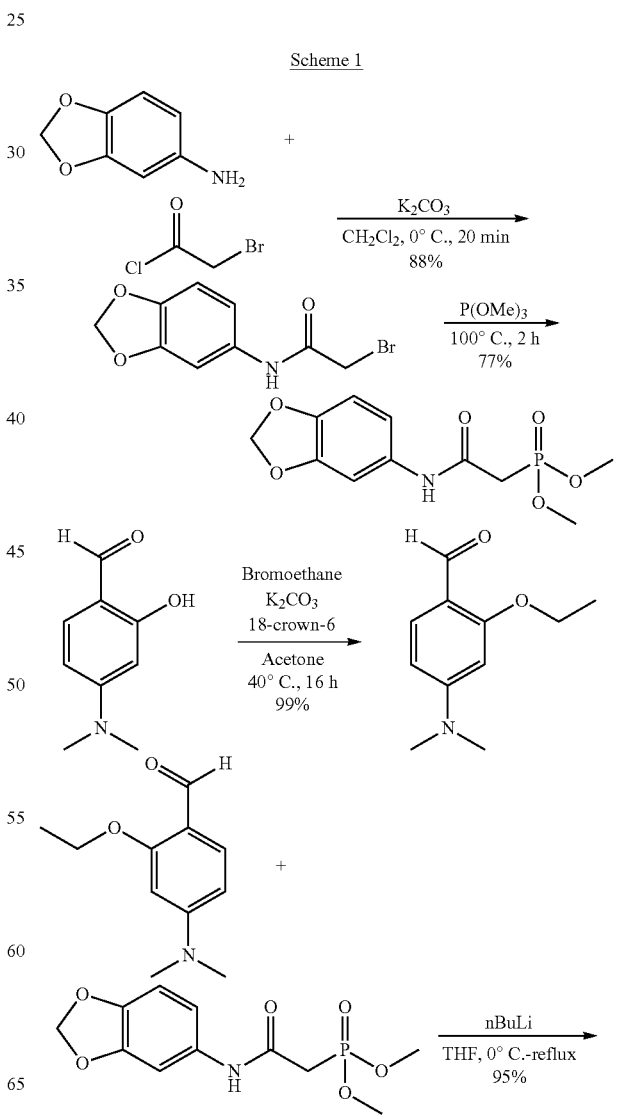

Scheme 1

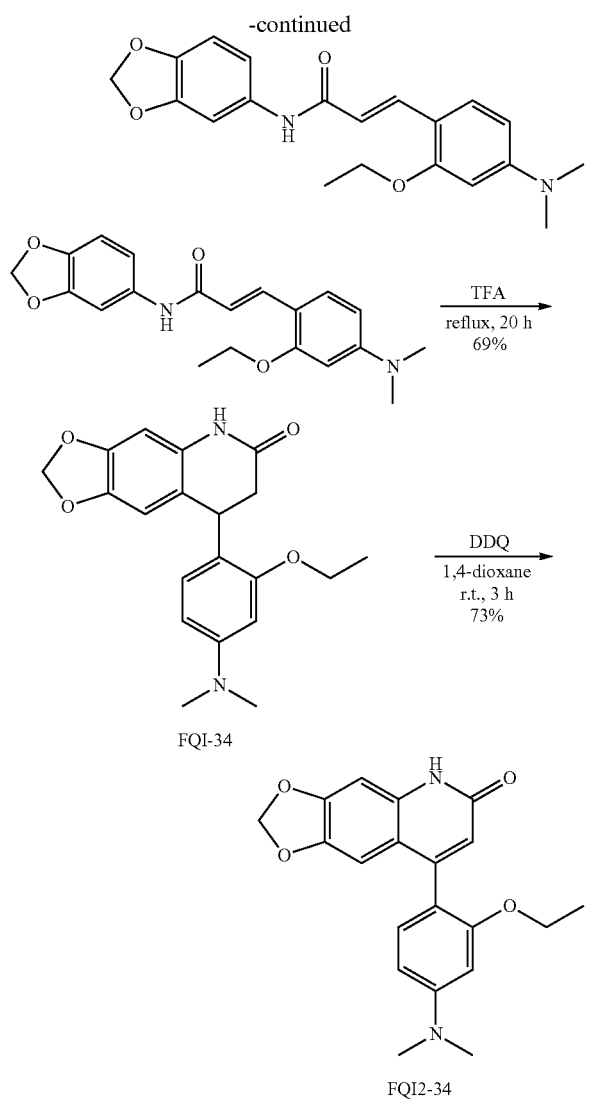

FQI-34

FQI2-34

Supplementary Methods

FQI2-34 Synthesis and Characterization: 41 NMR spectra were obtained at 400 MHz and referenced to the CHC13 singlet at 7.26 ppm, or the DMSO singlet at 2.50 ppm. $^{13}$C NMR spectra were obtained at 100 MHz, and referenced to the center peak of the CDCl$_3$ triplet at 77.16 ppm, or the center of the DMSO-d$_6$ septet at 39.51 ppm. Chemical shifts are reported in parts per million as follows: chemical shift, multiplicity (s=singlet, d=doublet, t=triplet, q=quartet, m=multiplet), coupling constant, and integration. High resolution mass spectrometry data were obtained on a Waters Qtof (hybrid quadrupolar/time-of-flight) API US system by electrospray (ESI) in the positive mode. Mass correction was done by an external reference using a Waters Lockspray accessory. Mobile phases were water and acetonitrile with 0.1% formic acid. The MS settings were: capillary voltage=3 kV, cone voltage=35, source temperature=120° C. and dissolvation temperature=350° C. Flash column chromatography was performed on Sorbent Technologies 60 Å silica gel.

FQI-34 and FQI2-34 were generally prepared according to patented procedures (Hansen et al., 2019; Schaus et al., 2020), with a few modifications as detailed in the following step-by-step protocol (Scheme 1).

N-(benzo[d][1,3]dioxol-5-yl)-2-bromoacetamide: A flame-dried 500-mL round bottomed flask equipped with a Teflon-coated magnetic stirbar under an argon atmosphere was charged with 3,4-(methylenedioxy)aniline (5.88 g, 42.9 mmol) and dry dichloromethane (100 mL, 0.43 M). (Note: 3,4-(methylenedioxy)aniline was recrystallized from hexanes prior to use). Vacuum oven-dried potassium carbonate (8.30 g, 60 mmol, 1.40 equiv) was added, and the reaction was cooled to 0° C. Bromoacetyl chloride (4.64 mL, 55.7 mmol, 1.30 equiv) was added via syringe and the reaction was stirred at 0° C. for 20 min and then allowed to warm to room temperature. Saturated aqueous sodium bicarbonate was added (100 mL) and the mixture was extracted with dichloromethane (3×150 mL). The combined organic layers were washed with saturated aqueous sodium chloride (100 mL), and dried over anhydrous sodium sulfate (Na$_2$SO$_4$). The filtrate was concentrated via rotary evaporation to afford N-(benzo[d][1,3]dioxol-5-yl)-2-bromoacetamide as a tan solid (9.73 g, 37.7 mmol, 88% yield, >97% purity), that was used without purification. $^1$H NMR (DMSO-d$_6$, 400 MHz) δ 10.30 (s, 1H), 7.27 (d, J=2.0 Hz, 1H), 6.96 (dd, J=8.4, 2.0 Hz, 1H), 6.87 (d, J=8.4 Hz, 1H), 5.98 (s, 2H), 4.00 (s, 2H). $^{13}$C NMR (DMSO-d$_6$, 100 MHz) δ 164.4, 147.1, 142.9, 133.0, 112.2, 108.1, 101.3, 101.1, 30.4. HRMS m/z 257.9771 [(M+H$^+$) calculated for C$_9$H$_9$BrNO$_3^+$: 257.9766].

Dimethyl (2-(benzo[d][1,3]dioxol-5-ylamino)-2-oxoethyl)phosphonate: A flame dried 50-mL round-bottomed flask equipped with a Teflon-coated magnetic stirbar under an argon atmosphere was charged with N-(benzo[d][1,3]dioxol-5-yl)-2-bromoacetamide (4.00 g, 15.5 mmol) and trimethyl phosphite (9.62 g, 9.16 mL, 77.5 mmol). The flask was fitted with a reflux condenser, rubber septum, and argon balloon. The reaction was heated to 100° C. for 2 hours, at which time the reaction was poured into a 500-mL separatory funnel, diluted with dichloromethane (250 mL), and washed with water (3×200 mL). The organic layer was rinsed with saturated aqueous sodium chloride (50 mL), and dried over anhydrous sodium sulfate (Na$_2$SO$_4$). The filtrate was concentrated in vacuo to afford a viscous oil that was left under high vacuum (0.4 mmHg) overnight. Then, the product was dissolved in dry toluene (50 mL) and concentrated via rotary evaporation to azeotrope any remaining trimethyl phosphite. The product was further dried under high vacuum (0.4 mmHg) to afford dimethyl (2-(benzo[d][1,3]dioxol-5-ylamino)-2-oxoethyl)phosphonate as a pale pink/purple solid (3.43 g, 77% yield, >98% purity) that was used without further purification. $^1$H NMR (CDCl3, 400 MHz) δ 8.89 (s, 1H), 7.18 (d, J=2.1 Hz, 1H), 6.79 (dd, J=8.4, 2.1 Hz, 1H), 6.65 (d, J=8.4 Hz, 1H), 5.91 (s, 2H), 3.82 (d=11.2 Hz, 6H), 3.01 (d, J=21.0 Hz, 2H). $^{13}$C NMR (CDCl3, 100 MHz) δ 161.7, 147.5, 144.0, 132.3, 112.8, 107.8, 102.4, 53.4, 35.9, 34.6. HRMS m/z 288.0630 [(M+H$^+$) calculated for C$_{11}$H$_{15}$BrNO$_6$P$^+$: 288.0637].

4-(dimethylamino)-2-ethoxybenzaldehyde: A flame-dried 250-mL round-bottomed flask equipped with a Teflon-coated magnetic stirbar under an argon atmosphere was charged with 4-(dimethylamino)-2-hydroxy-benzaldehye (4.13 g, 25 mmol) in acetone (83 mL, 0.30 M). Anhydrous potassium carbonate (5.18 g, 37.5 mmol), 18-crown-6 (330 mg, 1.25 mmol) and bromoethane (13.6 g, 125 mmol, 9.27 mL) were added to the reaction. The reaction mixture was fitted with a reflux glycol condenser and heated at 40° C. for 16 hours, then cooled to room temperature. The reaction was filtered and the filtered solid was washed with acetone. The filtrate was evaporated via rotary evaporation to yield 4-(dimethylamino)-2-ethoxy-benzaldehyde as a brown solid (3.87 g, >99% yield, 90% pure) that was used without further purification. $^1$H NMR (CDCl3, 400 MHz) δ 10.20 (s, 1H), 7.72 (d, J=8.8 Hz, 1H), 6.29 (dd, J=8.8, 2.3 Hz, 1H), 6.02 (d, J=2.3 Hz, 1H), 4.11 (q, J=7.0 Hz, 2H), 3.06 (s, 6H), 1.46 (t, J=7.0 Hz, 3H). $^{13}$C NMR (CDCl3, 100 MHz) 187.6, 163.4, 155.9, 129.8, 114.6, 104.50, 93.7, 70.0, 63.7, 40.2, 14.7. HRMS m/z 194.1176 [(M+H$^+$) calculated for $C_{11}H_{16}NO_2^+$: 194.1181].

(E)-N-(benzo[d][1,3]dioxol-5-yl)-3-(4-(dimethylamino)-2-ethoxyphenyl)acrylamide: A flame dried 25-mL round-bottomed flask equipped with a Teflon-coated magnetic stirbar was charged with dimethyl (2-(benzo[d][1,3]dioxol-5-ylamino)-2-oxoethyl)phosphonate (718 mg, 2.50 mmol) and THF (8.3 mL, 0.30 M). The flask was flushed with argon and fitted with a rubber septum and argon balloon, then cooled to 0° C. in an ice-water bath. n-Butyllithium (1.6 M in hexanes, 1.35 equiv) was added dropwise, and the mixture was allowed to warm to RT and stir for 30 min, at which time 4-(dimethylamino)-2-ethoxybenzaldehyde (387 mg, 2.0 mmol) was added as a single portion. The flask was fitted with a reflux condenser and argon balloon, and the mixture was heated to reflux for 22 h. The mixture was cooled to RT and quenched with saturated ammonium chloride (5 mL). The mixture was transferred to a 500-mL separatory funnel, and diluted with dichloromethane (150 mL) and water (50 mL). The dichloromethane layer was removed and washed with water (3×50 mL), then dried over anhydrous sodium sulfate ($Na_2SO_4$), filtered, and concentrated by rotary evaporation. The product was isolated as a yellow brown solid (671 mg, 95% yield, 5:1 E:Z) and used without further purification. $^1$H NMR (CDCl$_3$, 400 MHz) δ 7.90 (d, J=15.3 Hz, 1H), 7.07 (s, 1H), 7.35 (d, J=8.2 Hz, 1H), 6.84 (d, J=8.2 Hz, 1H), 6.73 (d, J=8.5 Hz, 1H), 6.44 (d, J=15.3 Hz, 1H), 6.27 (dd, J=8.5, 2.4 Hz, 1H), 6.14 (d, J=2.4 Hz, 1H), 5.93 (s, 2H), 4.09 (q, J=6.9 Hz, 2H), 3.00 (s, 6H), 1.47 (t, J=6.9 Hz, 3H). $^{13}$C NMR (CDCl$_3$, 100 MHz) 165.9, 159.7, 152.7, 147.6, 138.0, 135.2, 133.2, 130.3, 115.8, 112.8, 112.2, 108.0, 104.6, 102.7, 101.1, 97.2, 95.5, 63.7, 40.3, 14.9. HRMS m/z 355.1650 [(M+H$^+$) calculated for $C_{20}H_{23}N_2O_4^+$: 355.1650].

FQI-34 (8-(4-(dimethylamino)-2-ethoxyphenyl)-7,8-dihydro[1,3]dioxolo[4,5-g]quinolin-6(5H)-one): A flame-dried 25-mL round-bottomed flask equipped with a Teflon-coated magnetic stirbar was charged with (E)-N-(benzo[d][1,3]dioxol-5-yl)-3-(4-(dimethylamino)-2-ethoxyphenyl) acrylamide (580 mg, 1.64 mmol) and trifluoroacetic acid (11 mL, 0.15 M). The flask was flushed with argon, and fitted with a reflux condenser, a rubber septum, and an argon balloon and refluxed for 20 h. The resulting mixture was cooled to room temperature, and transferred to a 500-mL Erlenmeyer flask. The mixture was diluted with dichloromethane (150 mL) and cooled to 0° C. in an ice bath. The reaction mixture was quenched with saturated aqueous sodium bicarbonate (~100 mL) and then transferred to a 500-mL separatory funnel. The organic layer was removed, and the aqueous layer was extracted with dichloromethane (2×50 mL). The combined organic layers were washed with saturated aqueous sodium chloride (50 mL), dried over anhydrous sodium sulfate ($Na_2SO_4$), filtered, and concentrated via rotary evaporation. The crude product was purified via column chromatography (gradient from hexanes to 1:1 hexanes:ethyl acetate) to afford the desired product as a pale orange-yellow solid (400 mg, 69% yield, >99% pure). $^1$H NMR (CDCl3, 400 MHz) δ 7.79 (s, 1H), 6.73 (d, J=8.4 Hz, 1H), 6.47 (s, 1H), 6.35 (s, 1H), 6.27 (d, J=2.4 Hz, 1H), 6.22 (J=8.4, 2.4 Hz, 1H), 5.88 (s, 2H), 4.49 (dd, J=7.0, 7.0 Hz, 1H), 4.05 (m, 2H), 2.94-2.87 (overlap, 7H), 2.76 (dd, J=16.2, 6.4 Hz, 1H), 1.38 (t, 6.9 Hz, 3H). $^{13}$C NMR (CDCl$_3$, 100 MHz) δ 171.8, 157.1, 151.0, 147.2, 143.9, 131.5, 128.6, 119.8, 117.8, 108.4, 104.7, 108.4, 104.7, 101.1, 97.6, 97.0, 63.4, 40.8, 37.0, 35.1, 14.9. HRMS m/z 355.1648 [(M+H$^+$) calculated for $C_{20}H_{23}N_2O_4^+$: 355.1658].

FQI2-34 (8-(4-(dimethylamino)-2-ethoxyphenyl)-[1,3]dioxolo[4,5-g]quinolin-6(5H)-one): A flame-dried 25-mL round-bottomed flask equipped with a Teflon-coated magnetic stirbar was charged with 8-(4-(dimethylamino)-2-ethoxyphenyl)-[1,3]dioxolo[4,5-g]quinolin-6(5H)-one (280 mg, 0.79 mmol) and 1,4-dioxane (0.06 M). DDQ (179 mg, 1.0 equiv) was added and the reaction was stirred at room temperature for 3 hours and then concentrated via rotary evaporation. The resulting residue was dissolved in 2.5% aqueous potassium carbonate solution (30 mL) and extracted with dichloromethane (3×50 mL). The combined organic layers were washed with saturated sodium chloride, (50 mL), dried over anhydrous sodium sulfate (Na2SO4), and concentrated. The solid crude product was purified via column chromatography (gradient from 80% ethyl acetate in hexanes to 100% ethyl acetate to afford the desired product as an off-white solid (203 mg, 73% yield, >99% pure). $^1$H NMR (CDCl$_3$, 400 MHz) δ 12.14 (s, 1H), 7.10 (J=8.4 Hz, 1H), 6.92 (s, 1H), 6.76 (s, 1H), 6.53 (s, 1H), 6.41 (dd, J=8.4, 2.2 Hz, 1H), 6.33 (d, J=2.2 Hz, 1H), 5.99 (m, 1H), 5.96 (m, 1H), 4.00 (q, J=7.1 Hz, 2H), 3.04 (s, 6H), 1.19 (t, J=7.1 Hz, 3H). $^{13}$C NMR (CDCl$_3$, 100 MHz) δ 164.4, 156.8, 152.2, 151.5, 150.2, 143.9, 135.4, 131.2, 118.7, 115.4, 115.1, 105.1, 104.7, 101.5, 97.0, 96.2, 63.9, 40.5, 14.7. HRMS m/z 353.1494 [(M+H$^+$) calculated for $C_{20}H_{21}N_2O_4^+$: 353.1501].

MTS Cell Proliferation Assay: Three thousand FH-B cells were seeded per well in a 96-well plate and incubated at 37° C. for 20 hours. Compound dilutions were prepared in DMSO and added to the cell culture media to a final DMSO concentration of 1% for a 72 hour treatment. Cell growth inhibition was assessed by measuring absorbance at 490 nm using the Promega CellTiter 96® AQueous One Solution Cell Proliferation Assay (Promega, G358C). Percent growth inhibition was determined by the ratio of the absorbance of treatment wells to the absorbance of control wells. A non-linear regression plot of the percentage of growth inhibition versus compound concentration was prepared using Graph-Pad Prism software, using settings for the curves of variable slope and four parameters. The relative GI50 value was determined from the curve as the concentration of drug that provokes a response halfway between the top and bottom plateaus of the curve.

Cellular Thermal Shift Assay (CETSA): Huh7 cells obtained from JCRB (Japanese Cancer Resources Bank) were cultured in DMEM medium (Corning) supplemented with 10% fetal bovine serum (Gibco). The cells were cultured at 37° C. in 5% $CO_2$. Approximately 9×10$^5$ Huh7 cells were plated per 10 cm plate. After 20 hours, cells were treated for three hours with fresh media containing 50 μM FQI1, 50 μM FQI2-34, or 0.1% DMSO (FQI1 control) or 0.5% DMSO (FQI2-34 control). Subsequently, the cells were washed with PBS (137 mM NaCl, 2.7 mM KCl, 10 mM $Na_2HPO_4$, 2 mM $KH_2PO_4$, pH 7.2) supplemented with their respective treatments (FQI1, FQI2-34, or vehicle) and scraped from the dish in the presence of 5 mL of PBS supplemented with 1 mM Pefabloc (Sigma-Aldrich, 76307) plus the respective treatment. Pelleted cells were resuspended in 500 μL of PBS buffer with 1 mM Pefabloc plus the respective treatment. Aliquots of 50 μL of cell suspension from each treatment sample were incubated separately at the indicated temperatures for 3 minutes in a thermal cycler (Bio-rad, T100 Thermocyler), then cooled at the room temperature for 3 minutes. Lysates were prepared by four rounds of snap freezing and thawing. Soluble protein was separated from aggregates by centrifugation at 20,000×g for 10 minutes. 40 µL of each supernatant was used for immunoblot analysis. Lysates were separated by electrophoresis through 10% SDS polyacrylamide gels, in 25 mM Tris, 192 mM glycine, and 0.1% SDS. Gels were transferred to PVDF membranes and incubated in blocking buffer with 5% milk in TBST for 1 hour. Membranes were incubated overnight with anti-LSF antibody (1:1,000, BD Bioscience, 610818) at 4° C., and subsequently with goat anti-mouse HRP antibody (Thermo Fisher Scientific, 62-6520; 1:7,000) for 1 hour at room temperature. Films were scanned and band intensities were quantified by densitometry with Image J; a non-parametric t-test was used to determine statistical significance.

Example 3: Wound Healing Assay with FQI2-34

Methods

RPE-hTERT Flp-In cells, propagated in DME M:F12 media with 10% fetal bovine serum at 37° C. in a 5% $CO_2$ humidified incubator, were grown to confluence in 6-well tissue culture plates. One day prior to performing the wound healing assay, the medium was exchanged to also include 2 mM thymidine, so that the cells would stop dividing.

A cross-shaped wound was scratched into each well, and the cells imaged by phase contrast microscopy using at 4× magnification using a Olympus IX50 Inverted microscope. Then the cell media was exchanged to include vehicle (DMSO at 0.01%), 50 nM FQI2-34, 100 nM FQI2-34, or 200 nM FQI2-34; 2 mM thymidine was maintained throughout, as well. Cells were imaged again at 2 h, 4h, 6h, and 8h, in order to measure the migration of the cells into the wound.

Each of the 4 lines across the vertices of the "X" were individually measured from each set of images using ImageJ. Relative distances of cell migration into the wound were obtained by subtracting each of the lengths for 2-8 hour timepoints from the length at the 0 hour timepoint for that line and that sample. The averages of the four changes in lengths per sample were then plotted over time for each concentration of FQI2-34, from 0 to 100 nM, using Prism software. Triplicate technical replicates were performed for each concentration.

Results and Conclusions

Figure 4A:
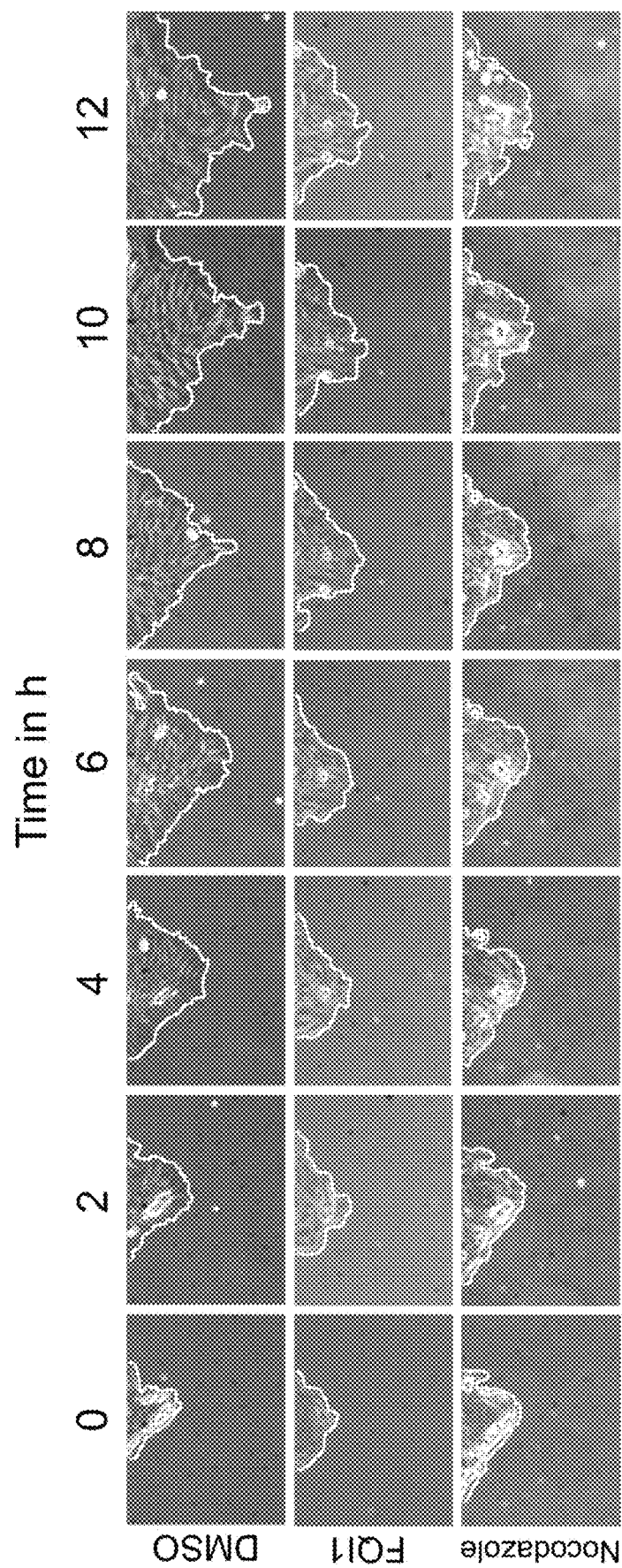
FIGS. 4A-4D show FQI1 impairs wound healing ability and cell motility.
Figure 4B:
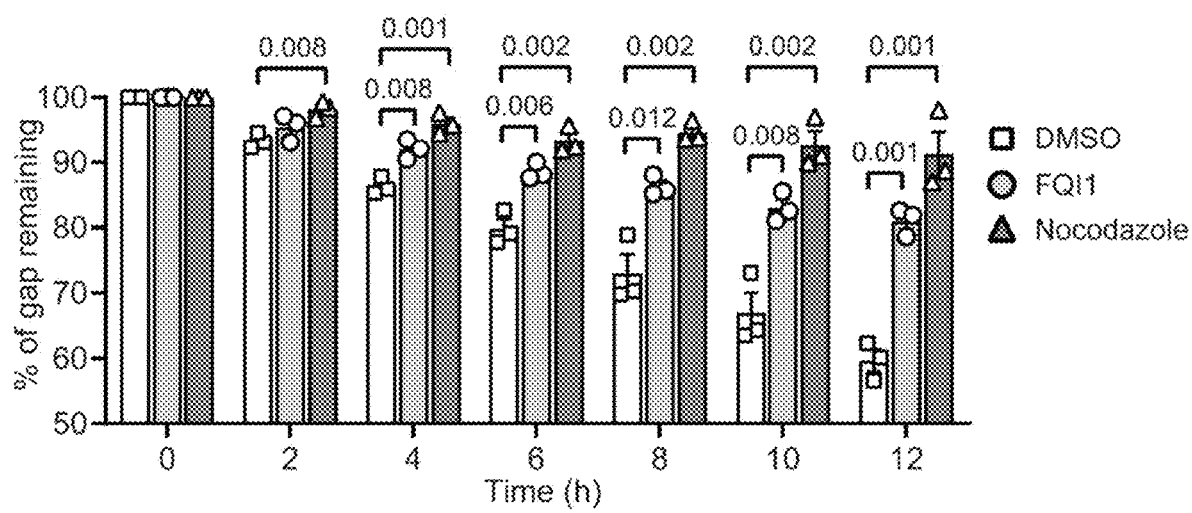
Figure 4C:
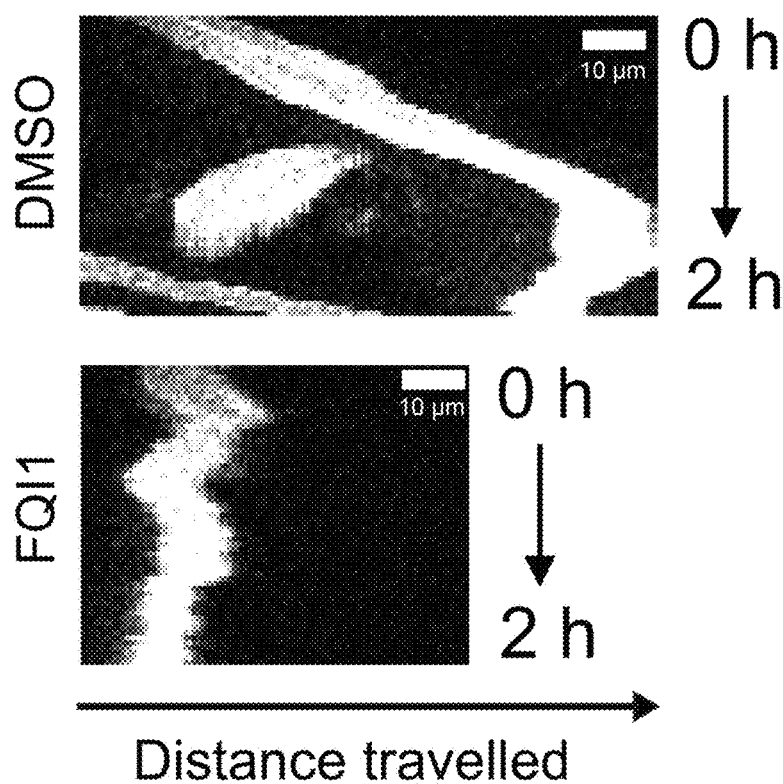
Figure 4D:
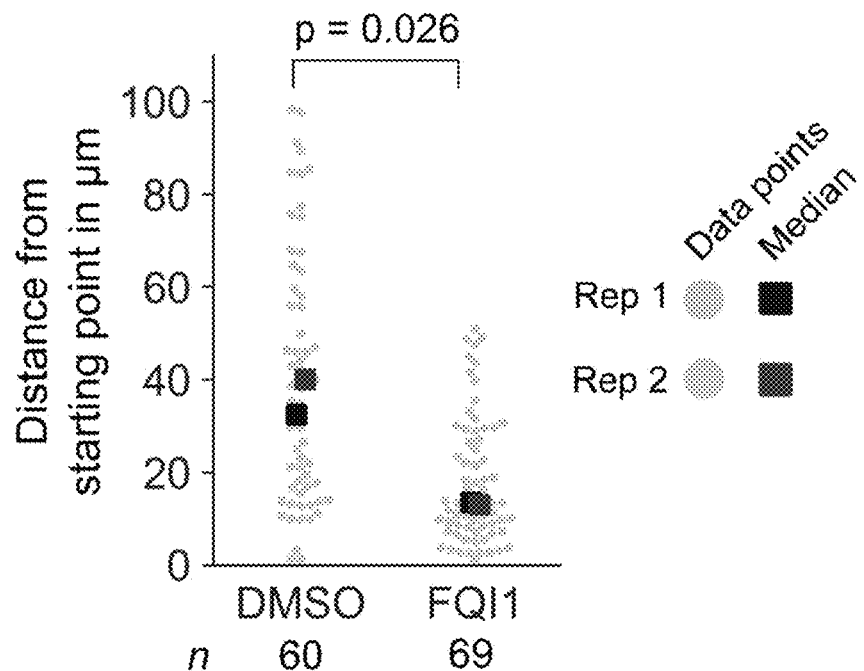
Figure 13:
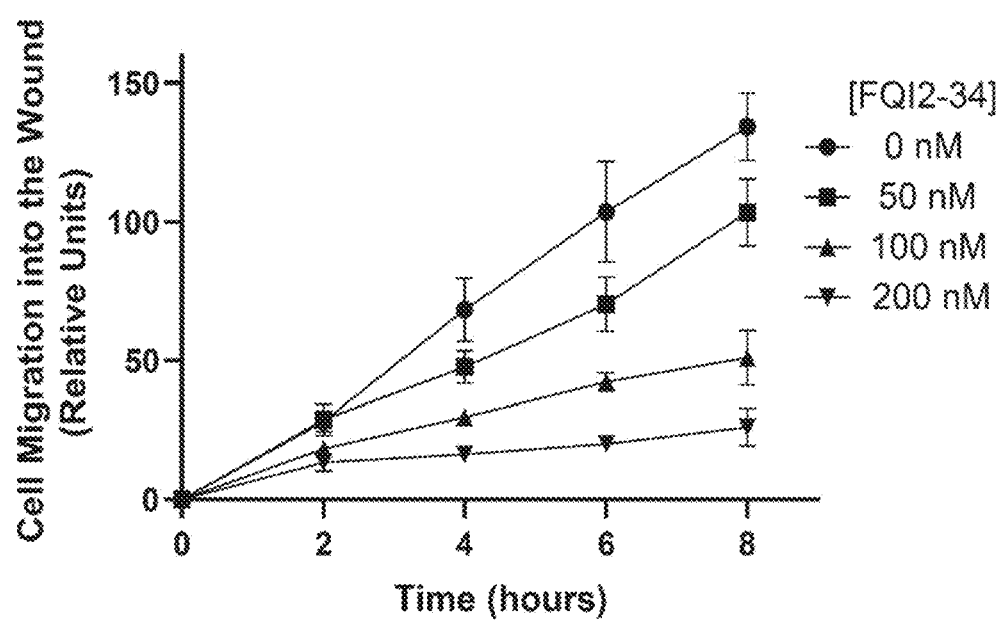
FIG. 13 shows FQI2-34 inhibits cell migration of RPE cells. Shown are measurements of the relative distances of cell migration of RPE cells in the presence of 0, 50, 100, and 200 nM FQI2-34. Means and standard deviations of technical triplicates are displayed. The data are representative of two independent biological experiments.
Figure 14B:
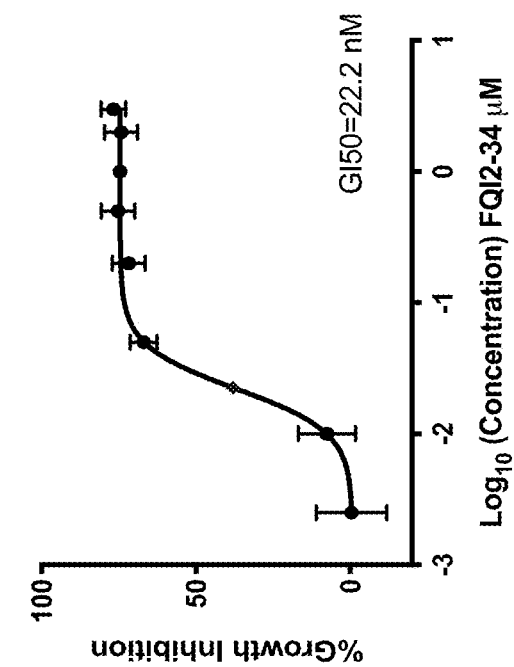
Figure 14A:
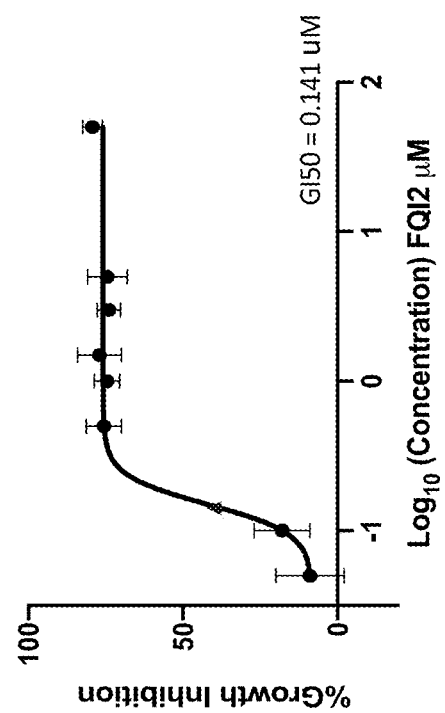
Figure 14E:
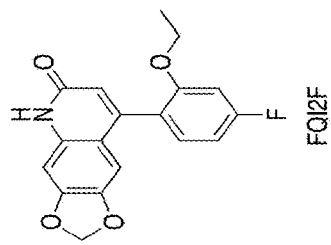
Figure 14E:
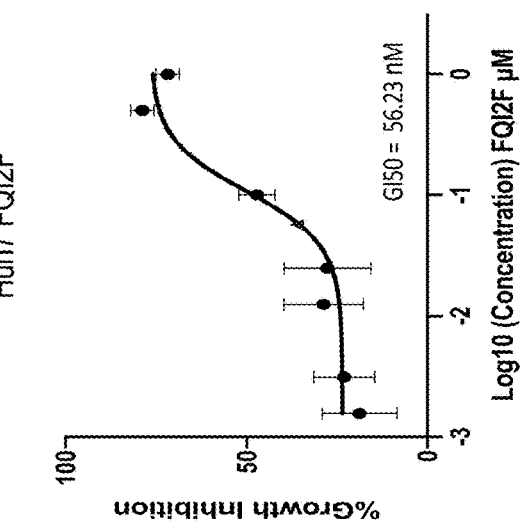
Figure 14D:
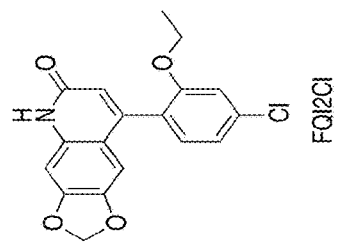
Figure 14D:
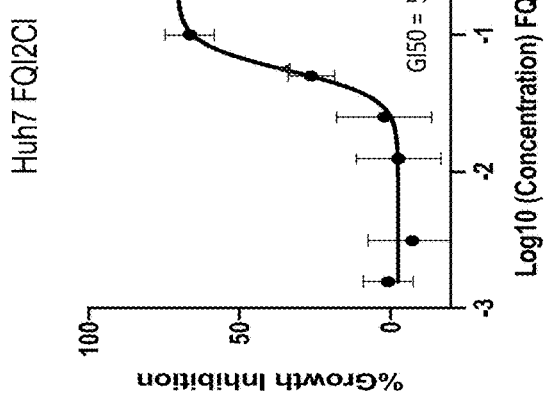
Figure 14C:
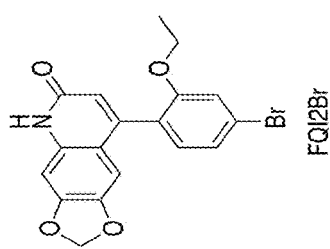
Figure 14C:
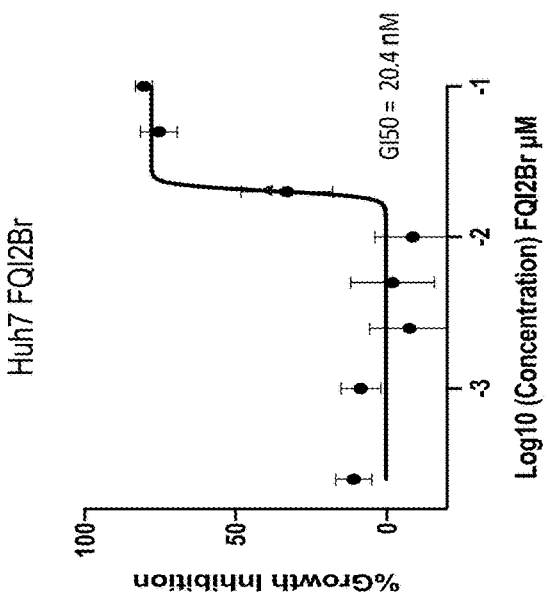
Figure 14H:
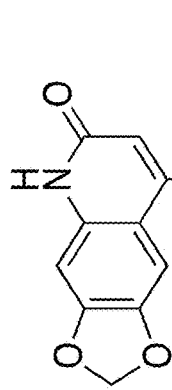
Figure 14H:
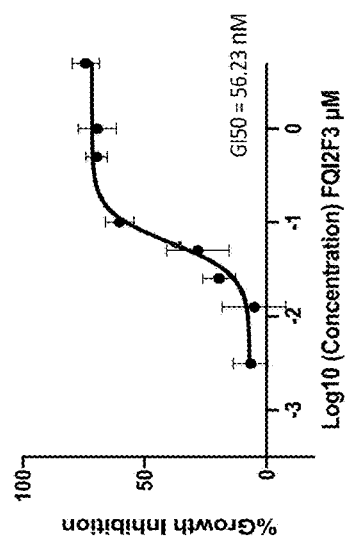
Figure 14G:
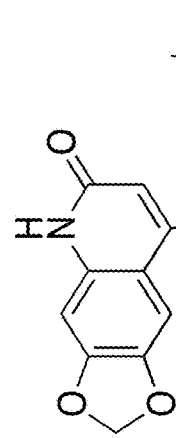
Figure 14G:
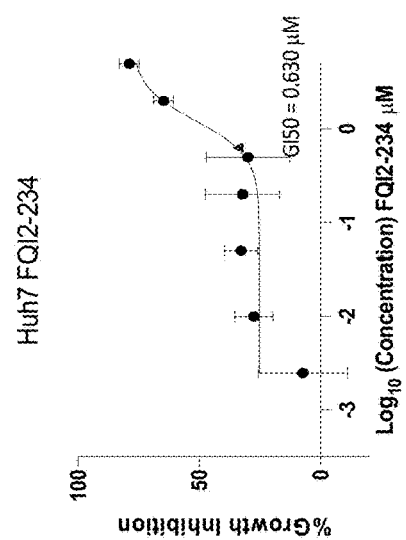
Figure 14F:
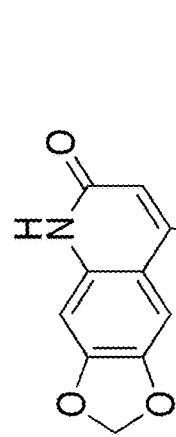
Figure 14F:
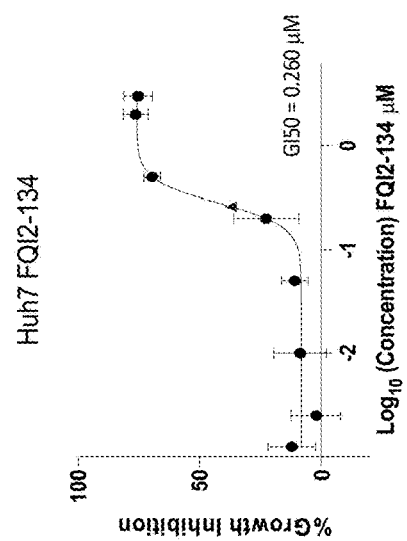
Figure 16A:
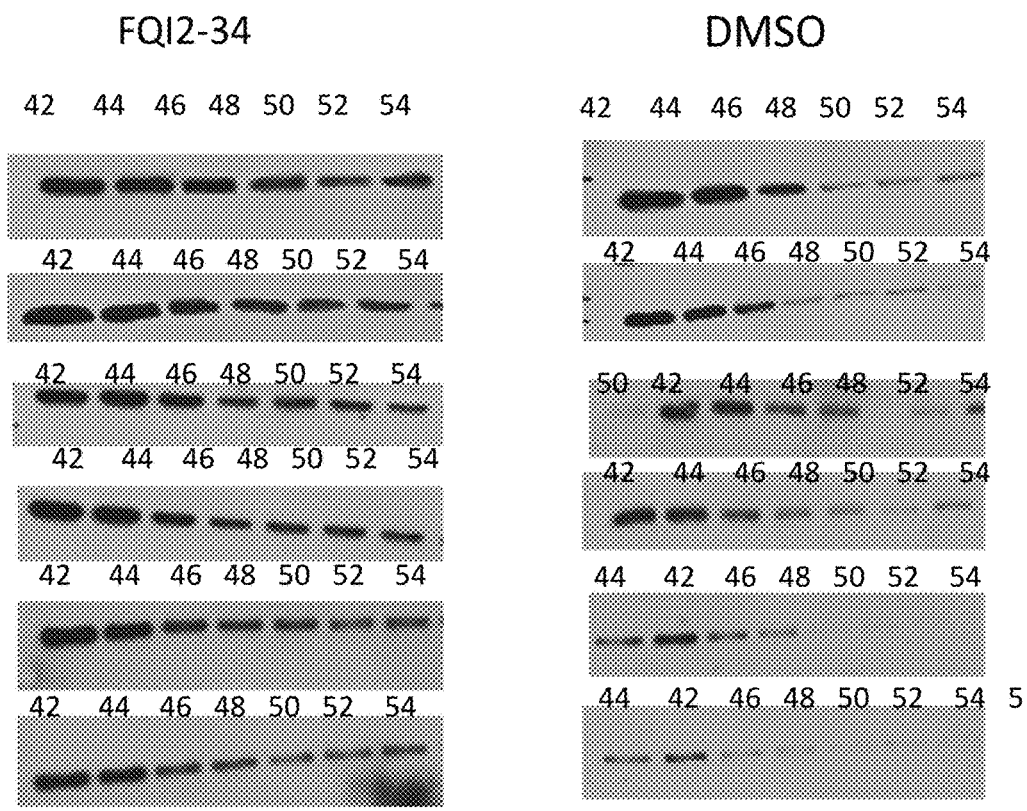
FIG. 16A-16C depict cellular thermal shift assay (CETSA) data for compound FQI2-34.
Figure 16B:
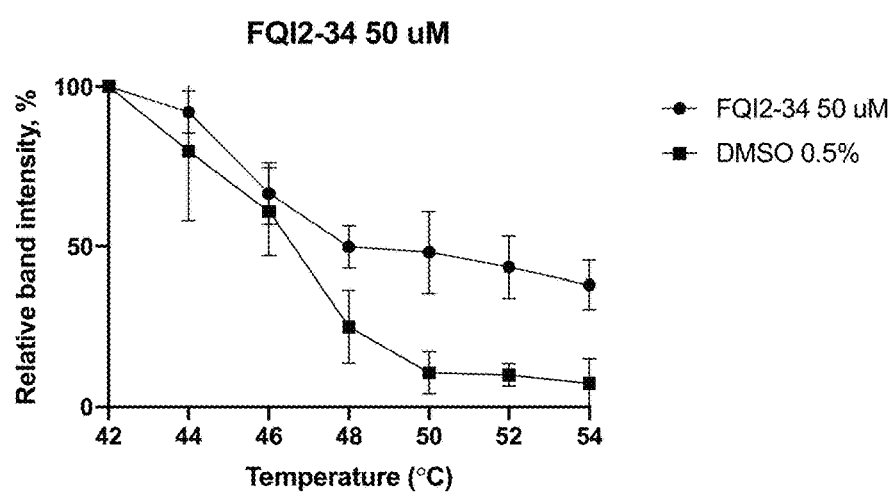
Figure 16C:
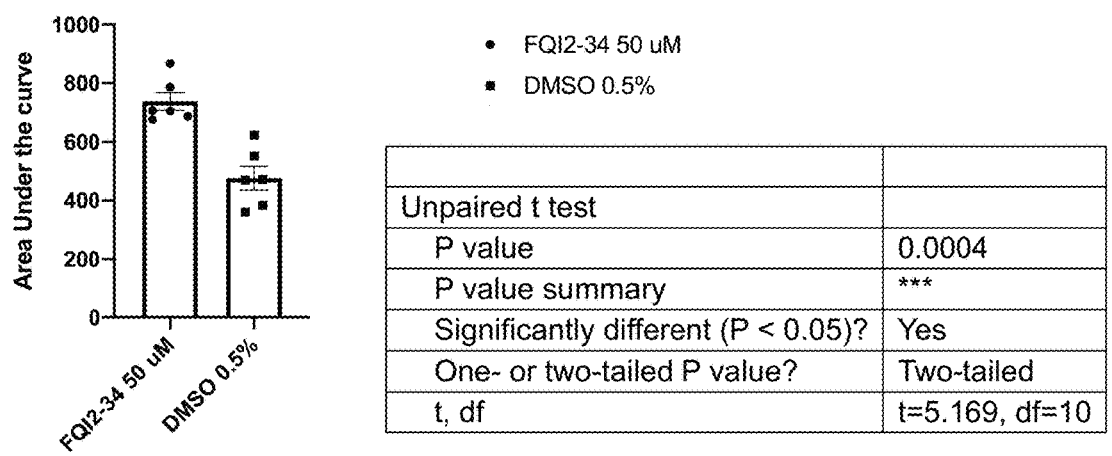
Figure 17A:
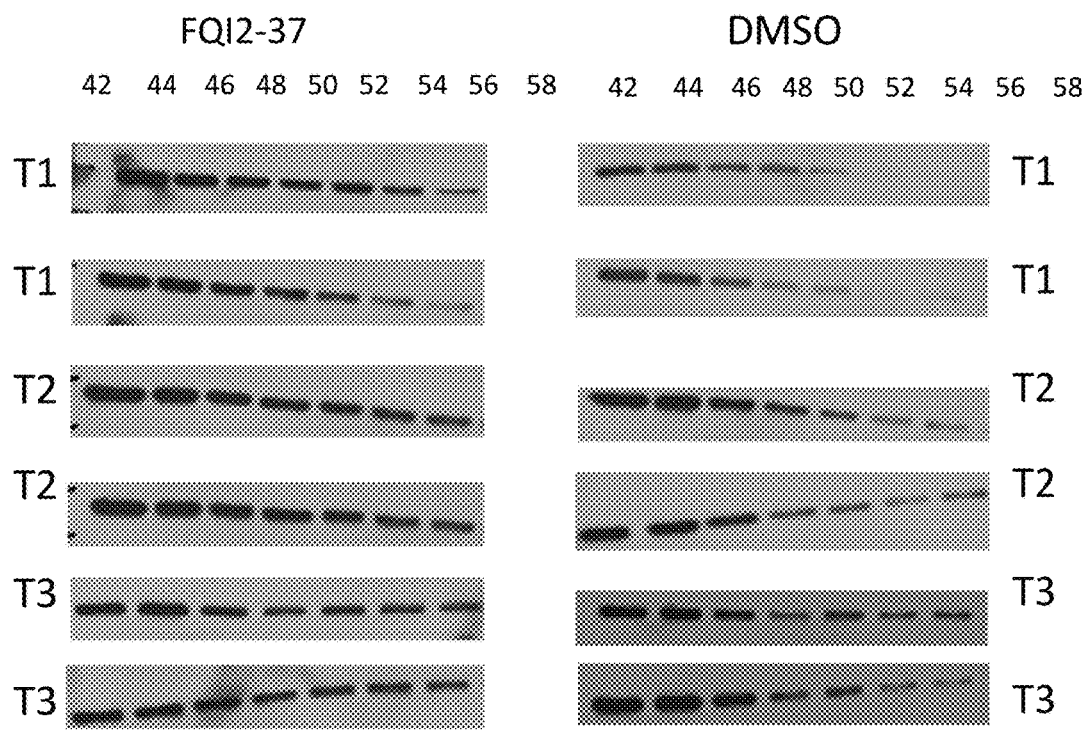
FIGS. 17A-17C depicts CETSA data for compound FQI2-37.
Figure 17B:
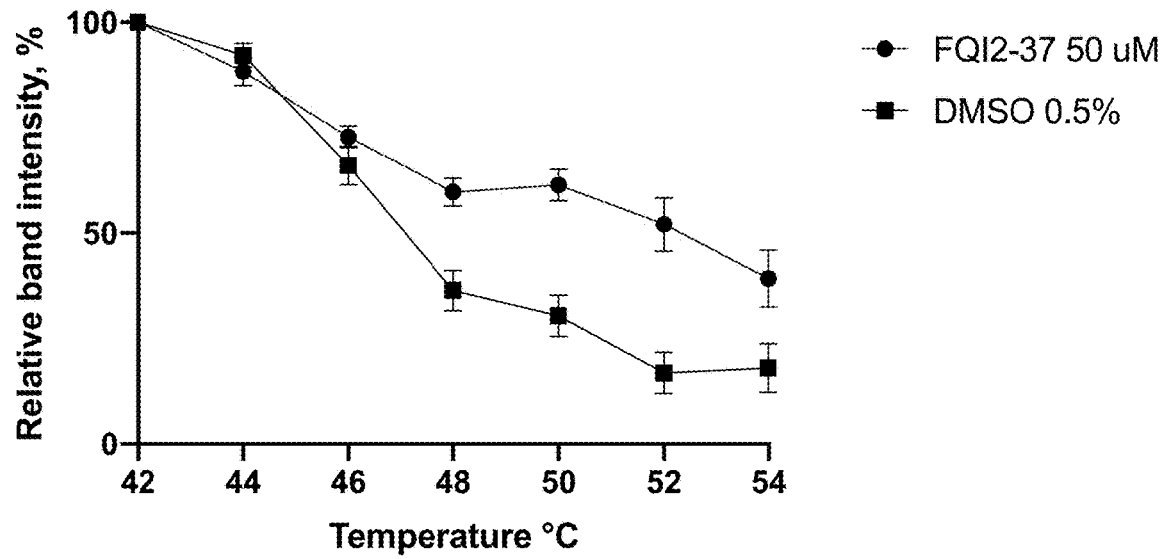
Figure 17C:
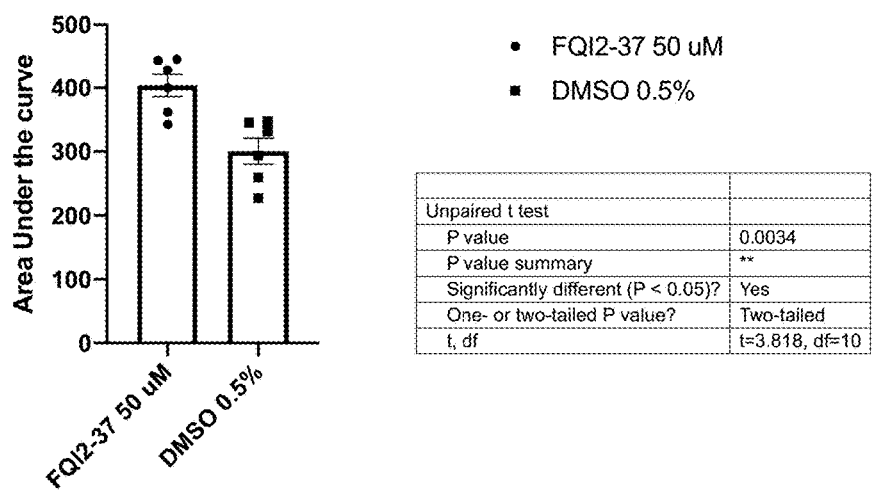
Figure 18A:
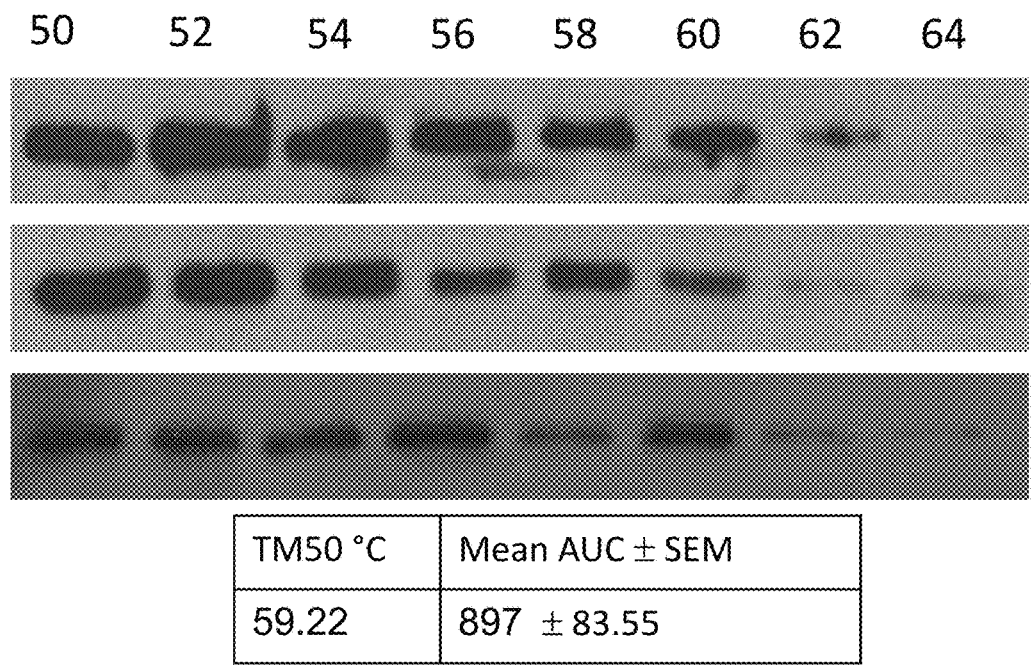
FIGS. 18A and 18B depict CETSA data for compound FQI-2.
Figure 18B:
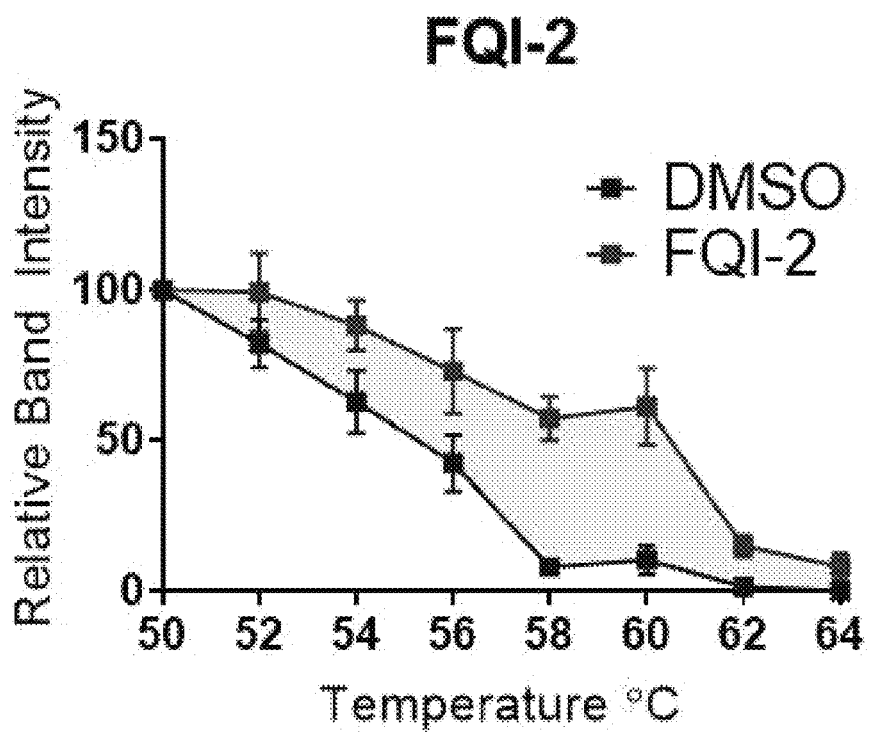
Figure 19:
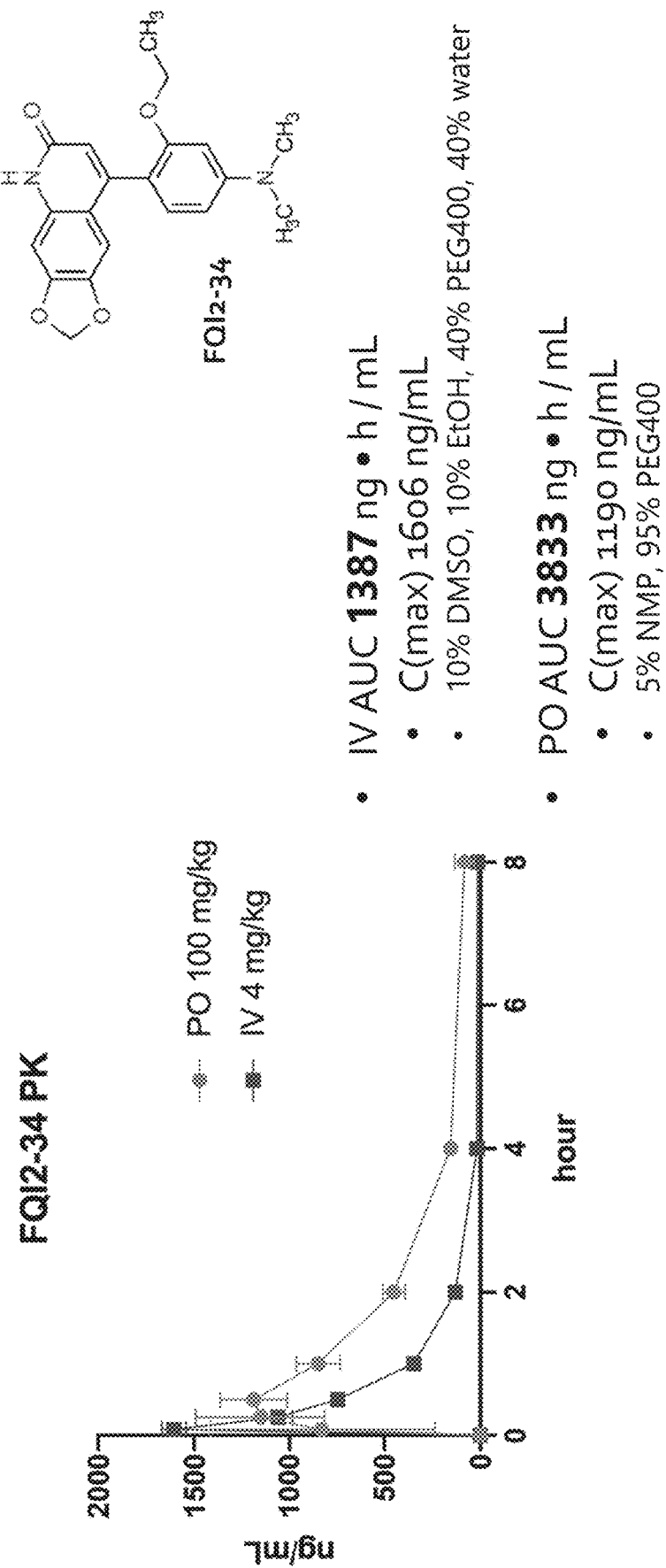
FIG. 19 depict bioavailability of FQI2-34 orally and intravenously.
Figure 20:
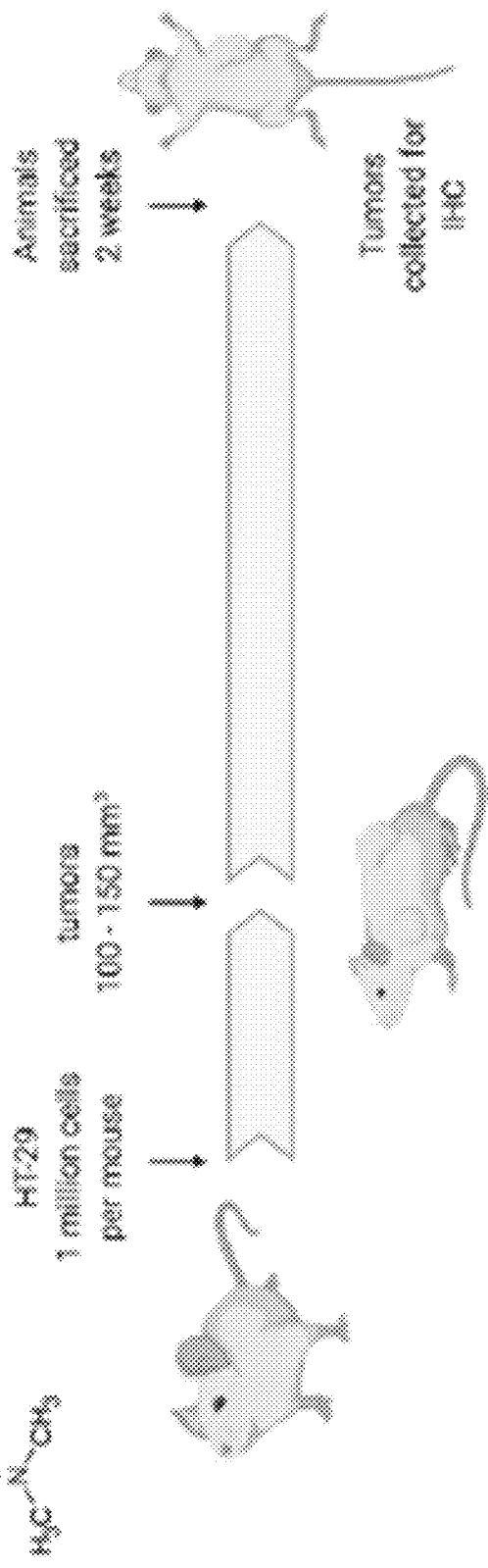
FIG. 20 depicts treatment of colorectal cancer with FQI-34.
Figure 21:
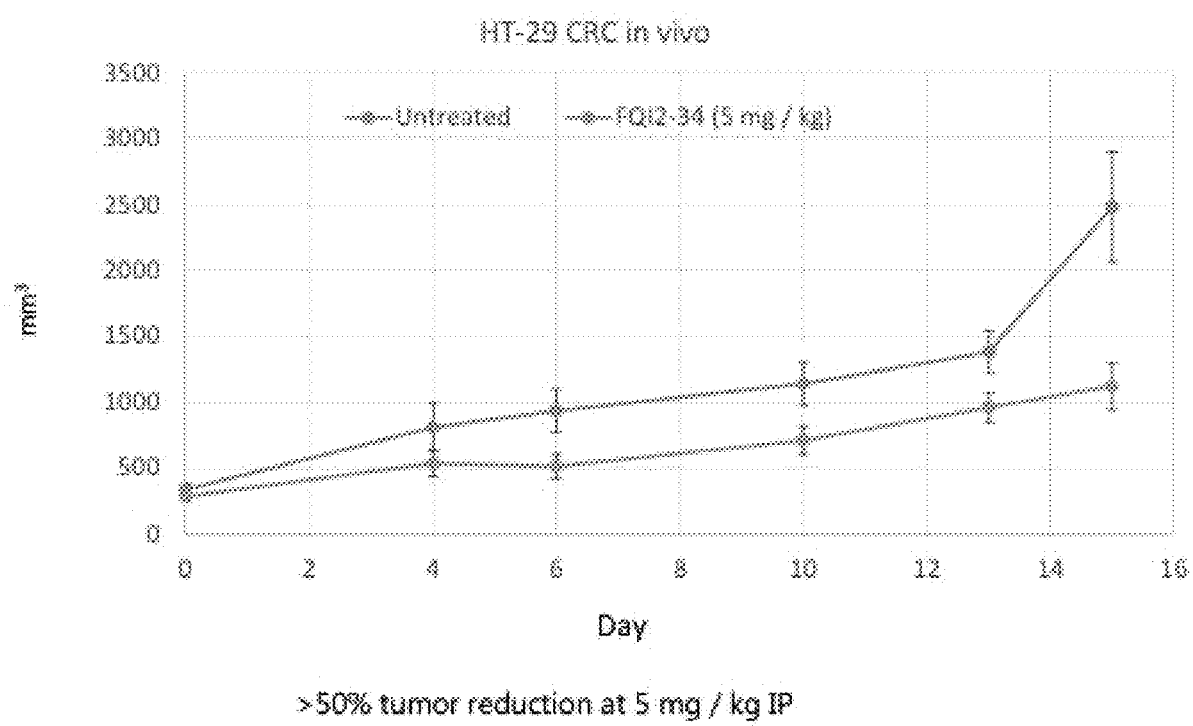
FIG. 21 depicts a line plot of colorectal cancer tumor size versus time without treatment and with FQI-34 treatment.
Figure 22:
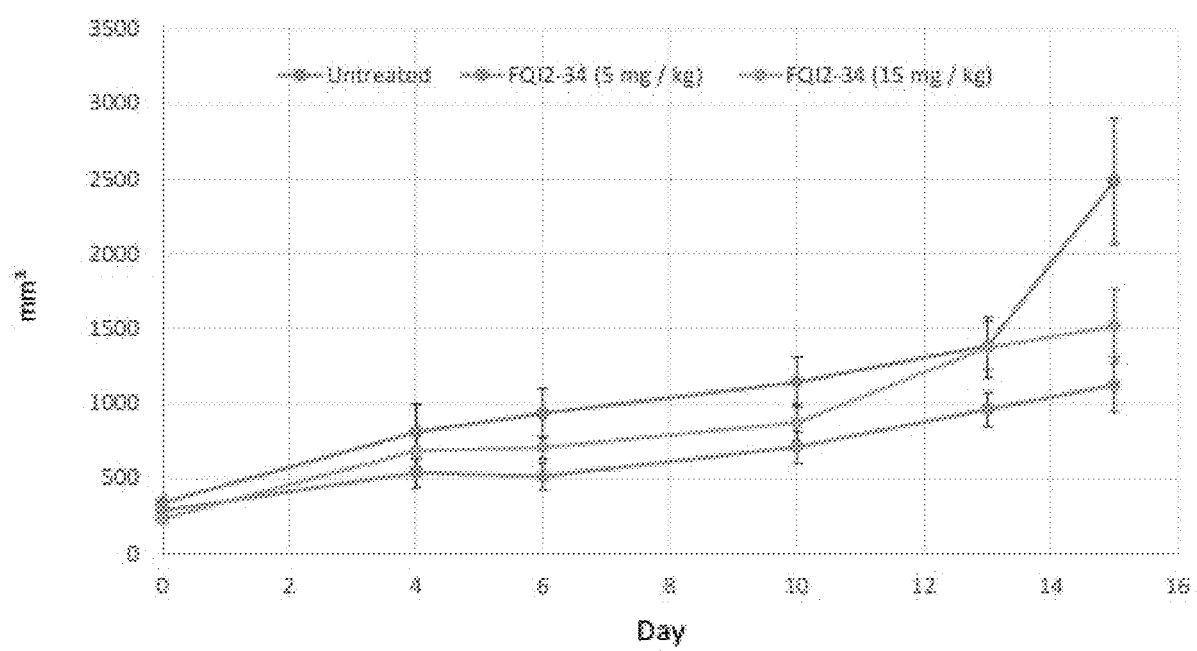
FIG. 22 depicts a line plot of colorectal cancer tumor size versus time without treatment and with FQI-34 treatment at two concentrations. 15 mg/kg treatment is not as effective due to compound solubility.
Figure 23:
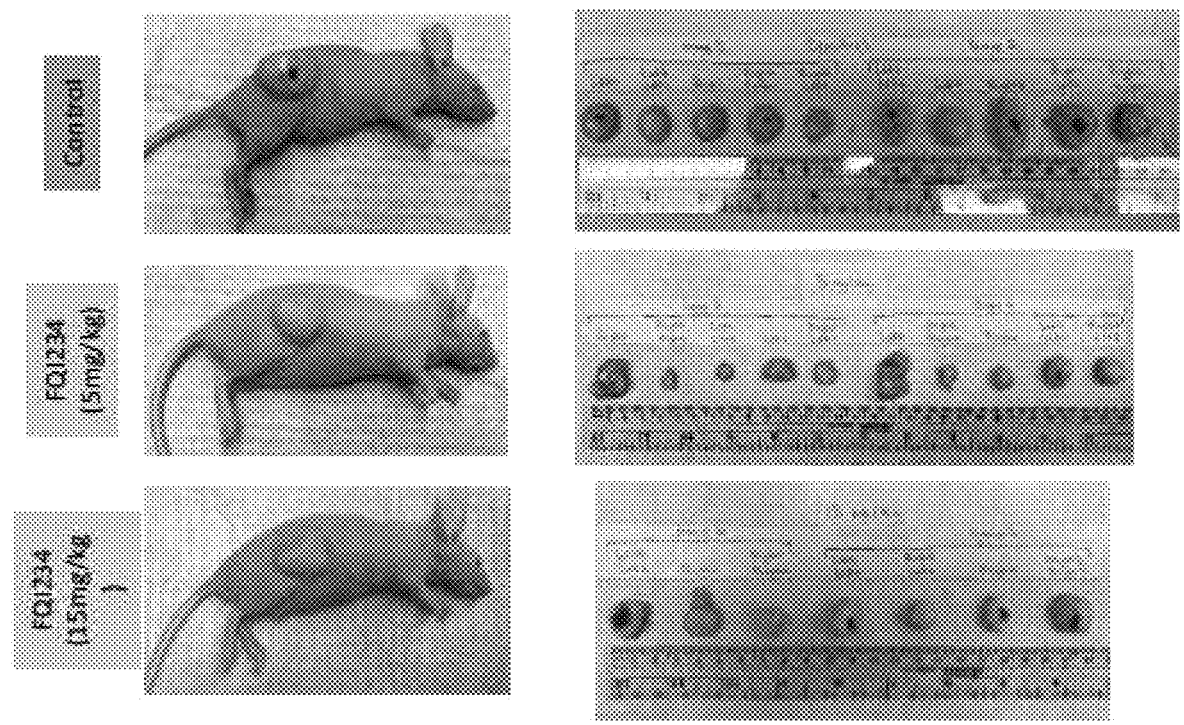
FIG. 23 depicts pictures of tumors for: control (top left mouse, top right sizes of tumors); 5 mg/Kg FQI234 (middle left mouse, top right sizes of tumors); and 15 mg/Kg FQI234 (top left mouse, top right sizes of tumors).
Figure 24:
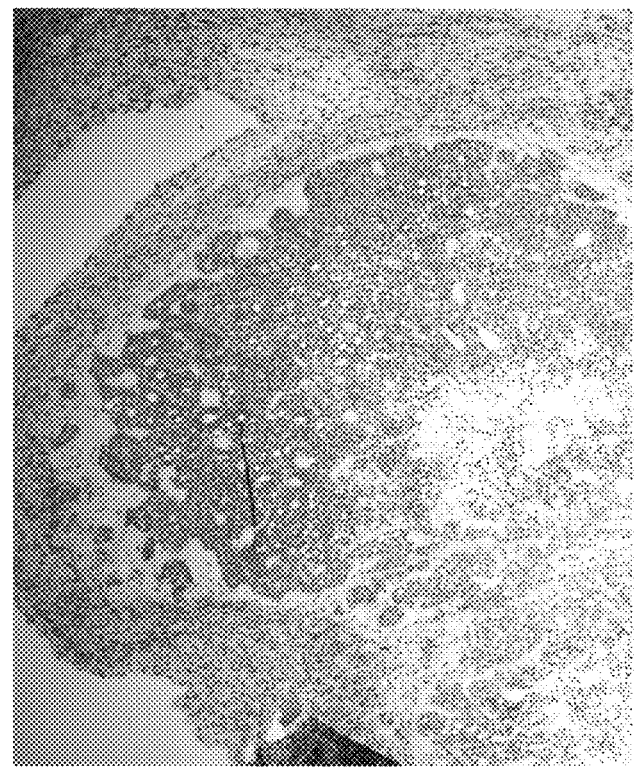
FIG. 24 depict microscope images of stained tumor tissue samples. Left is a control showing diffuse packed with cancer cells. Right shows a sample treated with FQI-234 showing more organized, interstitium and differentiated tumor.
Figure 24:
Figure 25:
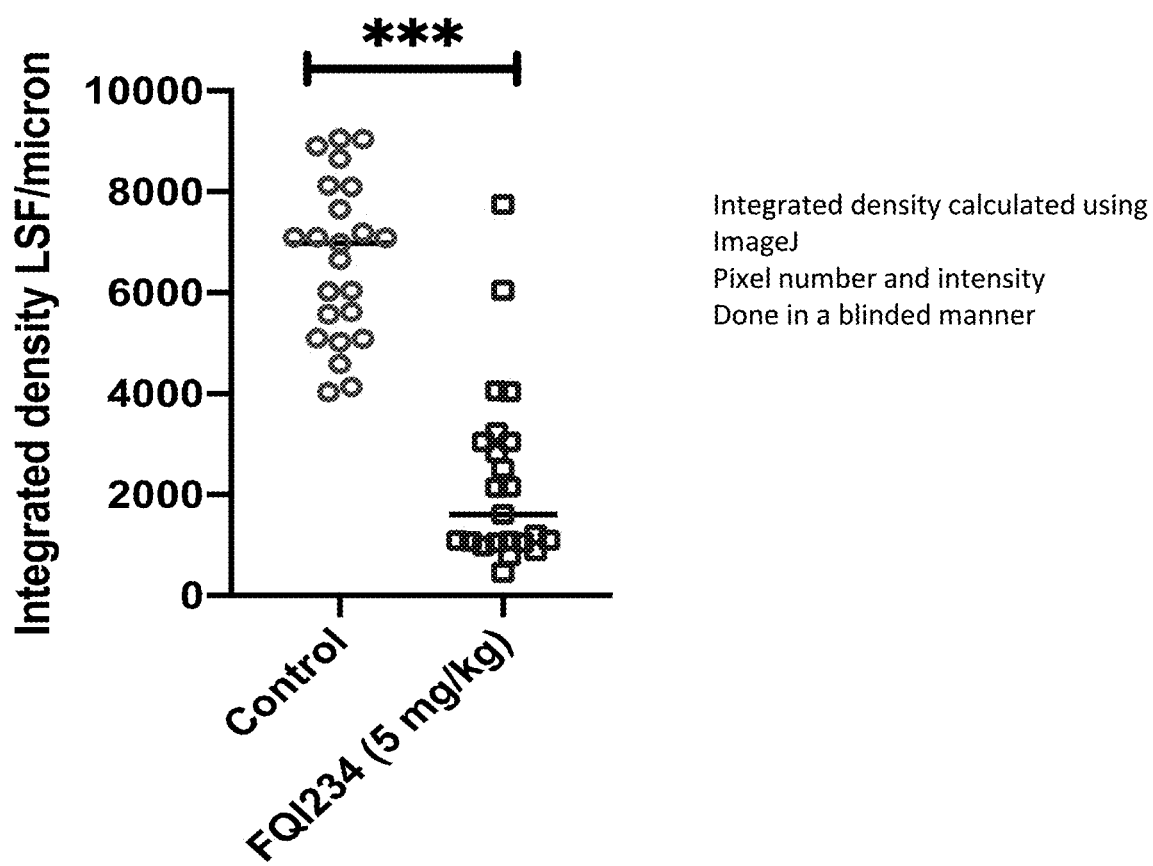
FIG. 25 is a plot showing integrated density LSF/micron for control and FQI235. The integrated density was calculated using ImageJ. Pixel number and intensity were done in a blinded manner.
Figure 26:
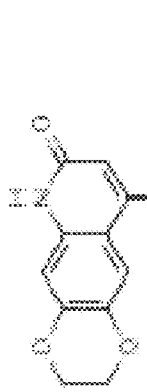
FIG. 26 depicts structures of compounds and plasma protein binding (PPB), according to some implementations. Left to right: FQI-34-human PPB 93%, mouse PPB 95%; FQI2-34 human PPB 90%, mouse PPB 93%; FQI-37-human PPB 93%, mouse PPB 95%; and FQI2-37-human PPB 92%, mouse 94%.
Figure 27:
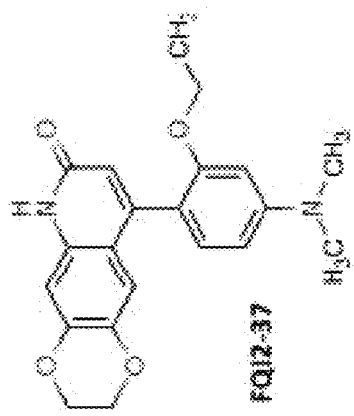
FIG. 27 depicts structures of compounds FQI2-34 and FQI2-37, and their CaCo-2 permeability, according to some implementations.
Figure 27:
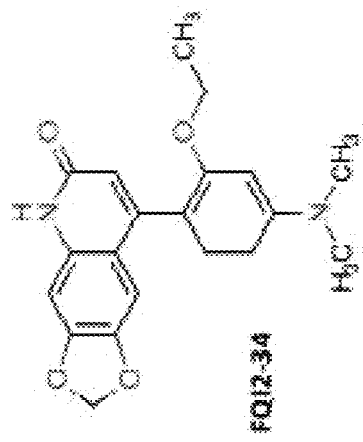
Figure 29:
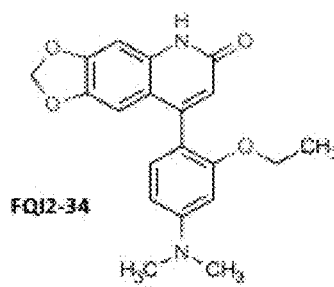
FIG. 29 depicts structures of compounds FQI2-34 and FQI2-37, and Parallel Artificial Membrane Permeability Assay (PAMPA) for the compounds, according to some implementations.
Figure 29:
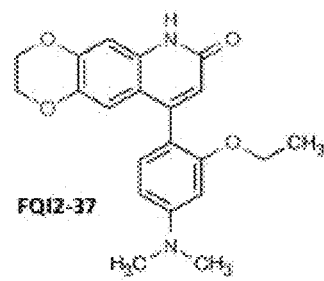
Figure 31:
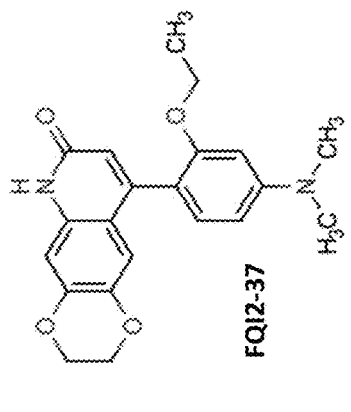
FIG. 31 depicts structures of compounds FQI2-34 and FQI2-37, and CYP34A Inhibition for the compounds, according to some implementations.
Figure 31:
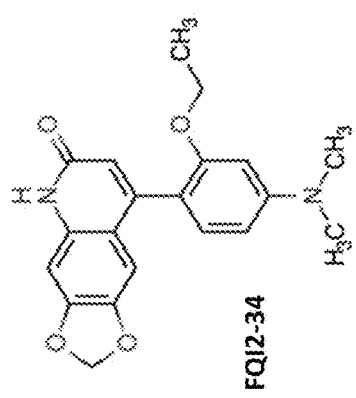
Figure 32:
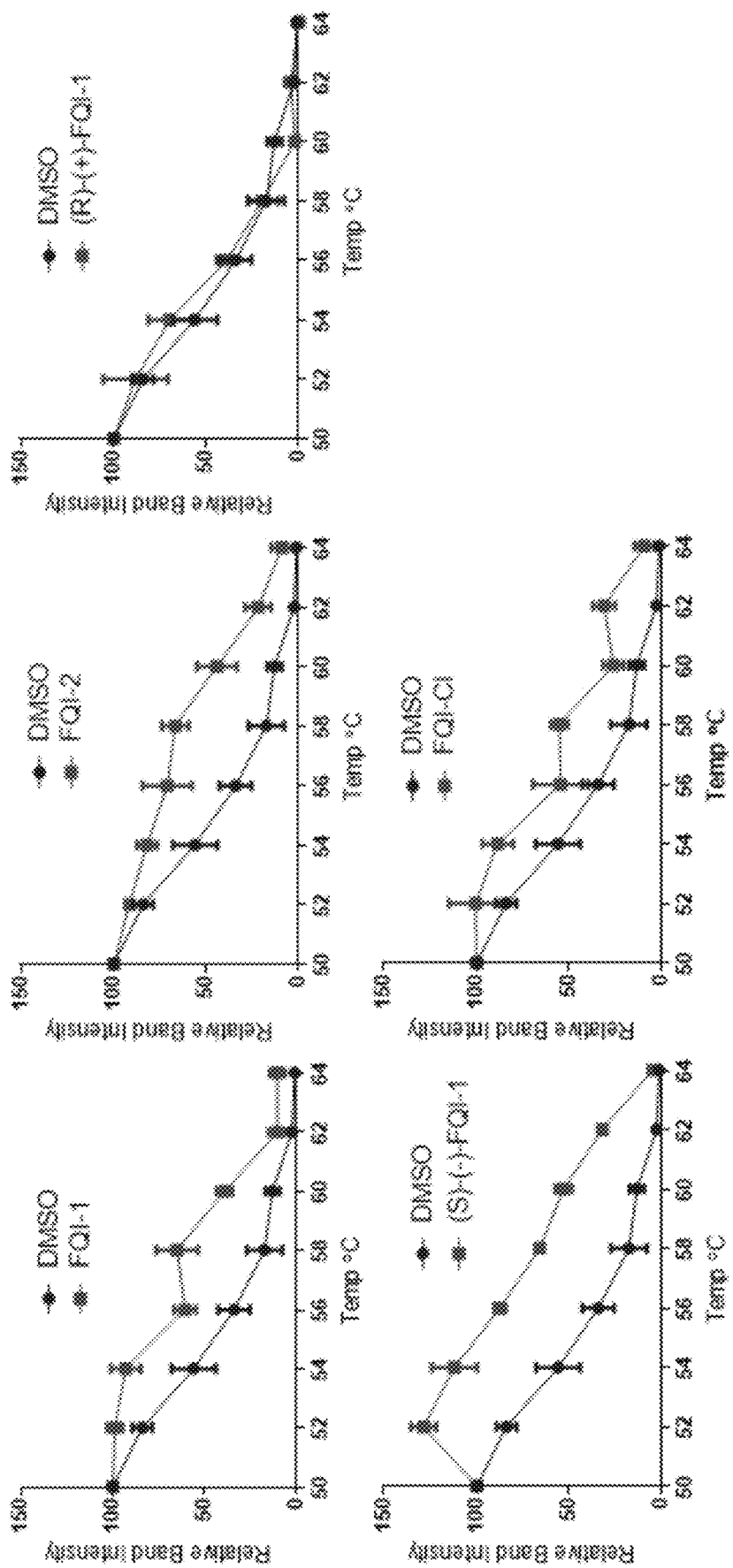
FIG. 32 depicts plots of CETSA for: FQI-1, FQI-2, (R)-(+)-FQI-1 (top); and (S)-(−)-FQI-1 and FQI-Cl (bottom FIG. 32). Comparison is to DMSO.

As seen from FIG. 13, FQI2-34 effectively inhibits cell migration at 200 nM, which is 20-fold lower than that used for FQI1 in the same assay (FIGS. 4A and 4B). Analysis with a 2-tailed, paired T-test indicated statistically significant differences from the control (vehicle) were achieved as follows. For 50 nM FQI2-34: $p=0.004$ at 8 h; for 100 nM FQI2-34: $p=0.042$ at 4 h, $p=0.021$ at 6 h, $p=0.021$ at 8 h; for 200 nM FQI2-34, $p=0.037$ at 2 h, $p=0.019$ at 4 h, $p=0.015$ at 6 h, $p=0.0059$ at 8 h.

Example 4: Pharmacological Manipulation of the Transcription Factor LSF Suppresses Wnt Signaling in Colon Cancer Cells and Inhibits Colon Tumor Growth in Mice Aberrant hyperactivation of Wnt signaling driven by nuclear β-catenin in the colonic epithelium represents the seminal event in the initiation and progression of colorectal cancer (CRC). Despite its established role in CRC tumorigenesis, clinical translation of Wnt inhibitors remains unsuccessful. LSF (encoded by TFCP2) is a transcription factor and a potent oncogene. We identified a chemotype, named Factor Quinolinone Inhibitors (FQIs) that specifically inhibits LSF DNA-binding, partner protein-binding, and transactivation activities. We examined the role of LSF and FQIs in CRC tumor growth. Here, we show that LSF and β-catenin interacted in a several CRC cell lines, which was disrupted by FQI2-34 treatment. FQI2-34 suppressed Wnt activity in CRC cell lines in a dose-dependent manner. Leveraging both allogeneic and syngeneic CRC xenograft models, we show that FQI2-34 suppressed CRC tumor growth, significantly reduced nuclear β-catenin, and suppressed Wnt targets such as AXIN-2 and SOX-9 in the xenograft cells. FQI2-34 augmented apoptosis and suppressed proliferation of xenograft cells. Adenocarcinomas from a series of stage 4 CRC patients revealed a positive correlation between LSF expression and Wnt targets (AXIN-2 and SOX-9) within the CRC cells. Collectively, this study uncovers the Wnt inhibitory and CRC growth suppressive effects of these LSF inhibitors in CRC cells, revealing a novel target in CRC therapeutics.

Introduction

In the United States, one in twenty-three women and one in twenty-one men will develop colorectal cancer (CRC)[1]. CRC is the second and third most common cause of cancer death in the United States in men and women, respectively, which is driven by the progression of CRC and its metastases[2,3]. While there are great advances in the early diagnostic techniques and targeted therapies, mortality and morbidity related to CRC still remain high[2,3]. CRC is characterized by mutations in the tumor suppressor Adenomatosis Polyposis Coli (APC), which is the primary trigger for CRC in approximately 85% of all CRC patients[4,5]. The inactivation of APC stabilizes β-catenin, which is a transcriptional co-activator. Nuclear β-catenin binds to DNA in concert with other transcriptional machinery to induce expression of pro-proliferative, angiogenic and anti-apoptotic genes to initiate transformation of colonic epithelium epithelial cells to adenoma[6].

The critical role of Wnt/β-catenin in CRC tumorigenesis makes it an attractive therapeutic target[7,8]. While several proteins regulating Wnt signaling have been explored as therapeutic targets, β-catenin is the prime target as its transcriptional activity drives, in large part, CRC tumor initiation and also contribute to progression, metastasis and cancer stem cells and influences therapeutic response. Furthermore, by targeting only nuclear activity of β-catenin, toxicities resulting from inhibition of upstream Wnt signaling proteins or the β-catenin/E cadherin cytoplasmic complex are avoided. Despite concerted attempts, Wnt pathway inhibitors, especially those targeting nuclear β-catenin, have not meaningfully progressed beyond the preclinical stage[9-12].

Over the last decade, our group has investigated Late SV40 Factor (LSF, TFCP2), a transcription factor and a potent oncogene, whose inhibition disrupts the oncogene addiction phenotype in various cancer types[13-18]. LSF is overexpressed in specific cancers such as CRC, hepatocellular carcinoma, and pancreatic cancer[19-23]. In CRC, elevated LSF expression correlated with poor overall survival, large tumors, advanced stage, higher rates of cell proliferation, and metastasis[19]. Gain-of-function and loss-of-function approaches have established a key role for LSF in generating other highly aggressive tumors[13-15,20,23,24]. At the cellular level, LSF regulates cell proliferation and migration and modulates several targets such as metalloproteases[14,25]. In addition, Yuedi et al showed that LSF interacts with β-catenin to enhance its binding to TCF4 and subsequent transcriptional activation in pancreatic cancer cell lines. This event, in turn, facilitated downstream events in Wnt signaling[22]. Loss of LSF inhibited Wnt activity, cell growth, migration and invasion[22].

We recently developed Factor Quinolinone Inhibitors (FQIs) that specifically inhibit LSF DNA-binding, partner protein-binding, and transactivation activities[13,16]. Given the critical role of Wnt signaling in CRC tumorigenesis, we set out to examine the effect of FQIs on Wnt signaling and CRC tumor growth.

Methods

Syngeneic and allogeneic xenograft models: We used 8-12 weeks-old athymic female mice for the allogeneic xenograft model and C57BL/6 mice for a syngeneic xenograft model, as described previously[26,27]. All the mice were obtained from The Jackson Laboratory and housed at Boston University Medical Center based on the approval from the Institutional Animal Care and Use Committee. Each mouse was implanted subcutaneously on the dorsal surface and was monitored for tumor growth as measured with a VWR Digital Caliper. The tumor volume was calculated twice a week using the equation: length×width×height.

The mice were randomly separated into two groups once tumor volumes reached 100 mm$^3$. The FQI2-34 was suspended in a mixture of ethanol and DMSO. The mixture was agitated until the compound had completely dissolved. This solution was further diluted in 20% PEG 400 and water to give a final concentration of 2 mg/ml. FQI2-34 or vehicle was injected intraperitoneally daily at 5 mg/kg for 5 days, followed by a break for 2 days. After 21 days, both groups of mice were sacrificed, and the tumors were harvested.

Cell culture and other reagents: HT-29 cells were obtained from ATCC and grown in the Roswell Park Memorial Institute (RPMI) medium supplemented with 10% FBS and penicillin and streptomycin. Cells were injected with the growth-factor poor Matrigel (Millipore, catalogue number DLW354263) using a 23-gauge needle for a total volume of 200 microliters. The MC38 cell line was obtained from ATCC and grown in RPMI medium supplemented with 10% FBS and penicillin and streptomycin.

FQI-34, FQI-37 and FQI2-34: Compounds FQI-34, FQI-37, and FQI2-34, were synthesized and characterized as previously described.

Immunohistochemistry:

IHC was performed on the paraffin-embedded tumors as described previously[26-28]. The manufacturer's protocol was used along with reagents from the Abcam Mouse and Rabbit Specific HRP/DAB IHC Detection Kit—Micro-polymer (ab236466). Primary antibodies and their dilutions used to detect the respective proteins were: Axin2 (Abcam, #ab32197, 1:100), β-catenin (BD Biosciences, #610154, 1:100), LSF (BD Biosciences, #610818, 1:100), SOX9 (Abcam, #ab185230, 1:100), Ki-67 (Cell Signaling, #8D5, 1:100).

Immunoprecipitation: The CRC cells were harvested. Proteins of interest were immunoprecipitated using the indicated antibodies at 1:100 concentration. The eluents were resolved by SDS polyacrylamide gel electrophoresis and probed with the indicated antibodies. All the antibodies for immunoblot and immunoprecipitation were acquired from Cell Signaling and were used at the recommended concentrations.

Wnt signaling assay: The CRC cells stably expressing β-catenin-responsive promoter tethered to a luciferase reporter (pBARLS) or a mutant construct (pfuBARLS), as described previously, were seeded in 96-well plates. After 48 h of transfection, luciferase assays was performed using the Dual-Luciferase Kit (Promega) and normalized using protein content determined by the Bradford assay (Bio-Rad) as described previously[26-28].

RNA extraction and quantitative RT-PCR analysis: Flash-frozen tumor sections were thawed. A section weighing approximately 50 mg was cut off. One mL of TRIzol™ reagent was added to each tissue sample followed by homogenization using an Omni Tissue Master 125 (TM12501051), taking care to clean thoroughly in between samples in order to avoid cross contamination. Samples were extracted with 0.2 mL chloroform and the aqueous phase was transferred to a fresh tube for precipitation of the RNA using isopropyl alcohol. After centrifugation, the RNA pellet was washed twice with 75% ethanol, air-dried, and dissolved in diethyl pyrocarbonate-treated water.

Using the Invitrogen SuperScript Frist-Stand Synthesis System of RT-PCR kit (Cat No: 11904-018), cDNA was prepared from 5 μg of each of the extracted tissue sample RNAs, according to the manufacturer's instructions. In preparation for the PCR reactions, 2 μl of cDNA was mixed with 10 μl of PowerTrack SYBR Green Master Mix (Cat Log: A46109), 0.5 μl of primer, and 7 μl of nuclease-free water. The following primers were obtained from ThermoFisher Scientific: AXIN2 (Hs00610344), CCND1 (Hs00765553), and SOX9 (Hs00165814). The components were centrifuged and samples were transferred to an optical plate in triplicate. The plate was sealed with an adhesive cover and briefly centrifuged to eliminate air bubbles.

The plate was then loaded into the real-time PCR machine and processed using the following protocol: 1 cycle at 95° C. for 2 minutes, and 40 cycles of 15 seconds at 95° C. followed by 60 seconds at 60° C. This was followed by a dissociation protocol: 15 seconds at 95° C. at a ramp rate of 1.6° C./second, followed by 1 minute at 60° C. at a ramp rate of 1.6° C./second, and finally 15 seconds at 95° C. at a ramp rate of 0.075° C./second. Results were analyzed by determining the baseline and threshold cycles for the amplification curves, checking for nonspecific amplification using melt curves, and performing relative quantification.

Patient samples acquisition and analysis: Patients with stage IV colorectal cancer treated at Boston Medical Center were included in the study using IRB protocol H-26367. The baseline characters and other clinical information were manually extracted from electronic medical record of [EPIC] (see Table 1). Samples were obtained from the Boston University School of Medicine core pathology facility and slides were stained by immunohistochemistry for the respective proteins.

TABLE 1

Baseline characteristics of CRC patients

| | |
|---|---|
| Median age (years) | 62 |
| % Male | 50.79 |
| Ethnic background (%) | |
| >White | 34.92 |
| African American | 33.33 |
| Hispanic | 20.63 |
| Other | 11.11 |
| Right sided colon cancer(%) | 30.16 |
| Histologic Type (%) | |
| Adenocarcinoma | 80.95 |
| Signet Ring | 1.96 |
| Presented with metastatic disease (%) | 76.19 |
| Mean number of organs metastasized | 1.66 |

All images and quantification were performed using the Nikon Eclipse TE2000 Inverted Microscope with the color camera at the Boston University School of Medicine (BUSM) Imaging Core. Random high-power field (hpf) images of every tumor sample were obtained. For quantification the signal was converted to grayscale, and the number and intensity of pixels were analyzed as integrated density by using Fiji. The integrated density of all the images was normalized to its area. The images were processed in ImageJ (National Institutes of Health, Bethesda, Md.) to quantitate the expression of SOX-9, AXIN-2, and LSF. Regions of interest were drawn and the expression was measured using integrated density normalized to the surface area. The average normalized integrated image densities from multiple hpfs were used to perform the correlational analysis between expression levels of pairs of proteins.

Statistical analysis: Summary statistics are presented using the mean, median, and SD, unless otherwise indicated. Either a Student's t-test with or without Welch's correction was performed to compare the groups as appropriate. Spearman rank correlation was performed to examine association between two variables. Statistical significance was assessed at the p<0.05.

Results

Figure 34C:
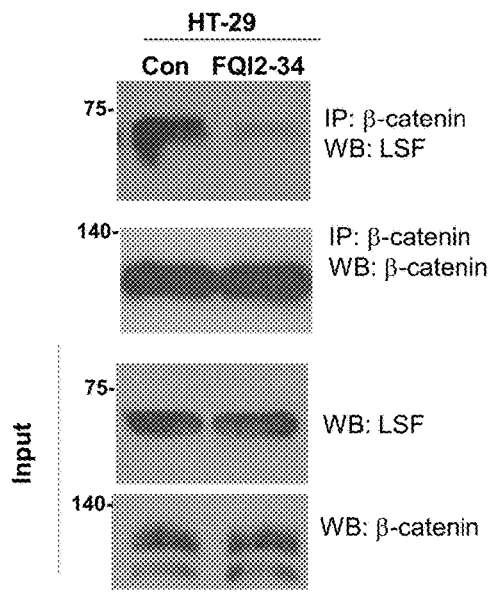
Figure 34D:
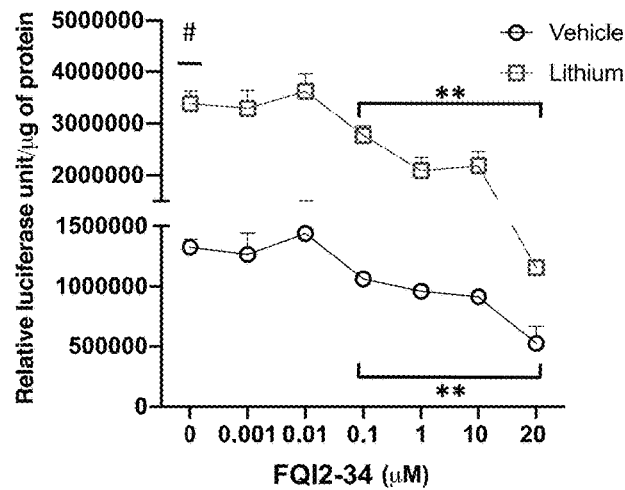

Interaction of LSF and β-catenin in CRC cells: β-catenin is a transcription coactivator of Wnt signaling[6] and LSF is a ubiquitously expressed transcription factor[25]. Given the precedent that these proteins associate in pancreatic cancer cells, we examined the interaction LSF and β-catenin in CRC cells and the effect of FQIs on it. For this purpose, we used a series of FQIs in different CRC cell lines. HT-29 and HCT-116 CRC cells lines were selected, as they represent mutations in APC and CCNB1[29], which constitute large percentage of mutations among human sporadic CRC[5]. An immunoprecipitation assay was performed using antibodies against β-catenin. In both these cell lines, LSF co-immunoprecipitated with β-catenin (FIGS. 34A-34C). Treatment with FQI-34, FQI-37 and FQI2-34 at 1 µM concentrations consistently reduced this interaction. Next, we posited that the FQIs will likely suppress Wnt activity. Increasing concentrations of FQI2-34 were added to a HCT-116 cell line that stably expresses the Wnt responsive element driving a luciferase reporter gene. The Wnt activity was examined at baseline and also upon activation with lithium chloride. Lithium chloride is a known Wnt signaling agonist that inhibits GSK-3β to activate Wnt signaling[30]. Our data showed high endogenous Wnt activity in HCT-116 consistent with our previous results that was further augmented by 2.5-fold with lithium chloride (FIG. 34D, #p<0.001). FQI2-34 inhibited Wnt activity in a monotonically decreasing manner over a range of concentrations, starting at 0.1 µM up to 20 µM. Also, FQI2-34 at concentrations of 0.1 µM or greater suppressed Wnt activity in HCT-116 cells induced by lithium chloride (FIG. 34D). Collectively these data showed that these LSF inhibitors disrupted the interaction between β-catenin and LSF and suppressed downstream Wnt signaling events in CRC cell lines.

Figure 35A:
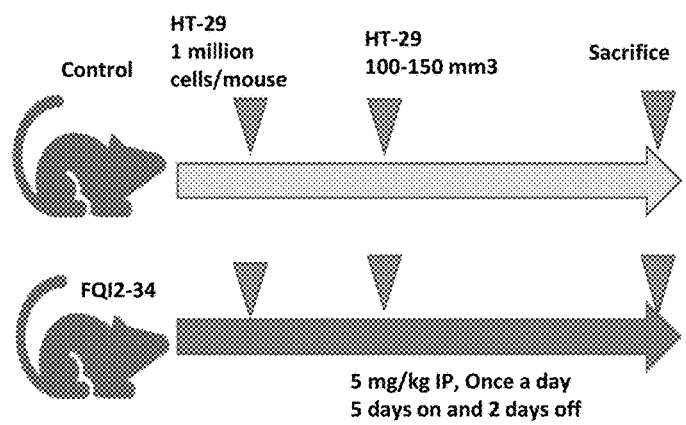
FIGS. 35A-35C show FQI2-34 suppresses CRC tumor growth in an allogeneic xenograft CRC model.
Figure 35B:
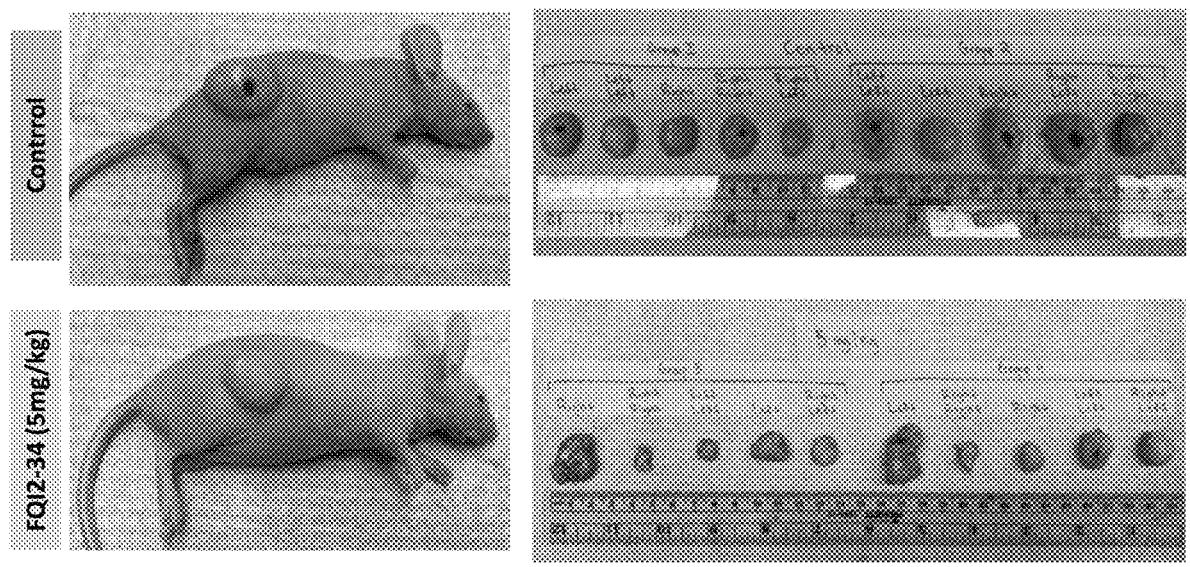
Figure 35C:
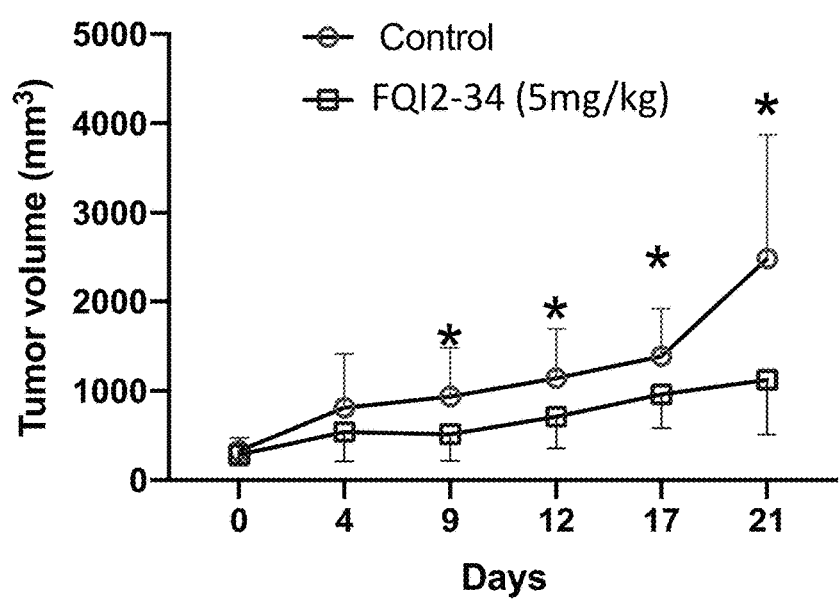

FQI2-34 suppressed allogeneic xenograft growth in athymic mice: As Wnt/β-catenin is critical for the CRC tumor growth, we posited that the FQIs would inhibit tumor growth of CRC. To this effect, we evaluated the HT-29 xenograft model, which widely-used[26] and well established model to evaluate efficacy of compounds. A group of twenty female athymic mice age of 8-12 weeks-old were injected subcutaneously with $10^6$ HT-29 cells. Once the xenografts reached 100 mm$^3$, mice were randomized for treatment with FQI2-34 (5 mg/kg daily for 5 consecutive days each week). Vehicle-treated mice served as controls (FIG. 35A). The mice in the control group displayed rapid tumor growth and ulceration, while FQI2-34-treated mice showed consistently smaller xenografts (FIG. 35B). There was no difference in tumor volumes between two groups at the time of randomization (day 0). Compared to the controls, FQI2-34-treated mice showed significantly lower tumor volumes on day 9 (p=0.05), day 12 (p=0.05) and day 17 (p=0.05) (FIG. 35C). At the time of harvest at day 21, the tumor volumes in control mice were 2480±440 mm$^3$, which was 2-times lower than those in FQI-treated mice (1120±193 mm$^3$, p=0.01).

Figure 36A:
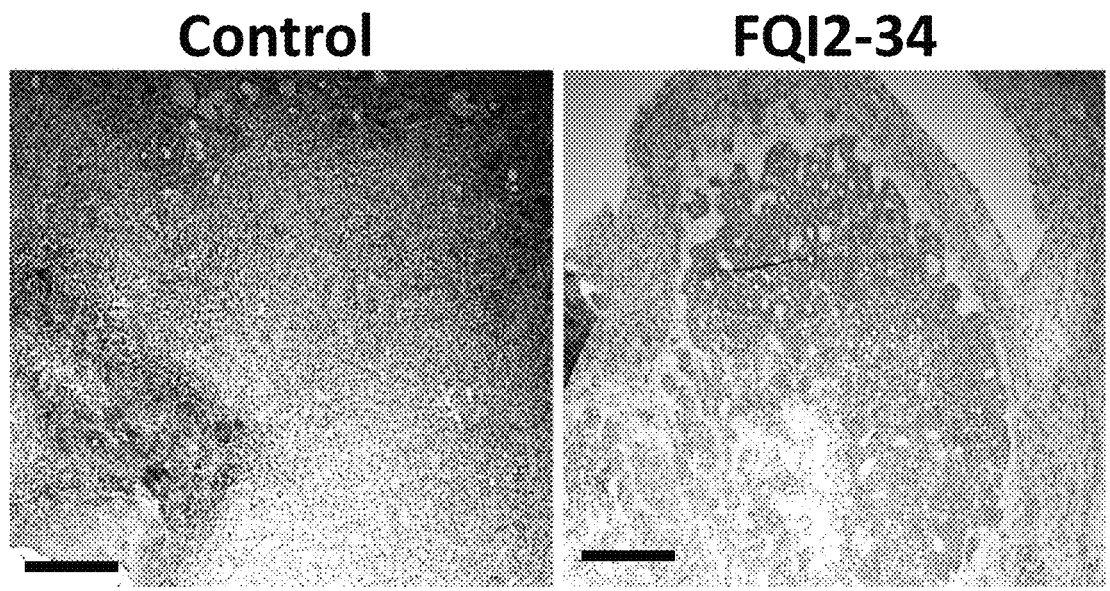
FIGS. 36A-36C show FQI2-34 treatment suppresses CRC tumor growth and reduces nuclear β-catenin expression in xenograft tumors.

Histopathological analysis of tumors revealed that mice treated with FQI2-34 had lower tumor mass organized in luminal regions interspersed within the interstitium. The control xenografts had a densely packed tumor areas with minimal interstitial area (FIG. 36A). Taken together, these data strongly suggested that FQI inhibited CRC xenograft growth in an athymic rodent model.

Figure 36B:
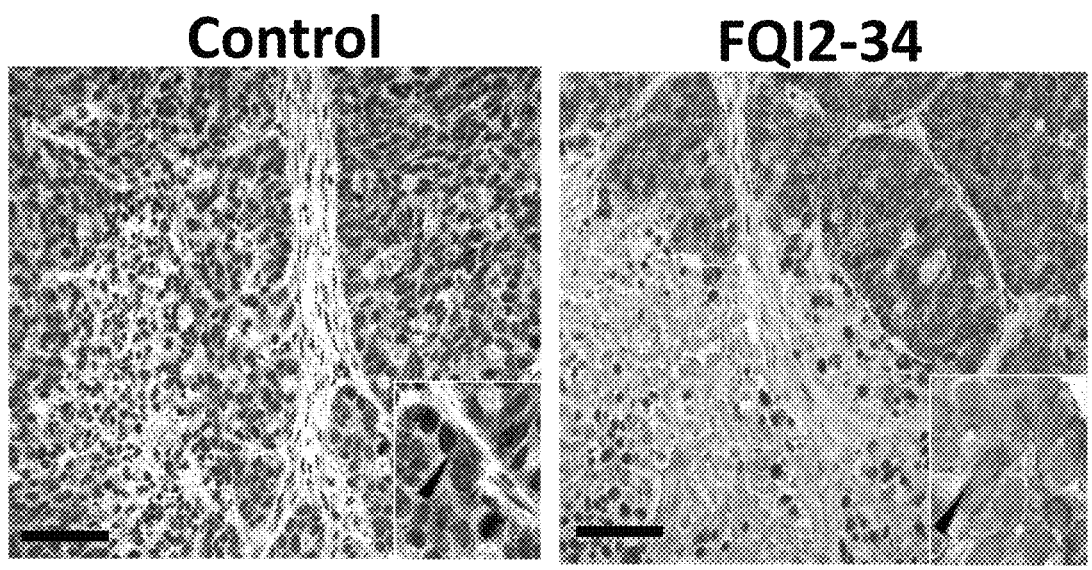
Figure 36C:
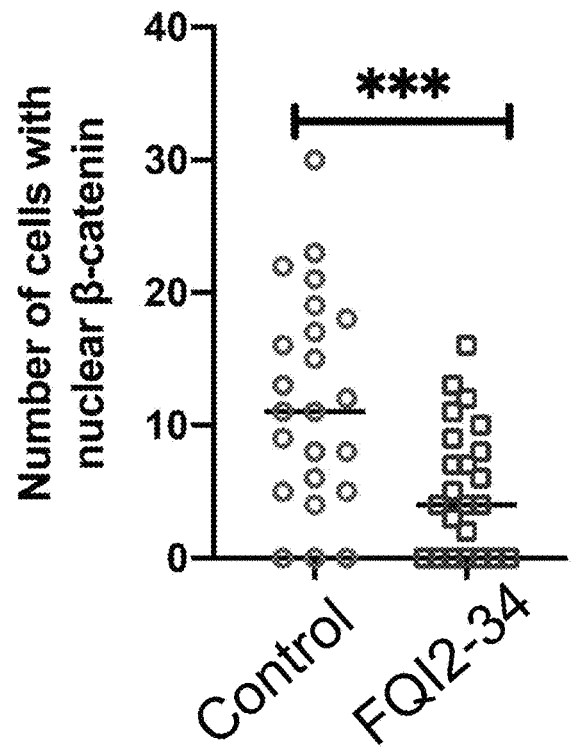

QI2-34 downregulated Wnt/β-catenin axis in xenografts in nude mice: To test whether FQIs affect Wnt signaling in vivo, as it did in vitro, we examined the effect of treatment by FQI2-34 on the Wnt/β-catenin axis in the xenografts. The control xenografts showed CRC cells with nuclear β-catenin (FIG. 36B). The FQI2-34-treated xenografts showed CRC cells predominantly with membrane β-catenin. The number of CRC cells with nuclear β-catenin were counted in xenografts in a manner blinded to the specimen (FIG. 36C). The cells positive for nuclear β-catenin from five randomly selected slides from 10 different mice from each group were averaged. There were 4-fold lower CRC cells with nuclear β-catenin in FQI2-34-treated mice compared to the control mice (p=0.0016). As nuclear β-catenin is considered the pathognomonic sign of Wnt activation in cells, these results suggested that FQI suppressed Wnt activity in CRC cells. These results are consistent with the suppression of Wnt activity by FQI compounds observed in CRC cell line.

Figure 37A:
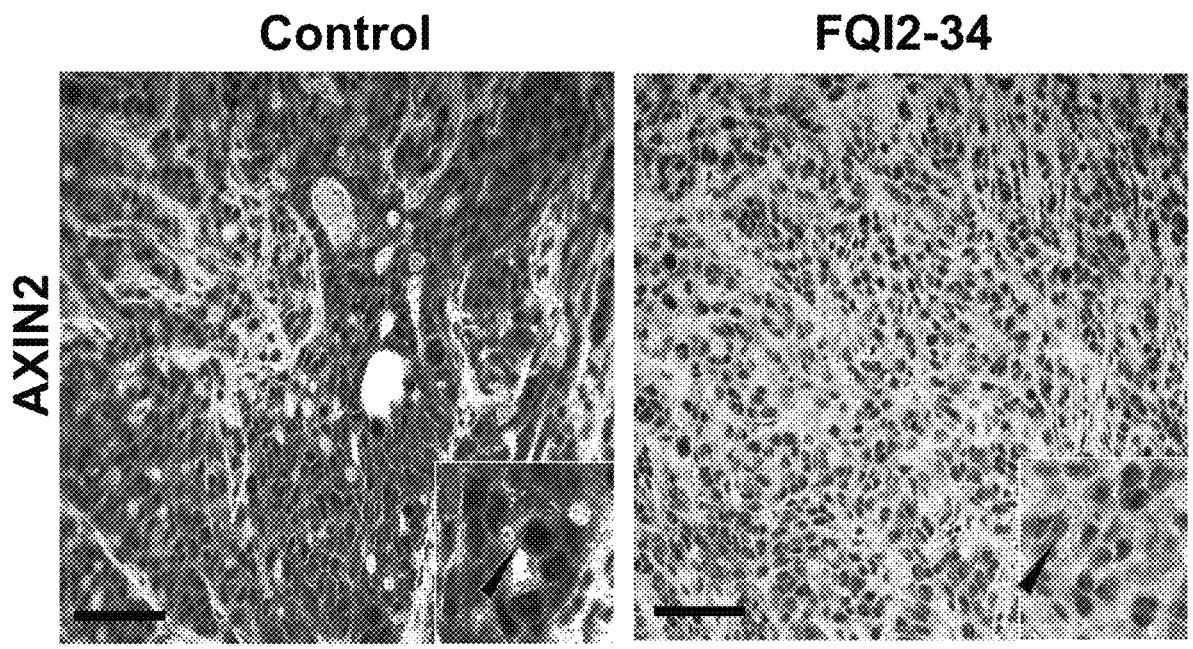
FIG. 37A-37E show FQI2-34 suppresses Wnt targets in the HT-29 xenograft cells.
Figure 37B:
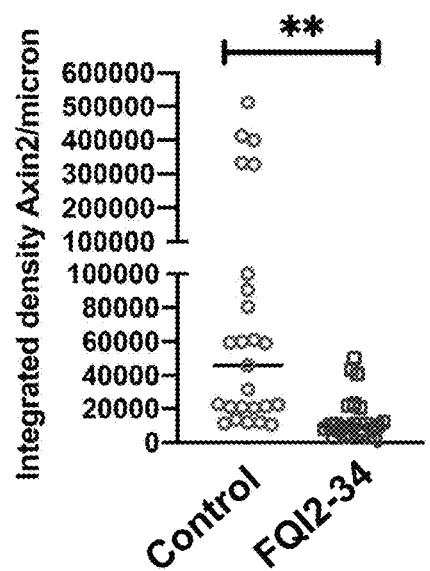
Figure 37C:
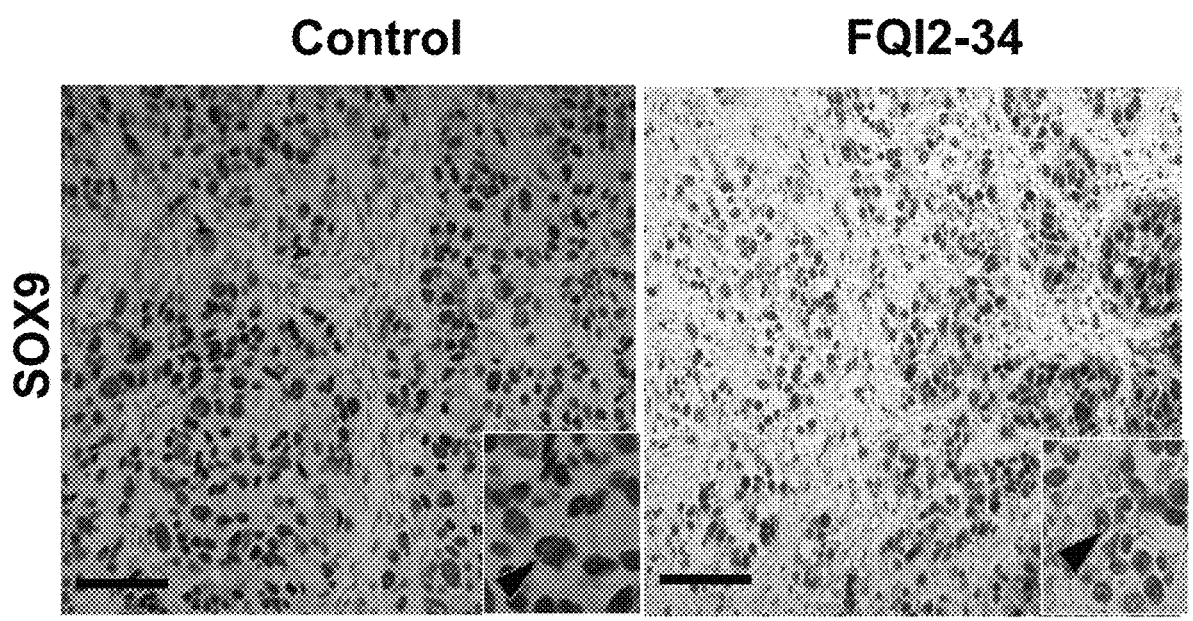
Figure 37D:
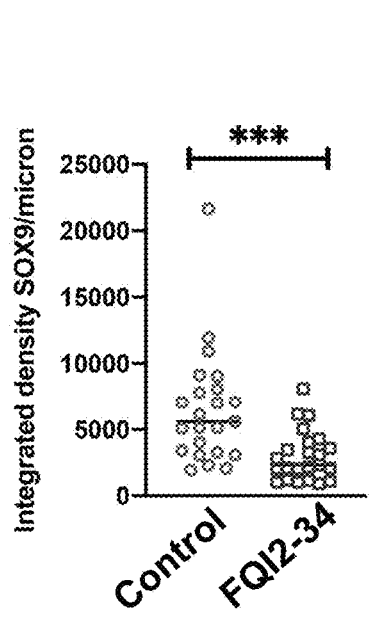
Figure 37E:
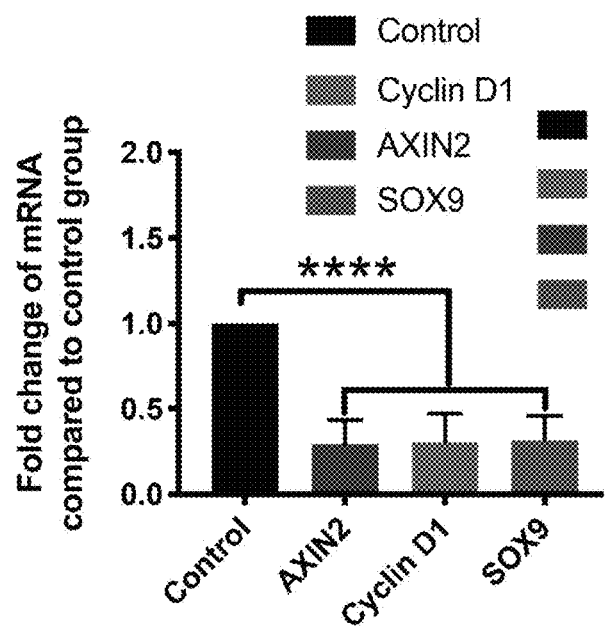

AXIN2 and SOX9 are cell-type specific Wnt target genes in CRC cells[31,32]. Both AXIN2 and SOX9 were observed in the nuclei of CRC cells and their expression was reduced in xenografts treated with FQI2-34. We further quantitated their expression levels using ImageJ and presented as integrated density (FIGS. 37A-37D). Integrated density estimates a pixel size and intensity and normalizes the signal to the area and can be used to compare expression of proteins in heterogenous tissues[33,34]. Two to three high-power field (hpf) images were randomly acquired from each xenograft. FQI2-34-treated xenografts showed 5-fold reduction in AXIN2 (p=0.0025) and 3.2-fold reduction in SOX9 (p=0.0009) compared to the vehicle-treated group (FIGS. 37B and 37D). We further validated these findings using qRT-PCR in the lysates of xenografts from both the groups at the end of treatment. Quantitative RT-PCR compared the Ct values of AXIN2, CCND1 (which encodes Cyclin D1), and SOX9. All three targets were significantly downregulated in the FQI2-34-treated group when compared to the control (FIG. 37E). Collectively, these results demonstrated that FQI2-34 treatment suppressed the Wnt/β-catenin axis in the xenografts of CRC.

Figure 38A:
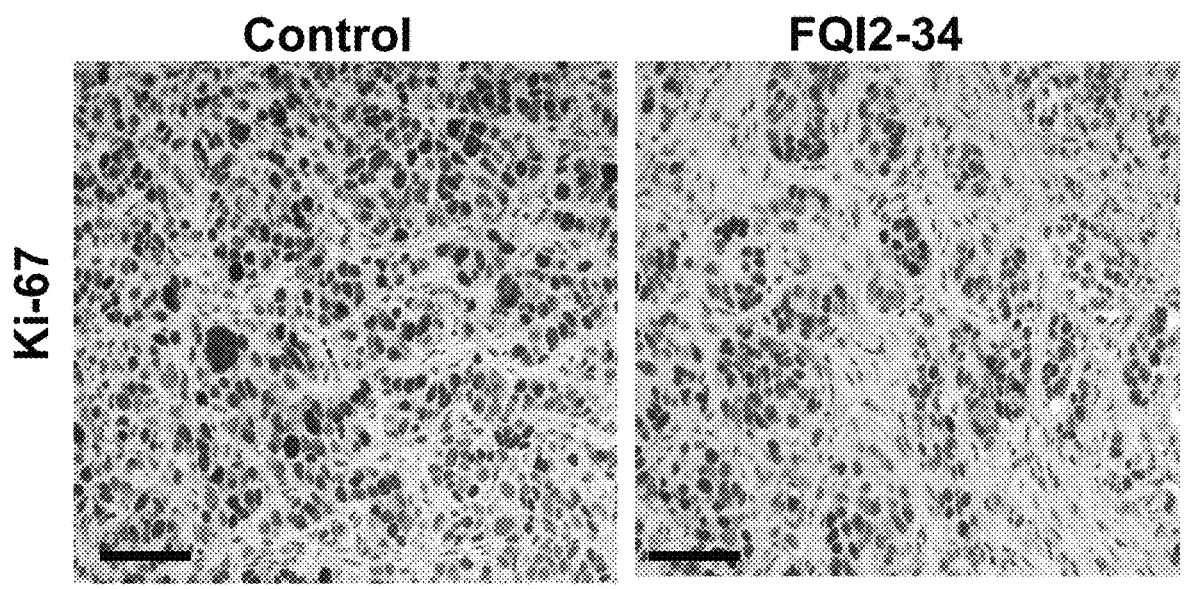
FIGS. 38A-38D show that FQI2-34 induces apoptosis and reduces the proliferation of CRC cells.
Figure 38B:
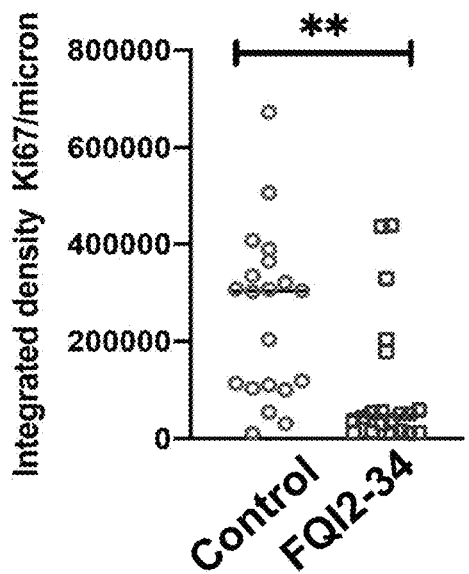
Figure 38C:
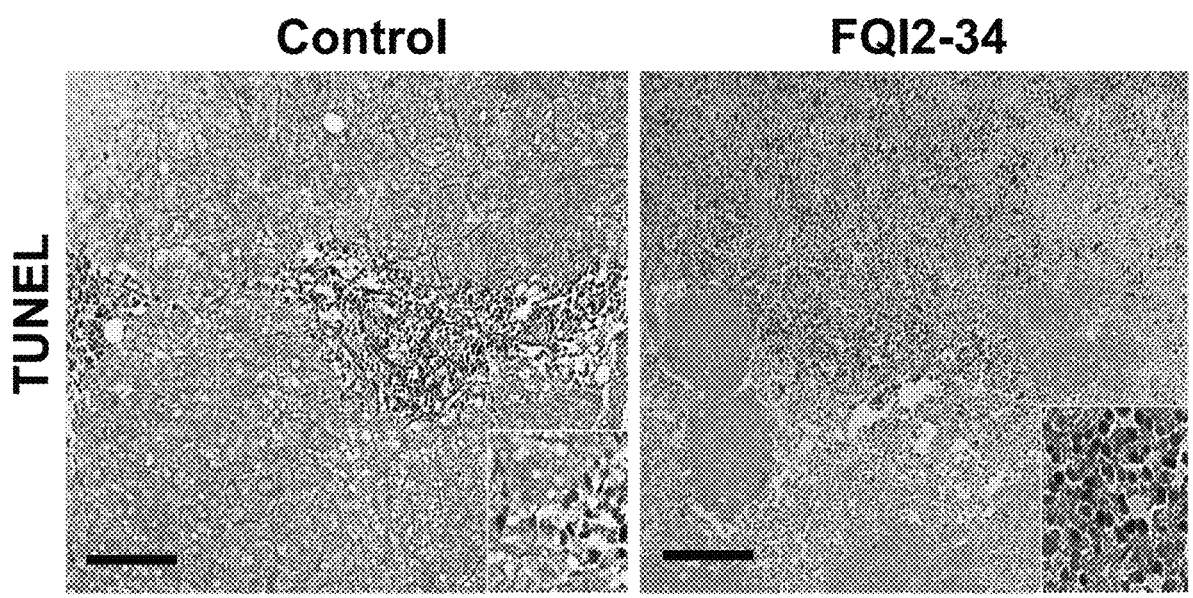
Figure 38D:
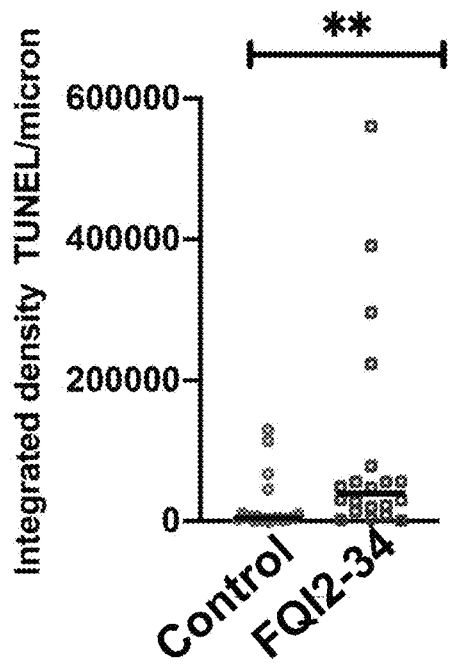

FQI2-34 suppressed CRC cell proliferation and enhanced apoptosis in xenografts: Tumor growth is regulated by two fundamental biological processes—proliferation and apoptosis, both of which were examined using immunohistochemistry by staining for Ki-67 and a TUNEL, respectively. Compared to the control, a 4.2-fold downregulation of Ki-67 was observed with FQI2-34 treatment (FIGS. 38A and 38B). On the other hand, TUNEL-positive cells were increased by 1.8-fold in FQI2-34 treated xenografts compared to the controls (FIGS. 38C and 38D). These data suggest that FQI2-34 treatment suppressed CRC cell proliferation and increased apoptosis.

Figure 39A:
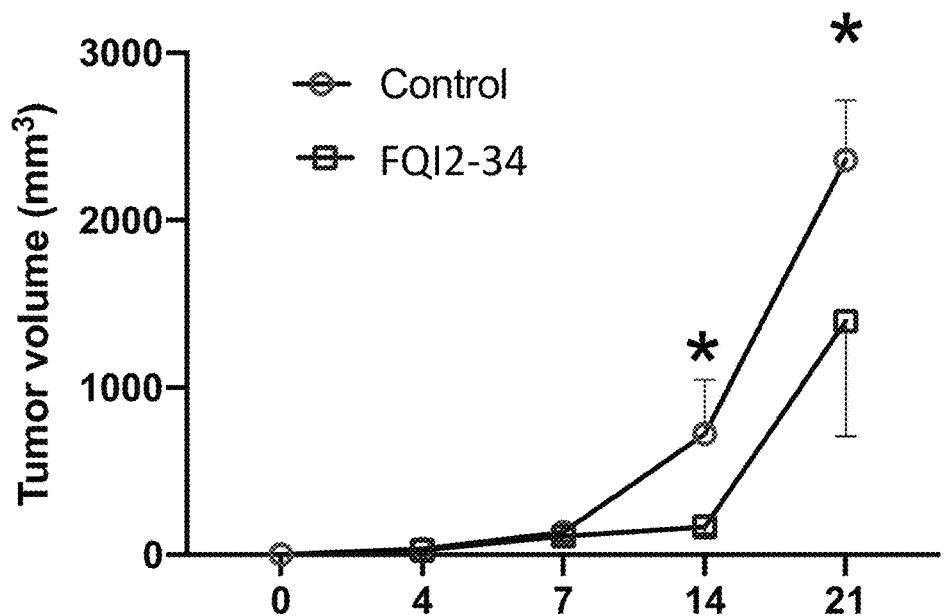
FIGS. 39A and 39B show FQI2-34 suppresses CRC tumor growth in a syngeneic xenograft CRC model (FIG. 39A) Approximately 0.25×10$^6$ MC38 cells were injected subcutaneously in twenty 8-12 week-old C57BL/6 female mice. The tumor volumes were calculated once to twice a week. The mice with tumor volumes of 100 mm$^3$ were randomized into two groups: control and FQI2-34 treated groups and were monitored for 21 days. Average tumor volumes from the control group and the FQI2-34 treatment group are shown. Error bars=SD. A Student's t test was performed. Compared to the controls, FQI2-34-treated mice showed significantly lower tumor volumes on day 14 (p<0.001), day 21 (p=0.01).
Figure 39B:
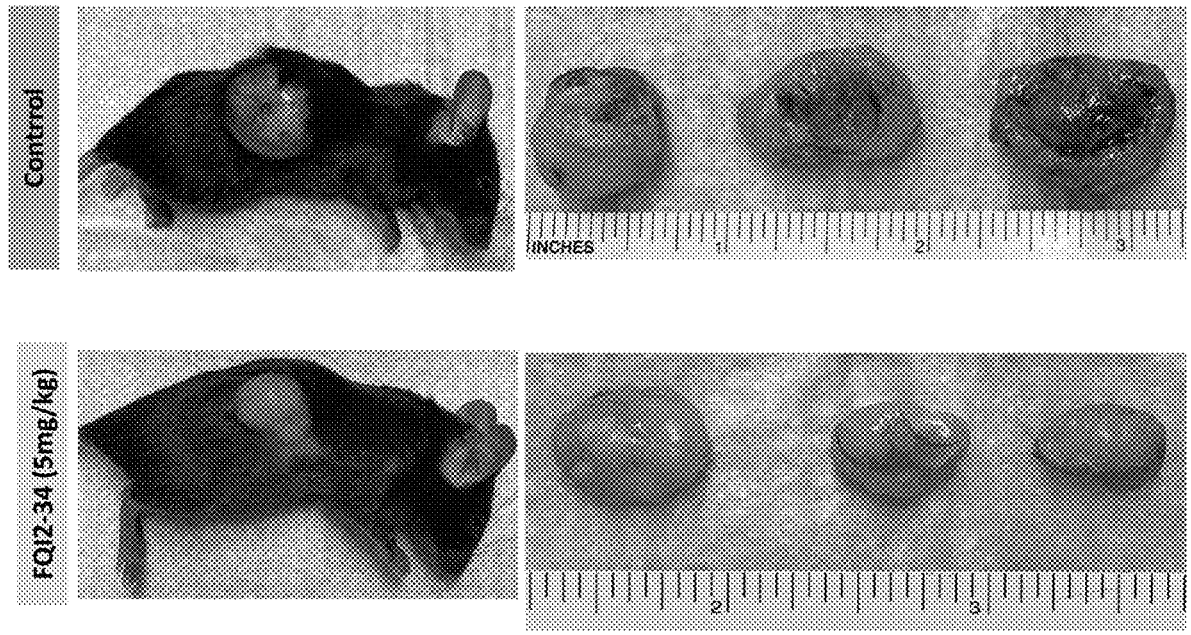
Figure 40A:
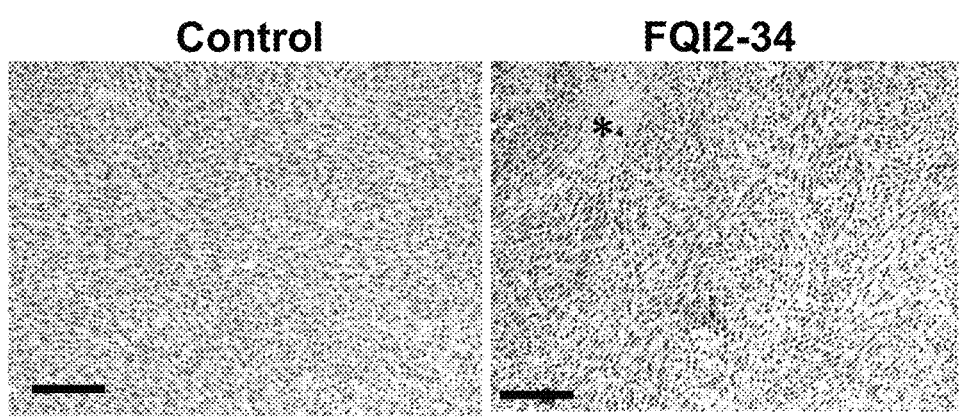
FIGS. 40A-40C show FQI2-34 treatment suppresses CRC tumor growth and reduces β-catenin expression in MC38 xenograft tumors.
Figure 40B:
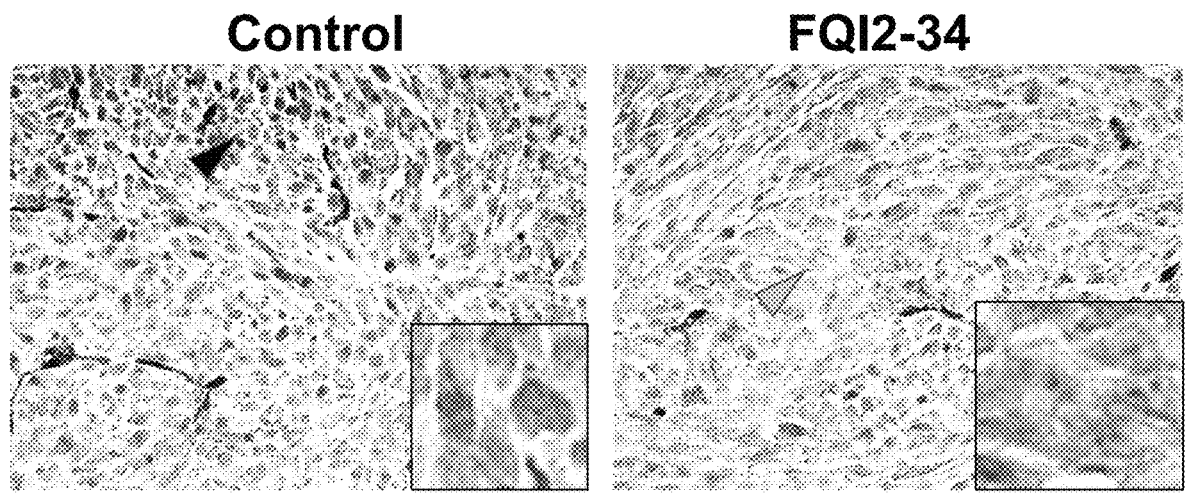
Figure 40C:
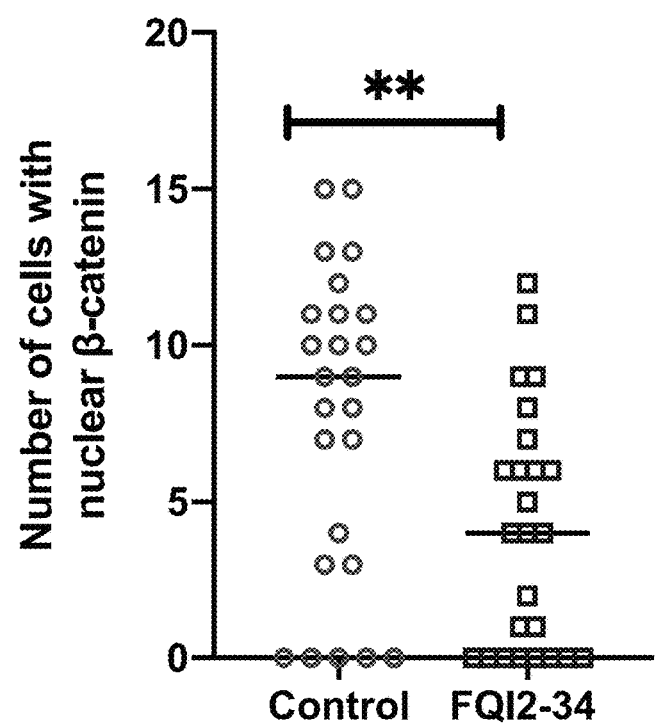
Figure 41A:
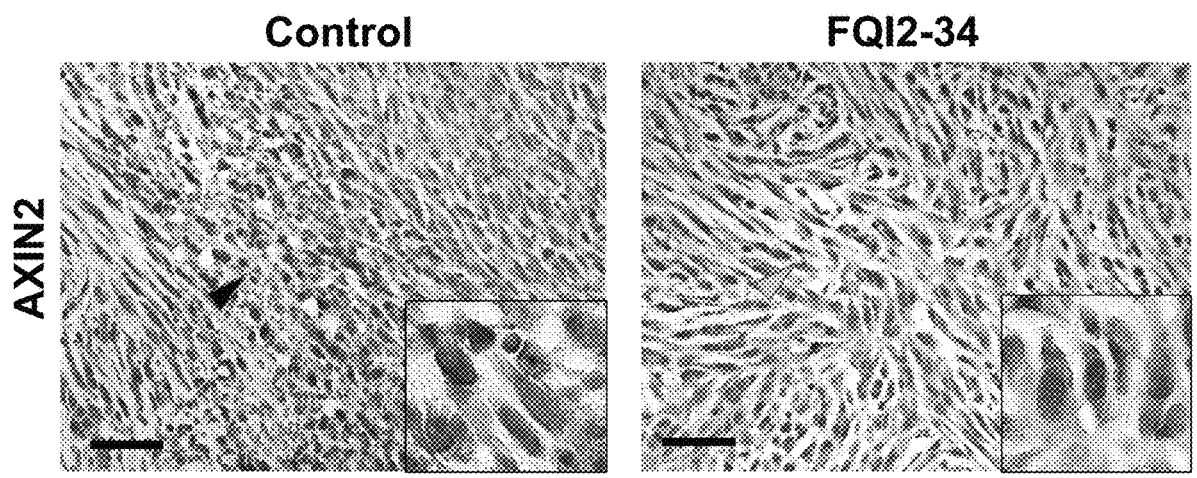
FIGS. 41A-41F show FQI2-34 suppresses Wnt targets in MC38 xenograft cells.
Figure 41B:
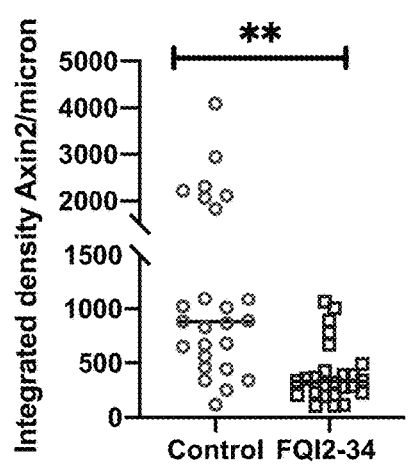
Figure 41C:
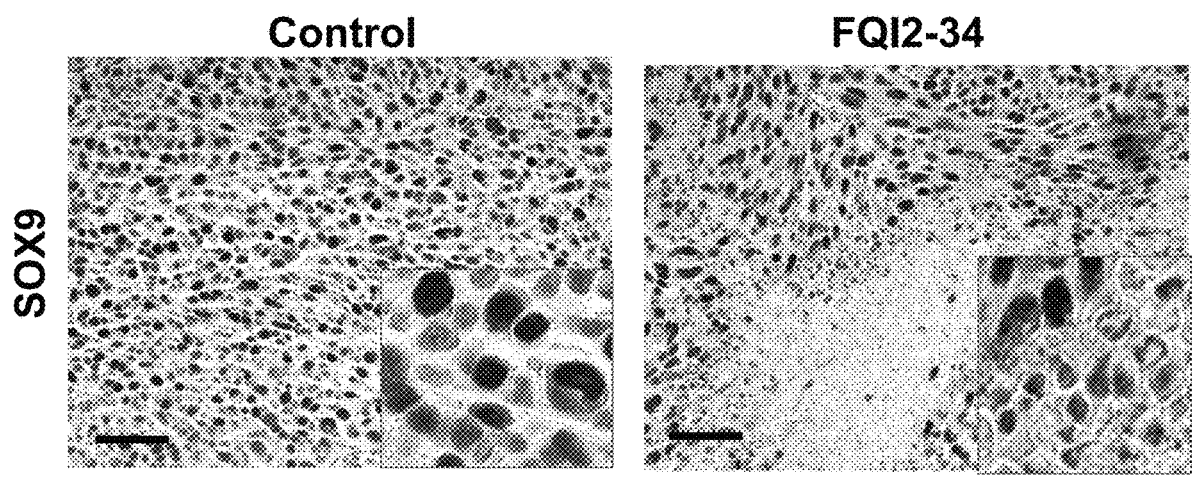
Figure 41D:
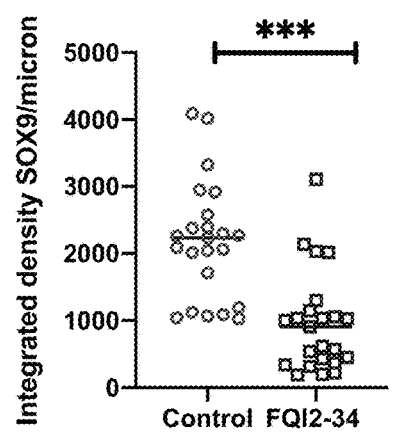
Figure 41E:
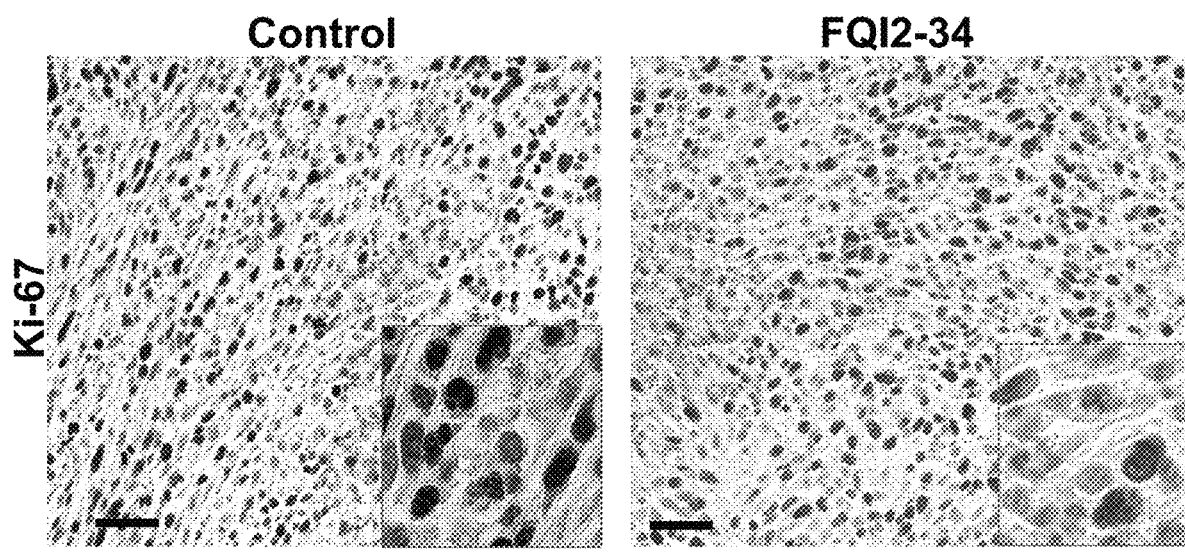
Figure 41F:
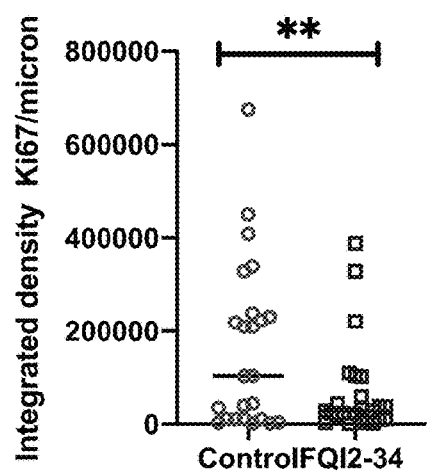

FQI2-34 down-regulated Wnt activity in the xenograft cells and xenograft growth in a syngeneic model: HT-29 is an allogeneic xenograft model of CRC, which requires athymic mice with the immunocompromised background. We further examined the effects of FQI2-34 in immunocompetent mice using a syngeneic model. The MC-38 cell line is a known colon cancer cell line obtained from C57BL6 mice (FIG. 39A)[27]. Our hypothesis was that FQIs will suppress Wnt signaling in xenograft cells and xenograft growth rate. To examine this hypothesis, twenty female C57BL6 mice age 8-12 weeks were injected subcutaneously with MC-38 cells, and ten randomly selected mice were started on FQI2-34 treatment after the xenografts reached 100 mm$^3$. Vehicle treated mice served as controls. The control mice demonstrated a rapid increase in tumor volume and developed skin ulceration in 9 out of 10 mice. In one mouse from this group, an excessive tumor growth >2 cm resulted in euthanasia within 15 days. On the other hand, FQI2-34 treated mice showed a significant reduction in the tumor size in mice (FIGS. 39A and 39B). Compared to the controls, FQI2-34-treated mice showed ~2-fold lower tumor volumes on day 14 (p<0.001) and day 21 (p=0.01). FQI2-34-treated xenografts had a substantial reduction in CRC mass on H&E stain (FIG. 40A). Xenografts from the control mice revealed areas of necrosis amidst the CRC cells. Randomly selected sections of xenografts from both the groups were stained for β-catenin (FIG. 40B) and Wnt targets AXIN2 and SOX9 to evaluate the effect on Wnt signaling in the xenograft cells (FIGS. 41A and 41C). The number of cells with nuclear β-catenin were counted from two randomly selected slides of 10 different mice in each group. A 2.3-fold reduction in number of cells with nuclear β-catenin was noted in FQI2-34 group compared to the control arm (p=0.0016) (FIG. 40C). In the same vein, a close to 2-fold reduction was noted in AXIN2 (p=0.0025) and SOX9 (p<0.001) expression levels in cells of mice treated with FQI2-34 compared to the control group (FIGS. 41A-41D). Ki-67 levels were also suppressed in FQI2-34-treated mice (FIGS. 41E and 41F). Collectively, the above results demonstrated that FQI2-34 suppressed Wnt signaling in the xenograft cells and tumor growth in a syngeneic model on an immunocompetent background.

Correlation of LSF expression and Wnt targets in patient colorectal tumors: The above data suggested that FQIs, disrupt the interaction of LSF with β-catenin to suppress Wnt signaling in the xenograft cells. Based on these observations, we posited that LSF levels will positively correlate with the state of Wnt signaling in cancer cells. To this end, we examined a set of nineteen AJCC stage 4 CRC patients who were managed at the Boston Medical Center. Most of the patients in this cohort were male, with predominate age of 50±16 years, who had left sided cancer. Adenocarcinoma constituted the predominant histopathologic type of the tumor.

Figure 42C:
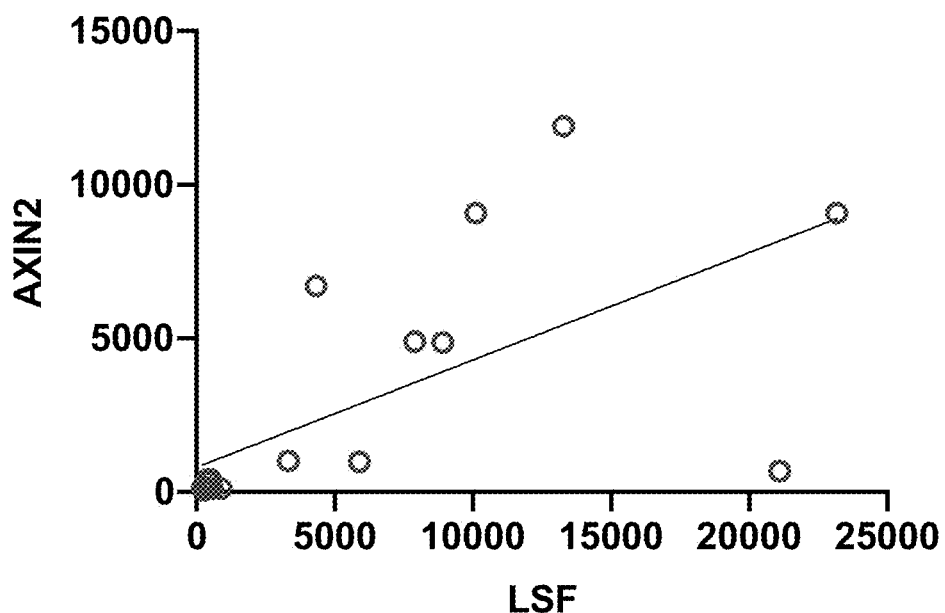
Figure 42D:
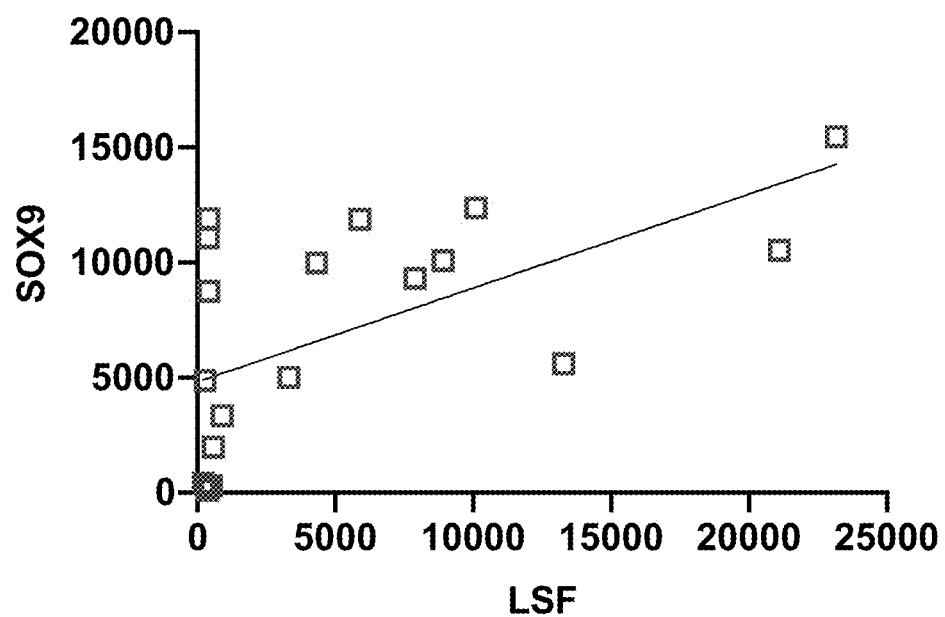

Serial sections from CRC from these patients were stained with LSF, AXIN2 and SOX9. We noted variability in LSF expression in CRC, with SOX9 and AXIN2 expression apparently higher in tumors with more LSF expression (FIG. 42A) compared to those with lower LSF expression (FIG. 42B). To quantitate the expression level of these proteins, whole slide scanning was performed and the amounts of these proteins were analyzed using ImageJ and demonstrated as integrated density. A correlation analysis was performed between LSF and these known Wnt targets. LSF positively correlated with both AXIN2 (correlation coefficient $R^2$=0.42, p=0.0026) and SOX9 (correlation coefficient $R^2$=0.35, p=0.0076) (FIGS. 42C and 42D).

Discussion

The oncogenic transcription factor LSF is overexpressed in multiple cancer types, including in colorectal cancer, in which LSF expression levels correlated with significantly worse survival[19,23]. In other cancer types, LSF is known to facilitate tumor cell proliferative and invasive properties, both in vitro and in vivo. Considering the critical importance of the Wnt pathway in CRC, combined with the recently reported requirement for LSF to effectively promote the β-catenin-mediated transcriptional response downstream of Wnt signaling in pancreatic cancer cell lines, we investigated whether LSF would also be a pharmacological target for treatment of CRC.

We previously identified and characterized a family of Factor Quinolinone Inhibitors (FQIs) as specific inhibitors of LSF, and demonstrated that these compounds inhibit tumor progression in multiple animal models[13,15]. FQIs not only inhibit LSF DNA-binding activity, which requires homo-oligomerization of LSF, but also interfere with other specific LSF-protein interactions (e.g. DNMT1)[13,16,35]. Both LSF oligomerization and the FQI1-sensitive LSF-DNMT1 interaction involve the C-terminal region of LSF. Here, we demonstrate in multiple CRC cell lines that LSF also associates with β-catenin. Furthermore, consistent with the β-catenin interaction mapping in LSF to its C-terminal region[22], we show that FQIs interfere with the association between these two proteins. Taken together, these in vitro findings suggested that inhibiting the transcriptional program downstream of Wnt signaling CRC would be possible through targeting of LSF.

Both our allogeneic and syngeneic CRC studies in mice verified that FQIs significantly reduce tumor growth. In addition, our data showed that FQI2-34 treatment inhibited the pathways downstream of Wnt signaling in the xenografts, with reduction in expression of AXIN2 and SOX9. Notably, FQI2-34 treatment also led to an increase in the amount of nuclear β-catenin, which can explain the higher expression of its target genes. Mechanistically, if the data are interpreted most parsimoniously, this suggests that LSF either facilitates nuclear transport of β-catenin, or stably maintains β-catenin in the nucleus. Although given the length of the FQI2-34 treatment in vivo prior to harvesting of the tumor, other secondary, downstream mechanisms could also be consistent with this result. The previous report regarding the binding of LSF to β-catenin had suggested that LSF then directly enhanced the interaction between β-catenin and its coactivator TCF4[22]. However, our findings suggest that since TCF4 is nuclear prior to β-catenin nuclear entry, the larger amount of β-catenin/TCF4 complexes detected after LSF overexpression could instead be due simply to a greater amount of nuclear β-catenin, rather than any direct consequence of LSF on the β-catenin/TCF4 affinity. Whether the FQI2-34-mediated diminishment in tumor growth was due solely to decreased β-catenin-mediated transcription is yet to be determined. FQIs are expected to also inhibit LSF-driven gene expression that is independent of the Wnt signaling pathway. It is possible that the combination of targeting these two types of transcriptional pathways may result in higher efficacy. In that regard, FQIs may be particularly efficacious in cancer types in which Wnt signaling is active and required for tumor progression, such as CRC.

Given the high unmet medical need for novel therapies for CRC, and the central role that the Wnt pathway plays in oncogenesis and tumor progression, a number of attempts have been made to identify inhibitors of the pathway that are clinically effective. It has been of particular interest to target the transcriptional activity of β-catenin, thereby preventing inhibition of upstream Wnt pathway and membrane-associated β-catenin functions that are essential for many critical aspects of normal cells[8-12]. Small molecules that disrupt interactions between β-catenin and some of its coactivators, TCF4 and CBP, have been characterized in vitro. Despite one CBP-targeted inhibitor, PRI-724, being tested in solid tumors in early phase clinical trials, one trial was withdrawn due to supply issues with the compound, and results from others were not compelling. As indicated above, our data strongly suggest that FQIs also inhibit the transcriptional activity of β-catenin in CRC cells and tumor xenografts, most likely through targeting of LSF/β-catenin interactions. FQIs may be able to overcome the setbacks that other β-catenin-targeted compounds have faced, given the relative ease of synthesis, acceptable pharmacological properties, and minimal toxicity detected to date in animal models. Thus, FQIs show promise as a novel chemotherapeutic for this devastating disease.

References

1 NCI/NIH. SEER Cancer Statistics Review (CSR) 1975-2017. SEER Program (2017)

2 Siegel, R. L., Miller, K. D. & Jemal, A. Cancer statistics, 2020. CA Cancer J Clin 70, 7-30, doi:10.3322/caac.21590 (2020)

3 Sung, H., Ferlay, J., Siegel, R. L., Laversanne, M., Soerjomataram, I., Jemal, A. & Bray, F. Global cancer statistics 2020: GLOBOCAN estimates of incidence and mortality worldwide for 36 cancers in 185 countries. CA Cancer J Clin, doi:10.3322/caac.21660 (2021)

4 Lynch, H. T. & de la Chapelle, A. Hereditary colorectal cancer. N Engl J Med 348, 919-932, doi:10.1056/NEJMra012242 (2003)

5 Vogelstein, B., Fearon, E. R., Hamilton, S. R., Kern, S. E., Preisinger, A. C., Leppert, M., Nakamura, Y., White, R., Smits, A. M. & Bos, J. L. Genetic alterations during colorectal-tumor development. N Engl J Med 319, 525-532, doi:10.1056/NEJM198809013190901 (1988)

6 Nusse, R. Wnt signaling in disease and in development. Cell Res 15, 28-32 (2005)

7 Ghosh, N., Hossain, U., Mandal, A. & Sil, P. C. The Wnt signaling pathway: a potential therapeutic target against cancer. Ann NY Acad Sci 1443, 54-74, doi:10.1111/nyas.14027 (2019)

8 Jung, Y. S. & Park, J. I. Wnt signaling in cancer: therapeutic targeting of Wnt signaling beyond beta-catenin and the destruction complex. Exp Mol Med 52, 183-191, doi:10.1038/s12276-020-0380-6 (2020) PMC7062731.

9 Kahn, M. Can we safely target the WNT pathway? Nat Rev Drug Discov 13, 513-532, doi:10.1038/nrd4233 (2014) PMC4426976.

10 Krishnamurthy, N. & Kurzrock, R. Targeting the Wnt/beta-catenin pathway in cancer: Update on effectors and inhibitors. Cancer Treat Rev 62, 50-60, doi:10.1016/j.ctrv.2017.11.002 (2018) PMC5745276.

11 Kim, M. J., Huang, Y. & Park, J. I. Targeting Wnt Signaling for Gastrointestinal Cancer Therapy: Present and Evolving Views. Cancers (Basel) 12, doi:10.3390/cancers12123638 (2020) PMC7761926.

12 Wang Z, Li Z, Ji H. Direct targeting of β-catenin in the Wnt signaling pathway: Current progress and perspectives. Med Res Rev. 2021 Jan. 21. doi: 10.1002/med.21787. Epub ahead of print. PMID: 33475177

13 Grant, T. J., Bishop, J. A., Christadore, L. M., Barot, G., Chin, H. G., Woodson, S., Kavouris, J., Siddiq, A., Gredler, R., Shen, X. N., Sherman, J., Meehan, T., Fitzgerald, K., Pradhan, S., Briggs, L. A., Andrews, W. H., Sarkar, D., Schaus, S. E. & Hansen, U. Antiproliferative small-molecule inhibitors of transcription factor LSF reveal oncogene addiction to LSF in hepatocellular carcinoma. Proc Natl Acad Sci USA 109, 4503-4508, doi: 10.1073/pnas.1121601109 (2012) PMC3311344.

14 Santhekadur, P. K., Rajasekaran, D., Siddiq, A., Gredler, R., Chen, D., Schaus, S. E., Hansen, U., Fisher, P. B. & Sarkar, D. The transcription factor LSF: a novel oncogene for hepatocellular carcinoma. Am J Cancer Res 2, 269-285 (2012) PMC3365805.

15 Rajasekaran, D., Siddiq, A., Willoughby, J. L., Biagi, J. M., Christadore, L. M., Yunes, S. A., Gredler, R., Jariwala, N., Robertson, C. L., Akiel, M. A., Shen, X. N., Subler, M. A., Windle, J. J., Schaus, S. E., Fisher, P. B., Hansen, U. & Sarkar, D. Small molecule inhibitors of Late SV40 Factor (LSF) abrogate hepatocellular carcinoma (HCC): Evaluation using an endogenous HCC model. Oncotarget 6, 26266-26277, doi:10.18632/oncotarget.4656 (2015) PMC4694900.

16 Chin, H. G., Ponnaluri, V. K., Zhang, G., Esteve, P. O., Schaus, S. E., Hansen, U. & Pradhan, S. Transcription factor LSF-DNMT1 complex dissociation by FQI1 leads to aberrant DNA methylation and gene expression. Oncotarget 7, 83627-83640, doi:10.18632/oncotarget.13271 (2016) PMC5347793.

17 Willoughby, J. L. S., George, K., Roberto, M. P., Chin, H. G., Stoiber, P., Shin, H., Pedamallu, C. S., Schaus, S. E., Fitzgerald, K., Shah, J. & Hansen, U. Targeting the oncogene LSF with either the small molecule inhibitor FQI1 or siRNA causes mitotic delays with unaligned chromosomes, resulting in cell death or senescence. BMC Cancer 20, 552, doi:10.1186/s12885-020-07039-1 (2020) PMC7296649.

18 Zhang, X., Sun, F., Qiao, Y., Zheng, W., Liu, Y., Chen, Y., . . . Wang, J. (2017). TFCP2 Is Required for YAP-Dependent Transcription to Stimulate Liver Malignancy. Cell Reports, 21(5), 1227-1239. https://doi.org/10.1016/j.celrep.2017.10.017. PMID: 29091762

19 Jiang, H., Du, J., Jin, J., Qi, X., Pu, Y. & Fei, B. LSF expression and its prognostic implication in colorectal cancer. Int J Clin Exp Pathol 7, 6024-6031 (2014) PMC4203218.

20 Yoo, B. K., L. Emdad, R. Gredler, C. Fuller, C. I. Dumur, K. H. Jones, C. Cook-Jackson, Z. Su, D. Chen, U. H. Saxena, U. Hansen, P. B. Fisher, and D. Sarkar (2010) Transcription factor Late SV40 Factor (LSF) functions as an oncogene in hepatocellular carcinoma. Proc. Natl. Acad. Sci. USA 107:8357-8362. PMID: 20404171, PMCID: PMC2889542

21 Broniarczyk, J. K., Warowicka, A., Kwasniewska, A., Wohun-Cholewa, M., Kwasniewski, W. & Gozdzicka-Jozefiak, A. Expression of TSG101 protein and LSF transcription factor in HPV-positive cervical cancer cells. Oncol Lett 7, 1409-1413, doi:10.3892/ol.2014.1967 (2014) PMC3997686.

22 Yuedi, D., Yuankun, C., having, Z., Han, L., Yueqi, W., Houbao, L. & Dexiang, Z. TFCP2 activates beta-catenin/TCF signaling in the progression of pancreatic cancer. Oncotarget 8, 70538-70549, doi:10.18632/oncotarget.19741 (2017) PMC5642575.

23 Kotarba, G., Krzywinska, E., Grabowska, A. I., Taracha, A. & Wilanowski, T. TFCP2/TFCP2L1/UBP1 transcription factors in cancer. Cancer Lett 420, 72-79, doi: 10.1016/j.canlet.2018.01.078 (2018)
24. Taracha, A., Kotarba, G. & Wilanowski, T. Neglected Functions of TFCP2/TFCP2L1/UBP1 Transcription Factors May Offer Valuable Insights into Their Mechanisms of Action. Int J Mol Sci 19, doi:10.3390/ijms19102852 (2018) PMC6213935.
25. Veljkovic, J. & Hansen, U. Lineage-specific and ubiquitous biological roles of the mammalian transcription factor LSF. Gene 343, 23-40, doi:10.1016/j.gene.2004.08.010 (2004) PMC3402097.
26. Shashar, M., Siwak, J., Tapan, U., Lee, S. Y., Meyer, R. D., Parrack, P., Tan, J., Khatami, F., Francis, J., Zhao, Q., Hartshorn, K., Kolachalama, V. B., Rahimi, N. & Chitalia, V. c-Cbl mediates the degradation of tumorigenic nuclear beta-catenin contributing to the heterogeneity in Wnt activity in colorectal tumors. Oncotarget 7, 71136-71150, doi:10.18632/oncotarget.12107 (2016) PMC5342068.
27. Lyle, C., Richards, S., Yasuda, K., Napoleon, M. A., Walker, J., Arinze, N., Belghasem, M., Vellard, I., Yin, W., Ravid, J. D., Zavaro, E., Amraei, R., Francis, J., Phatak, U., Rifkin, I. R., Rahimi, N. & Chitalia, V. C. c-Cbl targets PD-1 in immune cells for proteasomal degradation and modulates colorectal tumor growth. Sci Rep 9, 20257, doi:10.1038/s41598-019-56208-1 (2019) PMC6934810.
28. Kumaradevan, S., Lee, S. Y., Richards, S., Lyle, C., Zhao, Q., Tapan, U., Jiangliu, Y., Ghumman, S., Walker, J., Belghasem, M., Arinze, N., Kuhnen, A., Weinberg, J., Francis, J., Hartshorn, K., Kolachalama, V. B., Cifuentes, D., Rahimi, N. & Chitalia, V. C. c-Cbl Expression Correlates with Human Colorectal Cancer Survival and Its Wnt/beta-Catenin Suppressor Function Is Regulated by Tyr371 Phosphorylation. Am J Pathol 188, 1921-1933, doi:10.1016/j.ajpath.2018.05.007 (2018) PMC6099425.
29. Ahmed, D., Eide, P. W., Eilertsen, I. A., Danielsen, S. A., Eknaes, M., Hektoen, M., Lind, G. E. & Lothe, R. A. Epigenetic and genetic features of 24 colon cancer cell lines. Oncogenesis 2, e71, doi:10.1038/oncsis.2013.35 (2013) PMC3816225.
30. Chitalia, V. C., Foy, R. L., Bachschmid, M. M., Zeng, L., Panchenko, M. V., Zhou, M. I., Bharti, A., Seldin, D. C., Lecker, S. H., Dominguez, I. & Cohen, H. T. Jade-1 inhibits Wnt signalling by ubiquitylating beta-catenin and mediates Wnt pathway inhibition by pVHL. Nat Cell Biol 10, 1208-1216, doi:10.1038/ncb1781 (2008) PMC2830866.
31. Herbst, A., Jurinovic, V., Krebs, S., Thieme, S. E., Blum, H., Goke, B. & Kolligs, F. T. Comprehensive analysis of beta-catenin target genes in colorectal carcinoma cell lines with deregulated Wnt/beta-catenin signaling. BMC Genomics 15, 74, doi:10.1186/1471-2164-15-74 (2014) PMC3909937.
32. Blache, P., van de Wetering, M., Duluc, I., Domon, C., Berta, P., Freund, J. N., Clevers, H. & Jay, P. SOX9 is an intestine crypt transcription factor, is regulated by the Wnt pathway, and represses the CDX2 and MUC2 genes. J Cell Biol 166, 37-47, doi:10.1083/jcb.200311021 (2004) PMC2172132.
33. Belghasem, M., Roth, D., Richards, S., Napolene, M. A., Walker, J., Yin, W., Arinze, N., Lyle, C., Spencer, C., Francis, J. M., Thompson, C., Andry, C., Whelan, S. A., Lee, N., Ravid, K. & Chitalia, V. C. Metabolites in a mouse cancer model enhance venous thrombogenicity through the aryl hydrocarbon receptor-tissue factor axis. Blood 134, 2399-2413, doi:10.1182/blood.2019001675 (2019) PMC6933294.
34. Richards, S., Walker, J., Nakanishi, M., Belghasem, M., Lyle, C., Arinze, N., Napoleon, M. A., Ravid, J. D., Crossland, N., Zhao, Q., Rosenberg, D., Rahimi, N. & Chitalia, V. C. Haploinsufficiency of Casitas B-Lineage Lymphoma Augments the Progression of Colon Cancer in the Background of Adenomatous Polyposis Coli Inactivation. Am J Pathol 190, 602-613, doi:10.1016/j.ajpath.2019.10.024 (2020) PMC7074366.
35. Shirra, M. K., Hansen, U., 1998. LSF and NTF-1 share a conserved DNA recognition motif yet require different oligomerization states to form a stable protein—DNA complex. J. Biol. Chem. 273, 19260-19268. doi: 10.1074/jbc.273.30.19260. PMID: 9668115.

What is claimed is:

1. A compound of Formula (I):

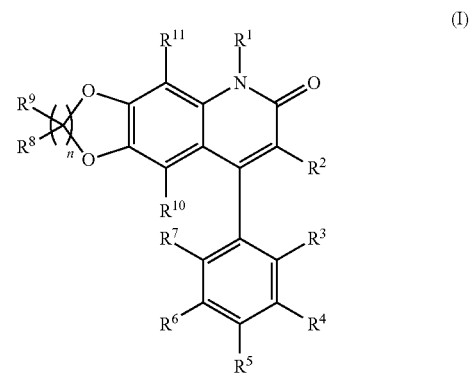

or enantiomers, prodrugs, and pharmaceutically acceptable salts thereof;
wherein:
$R^1$ is hydrogen, $C_1$-$C_6$ alkyl or $C_1$-$C_6$ haloalkyl;
$R^2$, $R^4$, $R^6$, $R^7$, $R^{10}$ and $R^{11}$ are each independently selected from the group consisting of hydrogen, halogen, OH, or amino ($NH_2$);
$R^3$ is $C_1$-$C_6$ alkoxy;
each $R^8$ and $R^9$ is selected independently from the group consisting of hydrogen and halogen; and
(i) n is 2 and $R^5$ is hydrogen, halogen, amino ($NH_2$), mono($C_1$-$C_6$)alkylamino, di($C_1$-$C_6$alkyl)amino, $C_1$-$C_6$ alkyl or $C_1$-$C_6$ haloalkyl; or
(ii) n is 1 and $R^5$ is $C_1$-$C_6$ haloalkyl.

2. The compound of claim 1, wherein $R^1$ and $R^2$ are hydrogen.

3. The compound of claim 1, wherein $R^{10}$ and $R^{11}$ are hydrogen.

4. The compound of claim 1, wherein $R^4$, $R^6$ and $R^7$ are hydrogen.

5. The compound of claim 1, wherein $R^3$ is $OCH_3$, $OCH_2CH_3$, $OCH_2CH_2CH_3$, $OCH(CH_3)_2$, $OCH_2CH_2CH_2CH_3$, $OCH_2CH(CH_3)_2$, $OCH_2CH_2CH_2CH_2CH_3$ or $OCH_2CH_2CH_2CH_2CH_2CH_3$.

6. The compound of claim 5, wherein $R^3$ is $OCH_2CH_3$, $OCH_2CH_2CH_3$ or $OCH_2CH(CH_3)_2$.

7. The compound of claim 1, wherein $R^5$ is hydrogen, halogen, amino, mono($C_1$-$C_6$)alkylamino, di($C_1$-$C_6$alkyl)amino or $C_1$-$C_6$ haloalkyl.

8. The compound of claim 7, wherein $R^5$ is H, Br, F, Cl, I, $N(CH_3)_2$, or trifluoromethane (—$CF_3$).

9. The compound of claim 8, wherein $R^5$ is $N(CH_3)_2$.

10. The compound of claim 8, wherein $R^5$ is trifluoromethane (—$CF_3$).

11. The compound of claim 1, wherein $R^8$ and $R^9$ are hydrogen.

12. The compound of claim 1, wherein n is 1.

13. The compound of claim 1, wherein n is 2.

14. The compound of claim 1, wherein the compound is selected from the group consisting of:

FQI2F3

FQI2-37

FQI2-137 and

FQI2-237

15. The compound of claim 14, wherein the compound is

FQI2-37

16. A method of increasing tubulin acetylation in a cell, inhibiting cell migration, or inducing cell compaction, the method comprising administering to the cell an effective amount of a compound of claim 1.

17. A method for treating cancer in a subject, the method comprising administering an effective amount of a compound of claim 1.

18. A compound of Formula (I):

(I)

or enantiomers, prodrugs, and pharmaceutically acceptable salts thereof;
wherein:
$R^1$ is hydrogen, $C_1$-$C_6$ alkyl or $C_1$-$C_6$ haloalkyl;
$R^2$, $R^4$, $R^6$, $R^7$, $R^{10}$ and $R^{11}$ are each independently selected from the group consisting of hydrogen, halogen, OH, or amino ($NH_2$);
$R^3$ is $C_1$-$C_6$alkoxy;
$R^5$ is halogen, amino ($NH_2$), mono($C_1$-$C_6$)alkylamino, di($C_1$-$C_6$ alkyl)amino, or $C_1$-$C_6$ alkyl;
each $R^8$ and $R^9$ is selected independently from the group consisting of hydrogen and halogen; and
n is 1.

19. The compound of claim 18, wherein $R^1$ and $R^2$ are hydrogen.

20. The compound of claim 18, wherein $R^{10}$ and $R^{11}$ are hydrogen.

21. The compound of claim 18, wherein $R^4$, $R^6$ and $R^7$ are hydrogen.

22. The compound of claim 18, wherein $R^3$ is $OCH_3$, $OCH_2$ $CH_3$, $OCH_2$ $CH_2$ $CH_3$, $OCH(CH_3)_2$, $OCH_2CH_2CH_2CH_3$, $OCH_2CH(CH_3)_2$, $OCH_2CH_2CH_2CH_2CH_3$ or $OCH_2CH_2CH_2CH_2CH_2CH_3$.

23. The compound of claim 18, wherein $R^5$ is hydrogen, halogen, amino, mono($C_1$-$C_6$)alkylamino, di($C_1$-$C_6$ alkyl)amino or $C_1$-$C_6$ haloalkyl.

24. The compound of claim 23, wherein $R^5$ is H, Br, F, Cl, I, or $N(CH_3)_2$.
25. The compound of claim 24, wherein $R^5$ is $N(CH_3)_2$.
26. The compound of claim 18, wherein $R^8$ and $R^9$ are hydrogen.
27. The compound of claim 18, wherein the compound is selected from the group consisting of:
FQI2-34
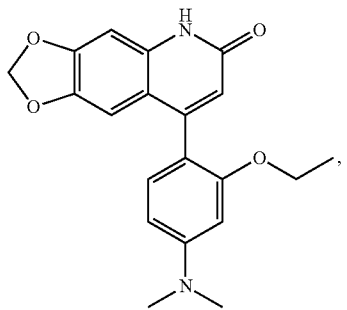
FQI2Br
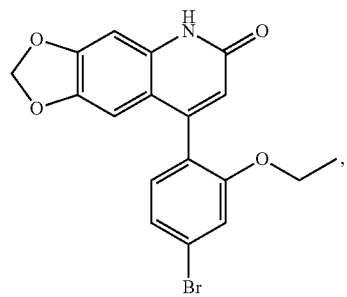
FQI2Cl
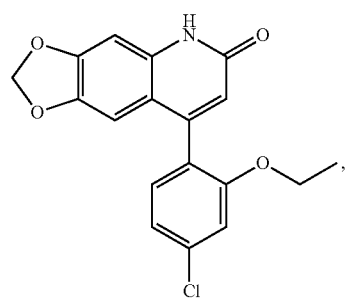
FQI2F
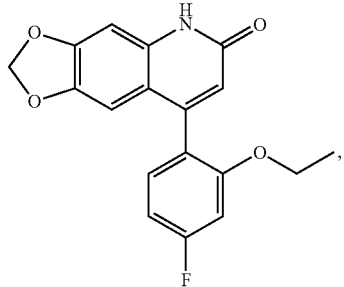
FQI2-134
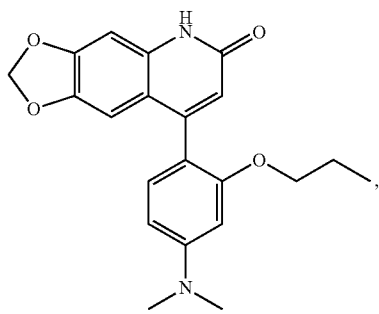
FQI2-234
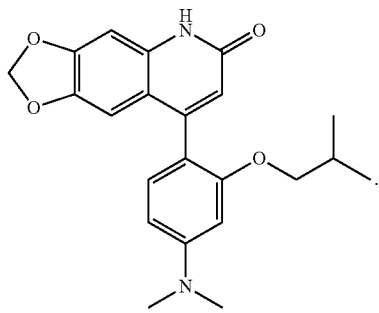
28. The compound of claim 27, wherein the compound is
FQI2-34
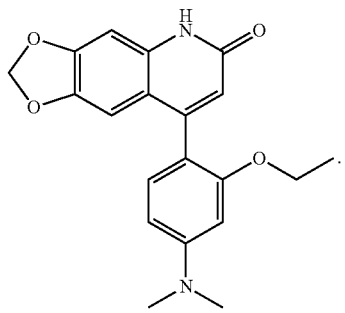
* * * * *